(12) United States Patent
Lazarides et al.

(10) Patent No.: US 8,236,315 B2
(45) Date of Patent: Aug. 7, 2012

(54) HUMANIZED ANTIBODIES SPECIFIC FOR VON WILLEBRAND FACTOR

(75) Inventors: Elias Lazarides, La Jolla, CA (US); Catherine Woods, La Jolla, CA (US); Xiaomin Fan, San Diego, CA (US); Samuel Hou, La Chaux-de-Fonds (CH); Harald Mottl, La Chaux-de-Fonds (CH); Stanislas Blein, La Chaux-de-Fonds (CH); Martin Bertschinger, La Chaux-de-Fonds (CH)

(73) Assignee: Glenmark Pharmaceuticals, S.A., La Chaux-de-Fonds (CH)

( * ) Notice: Subject to any disclaimer, the term of this patent is extended or adjusted under 35 U.S.C. 154(b) by 433 days.

(21) Appl. No.: 12/358,682

(22) Filed: Jan. 23, 2009

(65) Prior Publication Data

US 2009/0232804 A1    Sep. 17, 2009

Related U.S. Application Data

(60) Provisional application No. 61/023,025, filed on Jan. 23, 2008, provisional application No. 61/044,787, filed on Apr. 14, 2008.

(51) Int. Cl.
*A61K 39/395* (2006.01)

(52) U.S. Cl. ............... 424/145.1; 424/133.1; 424/141.1; 424/158.1; 530/387.3; 530/388.1; 530/388.25; 536/23.1; 435/337

(58) Field of Classification Search .................. None
See application file for complete search history.

(56) References Cited

U.S. PATENT DOCUMENTS

| | | |
|---|---|---|
| 3,773,919 A | 11/1973 | Boswell et al. |
| 4,275,149 A | 6/1981 | Litman et al. |
| 4,318,980 A | 3/1982 | Boguslaski et al. |
| RE30,985 E | 6/1982 | Cartaya |
| 4,419,446 A | 12/1983 | Howley et al. |
| 4,485,045 A | 11/1984 | Regen et al. |
| 4,544,545 A | 10/1985 | Ryan et al. |
| 4,560,655 A | 12/1985 | Baker et al. |
| 4,601,978 A | 7/1986 | Karin et al. |
| 4,657,866 A | 4/1987 | Kumar et al. |
| 4,737,456 A | 4/1988 | Weng et al. |
| 4,767,704 A | 8/1988 | Cleveland et al. |
| 4,927,762 A | 5/1990 | Darfler et al. |
| 4,965,199 A | 10/1990 | Capon et al. |
| 4,975,278 A | 12/1990 | Senter et al. |
| 5,013,556 A | 5/1991 | Woodle et al. |
| 5,122,469 A | 6/1992 | Mather et al. |
| 5,225,539 A * | 7/1993 | Winter ....................... 530/387.3 |
| 5,571,894 A | 11/1996 | Wels et al. |
| 5,587,458 A | 12/1996 | King et al. |
| 5,641,870 A | 6/1997 | Rinderknecht et al. |
| 5,965,709 A * | 10/1999 | Presta et al. .............. 530/387.3 |
| 6,180,370 B1 * | 1/2001 | Queen et al. ................ 435/69.6 |
| 6,228,360 B1 * | 5/2001 | Co et al. ..................... 424/145.1 |
| 6,251,393 B1 * | 6/2001 | Handin et al. ............. 424/135.1 |
| 7,572,621 B2 * | 8/2009 | Hu et al. ..................... 435/235.1 |
| 7,744,874 B2 * | 6/2010 | Korytko et al. ............ 424/130.1 |
| 7,786,264 B2 * | 8/2010 | Xia et al. .................... 530/387.1 |
| 2002/0028204 A1 | 3/2002 | Nagano et al. |
| 2003/0119104 A1 | 6/2003 | Perkins et al. |
| 2006/0246586 A1 | 11/2006 | Perkins et al. |
| 2007/0003547 A1 * | 1/2007 | Foote .......................... 424/141.1 |
| 2007/0065425 A1 | 3/2007 | Behrens et al. |

FOREIGN PATENT DOCUMENTS

| | | |
|---|---|---|
| EP | 0073657 A1 | 3/1983 |
| EP | 0183070 B1 | 6/1986 |
| EP | 0402226 A1 | 12/1990 |
| EP | 0616812 B1 | 11/1999 |
| EP | 0244234 B2 | 11/2001 |
| WO | 81/01145 A1 | 4/1981 |
| WO | 87/00195 A1 | 1/1987 |
| WO | 88/07378 A1 | 10/1988 |
| WO | 90/03430 A1 | 4/1990 |
| WO | 90/13646 A1 | 11/1990 |
| WO | 93/16185 A2 | 8/1993 |
| WO | 94/11026 A2 | 5/1994 |
| WO | 97/04801 A1 | 2/1997 |
| WO | 97/38731 A1 | 10/1997 |
| WO | WO 2005035577 A1 * | 4/2005 |
| WO | 2006/046935 | 5/2006 |
| WO | 2006/052591 A2 | 5/2006 |
| WO | WO 2006046935 | 5/2006 |

OTHER PUBLICATIONS

Bonnefoy et al., Blood, 2002, 101:1375-1383.*
Portolano et al., J Immunol. Feb. 1, 1993;150(3):880-7.*
Rudikoff et al., Proc Natl Acad Sci U S A. Mar. 1982;79(6):1979-83.*
Janeway et al., Immunobiology, 3rd edition, 1997, Garland Press, pp. 3:1-3:11.*
William E. Paul, M.D., editor, Fundamental Immunology, 3d ed. Raven Press, 1993, p. 242.*
Sugimoto et al., Int J Hematol. Jan. 1999;69(1):48-53.*
Carter et al., Opin Biotechnol. Aug. 1997;8(4):449-54.*
Anfossi, G. and Trovati, M., Eur. J. Clin. Invest., Role of catecholamines in platelet function: pathophysiological and clinical significance. 26:353-70 (1996).
Barnes, D. and Sato, G., Anal. Biochem., Methods for growth of cultured cells in serum-free medium. 102:255-70 (1980).
Brennan, M., et al., Science, Preparation of bispecific antibodies by chemical recombination of monoclonal immunoglobulin G1 fragments. 229:81-3 (1985).
Carter, P., et al., Biotechnology (N Y), High level *Escherichia coli* expression and production of a bivalent humanized antibody fragment. 10:163-7 (1992).

(Continued)

*Primary Examiner* — Michael Szperka
(74) *Attorney, Agent, or Firm* — K&L Gates LLP

(57) ABSTRACT

The present disclosure relates to humanized antibodies or binding fragments thereof specific for human von Willebrand factor (vWF), methods for their preparation and use, including methods for treating vWF mediated diseases or disorders.

126 Claims, 11 Drawing Sheets

OTHER PUBLICATIONS

Celikel, R., et al., Blood Cells Mol. Dis., Crystal structure of NMC-4 fab anti-von Willebrand factor A1 domain. 23:123-34 (1997).

Celikel, R., et al., Nat. Struct. Biol. Crystal structure of the von Willebrand factor A1 domain in complex with the function blocking NMC-4 Fab. 5:189-94 (1998).

Chari, et al., Cancer Research, Immunoconjugates containing novel maytansinoids: Promising anticancer drugs. 52: 127-31 (1992).

Cheng, Y. and Prusoff, W.H., Biochem. Pharmacol., Relationship between the inhibition constant (K1) and the concentration of inhibitor which causes 50 per cent inhibition (I50) of an enzymatic reaction. 22:3099-108 (1973).

Chothia, C., et al., J. Mol. Biol., Structural repertoire of the human VH segments. 227:799-817 (1992).

Dong, J.F., et al., Blood, ADAMTS-13 rapidly cleaves newly secreted ultralarge von Willebrand factor multimers on the endothelial surface under flowing conditions. 100:4033-9 (2002).

Epstein et al., Proc. Natl. Acad. Sci. USA, Biological activity of liposome-encapsulated murine interferon-gamma is mediated by a cell membrane receptor. 82: 3688-92 (1985).

Fleer et al., Bio/Technology, Stable multicopy vectors for high-level secretion of recombinant human serum albumin by kluyveromyces yeasts. 9: 968-75 (1991).

Foote, J. and Winter, G., J. Mol. Biol., Antibody framework residues affecting the conformation of the hypervariable loops. 224:487-99 (1992).

Fujimura, Y., et al., Blood, Studies on anti-von Willebrand factor (vWF) monoclonal antibody NMC-4, which inhibits both ristocetin- and botrocetin-induced vWF binding to platelet glycoprotein Ib. 77:113-20 (1991).

Gabizon et al., J. National Cancer Inst, Pharmacokinetics and tissue distribution of doxorubicin encapsulated in stable liposomes with long circulation times. 81: 1484-8 (1989).

Garber, E. and Demarest, S.J., Biochem. Biophys. Res. Commun., A broad range of Fab stabilities within a host of therapeutic IgGs. 355:751-757 (2007).

Graham, F.L., et al., J. Gen. Virol., Characteristics of a human cell line transformed by DNA from human adenovirus type 5. 36:59-74. (1977).

Guss, B., et al., EMBO J., Structure of the IgG-binding regions of streptococcal protein G. 5:1567-75 (1986).

Haas, I.G. and Wabl, M.R., Proc. Natl. Acad. Sci. U S A, Immunoglobulin heavy chain toxicity in plasma cells is neutralized by fusion to pre-B cells. 81:7185-8 (1984).

Ham, R.G. and McKeehan, W.L., Methods Enzymol., Media and growth requirements. 58:44-93 (1979).

Hansen, R.J. and Balthasar, J.P., J. Pharmacol. Exp. Ther., Pharmacokinetics, pharmacodynamics, and platelet binding of an anti-glycoprotein IIb/IIIa monoclonal antibody (7E3) in the rat: a quantitative rat model of immune thrombocytopenic purpura. 298:165-71 (2001).

Holmes, M.A., et al., J. Immunol., Structural Effects of Framework Mutations on a Humanized Anti-Lysozyme Antibody. 167:296-301 (2001).

Hwang et al., Proc. Natl. Acad. Sci. USA, Hepatic uptake and degradation of unilamellar sphingomyelin/cholesterol liposomes: A kinetic study. 77: 4030-4 (1980).

Jones, Genetics, Bipartite structure of the ade3 locus of *S. cerevisiae*. 85: 209-23 (1977).

Kabat, E.A., Adv. Protein Chem., The structural basis of antibody complementarity. 32:1-75 (1978).

Lind, S. E. and Kurkjian, C.D., The Bleeding Time, Platelets (second edition), Academic Press, Edited by: MD Alan D. Michelson, pp. 485-493, ISBN: 978-0-12-369367-9 (2007).

Lindenbaum, M., et al., Nucleic Acids Res., A mammalian artificial chromosome engineering system (ACE System) applicable to biopharmaceutical protein production, transgenesis and gene-based cell therapy. 32:e172 (2004).

Lindmark, R., et al., J. Immunol. Methods, Binding of immunoglobulins to protein A and immunoglobulin levels in mammalian sera. 62:1-13 (1983).

Martin et al., J. Biol. Chem., Irreversible coupling of immunoglobulin fragments to preformed vesicles. 257: 286-8 (1982).

Massey, R. J. Nature, Catalytic antibodies catching on. 457-8 (1987).

Mather, J.P., Biol. Reprod., Establishment and characterization of two distinct mouse testicular epithelial cell lines. 23:243-52 (1980).

Mather, J.P., et al., Ann. N.Y. Acad. Sci., Culture of testicular cells in hormone-supplemented serum-free medium. 383:44-68 (1982).

Moake, J.L., et al., J. Clin. Invest, Involvement of large plasma von Willebrand factor (vWF) multimers and unusually large vWF forms derived from endothelial cells in shear stress-induced platelet aggregation. 78:1456-61 (1986).

Morimoto, K. and Inouye, K., J. Biochem. Biophys. Methods, Single-step purification of F(ab')2 fragments of mouse monoclonal antibodies (immunoglobulins G1) by hydrophobic interaction high performance liquid chromatography using TSKgel Phenyl-5PW. 24:107-17 (1992).

Neuberger, et al, Nature, Recombinant antibodies possessing novel effector functions. 312: 604-8 (1984).

O'Sullivan, M.J. and Marks, V., Methods Enzymol., Methods for the preparation of enzyme-antibody conjugates for use in enzyme immunoassay.73(Pt B):147-66 (1981).

Reyes, G.R., et al., Nature, Expression of human beta-interferon cDNA under the control of a thymidine kinase promoter from herpes simplex virus. 297:598-601 (1982).

Serebruany, V.L. and Atar A., Am. J. Cardiol., Assessment of Bleeding Events in Clinical Trials—Proposal of a New Classification. 99:288-90 (2007).

Shima, M., et al., J. Nara Med. Assoc., Production and characterization of monoclonal antibodies against von Willebrand factor (vWF). 36:662-69 (1985).

Simmons, N.L., Exp. Physiol., A cultured human renal epithelioid cell line responsive to vasoactive intestinal peptide. 75:309-19 (1990).

Stinchcomb et al., Nature, Isolation and characterization of yeast chromosomal replicator. 282: 39-43 (1979).

Tan, P., et al., J Immunol., "Superhumanized" Antibodies: Reduction of Immunogenic Potential by Complementarity-Determining Region Grafting with Human Germline Sequences: Application to an Anti-CD28. 169:1119-1125 (2002).

Thiagarajan, P. and Benedict, C.R., Circulation, Inhibition of arterial thrombosis by recombinant annexin V in a rabbit carotid artery injury model. 96:2339-47 (1997).

Urlaub, G. and Chasin, L.A., Proc. Natl. Acad. Sci. U S A, Isolation of Chinese hamster cell mutants deficient in dihydrofolate reductase activity. 77:4216-20 (1980).

Urlaub, G. et al., Somat. Cell Mol. Genet., Effect of gamma rays at the dihydrofolate reductase locus: deletions and inversions. 12:555-66 (1986).

Van Den Berg et al., Bio/Technology, Kluyveromyces as a host for heterologous gene expression: Expression and secretion of prochymosin. 8: 135-9 (1990).

Vitetta, et al., Science, Redesigning nature's poisons to create anti-tumor agents. 238: 1098-1104 (1987).

Wu, T.T. and Kabat E. A., J. Exp. Med., An analysis of the sequences of the variable regions of Bence Jones proteins and myeloma light chains and their implications for antibody complementarity. 132:211-50 (1970).

Xiang, J., et al., J. Mol. Biol., Framework residues 71 and 93 of the chimeric B72.3 antibody are major determinants of the conformation of heavy-chain hypervariable loops. 253:385-90 (1995).

Yaniv, M., Nature, Enhancing elements for activation of eukaryotic promoters. 297:17-8 (1982).

Kageyama, et al., Pharmacokinetics and Pharmacodynamics of AJW200, a Humanized Monoclonal Antibody to von Willebrand Factor, in Monkeys, Arterioscler Throm Vasc Biol 2002;22;187-192.

International Search Report and Written Opinion for International Application No. PCT/IB2009/000124, dated May 6, 2009.

Kageyama et al., Pharmacokinetics and Pharmacodynamics of AJW200, a Humanized Monoclonal Antibody to von Willebrad Factor, in Monkeys' Arteriosclerosis, Thrombosis, and Vascular Biology, Journal of the American Heart Association, Vol. 22, No. 1, Jan. 1, 2002, 187-192.

* cited by examiner

A.

B.

US 8,236,315 B2

HUMANIZED ANTIBODIES SPECIFIC FOR VON WILLEBRAND FACTOR

FIELD

The present disclosure relates generally to humanized antibodies or binding fragments thereof specific for von Willebrand factor. More specifically, the disclosure relates generally to humanized antibodies or binding fragments thereof specific for von Willebrand factor, including those comprising CDRs corresponding to the CDRs present in murine antibody NMC-4.

BACKGROUND

The regulation of platelet adhesion to sites of vascular injury involves a well-orchestrated interaction of several proteins and plays an important role in both hemostasis and thrombosis. One such protein that contributes to platelet adhesion is von Willebrand Factor (vWF), a large multimeric glycoprotein present in blood plasma. VWF is hypothesized to interact with platelet receptor GPlb-α through its A1 domain thereby promoting platelet rolling and adhesion (Moake et al. (1986) J. Clin. Invest. 78:1456-61). Subsequent to platelet rolling and adhesion, a platelet/fibrin plug may form which results in the cessation of bleeding. However, an excessive platelet and/or coagulation response may lead to pathological thrombotic conditions.

Given that current therapies directed towards inhibiting platelet activation (e.g., GPllbllla, ADP receptor, cyclo-oxygenase or phosphodiesterase antagonists) or coagulation (e.g., thrombin and factor Xa inhibitors) are associated with bleeding complications, there exists a need to develop agents that are able to substantially inhibit thrombosis without significantly impairing hemostasis.

SUMMARY

The present disclosure relates generally to humanized antibodies or binding fragments thereof specific for human von Willebrand factor (vWF), methods for their preparation and use, including methods for treating vWF mediated diseases or disorders. The humanized antibodies or binding fragments thereof specific for human vWF may comprise complementarity determining regions (CDRs) from a non-human antibody (e.g., mouse CDRs) and human framework regions.

The present disclosure provides a humanized antibody or binding fragment thereof specific for vWF that comprises a heavy chain variable region sequence as set forth in SEQ ID NO: 19 and a light chain variable region sequence as set forth in SEQ ID NO: 28.

The present disclosure provides a humanized antibody or binding fragment thereof specific for vWF that comprises a heavy chain sequence as set forth in SEQ ID NO: 237 and a light chain sequence as set forth in SEQ ID NO: 238.

The present disclosure provides a humanized antibody or binding fragment thereof specific for vWF that comprises (a) heavy and light chain complementarity determining regions (CDRs) corresponding to the CDRs present in the heavy and light chain variable regions of murine antibody NMC-4 (SEQ ID NO: 1 and 2, respectively); and (b) a heavy chain framework region corresponding to the framework region present in the variable region of VH 4-59 derived human antibodies, such as antibody AAC18165.1 (SEQ ID NO: 4) and/or a light chain framework region corresponding to the framework region present in the variable region of human antibody AAK94808 (VL 018) (SEQ ID NO: 6).

The present disclosure provides a humanized antibody or binding fragment thereof specific for vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9).

The present disclosure also provides a humanized antibody or binding fragment thereof specific for vWF that comprises HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9). In some embodiments, the humanized antibody or binding fragment thereof may further comprise a heavy chain framework region from the variable region of human antibody AAC18165.1 (SEQ ID NO: 4).

The present disclosure also provides a humanized antibody or binding fragment thereof specific for vWF that comprises one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12).

The present disclosure provides a humanized antibody or binding fragment thereof specific for vWF that comprises the following light chain CDRs: LCDR1: SASQDINKYLN (SEQ ID NO: 10), LCDR2: YTSSLHS (SEQ ID NO: 11) and LCDR3: QQYEKLPWT (SEQ ID NO: 12). In some embodiments, the humanized antibody or binding fragment thereof may further comprise a light chain framework region from the variable region of human antibody AAK94808 (SEQ ID NO: 6).

The present disclosure also provides a humanized antibody or binding fragment thereof specific for vWF that comprises: heavy chain CDRs, HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9); and light chain CDRs, LCDR1: SASQDINKYLN (SEQ ID NO: 10), LCDR2: YTSSLHS (SEQ ID NO: 11) and LCDR3: QQYEKLPWT (SEQ ID NO: 12). In some embodiments, the humanized antibody or binding fragment thereof may further comprise a light chain framework region from the variable region of human antibody AAK94808 (SEQ ID NO: 6) and/or a heavy chain framework region from the variable region of human antibody AAC18165.1 (SEQ ID NO: 4).

The present disclosure provides a humanized antibody or binding fragment thereof specific for vWF that comprises one or more of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146).

The present disclosure provides a humanized antibody specific for vWF that comprises one or more of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides a humanized antibody or binding fragment thereof specific for vWF that comprises one or more of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146); and one or more of the following light chain variable regions: L5 (SEQ ID NO: 23), L4 (SEQ ID NO: 24), L6 (SEQ ID NO: 25), L7 (SEQ ID NO:

26), L8 (SEQ ID NO: 27), L9 (SEQ ID NO: 28), L10 (SEQ ID NO: 29) or L11 (SEQ ID NO: 30).

For example, humanized antibodies or binding fragments thereof may comprise L5 (SEQ ID NO: 23) and H2 (SEQ ID NO: 13); L5 (SEQ ID NO: 23) and H4 (SEQ ID NO: 14); L5 (SEQ ID NO: 23) and H5 (SEQ ID NO: 15); L5 (SEQ ID NO: 23) and H6 (SEQ ID NO: 16); L5 (SEQ ID NO: 23) and H7 (SEQ ID NO: 17); L5 (SEQ ID NO: 23) and H8 (SEQ ID NO: 18); L4 (SEQ ID NO: 24) and H2 (SEQ ID NO: 13); L6 (SEQ ID NO: 25) and H2 (SEQ ID NO: 13); L11 (SEQ ID NO: 30) and H2 (SEQ ID NO: 13); L7 (SEQ ID NO: 26) and H2 (SEQ ID NO: 13); L9 (SEQ ID NO: 28) and H9 (SEQ ID NO: 19); L8 (SEQ ID NO: 27) and H9 (SEQ ID NO: 19); L7 (SEQ ID NO: 26) and H9 (SEQ ID NO: 19); L6 (SEQ ID NO: 25) and H9 (SEQ ID NO: 19); L4 (SEQ ID NO: 24) and H9 (SEQ ID NO: 19); L5 (SEQ ID NO: 23) and H9 (SEQ ID NO: 19); L10 (SEQ ID NO:29) and H9 (SEQ ID NO: 19); L9 (SEQ ID NO: 28) and H9 (SEQ ID NO:19); L9 (SEQ ID NO: 28) and H12 (SEQ ID NO: 20); L9 (SEQ ID NO: 28) and H13 (SEQ ID NO: 21); L9 (SEQ ID NO: 28) and H14 (SEQ ID NO: 22); L11 (SEQ ID NO: 30) and H9 (SEQ ID NO: 19); or L11 (SEQ ID NO: 30) and H14 (SEQ ID NO: 22).

The present disclosure also provides a humanized antibody or binding fragment thereof specific for vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9); and one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12). In some embodiments, the humanized antibody or binding fragment thereof may further comprise a light chain framework region from the variable region of human antibody AAK94808 (SEQ ID NO: 6) and/or a heavy chain framework region from the variable region of human antibody AAC18165.1 (SEQ ID NO: 4).

The present disclosure provides a humanized antibody or binding fragment as described herein, that binds to vWF with an affinity (Kd) of 10 nM or less, preferably 5 nM or less, more preferably 1 nM or less, most preferably at least about 0.2 nM to about 0.4 nM. The present disclosure also provides a humanized antibody or binding fragment as described herein, that competes for binding to vWF with an affinity (Ki) of 100 nM or less, preferably 50 nM or less, more preferably 10 nM or less, most preferably at least about 0.2 nM to about 5.0 nM.

The present disclosure also provides a humanized antibody or binding fragment thereof that binds to the A1 domain of vWF with an affinity (Kd) of 10 nM or less, preferably 5 nM or less, more preferably 1 nM or less, most preferably at least about 0.2 nM to about 0.4 nM. The present disclosure also provides a humanized antibody or binding fragment thereof that competes for binding to the A1 domain of vWF with an affinity (Ki) of 100 nM or less, preferably 50 nM or less, more preferably 10 nM or less, most preferably at least about 0.2 nM to about 5.0 nM.

The present disclosure also provides a humanized antibody or binding fragment thereof which has a FAB fragment thermostability temperature greater than 65° C.

The present disclosure provides a humanized antibody or binding fragment thereof specific for vWF that comprises: HCDR1 (GFSLTDYGVD; SEQ ID NO: 7), HCDR2 (MIWGDGSTDYNSALKS; SEQ ID NO: 8), HCDR3 (DPADYGNYDYALDY; SEQ ID NO: 9) and a light chain CDR1, a light chain CDR2 and LCDR3 (QQYEKLPWT; SEQ ID NO: 12), with the proviso that at least one of LCDR1 and/or LCDR2 is not SASQDINKYLN (SEQ ID NO: 10) or YTSSLHS (SEQ ID NO: 11), respectively.

The present disclosure also provides a humanized antibody or binding fragment thereof specific for vWF that comprises, HCDR1 (GFSLTDYGVD; SEQ ID NO: 7), HCDR2 (MIWGDGSTDYNSALKS; SEQ ID NO: 8), HCDR3 (DPADYGNYDYALDY; SEQ ID NO: 9), LCDR1 (SASQDINKYLN; SEQ ID NO: 10), LCDR2 (YTSSLHS; SEQ ID NO: 11) and LCDR3 (QQYEKLPWT; SEQ ID NO: 12); heavy chain framework regions 1, 2 and 3 corresponding to framework regions 1, 2 and 3 in human antibody germline family VH4; and light chain framework regions 1, 2 and 3 corresponding to framework regions 1, 2 and 3 in human antibody germline family VK1.

The present disclosure also relates generally to isolated nucleic acids encoding the presently disclosed humanized antibodies specific for human vWF. In some embodiments, a vector may comprise the presently disclosed nucleic acids. In another embodiment, a host cell may comprise the disclosed nucleic acids.

The present disclosure also relates generally to methods of producing a humanized antibody specific for vWF comprising culturing the host cell of the present disclosure so that the nucleic acid is expressed and the antibody produced. In some embodiments, the method further comprises recovering the antibody from the host cell culture. In some embodiments, the antibody is recovered from the host cell medium. In some embodiments, before culturing, the host cell is co-transfected with a vector comprising nucleic acid encoding a heavy chain variable region and with a vector comprising nucleic acid encoding light chain variable region.

The present disclosure relates generally to compositions comprising a humanized antibody specific for vWF and a pharmaceutically acceptable carrier.

Compositions are also provided that comprise a first humanized antibody or binding fragment thereof as described herein and a second antibody that binds to the A1 domain of vWF. In some embodiments, the second antibody is AJW-200.

The present disclosure also relates generally to methods for treating a vWF mediated disease or disorder (e.g., a thrombotic disease or disorder) in a subject (e.g., a patient) by administering to the subject a therapeutically effective amount of a humanized antibody or fragment thereof specific for vWF. In some embodiments, the subject is a human. In some embodiments, a therapeutically effective amount is sufficient to inhibit platelet aggregation but insufficient to cause significant clinical signs of bleeding.

The present disclosure also provides uses of a humanized antibody or binding fragment thereof as described herein as a medicament. The present disclosure also provides uses of a humanized antibody or binding fragment thereof as described herein in the preparation of a medicament for the treatment of a vWF mediated disease or disorder. In some embodiments, a therapeutically effective amount is sufficient to inhibit platelet aggregation but insufficient to cause significant clinical signs of bleeding.

In some embodiments, the vWF mediated disease or disorder is a thrombotic disease or disorder. In some embodiments, the thrombotic disorder is cardiovascular disease or cerebrovascular disease such as ischemic stroke. In some embodiments, the cardiovascular disease is atherosclerosis, restenosis, angina, acute myocardial infarction, acute coronary syndrome or cardiovascular disorders associated with diabetes. In some embodiments, the thrombotic disease or disorder is vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes. In some embodiments, the cerebrovascular disease is vascular dementia, ischemic stroke, or prevention of recurrent strokes.

In some embodiments, the humanized antibody or binding fragment thereof specific for vWF lacks effector function. In some embodiments, the humanized antibody comprises an Fc region derived from IgG4.

In some embodiments, the humanized antibody or binding fragment thereof specific for vWF binds to the A1 domain of von Willebrand factor.

In some embodiments, the antibody binding fragment specific for vWF is a Fab, Fab', Fab'-SH, Fv, scFv, F(ab')2 or a diabody.

In some embodiments, the antibody binding fragment specific for vWF is not a Fab.

In some embodiments, the humanized antibody specific for vWF is a full length antibody.

In some embodiments the humanized antibody may comprise one or more substitutions, for example, F27G, L29I, T30S and/or V34W substitutions, in HCDR1. In some embodiments, the humanized antibody may comprise one or more substitutions, for example, S61P and/or A62S substitutions, in HCDR2. In some embodiments, the humanized antibody may comprise one or more substitutions, for example, S24Q, N30S and/or K31N substitutions, in LCDR1. In some embodiments, the humanized antibody may comprise one or more substitutions, for example, Y50D, T51A, S53N, H55E and/or S56T substitutions, in LCDR2. In some embodiments, the humanized antibody may comprise one or more substitutions, for example, F27G, L29I, T30S and/or V34W substitutions, in HCDR1; one or more substitutions, for example, S61P and/or A62S substitutions, in HCDR2; one or more substitutions, for example, S24Q, N30S and/or K31N substitutions, in LCDR1; and one or more substitutions, for example, Y50D, T51A, S53N, H55E and/or S56T substitutions, in LCDR2.

DETAILED DESCRIPTION

Figure 1:
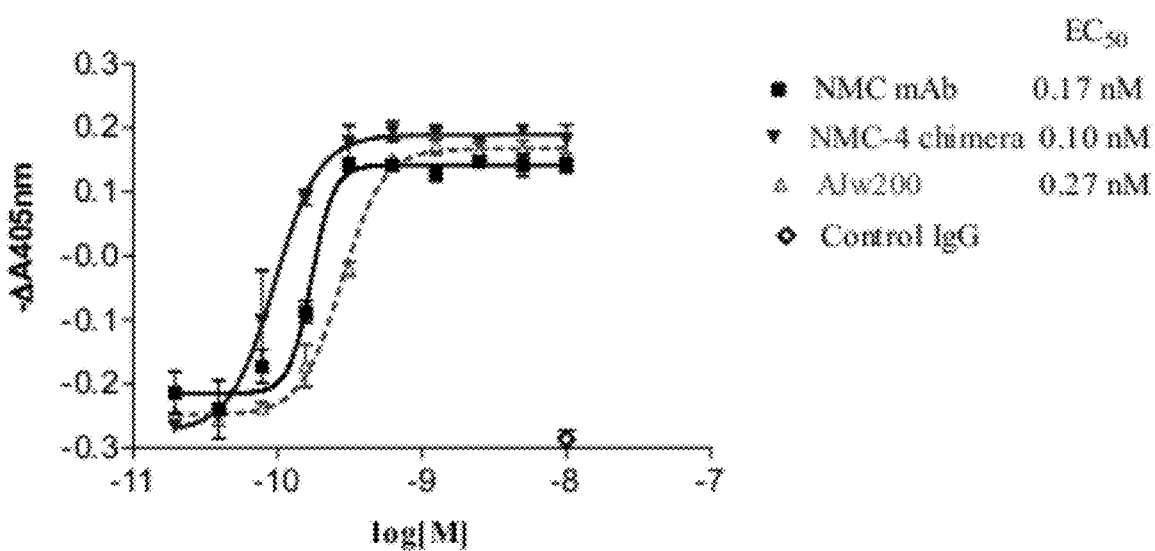
FIG. 1 shows inhibitory activity of an NMC-4 chimeric antibody compared to the original NMC-4 monoclonal antibody and a different anti-vWF antibody, AJW200, in a ristocetin-induced vWF-mediated platelet agglutination assay.

The present disclosure provides humanized antibodies or binding fragments thereof specific for human von Willebrand Factor (vWF), including those that comprise CDR regions corresponding to one or more of the CDRs or portions of the CDRs present in murine antibody NMC-4. The NMC-4 antibody binds the GP1b-α binding site on the A1 domain of vWF (see, e.g., Fujimura et al Blood, 77:113-20, 1991; Shima et al, J Nara Med. Assoc., 36:662, 1985). The humanized antibodies of the present disclosure may further comprise modified or unmodified human framework regions, such as a heavy chain framework region corresponding to the framework region in the variable region of human antibody AAC18165.1 (SEQ ID NO: 4) and a light chain framework region corresponding to the framework region in the variable region of human antibody AAK94808 (SEQ ID NO: 6). A large variety of human framework regions, including those that demonstrated high homology to the subfamilies to which the murine NMC-4 heavy and light chain regions belonged, were considered as potential acceptor molecules for the NMC-4 CDRs. Most surprisingly, grafting of NMC-4 CDRs onto one of the selected heavy chain variable region human frameworks and one of the selected light chain variable region human frameworks without additional changes (e.g., mutating human framework residues to murine residues), is sufficient to retain the potency of the humanized antibody in blocking vWF-mediated platelet responses.

The term "chimeric antibody" includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "human antibody" includes antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g. mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody comprises heavy or light chain variable regions that is "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "derived from" a particular human germline immunoglobulin sequence may contain amino acid differences as compared to the germline sequence, due to, for example, naturally-occurring somatic mutations or intentional introduction of site-directed mutation. However, a selected human antibody or fragment thereof typically is at least 80% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 90%, or even at least 95%, 96%, 97%, 98%, or 99% identical in amino acid sequence to the amino acid sequence encoded by the germline immunoglobulin gene including for example, 80%, 81%, 82%, 83%, 84%, 85%, 86%, 87%, 88%, 89%, 90%, 91%, 92%, 93%, 94%, 95%, 96%, 97%, 98%, 99%, and 100%.

The present disclosure provides a humanized antibody or binding fragment thereof (e.g., Fab, Fab', Fab'-SH, Fv, scFv, F(ab')$_2$, a diabody or a single chain antibody) specific for vWF that comprises a heavy chain variable region sequence as set forth in SEQ ID NO: 19 and a light chain variable region sequence as set forth in SEQ ID NO: 28. The present disclosure also provides a humanized antibody or binding fragment thereof specific for vWF, that comprises a heavy chain sequence as set forth in SEQ ID NO: 237 and a light chain sequence as set forth in SEQ ID NO: 238.

The present disclosure also provides a humanized antibody or binding fragment thereof specific for vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9); and one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12).

The present disclosure also provides a humanized antibody or binding fragment thereof specific for vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9); or one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12).

The present disclosure provides a humanized antibody or binding fragment thereof specific for vWF that comprises: heavy chain CDRs, HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9); and light chain CDRs, LCDR1: SASQDINKYLN (SEQ ID NO: 10), LCDR2: YTSSLHS (SEQ ID NO: 11) and LCDR3: QQYEKLPWT (SEQ ID NO: 12).

The present disclosure provides a humanized antibody or binding fragment thereof specific for vWF that comprises: heavy chain CDRs, HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9); or light chain CDRs, LCDR1: SASQDINKYLN (SEQ ID NO: 10), LCDR2: YTSSLHS (SEQ ID NO: 11) and LCDR3: QQYEKLPWT (SEQ ID NO: 12).

In some embodiments, the humanized antibody or binding fragment thereof may comprise a heavy chain variable region framework region wherein the framework region comprises one or more (e.g., one, two, three and/or four) heavy chain framework sequences (e.g., framework 1 (FW1), framework 2 (FW2), framework 3 (FW3) and/or framework 4 (FW4)) present in an antibody from the human VH4 family.

In some embodiments, the humanized antibody or binding fragment thereof may comprise a light chain variable region framework region wherein the framework region comprises one or more (e.g., one, two, three and/or four) light chain framework sequences (e.g., framework 1 (FW1), framework 2 (FW2), framework 3 (FW3) and/or framework 4 (FW4)) present in an antibody from the human VK1 family.

In some embodiments, the humanized antibody or binding fragment thereof may comprise one or more (e.g., one, two, three and/or four) heavy chain framework region sequences (e.g., framework 1 (FW1), framework 2 (FW2), framework 3 (FW3) and/or framework 4 (FW4)) present in an antibody from the human VH4 family and one or more (e.g., one, two, three and/or four) light chain framework region sequences (e.g., framework 1 (FW1), framework 2 (FW2), framework 3 (FW3) and/or framework 4 (FW4) present in an antibody from the human VK1 family.

Members of the VH4 family and their respective heavy chain framework regions 1, 2 and 3 include: 4-04 (SEQ ID NO: 147, 148 and 149, respectively), 4-28 (SEQ ID NO: 150, 151 and 152, respectively), 4-30.1 (SEQ ID NO: 153, 154 and 155, respectively), 4-30.2 (SEQ ID NO: 156, 157 and 158, respectively), 4-30.4 (SEQ ID NO: 159, 160 and 161, respectively), 4-31 (SEQ ID NO: 162, 163 and 164, respectively), 4-34 (SEQ ID NO: 165, 166 and 167, respectively), 4-39 (SEQ ID NO: 168, 169 and 170, respectively), 4-59 (SEQ ID NO: 171, 172 and 173, respectively), 4-61 (SEQ ID NO: 174, 175 and 176, respectively) and 4-b (SEQ ID NO: 177, 178 and 179, respectively).

Members of the VK1 family and their respective light chain framework regions 1, 2 and 3 include: 012 (SEQ ID NO: 180, 181 and 182, respectively), 02 (SEQ ID NO: 183, 184 and 185, respectively), 018 (SEQ ID NO: 186, 187 and 188, respectively), 08 (SEQ ID NO: 189, 190 and 191, respectively), A20 (SEQ ID NO: 192, 193 and 194, respectively), A30 (SEQ ID NO: 195, 196 and 197, respectfully), L14 (SEQ ID NO: 198, 199 and 200, respectively), L1 (SEQ ID NO: 201, 202 and 203, respectively), L15 (SEQ ID NO: 204, 205 and 206, respectively), L4 (SEQ ID NO: 207, 208 and 209, respectively), L18 (SEQ ID NO: 210, 211 and 212, respectively), L5 (SEQ ID NO: 213, 214 and 215, respectively), L19

(SEQ ID NO: 216, 217 and 218, respectively), L8 (SEQ ID NO: 219, 220, and 221, respectively), L23 (SEQ ID NO: 222, 223 and 224, respectively), L9 (SEQ ID NO: 225, 226 and 227, respectively), L24 (SEQ ID NO: 228, 229 and 230, respectively), L11 (SEQ ID NO: 231, 232 and 233, respectively) and L12 (SEQ ID NO: 234, 235 and 236, respectively).

The present disclosure provides a humanized antibody or binding fragment thereof specific for the vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9).

The present disclosure provides a humanized antibody or binding fragment thereof specific for the vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9) and a heavy chain framework region from human antibody AAC18165.1 (SEQ ID NO: 4).

The present disclosure provides a humanized antibody or binding fragment thereof specific for the vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9) and a heavy chain framework region from human antibody AAC18165.1 (SEQ ID NO: 4), wherein the heavy chain framework region does not comprise one or more murine residues.

The present disclosure provides a humanized antibody or binding fragment thereof specific for the vWF that comprises one or more of the following heavy chain CDRs: HCDR1: GFSLTDYGVD (SEQ ID NO: 7), HCDR2: MIWGDGSTDYNSALKS (SEQ ID NO: 8) and/or HCDR3: DPADYGNYDYALDY (SEQ ID NO: 9) and a heavy chain framework region from human antibody AAC18165.1 (SEQ ID NO: 4), wherein the heavy chain framework region further comprises one or more murine residues.

The present disclosure also provides a humanized antibody or binding fragment thereof specific for vWF that comprises HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9).

The present disclosure also provides a humanized antibody or binding fragment thereof specific for vWF that comprises HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9) and a heavy chain framework region from human antibody AAC18165.1 (SEQ ID NO: 4).

The present disclosure also provides a humanized antibody or binding fragment thereof specific for vWF that comprises HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9) and a heavy chain framework region from human antibody AAC18165.1 (SEQ ID NO: 4), wherein the heavy chain framework region does not comprise one or more murine residues.

The present disclosure also provides a humanized antibody or binding fragment thereof specific for vWF that comprises HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9) and a heavy chain framework region from human antibody AAC18165.1 (SEQ ID NO: 4), wherein the heavy chain framework region further comprises one or more murine residues.

The present disclosure also provides a humanized antibody or binding fragments thereof specific for vWF that comprise one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12).

The present disclosure also provides a humanized antibody or binding fragments thereof specific for vWF that comprise one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12) and a light chain framework region from human antibody AAK94808 (SEQ ID NO: 6).

The present disclosure also provides a humanized antibody or binding fragments thereof specific for vWF that comprise one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12) and a light chain framework region from human antibody AAK94808 (SEQ ID NO: 6), wherein the light chain framework region does not comprise one or more murine residues.

The present disclosure also provides a humanized antibody or binding fragments thereof specific for vWF that comprise one or more of the following light chain CDRs: LCDR1: SASQDINKYLN (SEQ ID NO: 10), LCDR2: YTSSLHS (SEQ ID NO: 11) and/or LCDR3: QQYEKLPWT (SEQ ID NO: 12) and a light chain framework region from human antibody AAK94808 (SEQ ID NO: 6), wherein the light chain framework region further comprises one or more murine residues.

The present disclosure provides a humanized antibody or binding fragment thereof specific for vWF that comprises, light chain CDRs LCDR1: SASQDINKYLN (SEQ ID NO: 10), LCDR2: YTSSLHS (SEQ ID NO: 11) and LCDR3: QQYEKLPWT (SEQ ID NO: 12).

The present disclosure provides a humanized antibody or binding fragment thereof specific for vWF that comprises, light chain CDRs LCDR1: SASQDINKYLN (SEQ ID NO: 10), LCDR2: YTSSLHS (SEQ ID NO: 11) and LCDR3: QQYEKLPWT (SEQ ID NO: 12) and a light chain framework region from human antibody AAK94808 (SEQ ID NO: 6).

The present disclosure provides a humanized antibody or binding fragment thereof specific for vWF that comprises, light chain CDRs LCDR1: SASQDINKYLN (SEQ ID NO: 10), LCDR2: YTSSLHS (SEQ ID NO: 11) and LCDR3: QQYEKLPWT (SEQ ID NO: 12) and a light chain framework region from human antibody AAK94808 (SEQ ID NO: 6), wherein the light chain framework region does not comprise one or more murine residues.

The present disclosure provides a humanized antibody or binding fragment thereof specific for vWF that comprises, light chain CDRs LCDR1: SASQDINKYLN (SEQ ID NO: 10), LCDR2: YTSSLHS (SEQ ID NO: 11) and LCDR3: QQYEKLPWT (SEQ ID NO: 12) and a light chain framework region from human antibody AAK94808 (SEQ ID NO: 6), wherein the light chain framework region further comprises one or more murine residues.

The present disclosure provides a humanized antibody or binding fragment thereof specific for vWF that comprises heavy chain CDRs: HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9); light chain CDRs: LCDR1: SASQDINKYLN (SEQ ID NO: 10), LCDR2: YTSSLHS (SEQ ID NO: 11) and LCDR3: QQYEKLPWT (SEQ ID NO: 12); and optionally a light chain framework region from the variable region of human antibody AAK94808 (SEQ ID NO: 6) and/or a heavy chain framework region from the variable region of human antibody AAC18165.1 (SEQ ID NO: 4).

The present disclosure also provides amino acid sequence variants of a humanized antibody or binding fragment thereof specific for vWF. Usually, the amino acid sequence variants of a humanized antibody or binding fragment thereof specific for vWF will have an amino acid sequence of the heavy and/or light chain framework region, which is at least 80% identical (having at least 80% amino acid sequence identity) to the amino acid sequence of the heavy and/or light chain framework region of the original humanized antibody of either the heavy or the light chain e.g., of either the heavy and light variable region sequences as in SEQ ID NO:19 or SEQ ID NO:28, respectively. Preferably the amino acid sequence identity of the heavy and/or light chain framework region sequence is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the humanized antibody or binding fragment thereof specific for vWF residues, after aligning the sequences and introducing gaps, if necessary, to achieve the maximum percent sequence identity. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3 (1978)) can be used in conjunction with the computer program. For example, the percent identity can the be calculated as: the total number of identical matches multiplied by 100 and then divided by the sum of the length of the longer sequence within the matched span and the number of gaps introduced into the longer sequences in order to align the two sequences.

Thus the present disclosure provides a humanized antibody or binding fragment thereof specific for vWF, wherein the humanized antibody or binding fragment thereof comprises a heavy chain variable region sequence which comprises a framework region which is at least 80% identical to the framework region of SEQ ID NO: 19 and/or a light chain variable region sequence which comprises a framework region which is at least 80% identical to the framework region of SEQ ID NO: 28. The present disclosure provides as well a humanized antibody or binding fragment thereof specific for vWF, wherein the humanized antibody or binding fragment thereof comprises a heavy chain variable region sequence which comprises a framework region which is at least 80% identical to the framework region of SEQ ID NO: 237 and/or a light chain variable region sequence which comprises a framework region which is at least 80% identical to the framework region of SEQ ID NO: 238.

Optionally, the humanized antibody may comprise one or more substitutions, for example, F27G, L291, T30S and/or V34W substitutions, in HCDR1. In some embodiments, the humanized antibody may comprise one or more substitutions, for example, S61P and/or A62S substitutions, in HCDR2. In some embodiments, the humanized antibody may comprise one or more substitutions, for example, S24Q, N30S and/or K31N substitutions, in LCDR1. In some embodiments, the humanized antibody may comprise one or more substitutions, for example, Y50D, T51A, S53N, H55E and/or S56T substitutions, in LCDR2. In some embodiments, the humanized antibody may comprise one or more substitutions, for example, F27G, L291, T30S and/or V34W substitutions, in HCDR1; one or more substitutions, including S61P and/or A62S substitutions, in HCDR2; one or more substitutions, including S24Q, N30S and/or K31N substitutions, in LCDR1; one or more substitutions, for example, Y50D, T51A, S53N, H55E and/or S56T, in LCDR2.

The present disclosure also provides a humanized antibody or binding fragment thereof specific for vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146) (polynucleotides encoding for the above-mentioned heavy chain variable regions are provided by SEQ ID NOs: 128, 129, 130, 131, 132, 133, 134, 135, 136, 137, 138 and 139, respectively).

The present disclosure provides a humanized antibody or binding fragment thereof specific for vWF that comprises one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30) (polynucleotides encoding for the above-mentioned light chain variable regions are provided by SEQ ID NO: 120, 121, 122, 123, 124, 125, 126 and 127, respectively).

The present disclosure also provides a humanized antibody or binding fragment thereof specific for vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146); and one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure provides humanized antibodies or binding fragments thereof specific for vWF that comprise L5 (SEQ ID NO: 23) and H2 (SEQ ID NO: 13); L5 (SEQ ID NO: 23) and H4 (SEQ ID NO: 14); L5 (SEQ ID NO: 23) and H5 (SEQ ID NO: 15); L5 (SEQ ID NO: 23) and H6 (SEQ ID NO: 16); L5 (SEQ ID NO: 23) and H7 (SEQ ID NO: 17); L5 (SEQ ID NO: 23) and H8 (SEQ ID NO: 18); L4 (SEQ ID NO: 24) and H2 (SEQ ID NO: 13); L6 (SEQ ID NO: 25) and H2 (SEQ ID NO: 13); L11 (SEQ ID NO: 30) and H2 (SEQ ID NO: 13); L7 (SEQ ID NO: 26) and H2 (SEQ ID NO: 13); L9 (SEQ ID NO: 28) and H9 (SEQ ID NO: 19); L8 (SEQ ID NO: 27) and H9 (SEQ ID NO: 19); L7 (SEQ ID NO: 26) and H9 (SEQ ID NO: 19); L6 (SEQ ID NO: 25) and H9 (SEQ ID NO: 19); L4 (SEQ ID NO: 24) and H9 (SEQ ID NO: 19); L5 (SEQ ID NO: 23) and H9 (SEQ ID NO: 19); L10 (SEQ ID NO:29) and H9 (SEQ ID NO: 19); L9 (SEQ ID NO: 28) and H9 (SEQ ID NO:19); L9 (SEQ ID NO: 28) and H12 (SEQ ID NO: 20); L9 (SEQ ID NO: 28) and H13 (SEQ ID NO: 21); L9 (SEQ ID NO: 28) and H14 (SEQ ID NO: 22); L11 (SEQ ID NO: 30) and H9 (SEQ ID NO: 19); or L11 (SEQ ID NO: 30) and H14 (SEQ ID NO: 22).

The present disclosure provides a humanized antibody or binding fragment thereof as described herein, that binds to vWF with an affinity (Kd) of 10 nM or less, preferably 5 nM or less, more preferably 1 nM or less, most preferably at least about 0.2 to about 0.4 nM (e.g., from about 0.21, 0.28 or 0.34 to about 0.25, 0.32 or 0.38 nM). The present disclosure also provides a humanized antibody or binding fragment as described herein, that competes for binding to vWF with an affinity (Ki) of 100 nM or less, preferably 50 nM or less, more preferably 10 nM or less, most preferably at least about 0.2 nM to about 5.0 nM (e.g., 0.22, 0.28 or 0.34 to about 2.3, 3.5 or 4.7 nM).

The present disclosure also provides a humanized antibody or binding fragment thereof as described herein, that binds to the A1 domain of vWF with an affinity (Kd) of 10 nM or less, preferably 5 nM or less, more preferably 1 nM or less, most preferably at least about 0.2 to about 0.4 nM (e.g., from about 0.21, 0.28 or 0.34 to about 0.25, 0.32 or 0.38 nM). The present disclosure also provides a humanized antibody or binding fragment thereof that competes for binding to the A1 domain of vWF with an affinity (Ki) of 100 nM or less, preferably 50 nM or less, more preferably 10 nM or less, most preferably at least about 0.2 nM to about 5.0 nM (e.g., 0.22, 0.28 or 0.34 to about 2.3, 3.5 or 4.7 nM).

The present disclosure also provides a humanized antibody or binding fragment thereof specific for vWF which has a FAB fragment thermostability temperature greater than 65° C., preferably greater than 70° C., more preferably greater than 75° C., most preferably greater than 80° C. For analysis of FAB fragment thermostability differential scanning calorimetry measurements are used, whereas a mid-point melting temperature of the FAB fragment in context of a full-length IgG is identified. This kind of calorimetric measurements are known to the skilled person and can be carried out according to e.g. Garber and Demarest (2007), BBRC 355:751-7. Surprisingly, it has been found that the humanized antibody of the present invention has a FAB fragment thermostability temperature greater than the parent non-humanized antibody. The parent non-humanized antibody is usually a murine antibody, in particular a murine antibody NMC-4. Thus the present disclosure also provides a humanized antibody or binding fragment thereof specific for vWF which has a FAB fragment thermostability temperature greater than the parent non-humanized antibody.

The present disclosure provides a humanized antibody or binding fragment thereof specific for vWF that comprises the following hypervariable region amino acid sequences: HCDR1 (GFSLTDYGVD; SEQ ID NO: 7), HCDR2 (MIWGDGSTDYNSALKS; SEQ ID NO: 8), HCDR3 (DPADYGNYDYALDY; SEQ ID NO: 9) and LCDR3 (QQYEKLPWT; SEQ ID NO: 12), with the proviso that at least one of LCDR1 and/or LCDR2 is not SASQDINKYLN (SEQ ID NO: 10) or YTSSLHS (SEQ ID NO: 11), respectively. Surprisingly, humanized NMC-4 antibodies lacking NMC-4 LCDR1 and/or LCDR2 retain nanomolar binding affinity for vWF.

In some embodiments, the humanized antibody may further comprise human antibody heavy chain framework regions. In some embodiments, the heavy chain framework regions correspond to heavy chain framework regions present in a 4-59 derived human antibody. In some embodiments, the heavy chain framework regions present in a 4-59 derived human antibody further comprise one or more murine residues. In some embodiments, the heavy chain framework regions present in a 4-59 derived human antibody does not comprise one or more murine residues.

In some embodiments, the humanized antibody may further comprise human antibody light chain framework regions. In some embodiments, the light chain framework regions correspond to the light chain framework regions present in a 018 derived human antibody. In some embodiments, the light chain framework regions present in a 018 derived human antibody further comprise one or more murine residues. In some embodiments, the light chain framework regions present in a 018 derived human antibody does not comprise one or more murine residues.

LCDR1 and/or LCDR2 may be obtained from a human source. In some embodiments, LCDR1 and/or LCDR2 may be obtained from the same antibody (e.g., one human antibody). In other embodiments, LCDR1 and/or LCDR2 may be obtained from different antibodies (e.g., two human antibodies). If LCDR2 is obtained from a human source, it is preferably DASNLET (SEQ ID NO: 118).

The present disclosure also provides a humanized antibody or binding fragment thereof specific for vWF that comprises: HCDR1 (GFSLTDYGVD; SEQ ID NO: 7), HCDR2 (MIWGDGSTDYNSALKS; SEQ ID NO: 8), HCDR3 (DPADYGNYDYALDY; SEQ ID NO: 9), LCDR1 (SASQDINKYLN; SEQ ID NO: 10), LCDR2 (YTSSLHS; SEQ ID NO: 11) and LCDR3 (QQYEKLPWT; SEQ ID NO: 12); heavy chain framework regions 1, 2 and 3 corresponding to framework regions present in human antibody heavy chain germline sequence 4-59, wherein heavy chain framework region 1 is QVQLQESGPGLVKPSETLSLTCTVS (SEQ ID NO: 171); heavy chain framework region 2 is WIRQPPGKGLEWIG (SEQ ID NO: 172); and heavy chain framework region 3 is RVTISVDTSKNQFSLKLSSVTAADTAVYYCAR (SEQ ID NO: 173); and light chain framework region 1, 2 and 3 corresponding to framework regions present in human antibody light chain germline sequence 018, wherein light chain framework region 1 is DIQMTQSPSSLSASVGDRVTITC (SEQ ID NO: 186); light chain framework region 2 is WYQQKPGKAPKLLIY (SEQ ID NO: 187); and light chain framework region 3 is GVPSRFSGSGSGTDFTFTISSLQPEDIATYYC (SEQ ID NO: 188).

The present disclosure provides a humanized antibody or binding fragment thereof specific for vWF that comprises: HCDR1 (GFSLTDYGVD; SEQ ID NO: 7), HCDR2 (MIWGDGSTDYNSALKS; SEQ ID NO: 8), HCDR3 (DPADYGNYDYALDY; SEQ ID NO: 9)), LCDR1 (SASQDINKYLN; SEQ ID NO: 10), LCDR2 (YTSSLHS; SEQ ID NO: 11) and LCDR3 (QQYEKLPWT; SEQ ID NO: 12); and heavy chain framework region 1, 2 and 3 corresponding to framework regions present in human antibody heavy chain germline sequence 4-34, wherein heavy chain framework region 1 is QVQLQQWGAGLLKPSETLSLTCAVY (SEQ ID NO:165); heavy chain framework region 2 is WIRQPPGKGLEWIG (SEQ ID NO: 166) and heavy chain framework region 3 is RVTISVDTSKNQFSLKLSSVTAADTAVYYCAR (SEQ ID NO: 167); and light chain framework region 1, 2 and 3 corresponding to framework regions present in human antibody light chain germline sequence 018, wherein light chain framework region 1 is DIQMTQSPSSLSASVGDRVTITC (SEQ ID NO: 186); light chain framework region 2 is WYQQKPGKAPKLLIY (SEQ ID NO: 187); and light chain framework region 3 is GVPSRFSGSGSGTDFTFTISSLQPEDIATYYC (SEQ ID NO: 188).

The present disclosure also provides a humanized antibody or binding fragment thereof specific for the A1 domain in vWF that comprises, HCDR1 (GFSLTDYGVD; SEQ ID NO: 7), HCDR2 (MIWGDGSTDYNSALKS; SEQ ID NO: 8), HCDR3 (DPADYGNYDYALD; SEQ ID NO: 9), LCDR1 (SASQDINKYLN; SEQ ID NO: 10), LCDR2 (YTSSLHS; SEQ ID NO: 11) and LCDR3 (QQYEKLPWT; SEQ ID NO: 12); heavy chain framework regions 1, 2 and 3 corresponding to framework regions 1, 2 and 3 present in an antibody from human antibody germline family VH4; and light chain framework regions 1, 2 and 3 corresponding to framework regions 1, 2 and 3 present in an antibody from human antibody germlne family VK1.

The humanized antibody or binding fragment thereof may comprise framework regions 1, 2 and 3 corresponding to framework regions 1, 2 and 3 present in heavy chain variable germlne sequence 4-04 (e.g., FW1: QVQLQESGPGLVKPS-GTLSLTCAVS (SEQ ID NO: 147), FW2: WVRQPPGK-GLEWIG (SEQ ID NO: 148) and FW3: RVTISVDKSKN-QFSLKLSSVTAADTAVYYCAR (SEQ ID NO: 149).

The humanized antibody or binding fragment thereof may comprise framework regions 1, 2 and 3 corresponding to framework regions 1, 2 and 3 present in heavy chain variable germlne sequence 4-28 (e.g., FW1: QVQLQESGPGLVKPS-DTLSLTCAVS (SEQ ID NO: 150), FW2: WIRQPPGK-GLEWIG (SEQ ID NO: 151) and FW3: RVTMSVDTSKN-QFSLKLSSVTAVDTAVYYCAR (SEQ ID NO: 152).

The humanized antibody or binding fragment thereof may comprise framework regions 1, 2 and 3 corresponding to framework regions 1, 2 and 3 present in heavy chain variable germlne sequence 4-30.1 (e.g., FW1: QVQLQESG-PGLVKPSQTLSLTCTVS (SEQ ID NO: 153), FW2: WIRQHPGKGLEWIG (SEQ ID NO: 154) and FW3: RVTISVDTSKNQFSLKLSSVTAADTAVYYCAR (SEQ ID NO: 155).

The humanized antibody or binding fragment thereof may comprise framework regions 1, 2 and 3 corresponding to framework regions 1, 2 and 3 present in heavy chain variable germlne sequence 4-30.2 (e.g., FW1: QLQLQESGS-GLVKPSQTLSLTCAVS (SEQ ID NO: 156), FW2: WIRQP-PGKGLEWIG (SEQ ID NO: 157) and FW3: RVTIS-VDRSKNQFSLKLSSVTAADTAVYYCAR (SEQ ID NO: 158).

The humanized antibody or binding fragment thereof may comprise framework regions 1, 2 and 3 corresponding to framework regions 1, 2 and 3 present in heavy chain variable germlne sequence 4-30.4 (e.g., FW1: QVQLQESG-PGLVKPSQTLSLTCTVS (SEQ ID NO: 159), FW2: WIRQPPGKGLEWIG (SEQ ID NO: 160) and FW3: RVTIS-VDTSKNQFSLKLSSVTAADTAVYYCAR (SEQ ID NO: 161).

The humanized antibody or binding fragment thereof may comprise framework regions 1, 2 and 3 corresponding to framework regions 1, 2 and 3 present in heavy chain variable germline sequence 4-31 (e.g., FW1: QVQLQESG-PGLVKPSQTLSLTCTVS (SEQ ID NO: 162), FW2: WIRQHPGKGLEWIG (SEQ ID NO: 163) and FW3: RVTISVDTSKNQFSLKLSSVTAADTAVYYCAR (SEQ ID NO: 164).

The humanized antibody or binding fragment thereof may comprise framework regions 1, 2 and 3 corresponding to framework regions 1, 2 and 3 present in heavy chain variable germline sequence 4-34 (e.g., FW1: QVQLQQW-GAGLLKPSETLSLTCAVY (SEQ ID NO: 165), FW2: WIRQPPGKGLEWIG (SEQ ID NO: 166) and FW3: RVTIS-VDTSKNQFSLKLSSVTAADTAVYYCAR (SEQ ID NO: 167).

The humanized antibody or binding fragment thereof may comprise framework regions 1, 2 and 3 corresponding to framework regions 1, 2 and 3 present in heavy chain variable germline sequence 4-39 (e.g., FW1: QLQLQESG-PGLVKPSETLSLTCTVS (SEQ ID NO: 168), FW2: WIRQPPGKGLEWIG (SEQ ID NO: 169) and FW3: RVTIS-VDTSKNQFSLKLSSVTAADTAVYYCAR (SEQ ID NO: 170).

The humanized antibody or binding fragment thereof may comprise framework regions 1, 2 and 3 corresponding to framework regions 1, 2 and 3 present in heavy chain variable germline sequence 4-59 (e.g., FW1: QVQLQESG-PGLVKPSETLSLTCTVS (SEQ ID NO: 171), e.g., FW2: WIRQPPGKGLEWIG (SEQ ID NO: 172) and FW3: RVTIS-VDTSKNQFSLKLSSVTAADTAVYYCAR (SEQ ID NO: 173).

The humanized antibody or binding fragment thereof may comprise framework regions 1, 2 and 3 corresponding to framework regions 1, 2 and 3 present in heavy chain variable germline sequence 4-61 (e.g., FW1: QLQLQESG-PGLVKPSETLSLTCTVS (SEQ ID NO: 174), FW2: WIRQPPGKGLEWIG (SEQ ID NO: 175) and FW3: RVTIS-VDTSKNQFSLKLSSVTAADTAVYYCAR (SEQ ID NO: 176).

The humanized antibody or binding fragment thereof may comprise framework regions 1, 2 and 3 corresponding to framework regions 1, 2 and 3 present in heavy chain variable germline sequence 4-b (e.g., FW1: QVQLQESG-PGLVKPSETLSLTCAVS (SEQ ID NO: 177), FW2: WIRQPPGKGLEWIG (SEQ ID NO: 178) and FW3: RVTIS-VDTSKNQFSLKLSSVTAADTAVYYCAR (SEQ ID NO: 179).

The humanized antibody or binding fragment thereof may comprise framework regions 1, 2 and 3 corresponding to framework regions 1, 2 and 3 present in kappa chain variable germline sequence O12 (e.g., FW1: DIQMTQSPSSLSAS-VGDRVTITC (SEQ ID NO: 180), FW2: WYQQKPGKAP-KLLIY (SEQ ID NO: 181) and FW3: GVPSRFSGSGSGT-DFTLTISSLQPEDFATYYC (SEQ ID NO: 182).

The humanized antibody or binding fragment thereof may comprise framework regions 1, 2 and 3 corresponding to framework regions 1, 2 and 3 present in kappa chain variable germline sequence O2 (e.g., FW1: DIQMTQSPSSLSAS-VGDRVTITC (SEQ ID NO: 183), FW2: WYQQKPGKAP-KLLIY (SEQ ID NO: 184) and FW3: GVPSRFSGSGSGT-DFTLTISSLQPEDFATYYC (SEQ ID NO: 185).

The humanized antibody or binding fragment thereof may comprise framework regions 1, 2 and 3 corresponding to framework regions 1, 2 and 3 present in kappa chain variable germline sequence O18 (e.g., FW1: DIQMTQSPSSLSAS-VGDRVTITC (SEQ ID NO: 186), FW2: WYQQKPGKAP-KLLIY (SEQ ID NO: 187) and FW3: GVPSRFSGSGSGT-DFTFTISSLQPEDIATYYC (SEQ ID NO: 188).

The humanized antibody or binding fragment thereof may comprise framework regions 1, 2 and 3 corresponding to framework regions 1, 2 and 3 present in kappa chain variable germline sequence O8 (e.g., FW1: DIQMTQSPSSLSAS-VGDRVTITC (SEQ ID NO: 189), FW2: WYQQKPGKAP-KLLIY (SEQ ID NO: 190) and FW3: GVPSRFSGSGSGT-DFTFTISSLQPEDIATYYC (SEQ ID NO: 191).

The humanized antibody or binding fragment thereof may comprise framework regions 1, 2 and 3 corresponding to the framework regions 1, 2 and 3 present in kappa chain variable germline sequence A20 (e.g., FW1: DIQMTQSPSSLSAS-VGDRVTITC (SEQ ID NO: 192), FW2: WYQQKPGKVP-KLLIY (SEQ ID NO: 193) and FW3: GVPSRFSGSGSGT-DFTLTISSLQPEDVATYYC (SEQ ID NO: 194).

The humanized antibody or binding fragment thereof may comprise framework regions 1, 2 and 3 corresponding to framework regions 1, 2 and 3 present in kappa chain variable germline sequence A30 (e.g., FW1: DIQMTQSPSSLSAS-VGDRVTITC (SEQ ID NO: 195), FW2: WYQQKPGKAP-KRLIY (SEQ ID NO: 196) and FW3: GVPSRFSGSGS-GTEFTLTISSLQPEDFATYYC (SEQ ID NO: 197).

The humanized antibody or binding fragment thereof may comprise framework regions 1, 2 and 3 corresponding to framework regions 1, 2 and 3 present in kappa chain variable germline sequence L14 (e.g., FW1: NIQMTQSPSAMSAS-VGDRVTITC (SEQ ID NO: 198), FW2: WFQQKPGKVP-KHLIY (SEQ ID NO: 199) and FW3: GVPSRFSGSGS-GTEFTLTISSLQPEDFATYYC (SEQ ID NO: 200).

The humanized antibody or binding fragment thereof may comprise framework regions 1, 2 and 3 corresponding to framework regions 1, 2 and 3 present in kappa chain variable germline sequence L1 (e.g., FW1: DIQMTQSPSSLSAS-VGDRVTITC (SEQ ID NO: 201), FW2: WFQQKPGKAPK-SLIY (SEQ ID NO: 202) and FW3: GVPSRFSGSGSGTD-FTLTISSLQPEDFATYYC (SEQ ID NO: 203).

The humanized antibody or binding fragment thereof may comprise framework regions 1, 2 and 3 corresponding to framework regions 1, 2 and 3 present in kappa chain variable germline sequence L15 (e.g., FW1: DIQMTQSPSSLSAS-VGDRVTITC (SEQ ID NO: 204), FW2: WYQQKPEKAPK-SLIY (SEQ ID NO: 205) and FW3: GVPSRFSGSGSGTD-FTLTISSLQPEDFATYYC (SEQ ID NO: 206).

The humanized antibody or binding fragment thereof may comprise framework regions 1, 2 and 3 corresponding to framework regions 1, 2 and 3 present in kappa chain variable germline sequence L4 (e.g., FW1: AIQLTQSPSSLSAS-VGDRVTITC (SEQ ID NO: 207), FW2: WYQQKPGKAP-KLLIY (SEQ ID NO: 208) and FW3: GVPSRFSGSGSGT-DFTLTISSLQPEDFATYYC (SEQ ID NO: 209).

The humanized antibody or binding fragment thereof may comprise framework regions 1, 2 and 3 corresponding to framework regions 1, 2 and 3 present in kappa chain variable germline sequence L18 (e.g., FW1: AIQLTQSPSSLSAS-VGDRVTITC (SEQ ID NO: 210), FW2: WYQQKPGKAP-KLLIY (SEQ ID NO: 211) and FW3: GVPSRFSGSGSGT-DFTLTISSLQPEDFATYYC (SEQ ID NO: 212).

The humanized antibody or binding fragment thereof may comprise framework regions 1, 2 and 3 corresponding to framework regions 1, 2 and 3 present in kappa chain variable germline sequence L5 (e.g., FW1: DIQMTQSPSSVSAS-VGDRVTITC (SEQ ID NO: 213), FW2: WYQQKPGKAP-KLLIY (SEQ ID NO: 214) and FW3: GVPSRFSGSGSGT-DFTLTISSLQPEDFATYYC (SEQ ID NO: 215).

The humanized antibody or binding fragment thereof may comprise framework regions 1, 2 and 3 corresponding to framework regions 1, 2 and 3 present in kappa chain variable germline sequence L19 (e.g., FW1: DIQMTQSPSSVSAS-VGDRVTITC (SEQ ID NO: 216), FW2: WYQQKPGKAP-KLLIY (SEQ ID NO: 217) and FW3: GVPSRFSGSGSGT-DFTLTISSLQPEDFATYYC (SEQ ID NO: 218).

The humanized antibody or binding fragment thereof may comprise framework regions 1, 2 and 3 corresponding to framework regions 1, 2 and 3 present in kappa chain variable germline sequence L8 (e.g., FW1: DIQLTQSPSFLSAS-VGDRVTITC (SEQ ID NO: 219), FW2: WYQQKPGKAP-KLLIY (SEQ ID NO: 220) and FW3: GVPSRFSGSGS-GTEFTLTISSLQPEDFATYYC (SEQ ID NO: 221).

The humanized antibody or binding fragment thereof may comprise framework regions 1, 2 and 3 corresponding to framework regions 1, 2 and 3 present in kappa chain variable germline sequence L23 (e.g., FW1: AIRMTQSPFSLSAS-VGDRVTITC (SEQ ID NO: 222), FW2: WYQQKPAKAP-KLFIY (SEQ ID NO: 223) and FW3: GVPSRFSGSGSGT-DYTLTISSLQPEDFATYYC (SEQ ID NO: 224).

The humanized antibody or binding fragment thereof may comprise framework regions 1, 2 and 3 corresponding to framework regions 1, 2 and 3 present in kappa chain variable germlne sequence L9 (e.g., FW1: AIRMTQSPSSFSAST-GDRVTITC (SEQ ID NO: 225), FW2: WYQQKPGKAP-KLLIY (SEQ ID NO: 226) and FW3: GVPSRFSGSGSGT-DFTLTISCLQSEDFATYYC (SEQ ID NO: 227).

The humanized antibody or binding fragment thereof may comprise framework regions 1, 2 and 3 corresponding to framework regions 1, 2 and 3 present in kappa chain variable germline sequence L24 (e.g., FW1: VIWMTQSPSLLSAST-GDRVTISC (SEQ ID NO: 228), FW2: WYQQKPGKAPEL-LIY (SEQ ID NO: 229) and FW3: GVPSRFSGSGSGTD-FTLTISCLQSEDFATYYC (SEQ ID NO: 230).

The humanized antibody or binding fragment thereof may comprise the framework regions 1, 2 and 3 corresponding to framework regions 1, 2 and 3 present in kappa chain variable germline sequence L11 (e.g., FW1: AIQMTQSPSSLSAS-VGDRVTITC (SEQ ID NO: 231), FW2: WYQQKPGKAP-KLLIY (SEQ ID NO: 232) and FW3: GVPSRFSGSGSGT-DFTLTISSLQPEDFATYYC (SEQ ID NO: 233).

The humanized antibody or binding fragment thereof may comprise framework regions 1, 2 and 3 corresponding to framework regions 1, 2 and 3 present in kappa chain variable germline sequence L12 (e.g., FW1: DIQMTQSPSTLSAS-VGDRVTITC (SEQ ID NO: 234), FW2: WYQQKPGKAP-KLLIY (SEQ ID NO: 235) and FW3: GVPSRFSGSGS-GTEFTLTISSLQPDDFATYYC (SEQ ID NO: 236).

The present disclosure also provides a humanized antibody or binding fragment thereof specific for the A1 domain in vWF that comprises: HCDR1 (GFSLTDYGVD; SEQ ID NO: 7), HCDR2 (MIWGDGSTDYNSALKS; SEQ ID NO: 8), HCDR3 (DPADYGNYDYALDY; SEQ ID NO: 9), LCDR1 (SASQDINKYLN; SEQ ID NO: 10), LCDR2 (YTSSLHS; SEQ ID NO: 11) and LCDR3 (QQYEKLPWT; SEQ ID NO: 12); heavy chain framework regions 1, 2 and 3 corresponding to framework regions 1, 2 and 3 present in human antibody 4-04 (SEQ ID NO: 147, 148 and 149, respectively), 4-28 (SEQ ID NO: 150, 151 and 152, respectively), 4-30.1 (SEQ ID NO: 153, 154 and 155, respectively), 4-30.2 (SEQ ID NO: 156, 157 and 158, respectively), 4-30.4 (SEQ ID NO: 159, 160 and 161, respectively), 4-31 (SEQ ID NO: 162, 163 and 164, respectively), 4-34 (SEQ ID NO: 165, 166 and 167, respectively), 4-39 (SEQ ID NO: 168, 169 and 170, respectively), 4-59 (SEQ ID NO: 171, 172 and 173, respectively), 4-61 (SEQ ID NO: 174, 175 and 176, respectively) or 4-b (SEQ ID NO: 177, 178 and 179, respectively); and light chain framework regions 1, 2 and 3 corresponding to framework regions 1, 2 and 3 present in human antibody 012 (SEQ ID NO: 180, 181 and 182, respectively), 02 (SEQ ID NO: 183, 184 and 185, respectively), 018 (SEQ ID NO: 186, 187 and 188, respectively), 08 (SEQ ID NO: 189, 190 and 191, respectively), A20 (SEQ ID NO: 192, 193 and 194, respectively), A30 (SEQ ID NO: 195, 196 and 197, respectively), L14 (SEQ ID NO: 198, 199 and 200, respectively), L1 (SEQ ID NO: 201, 202 and 203, respectively), L15 (SEQ ID NO: 204, 205 and 206, respectively), L4 (SEQ ID NO: 207, 208 and 209, respectively), L18 (SEQ ID NO: 210, 211 and 212, respectively), L5 (SEQ ID NO: 213, 214 and 215, respectively), L19 (SEQ ID NO: 216, 217 and 218, respectively), L8 (SEQ ID NO: 219, 220, and 221, respectively), L23 (SEQ ID NO: 222, 223 and 224, respectively), L9 (SEQ ID NO: 225, 226 and 227, respectively), L24 (SEQ ID NO: 228, 229 and 230, respectively), L11 (SEQ ID NO: 231, 232 and 233, respectively) or L12 (SEQ ID NO: 234, 235 and 236, respectively).

The present disclosure also provides a humanized antibody or binding fragment thereof as described herein that retains the same activity as the parent non-humanized antibody or as a chimeric antibody comprising variable regions from the parent non-humanized antibody and a human Fc region. The parent non-humanized antibody is usually a murine antibody, in particular a murine antibody NMC-4. The chimeric antibody comprising variable regions from the parent non-humanized is usually an antibody which comprises variable regions from a murine antibody, in particular from a murine antibody NMC-4 and a human Fc region. As human Fc region the human Fc regions as described in the present application are preferably used.

Activity of the humanized antibody or binding fragment thereof as described herein, of the parent non-humanized antibody and of the chimeric antibody can be measured as ristocetin-induced platelet agglutination activity by determining $EC_{50}$ activity as described, for example, in Example 1. A humanized antibody or binding fragment thereof as described herein can be considered to retain the same activity of the parent non-humanized antibody or of the chimeric antibody when the $EC_{50}$ activity of the humanized antibody or binding fragment thereof as described herein is identical to the $EC_{50}$ activity or is up to 50%, preferably up to 30%, preferably up to 20% different (e.g., higher or lower) from the $EC_{50}$ activity of the parent non-humanized antibody or of the chimeric antibody.

In a preferred embodiment of the present disclosure the humanized antibody or binding fragment thereof as described herein further comprises a heavy chain framework region from a human antibody, wherein the human heavy chain framework region does not comprise one or more murine residues.

In a further preferred embodiment of the present disclosure the humanized antibody or binding fragment thereof as described herein further comprises a light chain framework region from a human antibody, wherein the human light chain framework region does not comprise one or more murine residues.

"A human heavy chain framework region which does not comprise one or more murine residues" or "a human light chain framework region which does not comprise one or more murine residues" refers to a human heavy or light chain framework region which does not comprise one or more murine residues which exist only in murine, e.g. does not comprise backmutations to residues which exist only in murine and which does not exist in human. Human heavy or light chain framework regions which contain human residues which exists also in murine are not excluded by this definition. As well a human heavy or light chain framework region of which a residue has been mutated to common human, e.g. to a residue common to most human framework regions but which exists also in murine is not excluded by this definition.

In case of embodiments of the present disclosure where light or heavy chain framework regions from human antibodies further comprise one or more murine residues, they usually comprise 10 or less, preferably 9 or less, more preferably 8 or less, even more preferably 7 or less, most preferably 6 or less, in particular 5 or less, more particular 4 or less, even more particular 3 or less, most particular 2 or less, most particularly preferred 1 murine residues.

The present disclosure provides an isolated nucleic acid encoding a humanized antibody or binding fragment thereof specific for vWF that comprises a heavy chain variable region sequence as set forth in SEQ ID NO: 19 and a light chain variable region sequence as set forth in SEQ ID NO: 28.

The present disclosure provides an isolated nucleic acid encoding a humanized antibody or binding fragment thereof specific for vWF that comprises a heavy chain sequence as set forth in SEQ ID NO: 237 and a light chain sequence as set forth in SEQ ID NO: 238.

The present disclosure also provides an isolated nucleic acid encoding a humanized antibody or binding fragment thereof specific for human vWF that comprises CDR regions corresponding to the CDRs present in murine antibody NMC-4, a heavy chain framework region corresponding to the framework region present in the variable region of human antibody AAC18165.1 (SEQ ID NO: 4) and a light chain framework region corresponding to the framework region present in the variable region of human antibody AAK94808 (SEQ ID NO: 6).

The present disclosure also provides an isolated nucleic acid encoding a humanized antibody or fragment thereof specific for human vWF that comprises: HCDR1: GFSLT-DYGVD (SEQ ID NO: 7), HCDR2: MIWGDGSTDYN-SALKS (SEQ ID NO: 8) and HCDR3: DPADYGNYDY-ALDY (SEQ ID NO: 9) and a heavy chain framework region from the variable region of human antibody AAC18165.1 (SEQ ID NO: 4). A nucleotide sequence of an exemplary human heavy chain framework region is set forth in SEQ ID NO: 116.

The present disclosure also provides an isolated nucleic acid encoding a humanized antibody or binding fragment thereof specific for human vWF that comprises, light chain CDRs LCDR1: SASQDINKYLN (SEQ ID NO: 10), LCDR2: YTSSLHS (SEQ ID NO: 11) and LCDR3: QQYEK-LPWT (SEQ ID NO: 12) and a light chain framework region from the variable region of human antibody AAK94808 (SEQ ID NO: 6). A nucleotide sequence of an exemplary human light chain framework region is set forth in SEQ ID NO: 117.

The present disclosure also provides an isolated nucleic acid encoding a humanized antibody or binding fragment thereof specific for human vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146).

The present disclosure also provides an isolated nucleic acid encoding a humanized antibody or binding fragment thereof specific for human vWF that comprises one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides an isolated nucleic acid encoding a humanized antibody or binding fragment thereof specific for human vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146) and one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides an isolated nucleic acid comprising the light chain encoding nucleic acid sequence of the vector GS264 as deposited in a microorganism with DSMZ on Jan. 23, 2008, having accession No. DSM 21059.

The present disclosure also provides an isolated nucleic acid comprising the heavy chain encoding nucleic acid sequence of the vector GS265 as deposited in a microorganism with DSMZ on Jan. 23, 2008, having accession No. DSM 21060.

Thus the present disclosure also provides a humanized antibody or binding fragment thereof specific for vWF encoded by the light chain encoding nucleic acid sequence of the vector GS264 and by the heavy chain encoding nucleic acid sequence of the vector GS265.

The present disclosure provides a vector comprising an isolated nucleic acid encoding a humanized antibody or binding fragment thereof specific for vWF that comprises a heavy chain variable region sequence as set forth in SEQ ID NO: 19 and a light chain variable region sequence as set forth in SEQ ID NO: 28.

The present disclosure provides a vector comprising an isolated nucleic acid encoding a humanized antibody or binding fragment thereof specific for vWF that comprises a heavy chain sequence as set forth in SEQ ID NO: 237 and a light chain sequence as set forth in SEQ ID NO: 238.

The present disclosure also provides a vector comprising a nucleic acid encoding a humanized antibody or binding fragment thereof specific for human vWF that comprises CDR regions corresponding to the CDRs present within murine antibody NMC-4, a heavy chain framework region corresponding to the framework region in the variable region of human antibody AAC18165.1 (SEQ ID NO: 4) and a light chain framework region corresponding to the framework region in the variable region of human antibody AAK94808 (SEQ ID NO: 6).

The present disclosure also provides a vector comprising a nucleic acid encoding a humanized antibody or binding fragment thereof specific for human vWF that comprises: HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9) and a heavy chain framework region from the variable region of human antibody AAC18165.1 (SEQ ID NO 4).

The present disclosure also provides a vector comprising a nucleic acid encoding a humanized antibody or binding fragment thereof specific for human vWF that comprises: light chain CDRs LCDR1: SASQDINKYLN (SEQ ID NO: 10), LCDR2: YTSSLHS (SEQ ID NO: 11) and LCDR3: QQYEKLPWT (SEQ ID NO: 12) and a light chain framework region from the variable region of human antibody AAK94808 (SEQ ID NO: 6).

The present disclosure also provides a vector comprising a nucleic acid encoding a humanized antibody or binding fragment thereof specific for human vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146).

The present disclosure also provides a vector comprising a nucleic acid encoding a humanized antibody or binding fragment thereof specific for human vWF that comprises one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides a vector comprising a nucleic acid encoding a humanized antibody or binding fragment thereof specific for human vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146) and one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides a vector comprising an isolated nucleic acid comprising the light chain encoding nucleic acid sequence of the vector GS264 as deposited in a microorganism with DSMZ on Jan. 23, 2008, having accession No. DSM 21059.

The present disclosure also provides a vector comprising an isolated nucleic acid comprising the heavy chain encoding nucleic acid sequence of the vector GS265 as deposited in a microorganism with DSMZ on Jan. 23, 2008, having accession No. DSM 21060.

The present disclosure provides a host cell comprising a nucleic acid encoding a humanized antibody or binding fragment thereof specific for vWF that comprises a heavy chain variable region sequence as set forth in SEQ ID NO: 19 and a light chain variable region sequence as set forth in SEQ ID NO: 28.

The present disclosure provides a host cell comprising a nucleic acid encoding a humanized antibody or binding fragment thereof specific for vWF that comprises a heavy chain sequence as set forth in SEQ ID NO: 237 and a light chain sequence as set forth in SEQ ID NO: 238.

The present disclosure also provides a host cell comprising an isolated nucleic acid encoding a humanized antibody or binding fragment thereof specific for human vWF that comprises CDR regions corresponding to the CDRs present within murine antibody NMC-4, a heavy chain framework region corresponding to the framework region in the variable region of human antibody AAC18165.1 (SEQ ID NO: 4) and a light chain framework region corresponding to the framework region in the variable region of human antibody AAK94808 (SEQ ID NO: 6).

The present disclosure also provides a host cell comprising an isolated nucleic acid encoding a humanized antibody or binding fragment thereof specific for human vWF that comprises: HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9) and a heavy chain framework region from the variable region of human antibody AAC18165.1 (SEQ ID NO: 4).

The present disclosure also provides a host cell comprising an isolated nucleic acid encoding a humanized antibody or binding fragment thereof specific for human vWF that comprises: light chain CDRs LCDR1: SASQDINKYLN (SEQ ID NO: 10), LCDR2: YTSSLHS (SEQ ID NO: 11) and LCDR3: QQYEKLPWT (SEQ ID NO: 12) and a light chain framework region from the variable region of human antibody AAK94808 (SEQ ID NO: 6).

The present disclosure also provides a host cell comprising an isolated nucleic acid encoding a humanized antibody or binding fragment thereof specific for human vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146).

The present disclosure also provides a host cell comprising an isolated nucleic acid encoding a humanized antibody or binding fragment thereof specific for human vWF that comprises one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides a host cell comprising an isolated nucleic acid encoding a humanized antibody or binding fragment thereof specific for human vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146) and one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides a host cell comprising an isolated nucleic acid comprising the light chain encoding nucleic acid sequence of the vector GS264 as deposited in a microorganism with DSMZ on Jan. 23, 2008, having accession No. DSM 21059.

The present disclosure also provides a host cell comprising an isolated nucleic acid comprising the heavy chain encoding nucleic acid sequence of the vector GS265 as deposited in a microorganism with DSMZ on Jan. 23, 2008, having accession No. DSM 21060.

The present disclosure also provides methods for producing a humanized antibody or binding fragment thereof specific for vWF comprising culturing the host cells of the present disclosure so that the nucleic acid is expressed and the antibody produced. Methods for producing the humanized vWF antibody or binding fragment thereof of the present disclosure may further comprising recovering the antibody from the host cell culture. In some embodiments, the antibody may be recovered from the host cell medium. In some embodiments, before culturing, the host cell may be co-transfected with a vector comprising nucleic acid encoding a heavy chain variable region and with a vector comprising nucleic acid encoding a light chain variable region.

The present disclosure provides compositions comprising a humanized antibody or binding fragment thereof specific for vWF that comprises a heavy chain variable region sequence as set forth in SEQ ID NO: 19 and a light chain variable region sequence as set forth in SEQ ID NO: 28.

The present disclosure provides compositions comprising a humanized antibody or binding fragment thereof specific for vWF that comprises a heavy chain variable region sequence as set forth in SEQ ID NO: 19 and a light chain variable region sequence as set forth in SEQ ID NO: 28 and a pharmaceutically acceptable carrier.

The present disclosure provides compositions comprising a humanized antibody or binding fragment thereof specific for vWF that comprises a heavy chain sequence as set forth in SEQ ID NO: 237 and a light chain sequence as set forth in SEQ ID NO: 238.

The present disclosure provides compositions comprising a humanized antibody or binding fragment thereof specific for vWF that comprises a heavy chain sequence as set forth in SEQ ID NO: 237 and a light chain sequence as set forth in SEQ ID NO: 238 and a pharmaceutically acceptable carrier.

The present disclosure provides compositions comprising a humanized antibody or binding fragment thereof specific for human von Willebrand Factor (vWF) that comprises CDR regions corresponding to the CDRs present in murine antibody NMC-4, a heavy chain framework region corresponding to the framework region in the variable region of human antibody AAC18165.1 (SEQ ID NO: 4) and a light chain framework region corresponding to the framework region in the variable region of human antibody AAK94808 (SEQ ID NO: 6) and a pharmaceutically acceptable carrier.

The present disclosure also provides compositions comprising a humanized antibody or binding fragment thereof specific for vWF that comprises: HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9), a heavy chain framework region from the variable region of human antibody AAC18165.1 (SEQ ID NO: 4) and a pharmaceutically acceptable carrier.

The present disclosure provides compositions comprising a humanized antibody or binding fragment thereof specific for vWF that comprises, light chain CDRs, LCDR1: SASQDINKYLN (SEQ ID NO: 10), LCDR2: YTSSLHS (SEQ ID NO: 11) and LCDR3: QQYEKLPWT (SEQ ID NO: 12), a light chain framework region from the variable region of human antibody AAK94808 (SEQ ID NO: 6) and a pharmaceutically acceptable carrier.

The present disclosure provides compositions comprising a humanized antibody or binding fragment thereof specific for vWF that comprises: heavy chain CDRs: HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9); light chain CDRs: LCDR1: SASQDINKYLN (SEQ ID NO: 10), LCDR2: YTSSLHS (SEQ ID NO: 11) and LCDR3: QQYEKLPWT (SEQ ID NO: 12); optionally a light chain framework region from the variable region of human antibody AAK94808 (SEQ ID NO: 6) and/or a heavy chain framework region from the variable region of human antibody AAC18165.1 (SEQ ID NO: 4) and a pharmaceutically acceptable carrier.

The present disclosure also provides compositions comprising a humanized antibody or binding fragment thereof specific for vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146) and a pharmaceutically acceptable carrier.

The present disclosure provides compositions comprising a humanized antibody or binding fragment thereof specific for vWF that comprises one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30) and a pharmaceutically acceptable carrier.

The present disclosure also provides compositions comprising a humanized antibody or binding fragment thereof specific for vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146); one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30) and a pharmaceutically acceptable carrier.

Compositions are also provided that comprise a first humanized antibody or binding fragment thereof as described herein and a second antibody that binds to the A1 domain of vWF. In some embodiments, the second antibody is AJW-200.

The present disclosure also provides methods for treating a vWF mediated disease or disorder (e.g., a thrombotic disease or disorder) in a subject (e.g., a human), the method comprising administering to the subject a therapeutically effective amount of a humanized antibody or binding fragment thereof specific for human vWF that comprises a heavy chain variable region sequence as set forth in SEQ ID NO: 19 and a light chain variable region sequence as set forth in SEQ ID NO: 28.

The present disclosure also provides methods for treating a vWF mediated disease or disorder (e.g., a thrombotic disease or disorder) in a subject (e.g., a human), the method comprising administering to the subject a therapeutically effective amount of a humanized antibody or binding fragment thereof specific for human vWF that comprises a heavy chain sequence as set forth in SEQ ID NO: 237 and a light chain sequence as set forth in SEQ ID NO: 238.

The present disclosure also provides methods for treating a vWF mediated disease or disorder (e.g., a thrombotic disease or disorder) in a subject (e.g., a human), the method comprising administering to the subject a therapeutically effective amount of a humanized antibody or binding fragment thereof specific for human vWF that comprises CDR regions corresponding to the CDRs present within murine antibody NMC-4, a heavy chain framework region corresponding to the framework region in the variable region of human antibody AAC18165.1 (SEQ ID NO: 4) and a light chain framework region corresponding to the framework region in the variable region of human antibody AAK94808 (SEQ ID NO: 6).

The present disclosure also provides methods for treating a vWF mediated disease or disorder (e.g., a thrombotic disease or disorder) in a subject (e.g., a human), comprising, administering to the subject a therapeutically effective amount of a humanized antibody or binding fragment thereof specific for vWF that comprises: HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9) and a heavy chain framework region from the variable region of human antibody AAC18165.1 (SEQ ID NO: 4).

The thrombotic disease or disorder may be cardiovascular disease or cerebrovascular disorders such as ischemic stroke. In some embodiments, the cardiovascular disease is atherosclerosis, restenosis, angina, acute myocardial infarction, acute coronary syndrome or cardiovascular disorders associated with diabetes. In some embodiments, the thrombotic disease is vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes. In some embodiments cerebrovascular disorders may include ischemic stroke, resulting from both cerebral artery infarcts as well as small lacunar infarcts, and vascular dementia. Humanized vWF antibodies may also be used for prevention of recurrent strokes or initiation of strokes triggered by cerebrovascular inflammation.

In some embodiments, the thrombotic disease or disorder may include cancer.

The present disclosure provides methods for treating a vWF mediated disease or disorder (e.g., a thrombotic disease or disorder) in a subject (e.g., a human), comprising, administering to the subject a therapeutically effective amount of a humanized antibody or binding fragment thereof specific for vWF that comprises, light chain CDRs LCDR1: SASQDINKYLN (SEQ ID NO: 10), LCDR2: YTSSLHS (SEQ ID NO: 11) and LCDR3: QQYEKLPWT (SEQ ID NO: 12) and a light chain framework region from the variable region of human antibody AAK94808 (SEQ ID NO: 6).

The present disclosure also provides methods for treating a vWF mediated disease or disorder (e.g., a thrombotic disease or disorder) in a subject (e.g., a human), comprising: administering to the subject a therapeutically effective amount of a humanized antibody or fragment thereof specific for vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146).

The present disclosure provides methods for treating a vWF mediated disease or disorder (e.g., a thrombotic disease or disorder) in a subject (e.g., a human), comprising: administering to the subject a therapeutically effective amount of a humanized antibody or fragment thereof specific for vWF that comprises one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

The present disclosure also provides methods for treating a vWF mediated disease or disorder (e.g., a thrombotic disease or disorder) in a subject (e.g., a human), comprising: administering to the subject a therapeutically effective amount of a humanized antibody or fragment thereof specific for vWF that comprises one of the following heavy chain variable regions: H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146); and one of the following light chain variable regions: L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30).

In some embodiments, the humanized antibody lacks effector function. In some embodiments, the humanized antibody comprises an Fc region derived from $IgG_4$.

The present disclosure provides a human antibody or binding fragment thereof specific for von Willebrand factor (vWF), which can be administered in a therapeutically effective amount from about 1 to about 250 times of the $ED_{100}$ without causing significant clinical signs of bleeding. Preferably the human antibody or binding fragment thereof is specific for the A1 domain of human vWF. More preferably the human antibody or binding fragment thereof specific for vWF is a humanized antibody or a binding fragment thereof specific for vWF.

The present disclosure also provides a method for treating a vWF mediated disease or disorder by administering to a subject, preferably to human, a therapeutically effective amount of the humanized antibody or binding fragment thereof described herein from about 0.001 to about 100 mg/kg, preferably, from about 0.002 to about 20 mg/kg, more preferably from about 0.002 to about 10 mg/kg, more preferably, from about 0.002 to about 0.4 mg/kg, more preferably from about 0.005 to about 0.2 mg/kg, and most preferably from about 0.01 to about 0.1 mg/kg.

The present disclosure also provides a method for treating a vWF mediated disease or disorder by administering to a subject in need a therapeutically effective amount of the humanized antibody or binding fragment thereof described herein from about 1 to about 250 times the $ED_{100}$, preferably from about 1 to about 200 times the $ED_{100}$, more preferably from about 1 to about 100 times the $ED_{100}$.

The present disclosure also provides a method for treating a vWF mediated disease or disorder by administering a single or multiple sub-doses of a therapeutically effective amount of the humanized antibody or binding fragment thereof described herein to the subject in need of such treatment.

The present disclosure also provides a method for treating a vWF mediated disease or disorder by subcutaneously administering a therapeutically effective amount of the humanized antibody or binding fragment thereof described herein to a subject in need of such treatment.

The present disclosure also provides a method for treating a vWF mediated disease or disorder by intravenously administering a therapeutically effective amount of the humanized antibody or binding fragment thereof described herein to a subject in need of such treatment.

The present disclosure also provides a method for treating a vWF mediated disease or disorder by intravenously administering a therapeutically effective amount of the humanized antibody or binding fragment thereof described herein serially or in combination with radiological treatments (e.g., irradiation or introduction of radioactive substances—such as those referred to in UICC (Ed.), *Klinische Onkologie*, Springer-Verlag (1982)) to a subject in need of such treatment.

Although any methods and materials similar or equivalent to those described herein can be used in the practice or testing of the present disclosure, the preferred methods and materials are described.

Production of Humanized Von Willebrand Factor Antibodies

Methods are provided for producing a humanized von Willebrand Factor (vWF) antibody (e.g., murine NMC-4) or binding fragment thereof. A humanized antibody or binding fragment thereof specific for vWF may be produced by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for maintaining binding affinity. Optionally, non-human amino acid residues present in the CDRs may be replaced with human residues.

The classifications of frameworks and CDRs as described herein (except HFR1 and HCDR1) are based on the Kabat numbering system. In this definition, the CDRs of the heavy chain contain residues 31-35 (HCDR1), 50-65 (HCDR2) and 95-102 (HCDR3); those of the light chain are defined as being comprised of residues 24-34 (LCDR1), 50-56 (LCDR2) and 89-97 (LCDR3). The framework regions in VH (e.g., heavy chain framework region 1 (HFR1), heavy chain framework region 2 (HFR2), heavy chain framework region 3 (HFR3) and/or heavy chain framework region 4 (HFR4)) are defined as being comprised of residues 1-30 (HFR1), 36-49 (HFR2), 66-94 (HFR3); and 103-113 (HFR4); those in VL contain residue 1-23 (LFR1), 35-49 (LFR2), 57-88 (LFR3) and 98-107 (LFR4) (Wu and Kabat, 1970 *J. Exp. Med.* 132:211). However, based on the structure of CDRs, Chothia defined the CDR1-H as being comprising residues 26-32 (Chothia et al., 1992 *J. Mol. Biol.* 227: 799). The AbM (antibody modeling) definition is a compromise between the two used by Oxford Molecular's AbM antibody modeling software in which the CDR1-H contains the residues 26-35. This is the definition used for the humanization methods described herein using NMC-4.

A humanized antibody or binding fragment thereof specific for von Willebrand factor (vWF) may be produced by transferring heavy chain complementarity determining regions (CDRs) from NMC-4 to a heavy chain framework region corresponding to the framework region in the variable region of human antibody AAC18165.1 (SEQ ID NO: 4); and transferring light chain CDRs from NMC-4 to a light chain framework region corresponding to the framework region in the variable region of human antibody AAK94808 (SEQ ID NO: 6).

A humanized antibody specific for vWF may also be produced by transferring one of more heavy chain CDRs (e.g., HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9)) from murine NMC-4 to a human framework region (e.g., from the variable region of AAC18165.1 (SEQ ID NO: 4).

A humanized antibody specific for vWF may also be produced by transferring one of more light chain CDRs (e.g., LCDR1: SASQDINKYLN (SEQ ID NO: 10), LCDR2: YTSSLHS (SEQ ID NO: 11) and LCDR3: QQYEKLPWT (SEQ ID NO: 12)) to a human framework region (e.g., from the variable region of AAK94808 (SEQ ID NO: 6)).

A humanized antibody specific for vWF may be produced by transferring one of more heavy chain CDRs (e.g., HCDR1: GFSLTDYGVD (SEQ ID NO: 7), HCDR2: MIWGDGSTDYNSALKS (SEQ ID NO: 8) and HCDR3: DPADYGNYDYALDY (SEQ ID NO: 9)) from murine NMC-4 to a human framework region (e.g., the variable region of ACC18165.1.1 (SEQ ID NO: 4)), and transferring one of more light chain CDRs (e.g., LCDR1: SASQDINKYLN (SEQ ID NO: 10), LCDR2: YTSSLHS (SEQ ID NO: 11) and LCDR3: QQYEKLPWT (SEQ ID NO: 12)) to a human framework region (e.g., from the variable region of AAK93808 (SEQ ID NO: 6)).

A humanized antibody specific for vWF may be produced by transferring a modified heavy chain variable region comprising CDR's present in NMC-4 and human framework regions (e.g., H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146)) to a human constant region.

A humanized antibody specific for vWF may also be produced by transferring a modified light chain variable region comprising CDR's present in NMC-4 and human framework regions (e.g., L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30) to a human constant region.

A humanized antibody specific for vWF may be produced by transferring a modified heavy chain variable region comprising CDR's present in NMC-4 and human framework regions (e.g., H2 (SEQ ID NO: 13), H4 (SEQ ID NO: 14), H5 (SEQ ID NO: 15), H6 (SEQ ID NO: 16), H7 (SEQ ID NO: 17), H8 (SEQ ID NO: 18), H9 (SEQ ID NO: 19), H12 (SEQ ID NO: 20), H13 (SEQ ID NO: 21), H14 (SEQ ID NO: 22), H15 (SEQ ID NO: 145) or H16 (SEQ ID NO: 146) to a human constant region; and a modified light chain variable region comprising CDR's present in NMC-4 and human framework regions (e.g., L5 (SEQ ID NO: 23), L4 (SEQ ID NO: 24), L6 (SEQ ID NO: 25), L7 (SEQ ID NO: 26), L8 (SEQ ID NO: 27), L9 (SEQ ID NO: 28), L10 (SEQ ID NO: 29) or L11 (SEQ ID NO: 30) to a human constant region.

In an attempt to further reduce the antigenicity of the humanized antibodies, residues in the CDRs (e.g., murine residues) may be changed (e.g., substituted) for a human amino acid residue. For example, the humanized antibody may comprise one or more F27G, L29I, T30S and/or V34W substitutions in HCDR1. In some embodiments, the humanized antibody may comprise one or more S61P and/or A62S substitutions in HCDR2. In some embodiments, the humanized antibody may comprise one or more S24Q, N30S and/or K31N substitutions in LCDR1. In some embodiments, the humanized antibody may comprise one or more substitutions, for example, Y50D, T51A, S53N, H55E and/or S56T substitutions, in LCDR2. In some embodiments, the humanized antibody may comprise one or more F27G, L29I, T30S and/or V34W substitutions in HCDR1; one or more S61P and/or A62S substitutions in HCDR2; one or more S24Q, N30S and/or K31N substitutions in LCDR1; and one or more Y50D, T51A, S53N, H55E and/or S56T substitutions, in LCDR2.

Various forms of the humanized antibody are contemplated. For example, the humanized antibody may be an antibody fragment, such as a Fab, that is optionally conjugated with one or more cytotoxic agent(s) in order to generate an immunoconjugate. Alternatively, the humanized antibody or affinity-matured antibody may be an intact antibody, such as an intact IgG1 antibody.

Various techniques have been developed for the production of antibody fragments of humanized antibodies. Traditionally, these fragments were derived via proteolytic digestion of intact antibodies (see, e.g., Morimoto et al., *Journal of Biochemical and Biophysical Methods*, 24:107-117 (1992); and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology*, 10: 163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). See WO 1993/16185; U.S. Pat. No. 5,571,894; and U.S. Pat. No. 5,587,458. The antibody fragment may also be a "linear antibody", e.g., as described in U.S. Pat. No. 5,641,870, for example.

According to a different approach, antibody-variable domains with the desired binding specificities (antibody-antigen combining sites) may be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide optimized yields. It is, however, possible to insert the coding sequences for the two or three polypeptide chains in one expression vector when the expression of at least two polypeptide chains in equal ratios results in high yields or when the ratios are of no particular significance.

The disclosure also pertains to immunoconjugates comprising an antibody conjugated to a cytotoxic agent such as a chemotherapeutic agent, toxin (e.g. a small-molecule toxin or an enzymatically active toxin of bacterial, fungal, plant or animal origin, including fragments and/or variants thereof), or a radioactive isotope (i.e., a radioconjugate).

The present disclosure further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated humanized vWF antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 1994/11026. The linker may be a "cleavable linker" facilitating release of the cytotoxic drug in the cell. For example, an acid-labile linker, peptidase-sensitive linker, dimethyl linker, or disulfide-containing linker (Chari et al. *Cancer Research,* 52: 127-131 (1992)) may be used.

Alternatively, a fusion protein comprising the humanized vWF antibody and cytotoxic agent may be made, e.g. by recombinant techniques or peptide synthesis.

In yet another embodiment, the humanized vWF antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) that is conjugated to a cytotoxic agent (e.g. a radionucleotide).

The antibodies of the present disclosure may also be used in ADEPT by conjugating the humanized vWF antibody to a prodrug-activating enzyme that converts a prodrug (e.g. a peptidyl chemotherapeutic agent, see WO 1981/01145) to an active anti-cancer drug (see e.g., WO 1988/07378 and U.S. Pat. No. 4,975,278).

The enzyme component of the immunoconjugate useful for ADEPT includes any enzyme capable of acting on a prodrug in such a way so as to convert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain β-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the disclosure into free active drugs (see, e.g. Massey, *Nature*, 328:457-458 (1987)). Antibody-abzyme conjugates can be prepared as described herein for delivery of the abzyme to a tumor cell population.

Enzymes can be covalently bound to the humanized vWF antibodies by techniques well known in the art such as the use of the heterobifunctional crosslinking reagents discussed above. Alternatively, fusion proteins comprising at least the antigen-binding region of an antibody of the disclosure linked to at least a functionally active portion of a suitable enzyme can be constructed using recombinant DNA techniques well known in the art (see, e.g., Neuberger et al., *Nature*, 312: 604-608 (1984)).

Other modifications of the antibodies are contemplated herein. For example, an antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug-delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The humanized vWF antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO 1997/38731 published Oct. 23, 1997. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al. *J. Biol. Chem.*, 257: 286-288 (1982) via a disulfide-interchange reaction. A chemotherapeutic agent is optionally contained within the liposome. See Gabizon et al., *J. National Cancer Inst.*, 81(19): 1484 (1989).

Vectors, Host Cells and Recombinant Methods

The present disclosure provides isolated nucleic acids encoding humanized antibodies specific for vWF and binding fragments thereof, vectors and host cells comprising the nucleic acid, and recombinant techniques for the production of an antibody or binding fragment thereof.

For recombinant production of an antibody, the nucleic acid encoding it may be isolated and inserted into a replicable vector for further cloning (amplification of the DNA) or for expression. DNA encoding a monoclonal antibody may be isolated and sequenced using conventional procedures (e.g., by using oligonucleotide probes that are capable of binding specifically to genes encoding heavy and light chains of an antibody). Many vectors are available. Vector components generally include, but are not limited to, one or more of the following: a signal sequence, an origin of replication, one or more marker genes, an enhancer element, a promoter, and a transcription-termination sequence.

(i) Signal Sequence Component

Humanized vWF antibodies as described herein may be produced recombinantly not only directly, but also as a fusion polypeptide with a heterologous polypeptide, which is preferably a signal sequence or other polypeptide having a specific cleavage site at the N-terminus of the mature protein or polypeptide. A heterologous signal sequence preferably may be one that is recognized and processed (i.e., cleaved by a signal peptidase) by the host cell. For prokaryotic host cells that do not recognize and process the native humanized vWF antibody signal sequence, the signal sequence may be substituted by a prokaryotic signal sequence selected, for example, from the group of the alkaline phosphatase, penicillinase, lpp, or heat-stable enterotoxin II leaders. For yeast secretion a native signal sequence may be substituted by, e.g., a yeast invertase leader, a α-factor leader (including *Saccharomyces* and *Kluyveromyces* α-factor leaders), an acid-phosphatase leader, a *C. albicans* glucoamylase leader, or a signal described in WO 1990/13646. In mammalian cell expression, mammalian signal sequences as well as viral secretory leaders, for example, the herpes simplex gD signal, are available.

The DNA for such precursor region may be ligated in reading frame to DNA encoding a humanized vWF antibody.

(ii) Origin of Replication Component

Both expression and cloning vectors contain a nucleic acid sequence that enables the vector to replicate in one or more selected host cells. Generally, in cloning vectors this sequence may enable the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply necessary or desired nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the humanized vWF antibody-encoding nucleic acid, such as DHFR, thymidine kinase, metallothionein-I and -II, preferably primate metallothionein genes, aderosine deaminase, ornithine decarboxylase, etc.

For example, cells transformed with the DHFR selection gene are first identified by culturing transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding a humanized vWF antibody, wild-type DHFR protein, and another selectable marker such as aminoglycoside 3'-phosphotransferase (APH) may be selected by cell growth in medium containing a selection agent for the selectable marker such as an aminoglycosidic antibiotic, e.g., kanamycin, neomycin, or G418 (see, e.g., U.S. Pat. No. 4,965,199).

A suitable selection gene for use in yeast may be the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) may be complemented by known plasmids bearing the Leu2 gene.

In addition, vectors derived from the 1.6-µm circular plasmid pKD1 can be used for transformation of *Kluyveromyces* yeasts. Alternatively, an expression system for large-scale production of recombinant calf chymosin is reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technolog*, 9: 968-975 (1991).

(iv) Promoter Component

Expression and cloning vectors usually contain a promoter that may be recognized by the host organism and may be operably linked to the humanized vWF antibody-encoding nucleic acid. Promoters suitable for use with prokaryotic hosts include a phoA promoter, β-lactamase and lactose promoter systems, alkaline phosphatase, a tryptophan (trp) promoter system, and hybrid promoters such as a tac promoter. However, other known bacterial promoters are suitable. Promoters for use in bacterial systems also may contain a Shine-Dalgarno (S.D.) sequence operably linked to the DNA encoding a humanized vWF antibody.

Promoter sequences are known for eukaryotes. Eukaryotic genes have an AT-rich region located approximately 25 to 30 bases upstream from the site where transcription may be initiated. Another sequence found 70 to 80 bases upstream from the start of transcription of many genes is a CNCAAT (SEQ ID NO: 31) region where N may be any nucleotide. At the 3' end of most eukaryotic genes is an AATAAA (SEQ ID NO: 32) sequence that may be the signal for addition of the poly A tail to the 3' end of the coding sequence. These sequences may be suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, may be the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described (see, e.g., European Patent 73,657). Yeast enhancers also are advantageously used with yeast promoters.

Humanized vWF antibody transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), heterologous mammalian promoters, e.g., the actin promoter or an immunoglobulin promoter, and heat-shock promoters, provided such promoters are compatible with the host cell systems.

The early and late promoters of the SV40 virus may be conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector (see, e.g., U.S. Pat. No. 4,419,446). A modification of this system is described in, for example, U.S. Pat. No. 4,601,978. Reyes et al., *Nature,* 297:598-601 (1982) describes expression of human β-interferon cDNA in mouse cells under the control of a thymidine kinase promoter from herpes simplex virus. Alternatively, the rous sarcoma virus long-terminal repeat can be used as the promoter.

(v) Enhancer Element Component

Transcription of a DNA encoding humanized vWF antibodies of this disclosure by higher eukaryotes may be increased by inserting an enhancer sequence into the vector. Useful enhancer sequences are now known from mammalian genes (globin, elastase, albumin, α-fetoprotein, and insulin). Typically, however, one may use an enhancer sequence from a eukaryotic cell virus are also useful. Examples include the SV40 enhancer on the late side of the replication origin (bp 100-270), the cytomegalovirus early-promoter enhancer, the polyoma enhancer on the late side of the replication origin, and adenovirus enhancers. Yaniv, *Nature,* 297:17-18 (1982) also describes enhancing elements for activation of eukaryotic promoters. An enhancer may be spliced into the vector at a position 5' or 3' to the humanized vWF antibody-encoding sequence, but is preferably located at a site 5' from the promoter.

(vi) Transcription Termination Component

Expression vectors used in eukaryotic host cells (for example, yeast, fungi, insect, plant, animal, human, or nucleated cells from other multicellular organisms) may contain sequences necessary for the termination of transcription and for stabilizing the mRNA. Such sequences are commonly available from the 5' end, occasionally 3' end, of untranslated regions of eukaryotic or viral DNAs or cDNAs. These regions contain nucleotide segments transcribed as polyadenylated fragments in the untranslated portion of the mRNA encoding humanized vWF antibody. One useful transcription termination component is a bovine growth hormone polyadenylation region (see, e.g., WO 1994/11026 and expression vectors disclosed therein).

(vii) Selection and Transformation of Host Cells

Suitable host cells for cloning or expressing the DNA in vectors include various prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*. *E. coli* cloning hosts include *E. coli* 294 (ATCC 31,446), *E. coli* B, *E. coli* X1776 (ATCC 31,537), and *E. coli* W3110 (ATCC 27,325).

In addition to prokaryotes, eukaryotic microbes such as filamentous fungi or yeast are suitable cloning or expression hosts for humanized vWF antibody-encoding vectors. *Saccharomyces cerevisiae*, or common baker's yeast, is useful for expression. In addition, a number of other genera, species, and strains are commonly available and can be useful, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated humanized vWF antibody are derived from multicellular organisms. Examples of eukaryotic cells include plant, insect and vertebrate cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines include ChK2 cells (Chromos Molecular Systems Inc.); monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); baby hamster kidney cells (BHK, ATCC CCL 10); human embryonic kidney (HEK) 293 cells (Simmons, 1990 *Exp Physiol.* 75:309); SP2 spleen-myeloma fusion cells (Haas and Wabl, 1984, *PNAS* 81:7185); Chinese hamster ovary cells/−DHFR(CHO, Urlaub et al., *Proc. Natl. Acad. Sci. USA,* 77:4216 (1980), including DG44 (Urlaub et al., *Som. Cell and Mol. Gen.,* 12: 555-566 (1986)) and DP12 cell lines); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). Host cells are transformed with the above-described expression or cloning vectors for humanized vWF antibody production and cultured in conventional nutrient media modified as appropriate for inducing promoters, selecting transformants, or amplifying the genes encoding the desired sequences.

Stable cells lines that express high levels of antibody may also be used to produce the humanized antibody of the present disclosure. For example, a high yielding, mammalian protein expression system that is based on a murine Artificial Chromosome Expression (ACE) platform that has been engineered to contain multiple site-specific, recombination acceptor sites can be loaded with heterologous gene sequences using a mutant lambda integrase (e.g., ACE integrase) in combination with a targeting shuttle vector (Lindenbaum et al, (*Nucl. Acid Res.* 32 (21):e172 (2004); U.S. Patent Application Nos: 2003/0119104A1 and 2006/0246586 A1). This system may be used to generate stable cell lines for expression of selected humanized variants and the NMC-4 chimera.

(viii) Culturing the Host Cells

Host cells useful for producing a humanized vWF antibody may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described, for example, in Ham et al., *Meth. Enz.* 58:44 (1979); Barnes et al., *Anal. Biochem.,* 102:255 (1980); U.S. Pat. Nos. 4,767,704; 4,657,866; 4,927,762; 4,560,655; or 5,122,469; WO 1990/03430; WO 1987/00195; or U.S. Pat. No. 30,985 may be used as culture media for the host cells. Any of these media may be supplemented as necessary with hormones and/or other growth factors (e.g., insulin, transferrin, or epidermal growth factor), salts (e.g., sodium chloride, calcium, magnesium, and phosphate), buffers (e.g., HEPES), nucleotides (e.g., adenosine and thymidine), antibiotics (e.g., GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. A variety of culture conditions, such as temperature, pH, maybe used with the host cell selected for expression.

(ix) Purification of Humanized vWF Antibody

When using recombinant techniques, an antibody may be produced intracellularly or in the periplasmic space, or directly secreted into the medium. If an antibody is produced intracellularly, as a first step, particulate debris, either host cells or lysed fragments, may be removed, for example, by centrifugation or ultrafiltration. Carter et al., *Bio/Technology,* 10: 163-167 (1992) describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where an antibody is secreted into the medium, supernatants from such expression systems are generally first concentrated, including using a commercially available protein concentration filter, for example, an AMICON™ or MILLIPORE PELLICON™ ultrafiltration unit. A protease inhibitor such as phenylmethylsulphonyl fluoride (PMSF) may be included in any of the foregoing steps to inhibit proteolysis, and antibiotics may be included to prevent the growth of adventitious contaminants.

An antibody composition prepared from cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 62:1-13 (1983)). Protein G can be used for mouse isotypes and for human γ3 (Guss et al., *EMBO J.*, 5:15671575 (1986)). The matrix to which an affinity ligand is attached may be agarose, but other matrices are available. Mechanically stable matrices such as controlled-pore glass or poly(styrenedivinyl)benzene allow for faster flow rates and shorter processing times than can be achieved with agarose. Where an antibody comprises a $C_H3$ domain, the BAKERBOND ABX™ resin (J. T. Baker, Phillipsburg, N.J.) may be useful for purification. Other techniques for protein purification such as fractionation on an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation are also available depending on the antibody to be recovered.

Pharmaceutical Formulations

Pharmaceutical formulations comprising a humanized antibody specific for vWF are provided. Formulations of humanized vWF antibodies may be prepared for storage by mixing an antibody having the desired degree of purity with optional pharmaceutically acceptable carriers, excipients, or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized humanized vWF formulations are described in WO 1997/04801, expressly incorporated herein by reference.

The formulation herein may also contain more than one active compound as necessary for the particular indication being treated, preferably those with complementary activities that do not adversely affect each other. Alternatively, or additionally, the composition may further comprise a chemotherapeutic agent, cytotoxic agent, cytokine, growth-inhibitory agent, anti-hormonal agent, humanized vWF drug, antiangiogenic agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug-delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (e.g., poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), and poly-D-(−)-3-hydroxybutyric acid.

The formulations to be used for in vivo administration must be sterile. This may be accomplished by filtration through sterile filtration membranes.

Treatment with Humanized vWF Antibodies

Humanized vWF antibodies or binding fragments thereof may be used to treat various vWF related diseases or disorders. Exemplary conditions or disorders include thrombotic diseases or disorders. Thrombotic diseases or disorders may include cardiovascular disease or cerebrovascular disorders such as ischemic stroke. In some embodiments, a cardiovascular disease may be atherosclerosis, restenosis, angina, acute myocardial infarction, acute coronary syndrome or cardiovascular disorders associated with diabetes. In some embodiments, a thrombotic disease may be vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes. In some embodiments cerebrovascular disorders include ischemic stroke, resulting from both cerebral artery infarcts as well as small lacunar infarcts, and vascular dementia. Humanized vWF antibodies may also be used for prevention of recurrent strokes or initiation of strokes triggered by cerebrovascular inflammation. In case of acute coronary syndrome the humanized vWF antibodies or binding fragment thereof is particularly suited for the treatment of ST-segment diagnosed subjects. The humanized vWF antibodies or binding fragment thereof may also be used for post-surgical treatment to avoid formation of clots.

Moreover, vWF overexpression or amplification may be evaluated using an in vivo diagnostic assay, e.g. by administering a molecule (such as an antibody) that binds the molecule to be detected and is tagged with a detectable label (e.g. a radioactive isotope) and externally scanning the patient for localization of the label.

In certain embodiments, an immunoconjugate comprising a humanized vWF antibody conjugated with a cytotoxic agent may be administered to the patient. Preferably, an immunoconjugate and/or humanized vWF antibody to which it is bound is/are internalized by the cell, resulting in increased therapeutic efficacy of the immunoconjugate in killing the cancer cell to which it binds. In a preferred embodiment, a cytotoxic agent (including for example, maytansinoids, calicheamicins, ribonucleases, and DNA endonucleases) targets or interferes with nucleic acid in the cancer cell. In another embodiment a cytotoxic agent (e.g., taxanes or epothilones) may target or interfere with microtubules and microtubule-dependent mitosis in the cancer cell.

Humanized vWF antibodies or immunoconjugates may be administered to a human patient in accordance with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. Intravenous, intraperitoneal, or subcutaneous administration of the antibody is preferred, with subcutaneous or intraperitoneal routes being particular preferred. A preferred administration schedule may be a single dose for an acute disorder or about once every three to four weeks for a chronic disorder, depending on the particular mammal being treated, the type of antibody, and other factors well known to the practitioner. However, other administration schedules are operable herein.

Other therapeutic regimens may be combined with the administration of the humanized vWF antibody. A combined administration includes co-administration, using separate formulations or a single pharmaceutical formulation, and consecutive administration in either order, wherein preferably there may be a time period while both (or all) active agents simultaneously exert their biological activities.

In one embodiment, the treatment may involve the combined administration of a humanized anti-vWF antibody with fibrinolytic agents such as alteplase, desmoteplase or microplasmin and/or antiplatelet agents such as aspirin, dipyridamol or clopidogrel for the treatment of ischemia induced by myocardial infarction or cerebral infarction or other cerebrovascular disorders.

It may also be desirable to combine administration of a humanized vWF antibody or antibodies with administration of an antibody directed against another tumor-associated antigen.

In one embodiment, the treatment of the present disclosure involves the combined administration of a humanized vWF antibody (or antibodies) and one or more regulators of immune function in a mammal, such as cytokines, as well as chemotherapeutic agents or growth-inhibitory agents, including co-administration of cocktails of different chemotherapeutic agents. Preferred chemotherapeutic agents include taxanes (such as paclitaxel and docetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service, Ed., M. C. Perry, Williams & Wilkins, Baltimore, Md. (1992).

A humanized vWF antibody may be combined with an anti-hormonal compound, e.g. an anti-estrogen compound such as tamoxifen or an aromatase inhibitor such as anastrozole; an anti-progesterone such as onapristone (see, EP 616 812); or an anti-androgen such as flutamide, in dosages known for such molecules. Where the cancer to be treated is hormone-independent cancer, a patient may previously have been subjected to anti-hormonal therapy and, after the cancer becomes hormone independent, the humanized vWF antibody (and optionally other agents as described herein) may be administered to the patient.

For the prevention or treatment of disease, the appropriate dosage of antibody will depend on the type of disease to be treated, as defined above, the severity and course of the disease, whether the antibody may be administered for preventive or therapeutic purposes, previous therapy, the patient's clinical history and response to the antibody, and the discretion of the attending physician. The antibody may be suitably administered to the patient at one time or over a series of treatments. Depending on the type and severity of the disease, and the rate of clearance of the antibody, about 1 μg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment may be sustained until a desired suppression of disease symptoms occurs.

A preferred dosage of a humanized vWF antibody may be in the range from about 0.05 mg/kg to about 10 mg/kg. Thus, one or more doses of about 0.3 mg/kg, 0.5 mg/kg, 2.0 mg/kg, 4.0 mg/kg or 10 mg/kg (or any combination thereof) may be administered to the patient. Such doses may be administered intermittently, e.g. every week, every two weeks, every three weeks or every four weeks (e.g. such that the patient receives from about two to about twenty, e.g. about six doses, of the humanized vWF antibody). An initial higher loading dose, followed by one or more lower doses, may be administered. An exemplary dosing regimen comprises administering an initial loading dose of about 4 mg/kg, followed by a weekly maintenance dose of about 2 mg/kg of a humanized vWF antibody or binding fragment thereof. However, other dosage regimens may be useful. The progress of this therapy may be readily monitored by conventional techniques and assays.

In studies to evaluate efficacy and safety of a humanized vWF antibody or binding fragment thereof as described herein in baboons, it has been surprisingly found that such a humanized antibody is effective in preventing (e.g., reducing, decreasing or ameliorating) platelet aggregation in vivo at a very low dose e.g. in the low μg/kg range which is an unexpected and unprecedented result for treating a vWF mediated disease or disorder. Clinical signs of bleeding, with the exception of an increase bleeding from small cuts (e.g., prolongation of the template bleeding time and/or bleeding volume as measured in the incisional bleeding test), are not observed at these concentrations. Even more surprisingly, at doses from about 1 to about 250 times the $ED_{100}$, no significant clinical signs of bleeding is observed, although an increase in bleeding from small cuts is observed. Consequently, a humanized vWF antibody or a binding fragment thereof as described herein appears to be effective for treating a vWF mediated disease or disorder in humans.

A humanized antibody or binding fragment thereof as described herein can be thus administered to a subject, preferably to human, at a therapeutically effective amount ranging from about 0.001 to about 100 mg/kg. Preferably, a therapeutically effective amount ranging from about 0.002 to about 20 mg/kg, more preferably a therapeutically effective amount ranging from about 0.002 to about 10 mg/kg, in particular from about 0.002 to about 0.4 mg/kg, more particular from about 0.005 to about 0.2 mg/kg, and most particular from about 0.01 to about 0.1 mg/kg is administered to a subject, preferably to human. A therapeutically effective amount of the humanized antibody or binding fragment thereof can be administered to a subject in one or more therapeutically effective doses. A therapeutically effective amount administered is usually insufficient to cause significant clinical signs of bleeding but sufficient to inhibit platelet aggregation, i.e. a therapeutically effective amount can be administered without causing significant clinical signs of bleeding (e.g., without causing clinical signs of bleeding except for an increased bleeding from small cuts).

A humanized antibody or binding fragment thereof as described herein can be administered to a subject, preferably to human, at a therapeutically effective dose ranging from about 0.002 to about 0.4 mg/kg or in particular from about 0.005 to about 0.2 mg/kg, more particular from about 0.01 to about 0.1 mg/kg to produce a therapeutic effect (e.g., a reduction in thrombus formation) in a subject.

A humanized antibody or binding fragment thereof as described herein can be administered in a therapeutically effective amount ranging from between about 1 to about 250 times the $ED_{100}$, preferably from between about 1 to about 200 times the $ED_{100}$, more preferably from between about 1 to about 100 times the $ED_{100}$ without causing significant clinical signs of bleeding (e.g., without causing clinical signs of bleeding except for an increased bleeding from small cuts). A therapeutically effective amount of a humanized antibody or binding fragment thereof as described herein can be administered as a single or multiple sub-doses to the subject. The above therapeutically effective dosages are preferred for intravenous administration. In administration via the subcutaneous route, the preferred total amount administered can be in the range of about one to three times the amount administered via the intravenous route, preferably about two times.

Clinical signs of bleeding can refer to the BleedScore classification as described by Serebruany and Atar (American Journal of Cardiology, 2007, Volume 99, Issue 2, 15 Jan. 2007, Pages 288-290) and applied to animal models. The BleedScore has been specifically developed to score the type of bleeding which is characteristic for antiplatelet therapies. The BleedScore is based on assigning points to clinical findings depending on the severity of hemorrhage. By adding all points of all findings up, a resulting score is derived. The bleeding symptoms are divided into three categories of increasing severity: 1) superficial bleeding (one score point per event) 2) internal bleeding (3 score points per event) 3) alarming bleeding, or a combination of these (6 score points per event). This approach is particularly useful in the determination and reporting of mild to moderate bleeding events associated with modern antiplatelet and antithrombotic therapies, while accounting for the most severe bleeding complications as well. Superficial bleeding comprises the following criteria: Easy bruising, bleeding from small cuts (e.g prolonged template bleeding time) petechia, ecchymosis. Internal Bleeding comprises the following criteria: Hematoma, epistaxis, blood loss from mouth, vagina, melena, eye bleed, hematuria, hematemesis. Alarming bleeding comprises the following criteria: Transfusion needed, intracranial, life threatening.

Inhibition of platelet aggregation (inhibiting platelet aggregation or sufficient to inhibit platelet aggregation) can indicate that the therapeutically effective amount administered is sufficient to inhibit the formation of an occluding thrombus in an artificially injured artery in an animal model of arterial injury as measured by the monitoring of blood flow through the artery. One approach to determine in vivo inhibition of platelet aggregation in a quantitative way is through the measurement of cyclic flow reductions (CFRs) in an arterial injury model. Thus, for example, inhibition of platelet aggregation can indicate that the therapeutically effective amount administered is sufficient to reduce the number of CFRs in an animal.

Therapeutically effective amount or effective amount can refer to an amount effective to ameliorate or prevent the symptoms, or prolong the survival of the subject being treated. Determination of a therapeutically effective amount is well within the capabilities of those skilled in the art, especially in light of the detailed disclosure provided herein. A therapeutically effective amount as described herein includes an amount of a vWF antibody effective to treat a vWF mediated disease or disorder in a subject. A therapeutically effective amount of the vWF antibody includes an amount needed to treat or inhibit platelet aggregation (e.g. during thrombosis in main arteries, peripheral arteries, arterioles or veins).

Therapeutically effective dose or effective dose can refer to a dose effective to ameliorate or prevent the symptoms, or prolong the survival of a subject being treated. A therapeutically effective dose as described herein includes a dose of a vWF antibody effective to treat a vWF mediated disease or disorder in a subject. A therapeutically effective dose as described herein includes a dose which inhibits platelet aggregation (e.g., during thrombosis in main arteries, peripheral arteries, arterioles or veins). A therapeutically effective dose includes an $ED_{100}$ which is the effective dose sufficient to reduce by 100% the formation of a thrombus as measured by the reduction of blood flow in a blood vessel. $ED_{100}$ as described herein includes an amount of vWF antibody sufficient to reduce the number of flow reductions over a period of 30 minutes to zero. Therapeutically effective doses include those doses which produce a reduction in thrombus formation, for example, a dose sufficient to reduce by at least about 15 percent, preferably by at least 30 percent, more preferably by at least 50 percent, most preferably by at least 80 percent, in particular by at least 100% the formation of a thrombus as measured by the reduction of blood flow in a blood vessel or by suitable ex vivo tests which measure the reduction of platelet aggregation.

Alternatively, a humanized vWF antibody may be suitably administered serially or in combination with radiological treatments (e.g., irradiation or introduction of radioactive substances-such as those referred to in UICC (Ed.), *Klinische Onkologie*, Springer-Verlag (1982)).

The present disclosure thus further provides a human antibody or binding fragment thereof specific for von Willebrand factor (vWF), which can be administered in a therapeutically effective amount ranging from between 1 time to around 250 times of the $ED_{100}$ without causing significant clinical signs of bleeding. Preferably the human antibody or binding fragment thereof is specific for the A1 domain of human vWF. Preferably the human antibody or binding fragment thereof specific for vWF is a humanized antibody or a binding fragment thereof specific for vWF.

Articles of Manufacture

In another embodiment of the disclosure, an article of manufacture containing materials useful for the treatment of the disorders described above (e.g., a humanized vWF antibody) is provided. The article of manufacture may comprise a container and a label or package insert on or associated with the container. Suitable containers include, for example, bottles, vials or syringes. The containers may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the humanized vWF antibody described herein. The label or package insert may indicate that the composition may be used for treating the condition of choice, such as cancer. In one embodiment, the label or package insert may indicate that the composition comprising the humanized vWF antibody may be used to treat a vWF-related disorder.

Moreover, the article of manufacture may comprise (a) a first container with a composition contained therein, wherein the composition comprises the humanized antibody herein, and (b) a second container with a composition contained therein, wherein the composition comprises a therapeutic agent other than the humanized antibody. The article of manufacture in this embodiment of the disclosure may further comprise a package insert indicating that the first and second compositions can be used in combination to treat a vWF related disease or disorder. Such therapeutic agent may be any of the adjunct therapies described in the preceding section (e.g., a thrombolytic agent, an anti-platelet agent, a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Non-Therapeutic Uses for the Humanized vWF Antibody

Humanized vWF antibodies or binding fragment thereof have further non-therapeutic applications. For example, the antibodies may be used as affinity-purification agents. In this process, the antibodies may be immobilized on a solid phase such as for example, a SEPHADEX™ resin or filter paper, using methods well known in the art. The immobilized antibody may be contacted with a sample containing the humanized vWF protein (or fragment thereof) to be purified, and thereafter the support may be washed with a suitable solvent that will remove substantially all the material in the sample except the humanized vWF protein, which may be bound to the immobilized antibody. Finally, the support may be washed with another suitable solvent, such as glycine buffer, pH 5.0, which will release the humanized vWF protein from the antibody.

Humanized vWF antibodies may also be useful in diagnostic assays for human vWF protein, e.g. detecting its expression in specific cells, tissues, or serum. For diagnostic applications, the antibody may be labeled with a detectable moiety. Numerous labels are available that can be generally grouped into the following categories:

(a) Radioisotopes, such as $^{35}$S, $^{14}$C, $^{125}$I, $^{3}$H, and $^{131}$I. The antibody can may be labeled with the radioisotope using the techniques described in *Current Protocols in Immunology*, Volumes 1 and 2, Coligen et al., Ed. Wiley-Interscience, New York, N.Y., Pubs. (1991), for example, and radioactivity can be measured using scintillation counting.

(b) Fluorescent labels such as rare-earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available (see, e.g., U.S. Pat. No. 4,275,149). These enzymes generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (e.g., using a chemiluminometer) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase and microperoxidase. Techniques for conjugating enzymes to antibodies are described in O'Sullivan et al, "Methods for the Preparation of Enzyme-Antibody Conjugates for use in Enzyme Immunoassay," in *Methods in Enzym.* (Ed., J. Langone & H. Van Vunakis), Academic Press, New York, 73:147-166 (1981).

Examples of enzyme-substrate combinations include, for example (i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-p-β-galactosidase.

Numerous other enzyme-substrate combinations are available to those skilled in the art (see, e.g., U.S. Pat. Nos. 4,275, 149 and 4,318,980).

Sometimes, the label may be indirectly conjugated with the antibody. The skilled artisan will be aware of various techniques for achieving this. For example, the antibody may be conjugated with biotin, and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody may be conjugated with a small hapten (e.g., digoxin) and one of the different types of labels mentioned above may be conjugated with an anti-hapten antibody (e.g., anti-digoxin antibody). Thus, indirect conjugation of the label with the antibody can be achieved.

In another embodiment of the disclosure, the humanized vWF antibody need not be labeled, and the presence thereof may be detected using a labeled antibody that binds to the humanized vWF antibody.

The antibodies of the present disclosure may be employed in any known assay method, such as competitive-binding assays, direct and indirect sandwich assays, and immunoprecipitation assays. Zola, *Monoclonal Antibodies: A Manual of Techniques*, pp. 147-158 (CRC Press, Inc. 1987).

For immunohistochemistry, the tumor sample may be fresh or frozen or may be embedded in paraffin and fixed with a preservative such as formalin, for example.

The antibodies may also be used for in vivo diagnostic assays. Generally, the antibody may be labeled with a radionuclide (such as $^{111}$In, $^{99}$Tc, $^{14}$C, $^{131}$I, $^{125}$I, $^{3}$H, $^{32}$P or $^{35}$S) so that, for example, a tumor can be localized using immunoscintigraphy.

As a matter of convenience, the antibodies of the present disclosure can be provided in a kit (e.g., a packaged combination of reagents in predetermined amounts with instructions for performing the diagnostic assay). Where the antibody is labeled with an enzyme, the kit may include substrates and cofactors required by the enzyme (e.g., a substrate precursor that provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration.

The humanized vWF antibodies may also be useful for in vivo imaging, where the labeled antibody may be administered to a host, preferably the bloodstream, and the presence and location of the labeled antibody in the host assayed. This imaging technique may be suitably used in localization of vascular emboli or the staging and treatment of neoplasms. The antibody may be suitably labeled with any moiety that is detectable in a host, including for example, non-radioactive indicators detectable by, e.g., nuclear magnetic resonance, or other means known in the art. Preferably, however, the label may be a radiolabel, including iodine, e.g., $^{125}$I and $^{131}$I, selenium, bifunctional chelates, copper, e.g., $^{67}$Cu, technetium, e.g., $^{99m}$Tc, and rhenium, e.g., $^{186}$Re and $^{188}$Re. The radioisotope may be conjugated to the protein by any means, including for example, metal-chelating compounds or lactoperoxidase, or iodogen techniques for iodination.

Deposit of Material:

The following materials have been deposited with the Deutsche Sammlung von Mikroorganismen und Zellkulturen GmbH (DSMZ), Inhoffenstr. 7 B, 38124 Braunschweig, Germany:

Microorganism (*E. coli*) deposited with DSMZ on Jan. 23, 2008, having accession No. DSM 21059, comprising the vector GS264 which comprises isolated nucleic acid comprising the light chain encoding nucleic acid sequence of humanized NMC-4 variant H9L91gG4. Microorganism (*E. coli*) deposited with DSMZ on Jan. 23, 2008, having accession No. DSM 21060, comprising the vector GS265 which comprises isolated nucleic acid comprising the heavy chain encoding nucleic acid sequence of humanized NMC-4 variant H9L91gG4. These deposits were made under the provisions of the Budapest Treaty on the International Recognition of the Deposit of Microorganisms for the Purpose of Patent Procedure and the Regulations thereunder (Budapest Treaty).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Construction of Chimeric Antibodies

Generating a NMC-4-human Fc chimera: A chimeric antibody comprising variable regions from the mouse antibody NMC-4 and a human Fc region is constructed as described below. In an exemplary method, the anti-vWF antibody, NMC-4 (e.g., an IgG1κ with variable region amino acid sequences that have been published) is used as a template to generate synthetic gene sequences for the VH and VL regions of NMC-4 (Celikel et al., 1997, Blood Cells, Molecules and Diseases 23:123-134). For example, synthetic gene sequences for NMC-4 VH and VL are generated by taking the amino acid sequences described in Celikel et al. and generating a corresponding nucleotide sequence using VECTOR NTI software.

TABLE 1

Primers used to generate the NMC-4 chimera expression plasmids.

| Forward Primer | Sequence | Reverse Primer | Sequence |
| --- | --- | --- | --- |
| Heavy Chain | | | |
| NMC-VH-EcoRI-F | 5'-GACGCGAATTCGCAGGTGCAGCTGAAGGAGAGC-3' (SEQ ID NO: 34) | NMC-VH-IgG1-R | 5'-CGGATGGGCCCTTGGTGGAAGCGCTGCTCACGGTCACGCTGGT-3' (SEQ ID NO: 35) |
| hIgG-F | 5'-GCTTCCACCAAGGGCCCATCCG-3' (SEQ ID NO: 36) | hIgG-R | 5'-CCAGAGACAGGGAGAGGCTCTTCTG-3' (SEQ ID NO: 37) |
| | | IgG1-BamHI-R | 5'-ATTAGGATCCTTATCATTTACCCAGAGACAGGGAGAGGCT-3' (SEQ ID NO: 38) |
| hFc-L235E-F | 5'-CTCGAGGGGGGACCGTCAGTCTTCCTCTT-3' (SEQ ID NO: 39) | hFc-L235E-R | 5'-AAGAGGAAGACTGACGGTCCCCCCTCGAG-3' (SEQ ID NO: 40) |
| CH2-C1q(-)-F | 5'-GGCGTACGCGTGCGCGGTCTCCAACAAAGC-3' (SEQ ID NO: 41) | CH2-C1q(-)-R | 5'-CCGCGCACGCGTACGCCTTGCCATTCAGCCA-3' (SEQ ID NO: 42) |

TABLE 1-continued

Primers used to generate the NMC-4 chimera expression plasmids.

| Forward Primer | Sequence | Reverse Primer | Sequence |
| --- | --- | --- | --- |
| 4-59 leader-Hind III-NMC-4 | 5'-ATTAAGCTTGCCGCCACCATGAAA CATCTGTGGTTCTTCCTTCTCCTGGTG GCAGCTCCCAGGTGGGTCCTGTCCCA GGTGCAGCTGAAGGAGAGC-3' (SEQ ID NO: 43) | IgG1-BamHI-R | 5'- TAAGGATCCTTATCATTTAC CCGGAGACAGGGAGAG-3' (SEQ ID NO: 44) |
| Light Chain | | | |
| NMC-VL-EcoRI-F | 5'-GACGCGAATTCGGACATCCA GATGACCCAGAGCC-3' (SEQ ID NO: 45) | NMC-VL-Kappa-R | 5'-GAAGACAGATGGTGCAGCCACAGT TCGCTTCACCTCCAGCTTGGTGCC-3' (SEQ ID NO: 46) |
| Kappa-F | 5'-CGAACTGTGGCTGCACCAT CTGTCTT-3' (SEQ ID NO: 47) | Kappa-BamHI-R | 5'AATTCGGATCCTTACTAACACT CTCCCCTGTTGAAGCTCTT-3' (SEQ ID NO: 48) |

In an exemplary method, PCR reactions may be carried out using the Accuprime PFX DNA POLYMERASE KIT (Invitrogen). For example, a 50 µl reaction mix is assembled including: 1×PFX buffer, 0.2 µM dNTP mix, 1 unit of PFX polymerase, 1 µM forward primer, 1 µM reverse primer and 100 ng DNA template(s). A standard PCR program consists of initial denaturation at 94° C. for 1 minute, followed by 30 cycles with each cycle being 94° C. for 30 seconds, 55° C. for 30 seconds, 68° C. for one minute and a final extension step at 68° C. for 10 minutes. PCR products are purified by agarose gel electrophoresis on a 0.8% TAE gel and one or more bands of the desired size are excised and purified with a Qiagen GEL EXTRACTION KIT. DNA fragments are ligated for 30 minutes at room temperature in a 10 µl volume including 1×T4 DNA ligase buffer (NEB), 0.5 µl T4 DNA Ligase (NEB) and 10 ng of each DNA. Next, one µl of the ligation reaction is used to transform JM109 E. coli cells and the PCR generated inserts are verified by sequencing using a Beckman CEQ 8000 DNA ANALYZER.

Such chimeric antibodies comprising a VH and/or a VL from murine antibody NMC-4 and a human Fc are synthesized by PCR according to standard protocols known in the art. In an exemplary method, a VH and/or a VL from NMC-4 is fused to a human Fc by performing PCR with a primer specific for NMC-4 and a primer specific for human Fc.

Optionally, amino acid substitutions (e.g., mutations) are introduced into the IgG1 Fc region to abolish the Fc and complement binding sites to eliminate cytotoxicity hypothesized to be mediated by the wild type γ1 Fc constant region (see, for example, SEQ ID NO: 143). For example, a human IgG1 constant region (e.g., Fc) derived from I.M.A.G.E. cDNA clone #476-4579 (ATCC) (SEQ ID NO: 33) is amplified using primers hIgG-F (SEQ ID NO: 36) and hIgG-R (SEQ ID NO: 37) (Table 1). Amino acid substitutions (e.g., L235E (the FcR binding site) and E318A, K320A, K332A (at the C1q complement binding site)) are introduced into the IgG1 Fc region by performing, for example, site directed mutagenesis (Duncan and Winter; Nature. 332(6166):738-40 (1988). For example, the L235E mutation is introduced into the constant region using primer pair hFc-L235E-F (SEQ ID NO: 39) and hFc-L235E-R (SEQ ID NO: 40); and the complement site mutations are introduced using primer pair CH2—C1q(−)—F (SEQ ID NO: 41) and CH2-C1q(−)—R) (SEQ ID NO: 42) (Table 1). The resulting PCR products comprising the four mutations are linked using two outer primers, hIgG-F (SEQ ID NO: 36) and IgG1-BamHI-R (SEQ ID NO: 38) to produce a PCR product encoding a modified IgG1 Fc region (termed IgG1 (dm)).

In an exemplary method, the heavy chain variable region of NMC-4 is fused to a modified IgG1 Fc region (e.g., IgG1 (dm)) by recombinant techniques known in the art. For example, the nucleotide sequence encoding the heavy chain variable region of NMC-4 (SEQ ID NO: 1) is amplified with primers NMC-VH-EcoRI-F (SEQ ID NO: 34) and NMC-VH-IgG1-R (SEQ ID NO: 35) which introduce an EcoR1 cloning site upstream from the N-terminus of NMC-VH. Briefly, the PCR product is linked with a heavy chain constant region, (e.g., IgG1(dm)), by recombinant PCR in two steps, first using the primer pair NMC-VH-EcoRI-F (SEQ ID NO: 34) and hIgG-R (SEQ ID NO: 37), followed by a PCR reaction using primer pair NMC-VH-EcoRI-F (SEQ ID NO: 34) and IgG1-BamHI-R (SEQ ID NO: 38). The final PCR product is digested with EcoRI and BamHI and cloned into EcoR1 and BamH1 sites of the pIRES2-EGFP-Igκ vector (Clontech, Palo Alto, Calif.), which is modified to comprise an Igκ leader sequence (METDTLLLWVLLLWVPGSTGD) (SEQ ID NO: 107) (encoded by the polynucleotide of SEQ ID NO: 140) cloned into the XhoI and EcoRI sites.

In an exemplary method, the light chain variable region of NMC-4 is fused to a modified IgG1 Fc region (e.g., IgG1 (dm)) by recombinant techniques as described below. For example, the Igκ light chain constant region (e.g., κC1 (SEQ ID NO: 141)) is amplified from DNA made from I.M.A.G.E clone #4704496 (ATCC) (SEQ ID NO: 108) using primers, Kappa-F (SEQ ID NO: 47) and Kappa-BamHI-R (SEQ ID NO: 48) which further introduces a BamH1 restriction site at the 3' end of the Igκ light chain constant region. Similarly, the light chain variable region is amplified from the synthesized VL gene with primers NMC-VL-EcoRI-F (SEQ ID NO: 45) and NMC-VL-Kappa-R (SEQ ID NO: 46) (Table 1) which introduces an EcoR1 site at the 5' end. Next, the NMC 4 variable region and κC1 fragments are linked by recombinant PCR using primers NMC-VL-EcoRI-F (SEQ ID NO: 45) and Kappa-BamHI-R (SEQ ID NO: 48). The final PCR product is digested with EcoRI and BamHI and cloned into pIRES2-DsRed2-Igκ vector in the same sites.

The expression level of the heavy chain in the pIRES2-EGFP vector may be low in comparison to the pIRES-DsRed plasmid expressing the light chain mouse-human chimera, despite the fact that the same Igκ leader sequence is used for both the light and heavy chains. Accordingly, to improve the expression level of the heavy chain, the Igκ leader sequence is replaced by the leader sequence from the human germline 4-59 VH (MKHLWFFLLLVAAPRWVLS) (SEQ ID NO: 109) using primer pair, 4-59 leader-HindIII-NMC-4 (SEQ ID NO: 43) and IgG1-BamHI-R (SEQ ID NO: 38) with the pIRES2-EGFP-NMC4-IgG(mut) vector serving as the template (Table 1). The fragment is digested with HindIII and PmeI and subcloned into the HindIII and PmeI sites of the pcDNA6-cMyc-A vector (Invitrogen, Carlsbad, Calif.).

Construction of an AJW200 Reference Antibody: AJW200 is another antibody directed against the A1 domain of vWF, with the ability to block the interaction of the vWF A1 domain with GPIbα. An AJW200 reference antibody is generated by engineering the VH and VL sequences described in U.S. Pat. No. 6,228,360 to comprise, for example, an additional functional Kozak sequence for improved expression. For example, the synthetic AJW200 VH gene is amplified using primers Hind III-Ko-AJW-F (SEQ ID NO: 49) and HuFab-H-R (SEQ ID NO: 50) (Table 2) and cloned into the HindIII and ApaI site of the HindIII-ApaI-digested pcDNA6-cMyc-A vector comprising the human IgG1 (dm) heavy chain constant region (thereby replacing the NMC-4 VH). The AJW200 VL is amplified using primer pair XhoI-Ko-AJW-F (SEQ ID NO: 51) and Kappa-BamHI-R (SEQ ID NO: 48) and subcloned into the XhoI and BamH1 sites of the pIRES-DsRed vector carrying the NMC light chain chimera (thereby replacing the VL of the NMC4).

in a total volume of 330 ml of FREESTYLE 293 MEDIA. The transfection mixture is composed of equal parts DNA/Opti-MEM (e.g., 165 μg HC expression plasmid, 165 μg LC expression plasmid, and room temperature OptiMEM (Invitrogen) to a total volume of 11 ml) and 293fectin/OptiMEM (e.g., 433 μl of 293fectin (Invitrogen) and room temperature OptiMEM (Invitrogen) to a total volume of 11 ml). The DNA mixture is added to the 293fectin mixture, then mixed and incubated for 20 minutes at room temperature, and added to the existing media containing the 293F cells. The cells are incubated at 37° C., 8% $CO_2$ with shaking at 120 rpm. At 72 hours post-transfection, the suspension is centrifuged for 5 minutes at 100×g to pellet the cells and the Mab-containing supernatant is filtered through a 0.2 μm filter and purified using a Protein-A affinity column.

Small volumes of conditioned medium (CM) from transiently transfected HEK-293F cells are applied to a 0.3 ml Protein A SEPHAROSE drip column which is been equilibrated with PBS. The column is washed with 10 ml PBS and proteins are eluted with 0.1 M Glycine, pH2.7. One milliliter fractions are collected into 0.1 ml 1M Tris-HCl, pH 8.0 with the majority of antibody being eluted in the first two eluate fractions. These two fractions are pooled and concentrated to a final volume (e.g., 0.2-0.3 ml) using, for example, a Vivaspin 0.5 ml centrifugal device. During this concentration step, intermediate dilutions with PBS are performed to exchange the buffer from Tris-Glycine to PBS. The final concentrate is sterilized by filtration through, for example, a 0.2 μm syringe filter and the protein concentration of the antibody-containing sample is determined using a Lowry protein assay (BioRad DC Protein Assay).

For large scale purification, 2 L of conditioned medium (CM) from transiently transfected adherent cells (e.g., HEK-293T) is concentrated by ultrafiltration on a hollow fiber

TABLE 2

Primers used to generate the AJW200 expression plasmids

| Forward Primer | Sequence | Reverse Primer | Sequence |
| --- | --- | --- | --- |
| Hind III-Ko AJW-F | TAAGCTTGCCGCCACCATGGA TTTTGGGCTGATTTTTTTTATTGTT-3' (SEQ ID NO: 49) | HuFab-H-R | 5'-GAATGGGCCCTTGGTGGAAGCGG AGGAAACGGTCACGAGGGTA-3' (SEQ ID NO: 50) |
| XhoI-Ko-AJW-F | 5'-AATCTCGAGGCCGCCACCATGA GTGTGCCCACTCAGGTCCTGG-3' (SEQ ID NO: 51) | Kappa-BamHI-R | 5'-AATTCGGATCCTTACTAACACT CTCCCCTGTTGAAGCTCTT-3' (SEQ ID NO: 48) |

Antibody production: Chimeric antibodies may be produced by any methods known in the art. In an exemplary method, HEK293F cells are cultured in Freestyle 293 expression media (Invitrogen) in shaker flasks at 120 rpm, 37° C., 8% $CO_2$. The cells are pelleted at 100×g, resuspended in 30 ml FREESTYLE 293 EXPRESSION MEDIA, and vortexed for 20 seconds to achieve a single cell suspension. The cells are counted and a 2 L shaker flask is seeded with $3.3 \times 10^8$ cells cartridge (e.g., Amersham Biosciences 30,000 NMWC/290 $cm^2$ hollow fiber column UFP-30-C-3×2MA) until the volume is reduced to ~200 ml. This concentrated material or, for smaller transfections, straight CM is pumped over a 12 ml Protein A SEPHAROSE column that has been equilibrated with 0.1 M Tris-HCl, pH8.0. The column is washed with 0.1 M Tris-HCl, pH 8.0 until the $UV_{280}$ reading has established a baseline. The antibody is eluted with 0.1 M Glycine, pH2.7 and 3 ml fractions are collected. The pH of the peak protein containing fractions is adjusted by addition of Tris-HCl pH 8.0 to a final concentration of 0.1 M. Peak fractions are pooled, concentrated to a volume of less than 7 ml by ultrafiltration (e.g., on an Amicon Ultra 15 ml centrifugation device), and then desalted into PBS using two separate runs on a PD-10 column (Amersham Biosciences/GE-Healthcare).

Proteins obtained from the culture supernatants are quantitated and analyzed by any method known in the art (e.g., Lowry protein assay (BioRad DC Protein Assay). In an exemplary method, culture supernatants are analyzed by SDS-PAGE. Briefly, proteins are transferred to a nitrocellulose membrane, blocked with 5% milk/PBS for 1 hour at room temperature, and incubated with HRP conjugated mouse anti-human IgG (e.g., γ-chain specific, 1:10,000) and mouse anti-human kappa (e.g., κ-chain specific, 1:1,000) (Southern Biotech, Cat#9042-05 and #9220-05, Birmingham, Ala.) and signals detected with an ECL kit.

In vitro inhibitory activity in the ristocetin-induced platelet agglutination assay: In an exemplary method, chimeric NMC-4 human Fc antibodies are tested for activity, including for example, binding specificity for vWF. For example, platelet agglutination assays are performed with a standard aggregometer (Bio/Data, model PAP-4) using lyophilized human platelets (Bio/Data, Horsham Pa.). Briefly, 50 µl of ristocetin (e.g., stock concentration=15 mg/mL) (Bio/Data) and 48.5 µl of TBS or test antibody is added to a tube containing 1×10$^8$ lyophilized platelets in a 400 µl volume. The baseline reading is recorded for 10 seconds before 1.5 µl purified vWF (e.g., final concentration of 1.5 µg/mL) is added into the tube to initiate agglutination. The $EC_{50}$ value of the test antibody is estimated as the concentration that inhibited 50% of platelet agglutination. In a comparison with the parent monoclonal antibody, the chimera demonstrated potency equivalent to that of the parental murine NMC4 antibody.

Further, to more accurately determine $EC_{50}$ values, chimeric antibodies are assayed using, for example, a plate reader method adapted from the microplate method. In an exemplary method, 4.5×10$^7$ paraformaldehyde-fixed platelets in 150 µl TBS (pH 7.5) per well are added using a 96-well COSTAR 3603 plate and purified human vWF (Calbiochem, San Diego, Calif.) is added to a final concentration of 1.5 µg/mL per well. Serial concentrations of test antibodies are added followed by addition of ristocetin to a final concentration of 1.5 mg/mL per well to initiate agglutination and the turbidity (e.g., absorbance at 405 nm) is monitored using a SPECTRAMAX PLUS PLATE READER (Molecular Devices) set at 37° C. for 6 minutes with 20 seconds on-board shaking between read cycles. Inhibitor compound or the reference MAb (e.g., AVW-3) is added (e.g., 20 µl/well) and the mixtures are incubated and monitored for 2 minutes. Finally, either ristocetin or botrocetin (20 µl/well) is added and the mixtures are incubated and monitored for 40 minutes. The agglutination signal is monitored as the extent of the decrease in absorbance (e.g., −ΔAbsorbance).

The NMC-4-human Fc chimera is compared with the original NMC-4 monoclonal antibody as well as the cloned AJW200 antibody. As shown in FIG. 1, the NMC-4 chimera is similar in activity to the original NMC-4 mAb and slightly more potent than AJW200 in the ristocetin-induced platelet agglutination assay, with $EC_{50}$ values of 0.1, 0.17 and 0.27 nM, respectively.

Example 2

Construction of Humanized Antibodies

Selection of human acceptor frameworks: Databases (e.g., a human germline database, V base, or the Kabat database) or publications (e.g., Kabat et al., Sequences of Proteins of Immunological Interest, 1992) may be used to identify the subfamilies to which the murine heavy and light chain V regions belong and determine the best-fit human germline framework to use as the acceptor molecule. Selection of which VH and VL sequences within these subfamilies may be used as acceptor sequences may be based upon sequence homology and/or a match of the canonical structure of the CDR1 and CDR2 regions to help preserve the appropriate relative presentation of the six CDRs after grafting.

For example, use of the V base indicates that the K light chain of NMC-4 is of the kappa 1 subfamily given that good homology is identified between the NMC-4 VL framework and the members of the K subfamily 1 (VK1). The highest homology and best preservation of canonical structures of the CDR loops is observed for the germline sequence O18 (SEQ ID NO: 5), which have a sequence identity of 78% for the whole sequence up to CDR3 and a sequence identity of 84% for the framework regions. The alignment of the NMC-4 light chain and human light chain O18 (SEQ ID NO: 5) and AAK94808 (an O18-derived mature antibody, used to provide a LCDR3 and framework 4 sequence for comparison with NMC-4 in this region) (SEQ ID NO: 6) is shown in Table 3, with the differences between the NMC and human antibody indicated as bolded letters (numbering based on Kabat numbering scheme (Kabat, 1978)).

Similarly, use of V base indicates that the VH sequence through to framework 3 falls in the VH subfamily IV. Within the human VH IV subfamily, the NMC-4 VH shows the highest sequence homology with the 4-59 germline sequence (SEQ ID NO: 3) which exhibits a 56% sequence identity to the murine VH for the entire VH through to CDR3 and 67% identity for the framework regions alone (Table 4). Without being bound by a theory of the disclosure, AAC18165.1 (SEQ ID NO: 4) is chosen to provide a HCDR3 and framework 4 comparator sequence because it shares identical amino acid sequences in frameworks 1 through 3 and HCDR1 and HCDR2 to the human germline 4-59 VH (SEQ ID NO: 3). HCDR3 and framework 4 regions are not included in the VH germline sequences in the V base database, given the HCDR3 regions are highly divergent and FW4 is a distinct domain derived from a separate gene product (J). The amino acid differences between the NMC-4 VH and AAC18165.1 (SEQ ID NO: 4) sequences are highlighted in bold and their positions by the asterisks in Table 4.

TABLE 3

Alignment of the NMC-4 VL with the human antibody AAK94808 that has identical amino acid framework and CDR1 and CDR2 sequences to the human germline VL, O18.

| Name | FW1 | CDR1 | FW2 | CDR2 |
|---|---|---|---|---|
| | ---------1----*----2-*-*------3*--- | | ----4**-*----* | 5*-*-** |
| Kabat No: | 12345678901234567890123 | 45678901234 | 567890123456789 | 0123456 |
| NMC-4 VL (SEQ ID NO: 2) | DIQMTQSPSSLSASLGDRVTISC | SASQDINKYLN | WYQQKPDGAVKLLIF | YTSSLHS |
| O18 (AAK94808) (SEQ ID NO: 6) | DIQMTQSPSSLSASVGDRVTITC | QASQDISNYLN | WYQQKPGKAPKLLIY | DASNLET |

| Name | FW3 | CDR3 | FW4 |
|---|---|---|---|
| | ---6---------7***---*-*8----------9-**--*- | | |
| Kabat No: | 78901234567890123456789012345678 | 901234567 | 8901234567 |
| NMC-4 VL | GVPSRFSGSGSGTDYSLTISNLEPEDIATYYC | QQYEKLPWT | FGGGTKLEVK |
| O18 (AAK94808) | GVPSRFSGSGSGTDFTFTISSLQPEDIATYYC | QQYDNLPLT | FGGGTKVEIK |

TABLE 4

Alignment of the NMC-4 VH with the human antibody, AAC18165.1, that has identical framework, CDR 1 and CDR2 amino acid sequences to the human germline 4-59.

| Name | FW1 | CDR1 | FW2 | CDR2 |
|---|---|---|---|---|
| | ----*----1--*--**--*------*-*3*-***-*--4-------*-5-***---*-6**--- | | | |
| Kabat No: | 12345678901234567890123456789012345678901234567890123456789012345 | | | |
| NMC-4 VH (SEQ ID NO: 1) | QVQLKESGPGLVAPSQSLSITCTVSGFSLTDYGVDWVRQPPGKGLEWLGMIWGDGSTDYNSALKS | | | |
| 4-59 (ACC18165.1) (SEQ ID NO: 4) | QVQLQESGPGLVKPSETLSLTCTVSGGSISSYYWSWIRQPPGKGLEWIGYIYYSGSTNYNPSLKS | | | |

| Name | FW3 | CDR3 | FW4 |
|---|---|---|---|
| | -**-7*-*--**8--****---*9---*- ***10****-- -------11-- | | |
| Kabat No: | 67890123456789012abc345678901234 | 567890abcdef12 | 34567890123 |
| NMC-4 VH | RLSITKDNSKSQVFLKMNSLQTDDTARYYCVR | DPADYGNYDYALDY | WGQGTSVTVSS |
| 4-59 (AAC18165.1) | RVTISVDTSKNQFSLKLSSVTAADTAVYYCAR | GYRPGVAAHSPFDY | WGQGTLVTVSS |

Since straight grafting of CDRs from a mouse antibody to human antibody frameworks is hypothesized to result in loss of affinity for antigen-binding (Foote and Winter *J. Mol. Biol.* 224: 487-499 (1992); Xiang et al. *J Mol. Biol.* 253:385-90 (1995); Homes et al, *J. Immunol.* 167:296-301 (2001)), it may be desirable to mutate certain residues in the frameworks back to the mouse residues at those positions, a process called back-mutation. For example, Table 5 shows the residues that may affect the conformations of CDRs and which may be potential candidates for back mutation to the murine residue (e.g., amino acid differences between the NMC-4 and the human frameworks at these positions are highlighted in italicized bold letters).

TABLE 5

Framework residues affecting the conformation of the CDRs; comparison of NMC-4 and the human acceptor variable regions

| VL | | | VH | | |
|---|---|---|---|---|---|
| Kabat Position | NMC-4 | O18 FW | Kabat Position | NMC-4 | 4-59 FW |
| 2 | I | I | 2 | V | V |
| 4 | M | M | 47-49 | W, L, G | W, *I*, G |
| 35-36 | W, Y | W, Y | 67 | L | *V* |
| 46-49 | L, L, I, *F* | L, L, I, *Y* | 69 | I | I |
| 64 | G | G | 71 | K | *V* |
| 66 | G | G | 73 | N | *T* |
| 68-69 | G, T | G, T | 78 | V | *F* |

TABLE 5-continued

Framework residues affecting the conformation of the CDRs; comparison of NMC-4 and the human acceptor variable regions

| VL | | | VH | | |
|---|---|---|---|---|---|
| Kabat Position | NMC-4 | O18 FW | Kabat Position | NMC-4 | 4-59 FW |
| 71 | *Y* | *F* | 93-94 | *V*, R | *A*, R |
| 98 | F | F | 103 | W | W |

Amino acid residues that may be involved in the pairing of the heavy and light chains to coordinate the presentation of CDRs have been identified (Holmes et al, J Immunol. 167: 296-301 (2001) and may be candidates for back mutation. Without being bound by a theory of the disclosure, within the VL region, residues 44, 96 and 98 are thought to be of importance, with additional contributions from residues 34, 36, 38, 46, 87, 89 and 91. Of these residues, the only one that differs markedly between NMC-4 and acceptor O18 for the VL region is residue 44, which is a valine in NMC-4 VL and a proline in the human O18 framework. Without being bound by a theory of the disclosure, for the VH, residues 45, and 103 are of importance with residues 35, 37, 39, 47, 91, 93, and 95 also contributing to interface packing of the VH with the VL. The only differences in these interface residues for NMC-4 VH and the acceptor 4-59 acceptor frameworks is at residue 93, where there is a conservative difference of a valine in NMC-4 compared to alanine in 4-59 (Table 5).

Comparison of the framework sequences of the murine and the human germline 4-59 VH sequences reveals that many of the differences in the residues that are hypothesized to be important for CDR presentation and interface packing are clustered in framework 3 (residues 67, 71, 73, 78, 93), with additional differences at residues 37 and 48 in framework 2. These residues are putative candidates for back-mutation in the prototype humanized sequence. However, the differences for the two framework 2 residues (37V vs 37I and 48L vs 48I) are conservative; therefore the first prototype VH sequence may focus on the differences in the framework 3 region and carry the following back-mutations from human to mouse: V67L, V71 K, T73N, F78V and A93V (Table 6). The synthetic gene is custom synthesized by Retrogen (San Diego Calif.) and designated H2 and is cloned into the Nhe1 and Xho1 sites of the bacterial vector pRSFDuet (Novagen, Madison Wis.) and used as a template to amplify the insert using the 4-59-huNMC-F (SEQ ID NO: 54) and hu-VH-R (SEQ ID NO: 55) primers (Tables 7 and 9). The resulting fragment is digested with ApaI. Plasmid pcDNA6-NMC-HC, which contains the NMC-4 chimeric heavy chain generated in Example 1, is digested with HindIII and ApaI and the DNA fragment containing the pcDNA-IgG1dm fragment is blunt ended with Klenow fragment in the presence of NTPs. The PCR product containing the VH is ligated to the blunt-ended pcDNA-IgG1dm fragment. The plasmid DNA is then used to transform the E. coli host strain, JM 109. Individual clones are sequenced using a Beckman CEQ 8000 DNA sequencer to identify a clone expressing the insert in the correct orientation and with the correct sequence (clone pcDNA-huVH-IgG1dm). This vector is used as the template for the H4, H5, H6, H7 and H8 variants, that are designed to evaluate the effect of individually reverting each residue back to the human residue (summarized in Table 6). These variants are constructed using the primer pairs indicated in Table 7 (corresponding sequences are shown in Table 9).

TABLE 6

Framework residue mutations incorporated into the germline 4-59 and O18 germline acceptor sequences for the different VL and VH variants.

| VH | Backmutations (Human to Murine) | VL | Backmutations (Human to Murine) | (Human to common human) |
|---|---|---|---|---|
| H2 | V67L, V71K, T73N, F78V, A93V | L5 | P44V, Y49F, F71Y | F73L, G100Q |
| H4 | V67L, V71K, T73N, F78V | L4 | Y49F, F71Y | F73L, G100Q |
| H5 | V71K, T73N, F78V, A93V | L6 | P44V, F71Y | F73L, G100Q |
| H6 | V67L, T73N, F78V, A93V | L7 | P44V, Y49F | F73L, G100Q |
| H7 | V67L, V71K, F78V, A93V | L8 | No backmutations | F73L, G100Q |
| H8 | V67L, V71K, T73N, A93V | L9 | No backmutations | F73L, I83F, G100Q |
| H9 | No backmutations | | | |

TABLE 7

Summary of templates and primers used to construct the humanized heavy chain variants.

| VH variants | Template | Fragment-1 PCR primers | Fragment-2 PCR primers | Final VH PCR primers | Vector | Cloning sites |
|---|---|---|---|---|---|---|
| H2 | Synthesized DNA from Retrogen | | | 4-59-huNMC-F and hu-VH-R | pcDNA6-IgG1(dm) | HindIII ApaI |
| H4 | H2 in pcDNA6-IgG1(dm) | pcDNA6-F and VH-V93A-Rev | VH-V93A-For and hFc-L235E-R | pcDNA6-F and hFc-L235E-R | pcDNA6-IgG1(dm) | HindIII ApaI |
| H5 | H2 in pcDNA6-IgG1(dm) | pcDNA6-F and HC-L67V-R | HC-L67V-F and hFc-L235E-R | pcDNA6-F and hFc-L235E-R | pcDNA6-IgG1(dm) | HindIII ApaI |
| H6 | H2 in pcDNA6-IgG1(dm) | pcDNA6-F and HC-K71V-R | HC-K71V-F and hFc-L235E-R | pcDNA6-F and hFc-L235E-R | pcDNA6-IgG1(dm) | HindIII ApaI |
| H7 | H2 in pcDNA6-IgG1(dm) | pcDNA6-F and HC-N73T-R | HC-N73T-F and hFc-L235E-R | pcDNA6-F and hFc-L235E-R | pcDNA6-IgG1(dm) | HindIII ApaI |
| H8 | H2 in pcDNA6-IgG1(dm) | pcDNA6-F and HC-V78F-R | HC-V78F-F and hFc-L235E-R | pcDNA6-F and hFc-L235E-R | pcDNA6-IgG1(dm) | HindIII ApaI |
| H9 | Synthesized DNA from Retrogen | | | 4-59-huNMC-F and hu-VH-R | pcDNA6-IgG1(dm) | HindIII ApaI |

Comparison of residues hypothesized to affect canonical structure and interface packing indicates that there are three differences between the NMC-4 VL and the O18 human VL acceptor framework (e.g., residues 44, 49 and 71). Therefore, a prototype humanized variant may be designed, L5, that carries three back-mutations to the murine residue (e.g., P44V, Y49F and F71Y) (Table 6). In addition, this variant is designed to have residue 73 changed from phenylalanine to a leucine, since leucine is a more common residue at this position in the human antibody repertoire. To generate this variant, a variant, designated VL4, carrying framework changes (e.g., Y49F, F71Y and F73V), is custom synthesized (Retrogen) and cloned into the pETDuet vector using primer pairs indicated in Table 8. The resulting L4-pETDuet vector is used as a template to introduce the P44V mutation of L5 using primer pairs listed in Table 8. The L5 variant is then subcloned into the EcoR1 and BamH1 sites of the pIRES DsRed2 vector in place of the murine NMC-4 VL. The L5-pIRES DsRed vector is then used as a template to generate the L6 and L7 vectors using primers indicated in Table 8.

TABLE 8

Summary of templates and primers used to construct the humanized light chain variants.

| VL variants | Template | Fragment-1 PCR primers | Fragment-2 PCR primers | Final VL PCR primers | Vector | Cloning sites |
|---|---|---|---|---|---|---|
| L4 | Synthesized DNA from Retrogen | | | NMC4-VL-EcoRI-F and Kappa-BamHI-R | pIRES-DsRed2-Igk | EcoRI BamHI |
| L5 | L4 in pETDuet-1 | Fab-L-For and LC-P44V-R | LC-P44V-F and Fab-L-Rev | Fab-L-For and Fab-L-Rev | pETDuet-1 | NdeI XhoI |
| L5 | L5 in pETDuet-1 | | | NMC4-VL-EcoRI-F and Kappa-BamHI-R | pIRES-DsRed2-Igk | EcoRI BamHI |
| L6 | L5 in pIRES-DsRed2-Igk | NMC4-VL-EcoRI-F and LC-F49Y-R | LC-F49Y-F and Kappa-BamHI-R | NMC4-VL-EcoRI-F and Kappa-BamHI-R | pIRES-DsRed2-Igk | EcoRI BamHI |
| L7 | L5 in pIRES-DsRed2-Igk | NMC4-VL-EcoRI-F and LC-Y71F-R | LC-Y71F-F and Kappa-BamHI-R | NMC4-VL-EcoRI-F and Kappa-BamHI-R | pIRES-DsRed2-Igk | EcoRI BamHI |
| L8 | L7 in pIRES-DsRed2-Igk | 5'IRES and HuLC-V44P-F49Y-R | HuLC-V44PF49Y-F and 3'IRES | 5'IRES and 3'IRES | pIRES-DsRed2-Igk | EcoRI BamHI |
| L9 | Synthesized DNA from Retrogen | | | NMC4-VL-EcoRI-F and Kappa-BamHI-R | pIRES-DsRed2-Igk | EcoRI BamHI |

TABLE 9

Sequences of primers used to construct the various variable regions.

| Forward Primer | Sequence | Reverse Primer | Sequence |
|---|---|---|---|
| 4-59-huNMC-F | 5'-GTTAAGCTTGCCGCCACCATGAA ACATCTGTGGTTCTTCCTTCTCCTGGT GGCAGCTCCCAGGTGGGTCCTGTCCC AGGTGCAGCTGCAGGAATCCGG-3' (SEQ ID NO: 54) | Hu-VH-R | 5'-GGATGGGCCCTTGGTGGAAGC GGAGGAAACGGTCACGAGGGTA-3' (SEQ ID NO: 55) |
| pcDNA6-F | 5'-CACTGCTTACTGGCTTATCG AAATTA-3' (SEQ ID NO: 56) | hFc-L235E-R | 5'-AAGAGGAAGACTGACGGTCCCCC CTCGAG-3' (SEQ ID NO: 40) |
| VH-93A-For | 5'-GACACCGCTGTTTACTACT GCGCTCGTGACCCGGCTGACT-3' (SEQ ID NO: 57) | VH-V93A-Rev | 5'-AGTCAGCCGGGTCACGACCGCA GTAGTAAACAGCGGTGTC-3' (SEQ ID NO: 58) |
| HC-L67V-F | 5'-CTGAAATCCCGTGTTACCATC TCCAAAGAC-3' (SEQ ID NO: 59) | HC-L67V-R | 5'-GTCTTTGGAGATGGTAACACGGG ATTTCAG-3' (SEQ ID NO: 60) |
| HC-N73T-F | 5'-ACCATCTCCAAAGACACCTCC AAAAAC-3' (SEQ ID NO: 61) | HC-N73T-R | 5'-GTTTTTGGAGGTGTCTTTGGA GATGGT-3' (SEQ ID NO: 62) |
| HC-V78F-F | 5'-AACTCCAAAAACCAGTTCT CCCTGAAAC-3' (SEQ ID NO: 63) | HC-V78F-R | 5'-GTTTCAGGGAGAACTGGTTTTT GGAGTT-3' (SEQ ID NO: 64) |
| HC-K71V-F | 5'-CTTACCATCTCCGTAGACAA CTCCAAAAAC-3' (SEQ ID NO: 65) | HC-K71V-R | 5'-GTTTTTGGAGTTGTCTACGGA GATGGTAAG-3' (SEQ ID NO: 66) |
| hu-VH-K71V-F (H9) | 5'-CGTGTTACCATCTCCGTAGA CACCTCCAAA-3' (SEQ ID NO: 67) | hu-VH-K71V-R (H9) | 5'-TTTGGAGGTGTCTACGGAGAT GGTAACACG-3' (SEQ ID NO: 68) |
| Fab-L-For | 5'-ATACATATGGACATCCAGATG ACCCAGAGC-3' (SEQ ID NO: 69) | Fab-L-Rev | 5'-AGACTCGAGTTATCAACACTC TCCCCTGTTGAAGCT-3' (SEQ ID NO: 70) |
| NMC4-VL-EcoRI-F | 5'-GACGCGAATTCGGACATCCA GATGACCCAGAGCC-3' (SEQ ID NO: 71) | Fab-L-Rev | 5'-AGACTCGAGTTATCAACACTC TCCCCTGTTGAAGCT-3' (SEQ ID NO: 70) |

TABLE 9-continued

Sequences of primers used to construct the various variable regions.

| Forward Primer | Sequence | Reverse Primer | Sequence |
| --- | --- | --- | --- |
| 5'-IRES | 5'-AGCTGGTTTAGTGA-3' (SEQ ID NO: 72) | 3'IRES | 5'-CAAGCGGCTTCGGCCAG-3' (SEQ ID NO: 73) |
| LC-Y49F-F | 5'-CCAAGCTGCTGATCTTCTAC ACCA-3' (SEQ ID NO: 74) | LC-Y49F-R | 5'-TGGTGTAGAAGATCAGCAG CTTGG-3' (SEQ ID NO: 75) |
| LC-F83I-F | 5'-CAGCCCGAGGACATCGCCAC CTACTACTGC-3' (SEQ ID NO: 76) | LC-F83I-R | 5'-GCAGTAGTAGGTGGCGATGTCCT CGGGCTG-3' (SEQ ID NO: 77) |
| LC-P44V-F | 5'-AAGCCCGGCAAGGCCGTC AAGCTGCTGATC-3' (SEQ ID NO: 78) | LC-P44V-R | 5'-GATCAGCAGCTTGACGGCCTTGC CGGGCTT-3' (SEQ ID NO: 79) |
| LC-F49Y-F | 5'-GCCGTCAAGCTGCTGATCTA CTACACCAG-3' (SEQ ID NO: 80) | LC-F49Y-R | 5'-CTGGTGTAGTAGATCAGCAGCT TGACGGC-3' (SEQ ID NO: 81) |
| LC-Y71F-F | 5'-GGCAGCGGCACCGACTTCA CCCTGACCATC-3' (SEQ ID NO: 82) | LC-Y71F-R | 5'-GATGGTCAGGGTGAAGTCGGTG CCGCTGCC-3' (SEQ ID NO: 83) |
| HuLC-V44P, F49Y-F | 5'-GGCAAGGCCCCCAAGCTGCT GATCTACTACACCAG-3' (SEQ ID NO: 84) | HuLC-V44P, F49Y-R | 5'-CTGGTGTAGTAGATCAGCAGC TTGGGGGCCTTGCC-3' (SEQ ID NO: 85) |

In parallel to the cloning of these first sets of variants, a computer-generated 3-dimensional model of the 4-59 acceptor germline sequence is made using the 1 DN0.pdb structure (e.g., 2.3 Å (angstrom) resolution) identified in a BLAST search as having the highest sequence identity (88%) for the whole sequence up through to HCDR3 and a sequence identity of 89% for the framework regions. The structure 1AOK-.pdb is selected as the template for the humanized VH sequence with a sequence identity of 81%. Two crystallographic structures of the murine NMC-4 Fv are available: 1OAK.pdb (e.g., 2.2 Å resolution), which has bound antigen (Celikel et al, Nat. Struct. Biol. 5:189-194 (1998)) and is also selected as the best fit in the VH domain for the prototype humanized variant, and 1 FNS.pdb (2.0 Å resolution), which has bound mutant antigen. Both 1OAK.pdb and 1FNS.pdb have virtually identical VH/VL interface angles, so 1OAK-.pdb is used for superimposition of the models of the human acceptor and humanized VH and VL sequences.

When the backbone structures of NMC-4 VH and 4-59 are superimposed, three areas of difference may be observed. First, differences exist from residues H27 to H33, which include part of HCDR1. Without being bound by a theory of the disclosure, these residues contact HCDR2 and HCDR3, which together form part of the antigen binding site. Residue 34, Val in the murine NMC-4 VH and Trp in the 4-59 sequence, is predicted as potentially responsible for the altered conformation of the H27-33 loop and therefore a candidate for back-mutation. Second, differences exist from residues H52 to H55, which form part of the CDR 2 loop. Framework residue 71 (Lys in mouse, Val in 4-59) is considered to potentially play a role in this difference and so is a candidate for back-mutation. Three additional residues are identified in the 4-59 structure as having the potential to hinder antigen binding. H37, which is a conservative change of Ile compared to Val in mouse; H73 (which represented a moderate change, Thr in 4-59 compared to Asp in mouse) and H78, which represented a large change (Phe in 4-59 compared to Val in mouse). Third, differences exist in CDR3, where diversity is expected.

For modeling of the germline O18 and prototype humanized VL domains, the structure 1 IGM.pdb (e.g., 2.3 Å resolution) has excellent sequence identity (e.g., 95%) with O18, with 4 differences at residues L34, L45, L47 and L92. The structure 01BJ1.pdb (e.g., 2.4 Å resolution) is selected as the template for the prototype humanized VL, since it matches 97/107 residues (e.g., 91% sequence identity).

The good fit of the VL backbones of the NMC-4 and O18 VL structures is consistent with the sequence identity. The only significant structural difference is in the loop comprised of residues L39-L45, which contact the VH and could therefore influence packing and in turn, the shape of the binding pocket. Without being bound by a theory of the disclosure, residue 44 (e.g., Val in mouse, Pro in 4-59) is likely responsible for this difference and is therefore a likely candidate for back-mutation based on computer modeling.

In vitro inhibitory activity in the ristocetin-induced platelet agglutination assay: To test whether the computer modeling predictions could accurately predict effects on activity, the VH2 prototype variant is paired with a VL variant, (e.g., L4, 5, 6 and 7) and the prototype L5 combined with a VH variant (e.g., H2, H4, H5, H6, H7 and H8). The antibody variants are produced by transient transfection of HEK293T cells and purified from filtered culture supernatant as described for the NMC-4 chimeric antibody in Example 1.

Ristocetin-induced platelet agglutination assays are performed using lyophilized platelets as described in Example 1. The change in absorbance (e.g., turbidity) is measured for serial dilutions of antibody in duplicate using a Spectromax plate reader (Molecular Devices) and the data analyzed using Prism software to determine $EC_{50}$ values for the various purified antibody variants (see, e.g., Table 9).

The first version of the humanized antibody, comprised of H2 and L5, showed equivalent activity (e.g., $EC_{50}$ of 0.13) to the parental chimera (e.g., $EC_{50}$ of 0.18 nM) (Table 10). The heavy chain variants with successive point mutations back to the human framework residues were then tested (e.g., variants H2 through H6). The variants showed very similar activity, except for L5-H8 variant that showed a 1.5-fold lower $EC_{50}$ (Table 9). Interestingly, the yield of this variant was low (e.g., $\frac{1}{10}$ of other variants) which suggests that the interaction between the humanized heavy and light chain could have been adversely affected by this combination of mutations, since the stability of the antibody is dependent on the correct assembly of the heavy and light chains. Similarly the L5 variant antibodies were generated and tested and similarly none of the changes back to human appeared to affect activity suggesting that, surprisingly, no framework changes were required. These results indicated that none of the differences between the acceptor frameworks and NMC-4 variable region frameworks that were anticipated to be problematic, had any effect on potency, including the most marked differences thought to underlie the structural differences observed by computer modeling, including the differences flagged as inducing the greatest conformational differences (e.g., V71 K and T73N of the VH and P44V of the VL). Given these results, a heavy chain variant carrying a completely human framework was constructed (e.g., H9), which represented a simple CDR-grafted VH. This variant was then tested in combination with the light chain variants as well as an additional variant, L9 that represented simple CDR grafting on a completely human framework. Surprisingly, the straight CDR-grafted antibody retained full activity ($EC_{50}$ of 0.08 nM; Table 10). These data demonstrated that, unexpectedly, straight grafting of the CDRs from the murine antibody onto the selected human frameworks retained the fully activity of the original murine antibody even though the published crystallographic data indicates that multiple CDRs contribute to antigen binding (Celikel et al, Blood Cells Mol Dis. 23:123; Celikel et al., Nat. Struct Biol 5:189) and therefore any perturbation in the relative presentation of the 6 CDRs would be anticipated to affect affinity.

TABLE 10

Comparison of the $EC_{50}$ values for the parental NMC-4 chimera compared to the humanized variants in the ristocetin-induced vWF-mediated platelet agglutination assay.

| Antibody (1st set) | $EC_{50}$ (nM) | Antibody (2nd set) | $EC_{50}$ (nM) |
|---|---|---|---|
| NMC4 chimera | 0.18 ± 0.03 (n = 9) | H9, L4 | 0.11 |
| L5, H2 | 0.13 (n = 2) | H9, L5 | 0.14 |
| L5, H4 | 0.15 | H9, L6 | 0.13 |
| L5, H5 | 0.18 | H9, L7 | 0.11 |
| L5, H6 | 0.18 | H9, L8 | 0.08 |
| L5, H7 | 0.16 | H9, L9 | 0.12 (n = 2) |
| L5, H8 | 0.28 | | |
| L4, H2 | 0.14 | | |
| L6, H2 | 0.14 | | |
| L7, H2 | 0.15 | | |

Humanizing the CDR Regions: Molecular modeling suggested that additional changes, designed to humanize CDR1 of the light and heavy chain may be tolerated in NMC-4 LCDR1 (e.g., residues 24, 30 and 31) and NMC-4 HCDR1 (e.g., residues 27, 29, 30 and 34). Additionally, two residues in the HCDR2 sequence (e.g., 61 and 62), are also considered to represent changes that may be tolerated (e.g., Ser to Pro for residue 61 and Ala to Ser for residue 62). Therefore, a series of so-called "super-humanized" variants (Tan et al, 2002 J. Immunol. 169:1119-1125) are constructed from the templates and primer pairs indicated in Table 12 (e.g., L10 which represents the variant with an entirely human LCDR1; H12 and H13 which represent partially humanized HCDR1 regions) (Table 11).

TABLE 11

Mutations changing murine CDR residues to their 4-59 counterparts

| VH | Surper-humanized (murine to human) | VL | Super-humanized (murine to human) |
|---|---|---|---|
| H12 | F27G, L29I, T30S | L10 | S24Q, N30S, K31N |
| H13 | F27G, L29I, T30S, V34W | L11 | S24Q, N30S, K31N, Y50D, T51A, S53N, H55E, S56T |
| H14 | F27G, L29I, T30S, V34W, S61P, A62S | | |
| H15 | F27G, L29I, T30S, D31S, G33Y V34W, G35S, S61P, A62S, | | |
| H16 | F27G, L29I, T30S, V34W, M50Y, W52Y, G53Y, D54S, D58N S61P, A62S | | |

In an exemplary method, the computer modeling predictions are tested by performing one or more assays to determine the activity of the humanized antibody. For example, the L11 variant is co-transfected with H9, and the antibody is tested in the ristocetin-induced platelet agglutination assay. As shown in Table 14, the introduction of the three mutations to convert the LCDR1 to be entirely that of O18 is tolerated and caused no significant loss in potency. When the H12, 13 and 14 variants are combined with L9, the H12-L9 variant antibody showed a slight loss in potency but the additional V34W mutation restored full potency and the addition of the S61P and A62S mutations had little effect on potency, indicating that these residues could be converted to the 4-59 sequence without impacting activity. Next, the importance of LCDR2 in maintaining vWF blocking activity is assessed by constructing a variant of the L10 chain where the entire LCDR2 (YTSSLHS) (SEQ ID NO: 11) is replaced with the human germline O18 LCDR2 (DASNLET) (SEQ ID NO: 118) using the plasmid encoding the VL variant L10 as the template and the primer pairs indicated in Tables 11 and 12. This newly constructed variant (L11) is then paired with H14 to produce the antibody variant L11-H14. While still exhibiting nanomolar potency, this variant showed a 10-fold lower activity compared to chimera in the platelet agglutination assay ($EC_{50}$ 1.63 nM), suggesting that LCDR2 may be required for optimal activity of the humanized antibody.

TABLE 12

Summary of how the "super-humanized" variants were constructed

| Variants | Template | Fragment-1 PCR primers | Fragment-2 PCR primers | Final VH PCR primers | Vector | Cloning sites |
|---|---|---|---|---|---|---|
| H12 | H9 in pcDNA6-IgG1(dm) | pcDNA6-F and huH12-R | huH12-F and hFc-L235E-R | pcDNA6-F and hFc-L235E-R | pcDNA6-IgG1(dm) | HindIII ApaI |
| H13 | H9 in pcDNA6-IgG1(dm) | pcDNA6-F and huH13-R | huH13-F and hFc-L235E-R | pcDNA6-F and hFc-L235E-R | pcDNA6-IgG1(dm) | HindIII ApaI |

TABLE 12-continued

Summary of how the "super-humanized" variants were constructed

| Variants | Template | Fragment-1 PCR primers | Fragment-2 PCR primers | Final VH PCR primers | Vector | Cloning sites |
|---|---|---|---|---|---|---|
| H14 | H13 in pcDNA6-IgG1(dm) | pcDNA6-F and huH14-R | huH14-F and hFc-L235E-R | pcDNA6-F and hFc-L235E-R | pcDNA6-IgG1(dm) | HindIII ApaI |
| H15 | H14 in pcDNA6-IgG1(dm) | pcDNA6-F and huH15-R | huH15-F And hFc-L235E-R | pcDNA6-F and hFc-L235E-R | pcDNA6-IgG1(dm) | HindIII ApaI |
| H16 | H15 in pcDNA6-IgG1(dm) | pcDNA6-F and huH16-R | huH16-F And hFc-L235E-R | pcDNA6-F and hFc-L235E-R | pcDNA6-IgG1(dm) | HindIII ApaI |
| L9 | L1 in pETDuet-1 | NMC4-VL-EcoRI-F and LC-Y71F-R | LC-Y71F-F and Kappa-BamHI-R | NMC4-VL-EcoRI-F and Kappa-BamHI-R | pIRES-DsRed2-Igκ | EcoRI BamHI |
| L10 | L9 in pIRES-DsRed2-Igk | 5'IRES and huL10-R | huL10-F and 3'IRES | 5'IRES and 3'IRES | pIRES-DsRed2-Igκ | EcoRI BamHI |
| L11 | L10 in pIRES-DsRed2-Igk) | 5'-IRES and huL11-R | huL11-F and 3'IRES | 5'-IRES and 3'IRES | pIRES-DsRed2-Igκ | EcoRI BamHI |

TABLE 13

Primers used to construct the humanized CDR variants

| Forward Primer | Sequence | Reverse Primer | Sequence |
|---|---|---|---|
| 5'-IRES | 5'-AGCTGGTTTAGTGA-3' (SEQ ID NO: 72) | 3'IRES | 5'-CAAGCGGCTTCGGCCAG-3' (SEQ ID NO: 73) |
| huL10-F | 5'-ACCATCACCTGCCAAGCCAGCCAGGACATCAGCAACTACCTGAACTGG-3' (SEQ ID NO: 86) | huL10-R | 5'-CCAGTTCAGGTAGTTGCTGATGTCCTGGCTGGCTTGGCAGGTGATGGT-3' (SEQ ID NO: 87) |
| huL11-F | 5'-CCCAAGCTGCTGATCTACGACGCCAGCAACCTGGAAACCGGCGTGCCC-3' (SEQ ID NO: 88) | huL11-R | 5'-GGGCACGCCGGTTTCCAGGTTGCTGGCGTCGTAGATCAGCAGCTTGGG-3' (SEQ ID NO: 89) |
| pcDNA6-F | 5'-CACTGCTTACTGGCTTATCGAAATTA-3' (SEQ ID NO: 56) | hFc-L235E-R | 5'-AAGAGGAAGACTGACGGTCCCCCCTCGAG-3' (SEQ ID NO: 40) |
| huH12-F | 5'-GTTTCCGGTGGCTCCATCTCCGACTACGGTGTTGACTGGA-3' (SEQ ID NO: 90) | huH12-R | 5'-TCCAGTCAACACCGTAGTCGGAGATGGAGCCACCGGAAAC-3' (SEQ ID NO: 91) |
| huH13-F | 5'-GTTTCCGGTGGCTCCATCTCCGATACGGTTGGGACTGGATCCGTCAG-3' (SEQ ID NO: 92) | huH13-R | 5'-CTGCAGGATCCAGTCCCAACCGTAGTCGGAGATGGAGCCACCGGAAAC-3' (SEQ ID NO: 93) |
| huH14-F | 5'-GTTCCACCGACTACAACCCCTCTCTGAAATCCGT-3' (SEQ ID NO: 94) | huH14-R | 5'-ACGGGATTTCAGAGAGGGGTTGTAGTCGGTGGAAC-3' (SEQ ID NO: 95) |
| huH15-F | 5'GTTTCCGGTGGCTCCATCTCCTCCTACTATTGGTCCTGGATCCGTCAG-3' (SEQ ID NO: 96) | huH15-R | 5'-CTGACGGATCCAGGACCAATAGTAGGAGGAGATGGAGCCACCGGAAAC-3' (SEQ ID NO: 97) |
| huH16-F | 5'-GAATGGATCGGTTATATCTATTATTCCGGTTCCACCAACTACAACCCCTCT-3' (SEQ ID NO: 98) | huH16-R | 5'-AGAGGGGTTGTAGTTGGTGGAACCGGAATAATAGATATAACCGATCCATTC-3' (SEQ ID NO: 99) |

Next the importance of the remaining murine residues (e.g., H31, H33, and H35) in the humanized HCDR1 in variant H14 is examined by changing these residues to their human counterparts in the VH germline 4-59 sequence (e.g., a D31S, G33Y and D35S change). The resulting construct, H15 has a sequence of GGSISSYYWS (SEQ ID NO: 110) for HCDR1 compared to the partially humanized sequence of GGSISDYGWD (SEQ ID NO: 111) in H14. Finally, the entire HCDR2 of is converted to its human counterpart in VH4-59 (from MIWGDGSTDYNSALKS (SEQ ID NO: 8) to YIYYSGSTNYNPSLKS (SEQ ID NO: 119), a total of 7 residue differences) to create another variant, H16, which has a completely human HCDR1 and HCDR2. Variant H15 and H16 are individually paired with the light chain variant L10 to produce antibody variants H15-L10 and H16-L10, respectively.

These variants are evaluated in a platelet agglutination assay to determine their activities. The data presented in Table 14 suggests that the replacement of the entire HCDR1 with human sequence abolishes anti-vWF activity. This suggests that the remaining three residues in the HCDR1 (e.g., D at position H31, G at position H33 and D at H35) are important for retaining activity, even if these residues may not contact the antigen directly, as suggested by the crystal structure reported by Celikel, et al (*Nat. Struct Biol* 5:189). Replacing HCDR2 entirely with the human 4-59 HCDR2 did not restore the lost activity of H15, consistent with the indications from the crystallographic studies of Celikel et al., which suggest that three of the residues in HCDR2 (e.g., H53, H54, and H58) interact directly with the vWF antigen.

TABLE 14

$EC_{50}$ values of the "superhumanized" variants

| Antibody | $EC_{50}$ (nM) |
| --- | --- |
| NMC-4 chimera | 0.18 ± 0.03 (n = 9) |
| Hg, L9 (CDR-grafted) | 0.12 (n = 2) |
| H12, L9 | 0.29 |
| H13, L9 | 0.16 (n = 2) |
| H14, L9 | 0.13 (n = 2) |
| H13, L10 | 0.20 |
| H14, L10 | 0.22 ± 0.05 (n = 5) |
| H14, L11 | 1.63 |
| H15, L10 | ND |
| H16, L10 | ND |

Example 3

Reformatting Isotypes of Antibodies

In an exemplary method, it may be desirable to reformat VH variants from the mutated IgG1 format into an IgG4 format since IgG1 is an active isotype with respect to complement activation and elicitation of effector responses, whereas IgG4 is relatively inactive. For example, candidate VH variants are converted from the mutated IgG1 format into an IgG4 format (see, for example, SEQ ID NO: 144) to generate candidates for development. In addition, the light and heavy chain open reading frames are redesigned to incorporate restriction endonuclease cleavage sites on the 5' (e.g., XhoI and HindIII sites) and 3' (e.g., BamHI and NotI sites) ends, to facilitate subcloning into the multiple cloning site of expression vector pSTO518 for downstream cell-line development and large scale antibody production (Table 15).

For example, two of the humanized VH variants, H9 and H14 are converted to an IgG4 format by replacing the IgG1 constant region with a IgG4 constant region and introducing XhoI and BamHI sites on the 5' end and HindIII and NotI sites on the 3' end of the heavy chain expression cassette. Both IgG1 and IgG4 contain a naturally occurring ApaI site near the junction of the variable and constant regions. This site is used to clone in the IgG4 in place of the IgG1. BamHI and NotI restriction sites are placed on the 3' end of the sequence to facilitate later subcloning into the pSTO518 vector. The intron-deleted IgG4 constant region sequence from the ApaI site to the termination codon, with the added BamHI and NotI sites, is custom synthesized by Blue Heron Biotechnology (Bothell, Wash.). Further, the signal sequence in the pSTO518 vector is changed to an Igκ leader sequence by conducting overlapping PCR with primers that are designed to incorporate XhoI and HindIII sites at the 5' end of the heavy chain variable regions and to insert the Igκ signal sequence.

H9 and H14 heavy chain sequences are identical in the primer regions, therefore the same primers and cloning strategy are used for both. Two separate PCR products are produced, each incorporating one of the changes required in the huNMC4-H9 (and huNMC4-H14) heavy chain variable region. A PCR reaction that incorporates XhoI and HindIII restriction sites on the forward primer and amplifies the Igκ signal peptide is performed using pIRESdsRed-HUL10 as the template and the primers, IgKLF (SEQ ID NO: 100) and IgKHnmcR (SEQ ID NO: 101) (see, Table 15a and Table 15b). This is followed by a second reaction step which uses pcDNA6-H9 (or pcDNA6-H14) as the template and primers 14VHF (SEQ ID NO: 102) and 14VHR (SEQ ID NO: 103) and overlaps the first PCR reaction by 30 nucleotides. The PCR product contains the H9 (or H14) variable region as well as the first five amino acids of the IgG1 constant region through the ApaI site. The first five amino acids of the constant region do not differ between IgG1 and IgG4. The reaction also adds a NotI site after the ApaI site to facilitate cloning of the variable region prior to insertion of the IgG4 constant region. The kappa leader is added upstream by the third PCR step which uses the reaction products of the first two steps as template with the forward primer is of the first reaction (IgKLF) and the reverse primer of the second reaction (14VHR). The product from this reaction is digested with XhoI/NotI and inserted into the similarly digested plasmid backbone pCIneo. This ligation produced the cloning intermediate pCI-NMC4-VH9var *or* (pCI-NMC4-VH14var), which contains the Igκ leader and variable region of NMC4-H9 (or H14). The plasmid from Blue Heron Biotechnology, containing the de novo synthesized IgG4 constant region, is digested with ApaI and NotI, the 1 kb IgG4 constant region fragment is gel-purified and ligated into the ApaI/NotI digested pCI-NMC4-VH9var *or* (pCI-NMC4-VH14var). This produced the plasmids pCI-NMC4-VH9 and pCI-NMC4-VH14. After transformation into DH5α cells, plasmid inserts from individual clones are sequenced to verify that they are correct.

TABLE 15a

Primers used in the heavy chain PCR reactions.

| Name | Sequence |
| --- | --- |
| IgKLF | 5'CCTATCTCGAGAAGCTTCCACCATGGAGACAGACACACTC CT (SEQ ID NO: 100) |
| IgKHnmcR | 5'ACCCGGACCGGATTCCTGCAGCTGCACCTGTCCAGTGGAA CCTGGAACCCAGAGC (SEQ ID NO: 101) |
| 14VHF | 5'CAGGTGCAGCTGCAGGAATCCGGTCCG (SEQ ID NO: 102) |
| 14VHR | 5'CCTATGCGGCCGCGGGCCCTTGGTGGAAGCGGAGGAAACG GT (SEQ ID NO: 103) |

TABLE 15b

PCR reactions used for the heavy chain construction

| PCR | Fwd Primer | Rev Primer | Template | Product |
|---|---|---|---|---|
| 1st | IgKLF | IgKHnmcR | pIRESdsRed-huL10 | XhoI, HindIII, IgK signal peptide |
| 2nd | 14VHF | 14VHR | pCDNA6-huH9, (or pCDNA6-huH14) | hu-H9 variable region, ApaI, NotI (or hu-H14 variable region, ApaI, NotI) |
| 3rd | IgKLF | 14VHR | Products of above two PCR reactions | Hu-VH9 (or VH14) variable region |

The changes in the L9 and L10 light chains are accomplished by PCR. Since the L9 and L10 light chains are identical in the primer regions, the same primers and the same strategy were used for both. Two separate PCR templates are produced for each light chain. The first PCR step incorporates XhoI and HindIII restriction sites on the 5' end. The second PCR step overlaps with the first by 30 nucleotides and incorporates BamHI and NotI sites at the 3' end of the fragment. These two separate overlapping PCR products are used as templates in the third PCR reaction to produce a final overlapping PCR product that incorporates these changes by amplifying them using the forward primer from the first PCR step and the reverse primer from the second step. The product from the third PCR reaction is digested with XhoI/NotI and inserted into the similarly digested plasmid pCI-neo (Invitrogen), producing plasmids and pCI-NMC4-VL10 (see, Table 16a and Table 16b for exemplary primers and strategy used for light chain construction).

TABLE 16a

Primers used in the light chain PCR reactions.

| Name | Sequence |
|---|---|
| IgKLF | 5' CCTATCTCGAGAAGCTTCCACCATGGAGACAGACACACTC CT (SEQ ID NO: 100) |
| IgKLNMCR | 5' GCTGCTGGGGCTCTGGGTCATCTGGATGTCTCCAGTGGAA CCTGGAACCCAGAGC (SEQ ID NO: 104) |
| 10VLF | 5' GACATCCAGATGACCCAGAGCC (SEQ ID NO: 105) |
| hKcR | 5' CCTATGCGGCCGCGGATCCTATCAACACTCTCCCCTGTTG AAGCTCT (SEQ ID NO: 106) |

TABLE 16b

PCR reactions for the light chain construction

| PCR | Fwd Primer | Rev Primer | Template | Product |
|---|---|---|---|---|
| 1st | 1 | 2 | pIRESdsRED-huL10 | XhoI, HindIII, Signal.peptide |
| 2nd | 3 | 4 | pIRESdsRED-huL9 or pIRESdsRED-huL10 | huL9 or huL10 variable region and hIgκ constant region, BamH1, Not1 |
| 3rd | 1 | 4 | Ist and 2$^{nd}$ PCR products | NMC4-VL9 or NMC4-VL10 IgG4 sequence cassettes |

The IgG4 isotypes of H9-L9 and H14-L10 are generated from HEK293T cells as described above in Example 1 and purified by Protein A affinity chromatography. The purified antibodies are then tested in the vWF-mediated platelet agglutination assay to determine relative potency. As shown in Table 17, conversion to the IgG4 isotype had no effect on potency.

TABLE 17

Comparison of the ristocetin-induced platelet agglutination activity of the lead anti-vWF IgG1 and IgG4 variants.

| Antibody variant | Isotype | Platelet agglutination EC$_{50}$ mean value (from 2 independent expts.) |
|---|---|---|
| NMC-4 Chimera | IgG1 Chimera | 1.25 nM (1.3 nM, 1.2 nM) |
| H9-L9 | IgG1 | 1.30 nM (1.3 nM, 1.3 nM) |
| H9-L9 | IgG4 | 1.40 nM (1.3 nM, 1.5 nM) |
| H14-L10 | IgG1 | 1.20 nM (1.1 nM, 1.3 nM) |
| H14-L10 | IgG4 | 2.15 nM (2.3 nM, 2.0 nM) |

Example 4

Binding of Antibodies to vWF or A1 Domain

Cloning His tagged A1 domain antigen: Without being bound by a theory of the disclosure, it is hypothesized that NMC-4 binds to the A1 domain of vWF, which normally is accessible only when vWF is activated (e.g. under high shear conditions). As an alternative approach it may be desirable to express the isolated A1 domain of vWF, which is reported to bind GP1bα with potency equivalent to that of intact activated vWF (Celikel et al, 1997). Therefore, the A1 domain is cloned to serve as a substrate for microwell binding studies. A plasmid clone containing the full-length human vWF cDNA is purchased from ATCC (Cat#67122). The vWF A1 domain (e.g., residues 499-729) is amplified from this clone with the primers vWF-A1-For (5'-CCCAGGAATTCCTCGGAAC-CGCGTTGCAC-3') (SEQ ID NO: 112) and vWF-A1-Rev (5'-CCGATGCGGCCGCTCACCTCTTGGGCCCCAG-3') (SEQ ID NO: 113). The PCR product is gel purified, digested with EcoR I and Not 1, and cloned into the pETDuet-1 vector. The ligated product is transformed into DH5α competent cells to produce the oxidized form of A1 domain.

To construct a plasmid expressing the rat A1 domain, rat genomic DNA is isolated from rat liver with DNAzoI reagent by following the manufacturer's protocol (Molecular Research Center, Inc., Cat# DN127, Cincinnati, Ohio). The genomic DNA is then used for a PCR reaction with the primers (Rat-vWF-A1-F (5'-AGCGAATTCCCCCGAAC-CCCCCCTGCACAACTTC-3') (SEQ ID NO: 114) and RatvWF-A1-R (5'-AGTGCGGCCGCTTATCAC-CTTTTGGGTCCTGGTGATGAAACC-3') (SEQ ID NO: 115). The PCR product is digested with EcoRI and NotI and cloned into the same sites of the pETDuct-1 vector. The ligated products are transformed into DH5α competent cells.

One liter of bacterial culture medium (LB or 2×YT) containing the antibiotics, Carbenicillin, Kanamycin, and Tetracycline, is inoculated with a 25 ml overnight bacterial culture (e.g., strain Origami B carrying plasmids p35 [pET-Duet-Rat-A1] or p36 [pET-Duet-human-A1]). The culture is grown at 37° C. in a shaker to an $OD_{600}$ of 0.6-0.8. Expression of the recombinant proteins is induced by addition of IPTG to a final concentration of 1 mM and growth of the culture is then continued at 37° C. for an additional 4-5 hours before bacteria are harvested by centrifugation at 6,000 rpm in a JA-10 rotor (Beckman). The cell pellet is either frozen at −80° C. or immediately processed by re-suspending the pellet in 20 ml PBS containing two dissolved tablets of complete Protease Inhibitors (Roche), subjecting the resulting cell suspension to two 2 minute cycles of cell disruption (e.g., Branson Sonifier 250 fitted with a micro-tip on a constant duty cycle setting and output control setting of 1-2) while on ice. The cell lysate is centrifuged at 16,000 rpm in a JA-20 rotor (Beckman) for 30 minutes at 4° C. The supernatant is filtered through a 0.45 μm syringe filter prior to application to a 2 ml column packed with His-Select HF Nickel Affinity gel (Sigma) which has been equilibrated in binding buffer (5 mM imidazole, 0.3 M NaCl, 50 mM Tris-HCl, pH 8.0). The chromatography is performed using a syringe pump that regulates the flow rate at 1 ml/min. After the column is washed with 20 ml binding buffer, the proteins are eluted with 250 mM imidazole, 0.3 M NaCl, 50 mM Tris-HCl, pH 8.0, and 1 ml fractions are collected. The majority of the protein elutes within the first 4 fractions of the elution. The size (~28 kD) and integrity of the proteins are monitored on a Coomassie stained SDS-polyacrylamide gel. Peak fractions are pooled, concentrated to 2.5 ml if necessary, and desalted into PBS using a PD-10 column (Amersham/GE-Healthcare). The protein concentration is determined using a Lowry protein assay (BioRad DC Protein Assay).

Binding kinetics: To assess $K_{on}$, $K_{off}$ and $K_d$ values, sensitive assays are performed whereby Europium (N1 chelate) antibody conjugates are synthesized and purified. Binding of these Eu-labelled NMC-4 chimera and isotype control antibodies to immobilized A1 antigen is measured using a dissociation-enhanced lanthanide fluoroimmunoassay (DELFIA).

For example, control antibody (e.g., isotype control MOPC-21, an IgG1/κ from human myeloma plasma; Sigma-Aldrich, St Louis Mo.) and NMC-4 chimera are Eu labeled. Briefly, antibody is added to sterile-filtered sodium phosphate buffer (96 mM, pH 7.4) and dialyzed extensively into Phosphate Buffered Saline (PBS; 1.47 mM $KH_2PO_4$, 8.1 mM $Na_2HPO_4$, pH 7.4, 138 mM NaCl and 2.67 mM KCl) to remove low-MW primary amines. Dialyzed antibodies are concentrated in a washed MicroSep concentrator at 9500 RPM (7000×g) in a JA-20 rotor for 20 minutes at 4° C. Antibody is adjusted to 4.0 mg/ml with PBS containing a final concentration of 100 mM $NaHCO_3$, pH 9.3. The mAb/bicarbonate mixture (0.250 ml) is mixed into a vial containing 0.2 mg $N^1$-(p-isothiocyanatobenzyl)-diethylenetriamine-$N^1$,$N^2$, $N^3$,$N^3$-tetraacetic acid chelated with $Eu^{3+}$ (Eu-N1-ITC; Perkin Elmer Life Sciences, Waltham Mass.) by gently pipetting up and down. The mixture of antibody and amine-reactive chelate is allowed to react overnight at 4° C. without stirring.

A labeled antibody mixture is applied to a separate NAP-10 column (Amersham Biosciences, Piscataway, N.J.) pre-equilibrated with PBS. Fractions (e.g., 0.5 ml) are collected using PBS for the column buffer. Samples are assayed for total protein (e.g., Bradford reagent; Bio-Rad Laboratories, Inc., Hercules, Calif.) using a SpectraMax 384 absorbance plate reader and assayed for Eu, after 1:10,000 dilution in DELFIA Enhancement Solution (Perkin-Elmer), by time-resolved fluorescence (TRF) using a Victor2 multi-label plate reader (Perkin-Elmer). The fractions that are positive for both protein and Eu label are pooled and applied to new NAP-10 columns pre-equilibrated with Running Buffer (50 mM Tris, pH 7.4 and 138 mM NaCl). Fractions from these columns that are positive for both protein and Eu label are pooled and applied to PD-10 columns pre-equilibrated with Running Buffer and fractions positive for protein and Eu label are pooled and assayed for total protein and for Eu content by TRF calibrated against a europium standard solution (Perkin-Elmer). The fluor:protein ratio is then calculated.

Wells of Immulon-4 plates are coated with His-A1 domain of vWF from human (e.g., 25 ng in 100 μl/well in 30 mM Tris, pH 7.4 and 300 mM NaCl or divalent cation-free PBS) or rat (e.g., 50 ng/well) by incubating overnight at 4° C. The plates are washed three times with Wash Buffer (e.g., 50 mM HEPES, pH 7.4, 150 mM NaCl, 0.5% Tween-20), blocked with 300 μl/well Blocking Buffer (e.g., Wash Buffer containing 3.0 mg/ml IgG-free BSA and 0.1% sodium azide) for 1 hour at room temperature and washed 5 times with Wash Buffer before use.

Equilibrium binding assays are performed as follows. Eu-antibody is pre-diluted into Binding Buffer (e.g., Wash buffer containing 100 μg/ml IgG-free BSA and 0.1% sodium azide) and applied to wells (e.g., 10 μl/well) of a 96-well plate and the plates sealed with SEALPLATE film. The plates are shaken (e.g., Titer Plate Shaker speed setting of 4 for ≧15 sec or 60 sec at RT), placed into nalgene boxes containing wet paper towels, and incubated in the closed boxes for 2 hours at 37° C. For the measurement of free label, supernatant samples (4.0 μl) are transferred from the wells containing binding mixtures into a parallel set of wells containing DELFIA Enhancement Solution (100 μl/well). To assess bound antibody, the A1-coated wells with the remaining binding mixtures are washed five times with Wash Buffer, tapped dry onto paper towels and DELFIA Enhancement Solution (100 μl/well) added to the empty wells for the measurement of bound label. For assay calibration, DELFIA Enhancement Solution (100 μl/well) is added to unused wells and Europium Standard (1.0 μl/well) is added. The plates are shaken (e.g., Titer Plate Shaker speed setting of 5 for 10 minutes at room temperature), and time-resolved fluorescent (TRF) intensities are read using a Victor2 multi-label plate reader (Perkin-Elmer Wallac, Boston, Mass.). Binding is normalized for Eu-chelate content by the fluor:protein ratio (F:P) for the respective antibodies. Specific binding is calculated by deducting non-specific binding (e.g., average binding by the Eu-labeled isotype control) from total binding (e.g., binding by Eu-NMC-4). The number of binding sites and the $K_d$ values are calculated by the method of Scatchard (1949). Hill plots are made to assess binding, by plotting $\log(\bar{v}/(n-\bar{v}))$ vs. the log of the free Eu-NMC-4 concentration, where n=the number of high affinity binding sites/well, $\bar{v}$=the average number of specifically-bound Eu-NMC-4 mAb/well, and free Eu-NMC-4 chimera is calculated from the TRF readings measured in the solution phase.

This analysis revealed two classes of binding sites, a high affinity site of $K_d$ 0.37 nM and a low affinity site of $K_d$ 5 nM. Similarly, binding to His-rA1 from rat vWF captured by anti-His mAb also exhibited two classes of binding sites, with $K_d$ values of 0.19 and 3.4 nM (Table 17).

Association kinetics are determined using the same protocol, except washing buffer is replaced at different time-points with europium-labeled antibody at the indicated concentrations (100 µl/well). The plates are promptly sealed, shaken (e.g., Titer Plate Shaker speed setting of 4 for 15 seconds at room temperature), and incubated for the indicated times at 37° C. The plates containing binding mixtures are washed five times with Wash Buffer, tapped dry onto paper towels, and the time of washing for each plate recorded. DELFIA Enhancement Solution (100 µl/well) is added to the empty wells for the measurement of bound label as described above. The apparent on-rate, $k_{on,app}$, for each antibody concentration is measured by fitting specific binding vs. time with the following equation using Prism software (GraphPad Software Inc., San Diego, Calif.).

$$B = B_{max} \cdot (1 - e^{-k_{on,app} \cdot t})$$

The apparent association rate ($k_{on,app}$) is plotted vs. Eu-mAb concentration. The data are fitted to the linear equation $$k_{on,app} = k_{on}[mAb] + k_{off}$$

Where on-rate constant $k_{on}$ is the fitted slope, [mAb] is the concentration of Eu-NMC-4, and the dissociation rate $k_{off}$ is the fitted intercept.

The calculated half-life for the dissociation of the NMC-4 chimera bound to His-A1 from human or rat vWF is calculated by the following equation:

$$t_{1/2,dissoc} = \frac{\ln(2)}{k_{off}}$$

Specific binding of Eu-NMC-4 to His-A1 of human and rat vWF fit a single-exponential association equation, from which the apparent rates of association $k_{on,app}$ (e.g., the constant k from the exponential association curve fit) for each concentration of labeled antibody are obtained. The rates of apparent association to both antigens are dose-dependent as shown in plots of the $k_{on,app}$ vs. Eu-NMC-4 concentration. The results are summarized in Table 17 and revealed that that the NMC-4 chimera had a $K_d$ of 0.32±0.07 nM for the human A1 domain and 0.28±0.01 nM for the rat A1 domain. In both cases these results are in close agreement with the $K_d$ values determined by equilibrium binding. The results also suggest that the antigen-antibody complex is long-lived for both A1 species, with in vitro half-lives for dissociation of 44 minutes and 69 minutes for human and rat antigens, respectively.

TABLE 18

Kinetics and equilibrium binding of Eu-NMC-4 chimera to His-A1 domain from human and rat vWF at 37° C.

|  | His-A1 (human) | His-A1 (rat) |
|---|---|---|
| Kinetic constants | | |
| $k_{on}$ (M$^{-1}$ min$^{-1}$) | 4.1 × 10$^7$ | 1.4 × 10$^7$ |
| $k_{off}$ (M$^{-1}$)† | 1.6 × 10$^{-2}$ | 1.0 × 10$^{-2}$ |
| Dissociation half-life (min) | 44 | 69 |
| $k_{on}/k_{off}$ | 0.39 nM | 0.70 nM |
| Equilibrium binding ($K_d$) | | |
| His-A1 | 0.316 ± 0.068 nM†† | 0.276 ± 0.011 nM†† |
|  | (n = 10) | (n = 5) |

TABLE 18-continued

Kinetics and equilibrium binding of Eu-NMC-4 chimera to His-A1 domain from human and rat vWF at 37° C.

|  | His-A1 (human) | His-A1 (rat) |
|---|---|---|
| Homologous competition ($K_i$) | | |
| His-A1 | 0.275 ± 0.064 nM | 0.297 ± 0.128 nM |
|  | (n = 4) | (n = 3) |

†Intercept from dose-dependence of $k_{on,apparent}$
††$K_d$ for EU-NMC-4 BINDING TO DIRECT-COATED ANTIGEN (HUMAN VS. RAT) NOT STATISTICALLY SIGNIFICANT BY THE T TEST OF SIGNIFICANCE (P = 0.6892).
ERRORS ARE DENOTED BY SEM.

Competitive binding studies may be performed to determine Ki values (e.g., a measure of relative affinity for antigen). The assays are performed as described above for association kinetics except in this case, 80 µl/well of Binding Buffer (e.g., Wash Buffer containing 100 µg/ml IgG-free BSA, 0.1% sodium azide) is applied followed by 10 µl/well of either Eu-NMC-4 or Eu-unlabeled competitor and 10 µl/well of unlabeled competitor antibody in a duplicate serial dilution series ranging from 10$^{-12}$M to 10$^{-7}$M. The final concentration of europium-labeled antibody is 100 pM. The level of non-specific background binding is significantly decreased in the presence of the chelating agent DTPA (1 µM) so this is included in the competitive binding assays. In addition, coating of the wells is optimized by using His-A1 that has been purified using iodoacetyl gel to remove any reduced A1 from the protein preparation. The mixture is incubated for 3.75 hours to allow the reaction to reach full equilibrium, washed and bound labeled-antibody determined by TRF as described above. The inhibition curves are fitted with the "one site competition" model using Prism software (GraphPad, Inc.) to obtain IC$_{50}$ values and to calculate the $K_i$ using the equations of Cheng and Prusoff (1973 Biochem Pharm. 22:3099) using the $K_d$ values measured by Scatchard analysis of the equilibrium binding experiment.

Standardization of the competitive binding assay is demonstrated by comparing the $K_i$ value obtained from homologous competition by unlabelled NMC-4 chimera with the affinity ($K_d$) measured for binding of Eu-NMC-4 to antigen. For homologous competition to human His-A1, NMC-4 chimera is a potent inhibitor of EU-NMC-4 binding with a $K_i$ of 0.28±0.06 nM (Table 19), which is consistent with the observed $K_d$ of 0.32±0.07 nM. Similarly, for homologous competition to rat His-A1, NMC-4 chimera had a $K_i$ of 0.297±0.128 nM (Table 18), which is consistent with the $K_d$ of 0.276±0.011 nM. In contrast, the unlabeled isotype control, IgG1/κ from human myeloma plasma, had no inhibitory effect on Eu-NMC-4 binding to A1 antigen.

TABLE 19

Comparison of the binding activity (Ki by competition assay) of selected humanized NMC variants.

| Antibody variant | Isotype | Ki (mean ± SEM) |
|---|---|---|
| NMC-4 mAb | mIgG1 | 0.60 ± 0.13 nM (n = 3) |
| NMC-4 Chimera | IgG1 Chimera | 0.28 ± 0.06 nM (n = 4) |
| IgGκ control | IgG1 | Not detectable |
| H2-L5 | IgG1 | 0.96 ± 0.27 nM (n = 3) |
| H9-L9 | IgG1 | 3.51 ± 1.21 nM (n = 4) |
| H9-L9 | IgG4 | 3.53 nM (n = 1) |

The competitive binding assay is then used to test the potency of the humanized NMC-4 variants H9L9 IgG1 and 4. The two isotypes of the CDR-grafted H9L9 variant showed identical nM activity, albeit less potent than the homologous NMC-4 chimera (Table 19).

Figure 2:
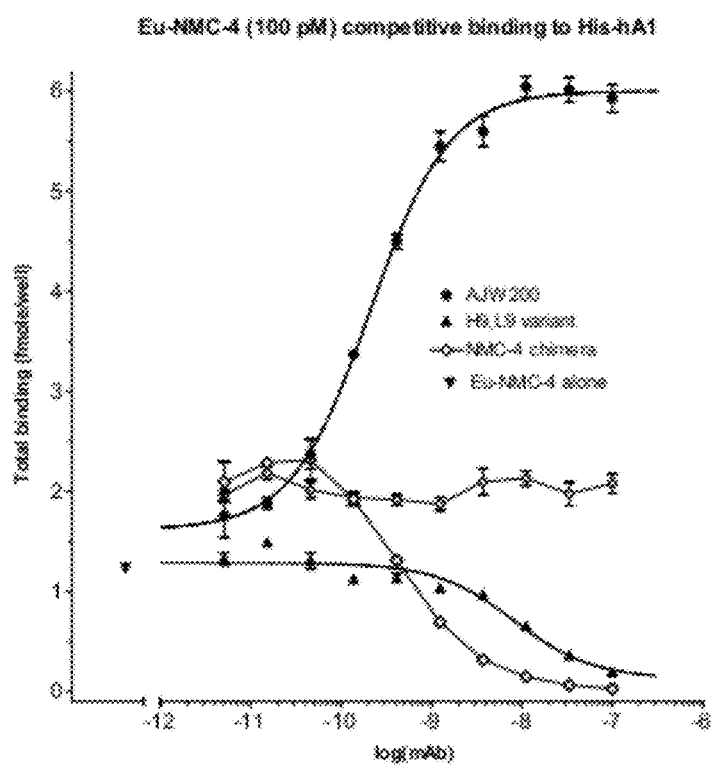
FIG. 2A-B shows competition for Eu-labeled NMC-4 binding by an unlabeled NMC-4 chimeric antibody (homologous competition) and AJW200, alone and in combination (FIG. 2A). Competition of an Eu-labelled NMC-4 chimeric antibody by unlabeled NMC-4 monoclonal antibody, isotype control IgG, AJW200 and a humanized derivative of the NMC-4 antibody with variable regions designated as H9, L9 (FIG. 2A). Hill plot of NMC-4 competition in the presence or absence of 20 nM AJW200 (FIG. 2B).
Figure 2:
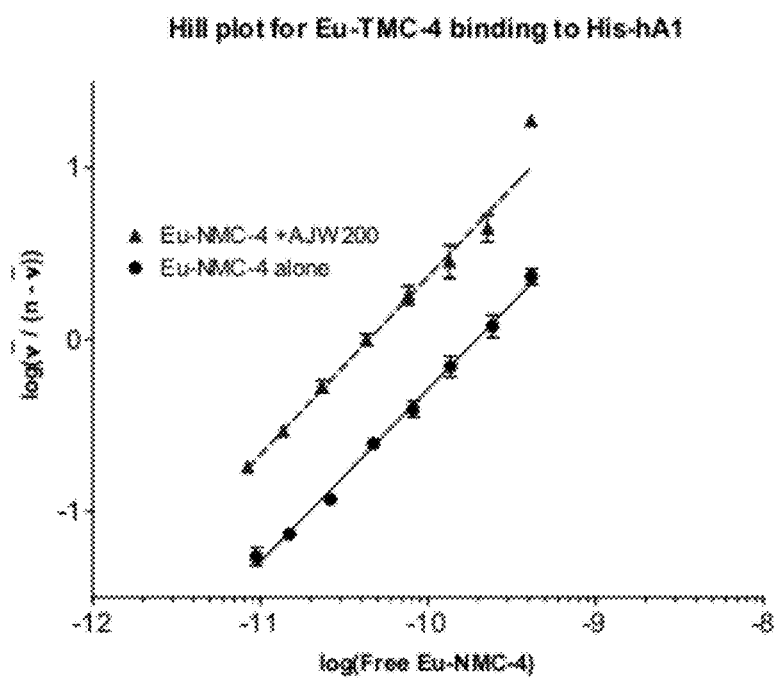

The AJW-200 antibody is tested in the competitive binding assay. In contrast to the humanized NMC-4 variants, which competed for Eu-NMC-4 binding to His-A1, binding of Eu-NMC-4 to His-A1 is enhanced by AJW200 with an $EC_{50}$ of 210 µM (FIG. 2). Hill plots of Eu-NMC-4 binding to His-A1 show Hill slopes near unity ($n_H$=0.984 and 0.957), consistent with binding to a single class of binding sites without cooperativity. By contrast, Hill plots of Eu-NMC-4 binding to His-A1 in the presence of either 1.8 nM or 20 nM AJW200 (FIGS. 2C and 2D, respectively) show Hill slopes greater than one ($n_H$=1.548 and 1.201), indicating positive cooperativity. Positive cooperativity mediated by AJW200 is observed in two independent experiments conducted on two different days. These results not only confirmed that NMC-4 binds to a separate binding site then AJW200 on the A1 domain of vWF but also indicate that, at least for the isolated A1 fragment, AJW200 potentiates NMC-4 binding to the GP1bα binding site.

Example 5

Ability of Antibodies to Block Platelet Adhesion

A confirmation that an antibody blocks the GP1bα receptor binding site on vWF is its ability to antagonize vWF-GP1b interactions under native conditions of flow. One approach that has been developed by Moake and colleagues (1986, *J Clin Invest.* 78:1456-61) exploits the fact that when endothelial cells are activated with histamine they secrete an ultra-large form of vWF (ULvWF), where the A1 domain is in the open (e.g., active) conformation. These rapidly break up upon introduction of plasma, due to ADAMS13-mediated cleavage of the ULvWF (Dong et al., 2002 *Blood* 100:4033-9).

Figure 3:
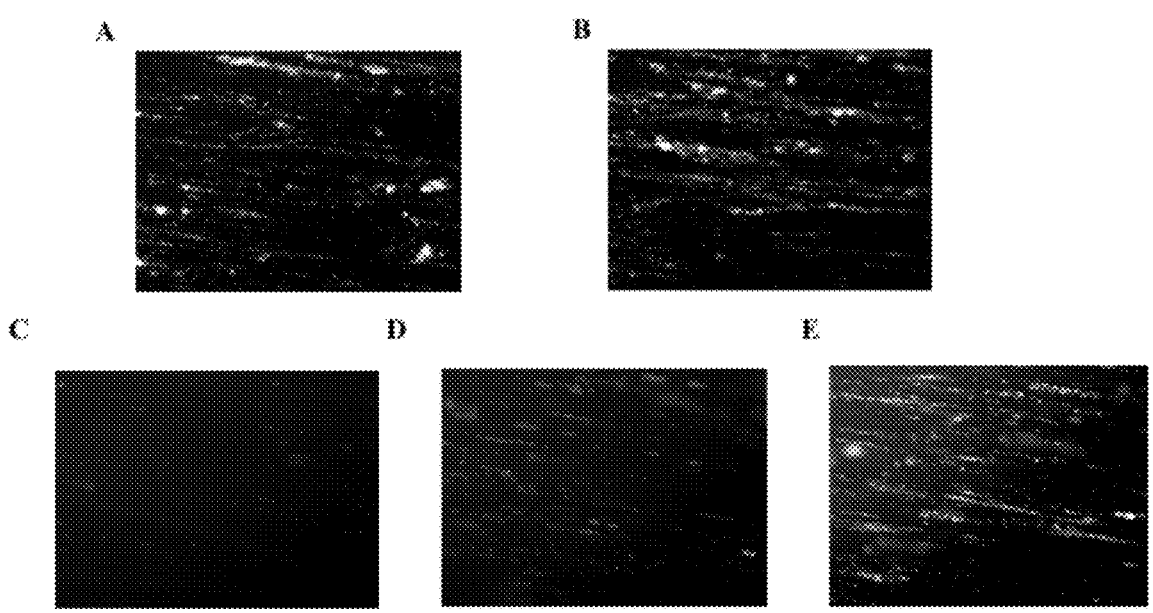
FIG. 3A-E shows the ability of NMC-4 to block platelet adhesion to endothelial vWF under shear flow conditions, including photomicrographs of platelets adhering to HUVEC cells. HUVEC cell monolayers were treated with PBS (FIG. A) or 25 µM histamine (FIGS. B-E), plus 10 µg/mL anti-vWF antibody, NMC-4 (FIG. C), 18 µg/ml anti-GPIbα antibody, AK2 (FIG. D), or 18 µg/ml mouse IgG (FIG. E). The different antibodies were also included in the corresponding platelet suspensions immediately prior to perfusion across the monolayers.

In an exemplary method, first passage (P1) HUVECs are split and seeded onto 35 mm dishes at a density of 1×10$^5$ cells/dish, cultured for 7 days, and used on day 7 (2-3 days after they are 100% confluent). CFSE-labeled human platelets readily adhere to HUVECs at a flow rate of 1.2 mL/min (FIG. 3A). Many more platelets attach to HUVECs when the cells are pre-treated with 25 µM histamine for 10 minutes at room temperature (FIG. 3B). This adhesion of platelets was completely inhibited when the platelets were perfused over the monolayer in buffer containing NMC-4, at a concentration of 10 µg/ml (FIG. 3C) and partially blocked when platelets were perfused in the presence of an anti-GPIbα antibody (e.g., AK2), at a concentration of 18 µg/ml (FIG. 3D). In contrast, mouse control IgG at a concentration of 18 µg/ml did not prevent platelet adhesion to vWF polymers (FIG. 3E), suggesting that the adhesion of platelets onto HUVECs is indeed mediated by the interaction between endothelial-derived vWF and platelet GPIbα. When the area covered by platelets from the 20 images captured per run were measured and quantified using Compix software, NMC-4 reduced platelet adhesion by >95% compared to a negligible effect by control antibody.

Example 6

Ability of Antibodies to Prevent Vascular Occlusion

The ferric chloride model of arterial thrombosis is used to assess the anti-thrombotic activity of the NMC-4 chimera and the humanized derivative (e.g., H14,L10) compared to AJW200. The contra-lateral carotid artery is isolated through the relocation of the salivary gland and accompanying adipose tissue to the cranial side of the incision. The carotid artery is exposed and placed on a piece of filter paper (e.g., 4 mm×5 mm) which is folded to cradle the carotid artery and provide a surface for the ferric chloride (7.5%) solution. After applying the FeCl$_3$ solution for 4 minutes, a flow probe is placed around the carotid artery and flow is measured using a Transonic Systems Inc. flow system (Ithaca, N.Y.) until time to occlusion (typically 10 minutes in control rats) or until 45 minutes. Groups of 4 rats (n=6 for saline) are administered IV doses ranging from, for example, 5 to 0.01 mg/kg of either NMC-4 chimera, V14 µL10, AJW200 or control IgG at a volume of 1 µl/g of rat body weight. The antibody preparations are sterile filtered and tested to ensure low endotoxin content using the LIMULUS AMOEBOCYTE ASSAY KIT (BioWhittaker) following the manufacturer's protocol as well as evaluated for mono-dispersity by HPLC analysis before being used for animal studies.

Figure 4:
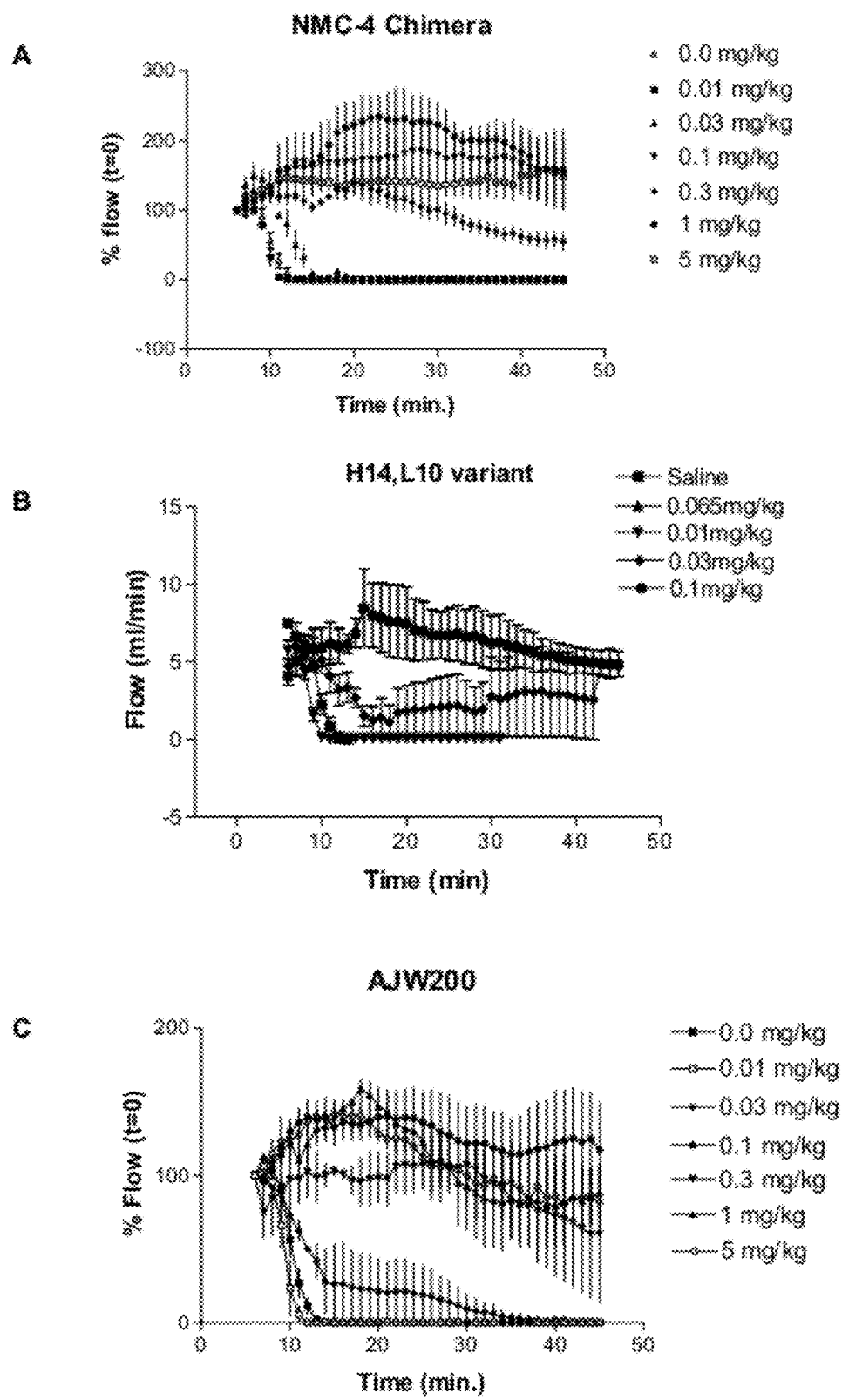
FIG. 4A-C shows activity of the NMC-4 chimera (FIG. 4A) and a humanized antibody with variable regions designated as H14, L10 (FIG. 4B) in the rat ferric chloride model of arterial thrombosis compared to AJW200 (FIG. 4C). The three antibodies were compared in a dose response study.

As shown in FIG. 4, both NMC-4 and AJW200 significantly inhibited vessel occlusion. NMC4 showed an $ED_{50}$ at a dose of 0.03 and 0.1 mg/kg similar to AJW200. The humanized derivative, H14,L10, also showed similar activity with an $ED_{50}$ also between 0.03 and 0.1 mg/kg dose (FIG. 4B).

Example 7

Effect of Antibodies on Bleeding Time and Blood Loss

Blood loss can sometimes be an adverse side effect associated with anti-platelet agents (e.g., anti-vWF antibodies). Accordingly, it may be necessary to evaluate humanized NMC-4 antibodies for their potential of contributing to bleeding complications. For this, a standard bleeding time assay is performed, where antibody control, NMC-4 chimera or AJW200 is administered 30 minutes prior to performing a tail transection. For the tail transection the terminal (e.g., 0.5 mm) of the tail is cut and the tail placed into a known volume of warm saline and the time required for bleeding to stop is measured. Blood loss is also measured by assessing hemoglobin content of the blood cells collected in saline during the assessment of bleeding time. For this, red cells are pelleted by low speed centrifugation, resuspended in saline containing 1% TritonX100, which is adjusted to a final volume of 5 ml, and hemoglobin concentration of the solution measured by determining the absorbance at 420 nm.

The NMC-4 chimera showed the same $ED_{50}$ dose of 0.09 mg/kg for a significant increase in bleeding time as the humanized derivative H14-L10. At the 0.03 mg/kg dose associated with efficacy for these two antibodies in the FeCl$_3$ model of arterial thrombosis, there was no significant prolongation of bleeding or increased blood loss. NMC-4 and its humanized derivative exhibits a slightly improved $ED_{50}$ dose response than AJW200 whose $ED_{50}$ dose in the rat for increased bleeding was much closer to its $ED_{50}$ dose for anti-thrombotic activity suggesting that NMC-4 offers an improved therapeutic window compared to AJW200.

TABLE 20

Effect of NMC-4 chimera and its humanized derivative, H14, L10, compared to AJW200 on bleeding time and blood loss in the rat.

| Antibody | Bleeding time (min) Mean ± SEM (n) | Blood loss (ML) Mean ± SEM (n) |
|---|---|---|
| Saline | 3.1 ± 0.3 (16) | 0.287 ± 0.088 (9) |
| NMC-4 (chimera) | $ED_{50}$ = 0.09 mg/kg | |
| 0.01 mg/kg | 2.7 ± 0.3 (2) | 0.059 ± 0.009 (2) |
| 0.03 mg/kg | 4.1 ± 0.2 (4) | 0.076 ± 0.014 (4) |
| 0.10 mg/kg | 19.7 ± 0.9 (2) | 1.503 ± 0.485 (2) |
| 0.30 mg/kg | 32.7 ± 4.4 (3) | 1.501 ± 0.213 (3) |
| 3.00 mg/kg | 32.3 ± 2.3 (2) | 1.106 ± 0.243 (4) |
| H14, L10 (humanized) | $ED_{50}$ = 0.09 mg/kg | |
| 0.03 mg/kg | 2.03 ± 0.35 (3) | 0.094 ± 0.035 (3) |
| 0.10 mg/kg | 15.30 ± 1.70 (4) | 0.630 ± 0.294 (4) |
| 0.30 mg/kg | 26.45 ± 3.09 (4) | 1.883 ± 0.312 (4) |
| AJW200 | $ED_{50}$ = 0.05 mg/kg | |
| 0.01 mg/kg | 2.8 ± 0.25 (2) | 0.177 ± 0.059 (2) |
| 0.03 mg/kg | 8.2 ± 1.56 (7) | 0.250 ± 0.059 (4) |
| 0.10 mg/kg | 25.1 ± 0.4 (5) | 1.943 ± 0.420 (2) |
| 0.30 mg/kg | 29.2 ± 0.72 (5) | 2.074 ± 0.521 (3) |
| 3.00 mg/kg | 30.9 ± 0.62 (3) | 2.912 ± 0.243 (4) |

Another parameter of adverse side effects of these antibodies on hemostasis is blood loss, which is assayed on the blood collected while determining bleeding times. Again, at doses higher than 0.1 mg/kg, these antibodies induced significant loss of blood. However, at doses of 0.3 and 3 mg/kg, AJW200 caused markedly higher blood loss than NMC-4 chimera at the same doses, although these differences only approached statistical significance for the 3.0 mg/kg groups where n=4 rather than 3 (Table 20). The H14, L10 antibody variant showed no significant difference to the parental NMC-4 chimera.

Example 8

Effect of Antibodies on Circulating Platelet and White Cell Count

Some anti-platelet agents are hypothesized to inhibit thrombosis formation while at the same time may cause thrombocytopenia (Hansen et al., *J Pharmacol Exp Ther.* 298:165-71 (2001)). To determine the effect of NMC-4 on the numbers of circulating white blood cells (WBC) and platelets in treated animals, a group of five rats weighing 230-260 g are injected (e.g., intra venously) with NMC-4 at 1 mg/ml and a control group of 3 rats are injected with a vehicle control (e.g., surgical-grade PBS). Prior to injection, a tail bleed is used to measure baseline blood cell counts using, for example, the HEMAVET HEMATOLOGY ANALYZER™ (Drew Scientific). Blood samples are collected at pre-specified time points up to 48 hours (e.g., 30 minutes, 2, 4, 24 and 48 hours) after antibody or saline injection from un-anaesthetized rats by retro-orbital draw using a capillary pipet. Approximately 40 µL of blood is then transferred to a tube containing 5 µL of acidified citrate dextrose anti-coagulant solution (ACD) and immediately sampled in a HEMAVET cell counter to determine the number of platelets and white blood cells. For each blood draw, samples are taken from alternating eyes.

NMC-4 had little effect on platelet count at any of the time points analyzed. A temporary decrease in white blood cell count of 37.5% (p=0.016) was observed at 30 minutes post injection, but a similar decrease was also observed upon injection of PBS vehicle. White blood cell levels returned to baseline between 2 and 4 hours post-injection in both the NMC-4 and control vehicle treated groups.

Example 9

Establishment of Cell Lines for Expression of Antibodies

A high yielding, mammalian protein expression system may be developed that is based on a murine Artificial Chromosome Expression (ACE) platform that has been engineered to contain multiple site-specific, recombination acceptor sites that can be loaded with heterologous gene sequences using a mutant lambda integrase (e.g., ACE integrase) in combination with a targeting shuttle vector (Lindenbaum et al, (*Nucl. Acid Res.* 32 (21):e172 (2004); U.S. Patent Application Nos: 2003/0119104A1 and 2006/0246586 A1). This system is used to generate stable cell lines for expression of selected humanized variants and the NMC-4 chimera.

The inserts of plasmids pCI-NMC4-VL10 and pCI-NMC4-VH14 are digested with Not 1 plus HindIII (light chain vector) or Xho1 and BamH1 (heavy chain vector) and cloned sequentially into the MCS 1 (light chain) and MCS 2 (heavy chain) of the pSTO518 vector. The pSTO518 vector carrying the heavy and light chain inserts in tandem serves as the shuttle vector for transfer into the ACE Targeting Vectors (ATVs) with different resistance genes, derived from the targeting vectors described by Lindenbaum et al, (*Nucl. Acid Res.* 32 (21):e172 (2004); U.S. Patent Application Nos: 2003/0119104A1 and 2006/0246586 A1). To transfer the cassette containing both heavy and light antibody chains into the ATVs, the pSTO518-VH14, VL10 vector is digested with I-Ceul and PI-Scel homing endonucleases (New England Biolabs, MA). The VH14 plus VL10 fragment is gel-purified and cloned into the equivalent sites of the pZeo and pHygro-ATV pre-digested with the same 1-Ceul and PI-Scel endonucleases. This yields the plasmids pNHT605-H14L10-IgG4 ($hyg^R$ gene) and pNHT607-H14L10-IgG4 (p $zeo^R$ gene).

Similarly, pSTO518 targeting vectors carrying the NMC-4 IgG4 chimera are constructed, and the tandem insert subcloned into the pZeo and pHygro ATV vectors which yields plasmids pNHT623 (human IgG4 chimera plus the $hyg^R$ gene) and pNHT624 (human IgG4 chimera plus the $zeo^R$ gene).

For targeted integration into the platform ACE, host ChK2 ACE platform cells are seeded at a density of $0.4 \times 10^5$ cells per well of a 6-well culture plate and cultured overnight. Three hours prior to transfection, the culture medium is replaced with serum-free medium and after 3 hours transfected with 1 µg of the vector and 1 µg of the ACE Integrase expression vector complexed with LipofectAMINE PLUS reagent (Invitrogen) according to the manufacturer's instructions. Twenty-four hours later, cells are expanded onto 15 cm culture dishes, and the following day, either 3.0 µg/ml of zeomycin or hygromycin (depending on the vector used) is added to the culture medium. After 14 days of selection, drug resistant colonies are isolated using cloning rings and individual clones amplified for analysis of antibody production.

Example 10

In Vivo Efficacy and Safety of NMC-4 Antibody

Efficacy and safety of humanized NMC-4 antibody is tested in an in vivo animal (e.g., baboon) model.

In an exemplary method, baboons are anaesthetized with ketamine hydrochloride (Anaket-V™ from the Premier Pharmaceutical Company) (10 mg/kg IM/30 minutes or when needed to maintain general anesthesia) and their body temperature is maintained at 37° C. with a heating table. Next, a 4-5 cm segment of the femoral vessels is gently dissected free from surrounding tissue. All nearby branches in the femoral artery and femoral vein are ligated. A small incision is then made in the femoral artery and femoral vein and vessel tips are inserted and secured with surgical silk. Silicone tubing is then attached to the vessel tips to shunt arterial blood into the femoral vein. The direct shunting from the arterial to the venous circulation while bypassing the capillaries increases blood flow to approximately 150-300 mL/minute. A tube-type ultrasonic flow probe (Transonic Systems Inc, Maastricht, The Netherlands) is attached to the silicone tubing and blood flow is allowed to stabilize for about twenty minutes. The mean and phasic blood flow is measured continuously throughout the experiment with the shunt used for drug administration as well as for blood sampling.

Next, the endothelium of the femoral artery is injured proximally to the vessel tip with a Martin needle holder (Hegar-Baumgartner TC Gold 14 cm, Product code 20.634.14) by pressing hard on the endothelium for ten seconds at maximum depression. Two overlapping injuries are made and an adjustable plastic constrictor is placed over the injury site to reduce blood flow to 10 to 20% of baseline value. A gradual decline in blood flow is observed due to thrombus formation. When blood flow is reduced to ≦5 mL/min, the constrictor is opened to dislodge the platelet-rich thrombus. Next, the external stenosis is applied again and the process of thrombus formation restarted. This repetitive pattern of decreasing blood flow following mechanical restoration is referred to as cyclic flow reductions (CFRs). The number of CFRs in function of time was measured. Baseline cyclic flow reductions (CFRs) are recorded for thirty minutes. Saline is injected and CFRs are monitored for a further thirty minutes. The humanized NMC-4 variant H9L9 IgG4 as described in Example 3 (referred further herein as GBR 600) is used.

Two methods may be used to assess bleeding upon drug administration. In a first method, the skin template bleeding time is determined at the surface of the forearm. A pressure cuff is applied around the arm and inflated at 40 mm Hg, after which a wound is induced with the Surgicut device (ITC, Edison, N.J.). The skin bleeding time is defined as the time between the induction of the wound and visual cessation of bleeding. The blood is carefully dabbed every fifteen seconds with filter paper while not touching the wound. Measurements are stopped when the skin bleeding time exceeded 900 seconds (e.g., 15 minutes) and are considered as 900 seconds.

In the second method, the blood loss from an incision is assessed by a recombinant annexin V in a rabbit carotid artery injury model (see, e.g., P. Thiagarajan et al. (1997) *Circulation* 96(7):2339-47). A 2 cm×0.8 cm incision is made in the groin and pre-weighed gauze swabs are inserted and replaced at the end of each thirty minute dose infusion period or when it is saturated with blood. All gauzes are weighed at the end of the study to yield the amount of blood loss. The value for each dose is expressed as a ratio of the saline control phase gauze. Heart rate and blood pressure is monitored continuously during the whole study at ten minute intervals.

At the end of each dose period one milliliter of EDTA blood, and ten milliliters of citrated blood are drawn, and a FBC platelet count, prothrombin time, activated partial thromboplastin time, Factor VIII and vWF are determined. Two aliquots of 300 µl each are frozen at −80° C. for shipment to the investigators for additional in vitro laboratory testing if necessary. Similarly, blood is drawn 0.5, 1, 2, 8, 24 and 48 hours after the end of the flow studies. At the end of the final dose, platelet aggregation tests are performed with test and control samples.

After the cumulative dose (e.g., when complete inhibition of CFRs is observed), epinephrine (Intramed) is infused at a dose of 2.2 µg/kg/min for twenty minutes and CFRs are again measured. Epinephrine alone does not cause platelet aggregation in baboons but can restore the abolished cyclic flow variations by enhancing other platelet aggregation factors (see, e.g., G. Anfossi et al. (1996) Eur J Clin Invest. 26:353-370).

Efficacy and Safety Studies of GBR 600: Studies 1 to 4, described below, are conducted to determine the efficacy and safety of GBR600.

Study 1: A pilot study is performed with n=1 animal to establish a dose response curve with increasing amounts of GBR 600 and identify the effective dose at which maximal inhibition of CFRs is observed. Template bleeding and incisional bleeding are determined for all doses tested. Blood samples are taken up to forty-eight hours to establish pharmacokinetics of the antibody at the highest dose.

The following ascending doses GBR 600 are injected at thirty minute intervals and flow is recorded for the duration of the study: Dose 1, 0.03 mg/kg; Dose 2. 0.1 mg/kg; Dose 3, 0.3 mg/kg; Dose 4, 1 mg/kg; and Dose 5, 10 mg/kg. Bleeding tests are then performed at ten minutes after injection of each dose.

Figure 5:
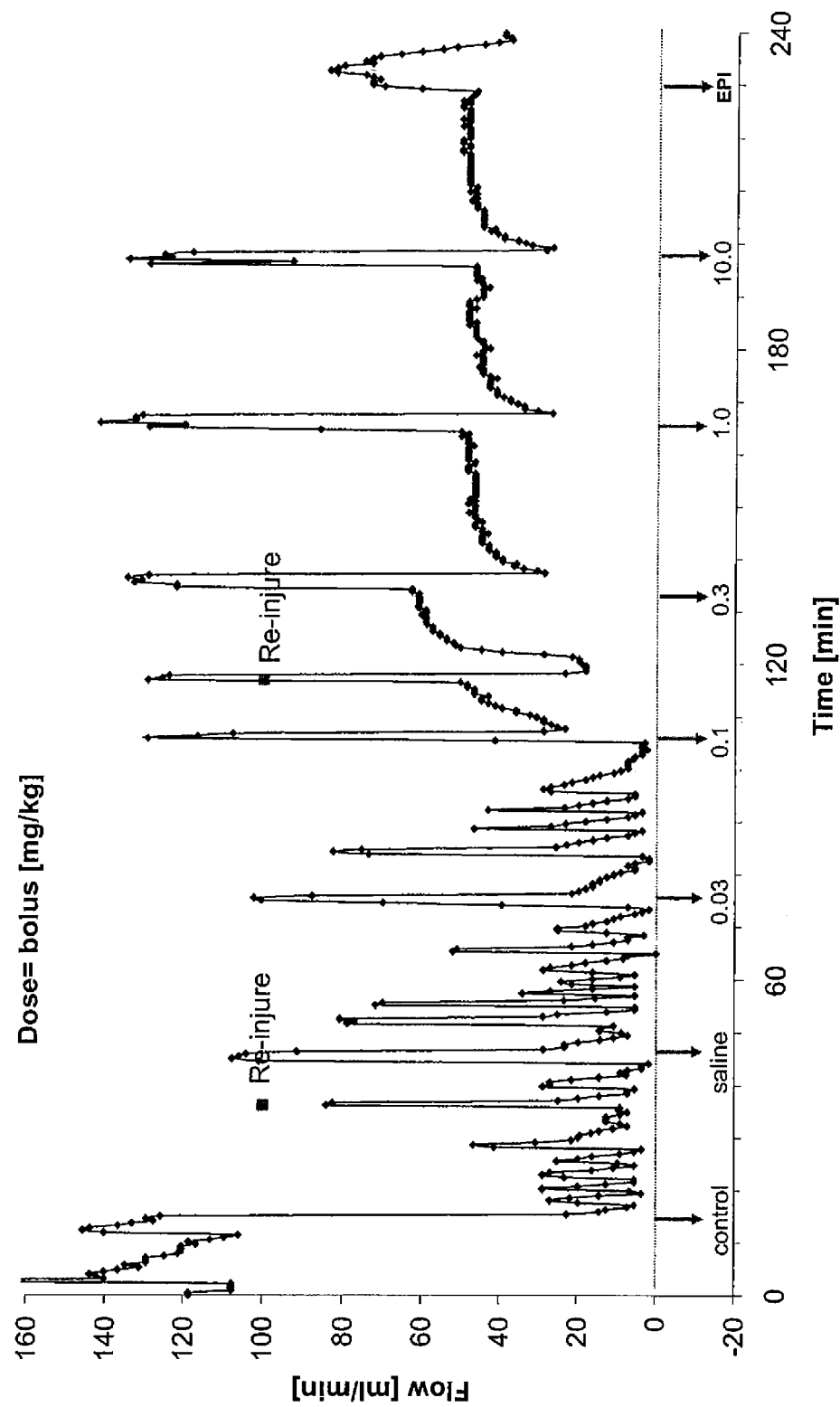
FIG. 5 shows the effect of increasing doses (0.03-10 mg/kg) of GBR600 on cyclic flow reductions (CFRs) in baboons.

FIG. 5 and Table 21 describe the effect of increasing doses of GBR 600 on CFRs. The artery is re-injured near the end of the thirty minute baseline phase as CFRs did not appear to be stable. 0.03 mg/kg GBR 600 decreased the number of CFRs to 5/30 minutes compared to 8/30 minutes for the saline phase. Infusion of an additional 0.1 mg/kg inhibited CFRs completely. This is confirmed by the fact that a re-injury of the artery did not cause a return of CFRs. The inhibition is observed for all following increasing doses. After infusion of the highest dose of GBR 600 (10 mg/kg) epinephrine is infused at a rate of 2.2 µg/kg/minutes to establish if strong or weak inhibition of platelet deposition is achieved. Infusion of epinephrine led to a temporary increase of blood flow due to its effect on blood pressure, but did not reverse the inhibition of CFRs.

TABLE 21

Effect of increasing doses of GBR 600 on CFRs (0.03-10 mg/kg)

| Dose (mg/kg) | Cumulative Dose (mg/kg) | Number of CFRs |
| --- | --- | --- |
| Baseline | 0 | 8 |
| Saline | 0 | 8 |
| 0.03 | 0.03 | 5 |
| 0.1 | 0.13 | 0 |
| 0.3 | 0.43 | 0 |
| 1 | 1.43 | 0 |
| 10 | 11.43 | 0 |

Study 2: Study 2 is carried out in a manner similar to Study 1, except that a dose of 0.01 mg/kg is included at the start of the dose escalation, before the 0.03 mg/kg dose, as a partial inhibition of CFRs at a dose of 0.03 mg/kg has been seen in Study 1.

Figure 6:
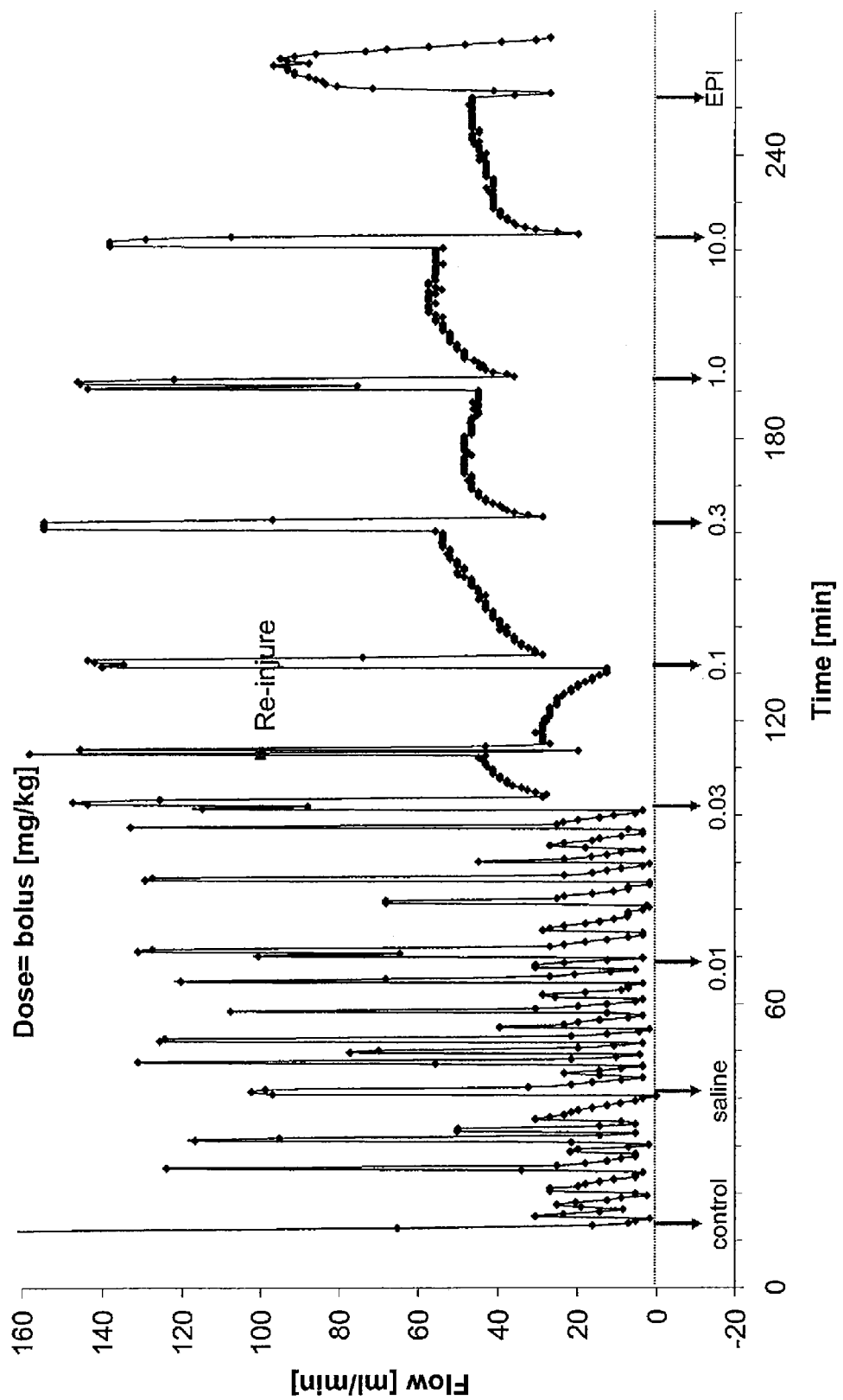
FIG. 6 shows the effect of increasing doses (0.01-10 mg/kg) of GBR600 on CFRs in baboons.

In Study 2 (see, e.g., FIG. 6 and Table 22), an effect on CFRs by 0.01 mg/kg GBR 600 (7CFRs/30 minutes compared to 9CFRs/30 minutes for saline) is observed. However, infusion of an additional 0.03 mg/kg (cumulative dose=0.04 mg/kg) caused complete inhibition of CFRs. The $ED_{100}$ of GBR 600 is therefore 0.04 mg/kg. Re-injury of the artery did not reverse the inhibition of CFRs, indicating a true inhibition. The inhibitory effect is maintained at the higher doses up to the maximal dose of 10 mg/kg. Infusion of epinephrine led to a temporary increase of blood flow due to its effect on blood pressure, but did not reverse the inhibition of CFRs.

TABLE 22

Effect of increasing doses of GBR 600 on CFRs (0.01-10 mg/kg)

| Dose (mg/kg) | Cumulative Dose (mg/kg) | Number of CFRs |
|---|---|---|
| Baseline | 0 | 9 |
| Saline | 0 | 9 |
| 0.01 | 0.01 | 7 |
| 0.03 | 0.04 | 0 |
| 0.1 | 0.14 | 0 |
| 0.3 | 0.44 | 0 |
| 1 | 1.44 | 0 |
| 10 | 11.44 | 0 |

Study 3: Study 3 is carried out in a manner similar to Study 1 with the exception that a starting dose of 0.005 mg/kg is administered followed by another dose of 0.005 mg/kg (cumulative dose=0.01 mg/kg) and then increased in 6 increments of 0.01 mg/kg.

Figure 7:
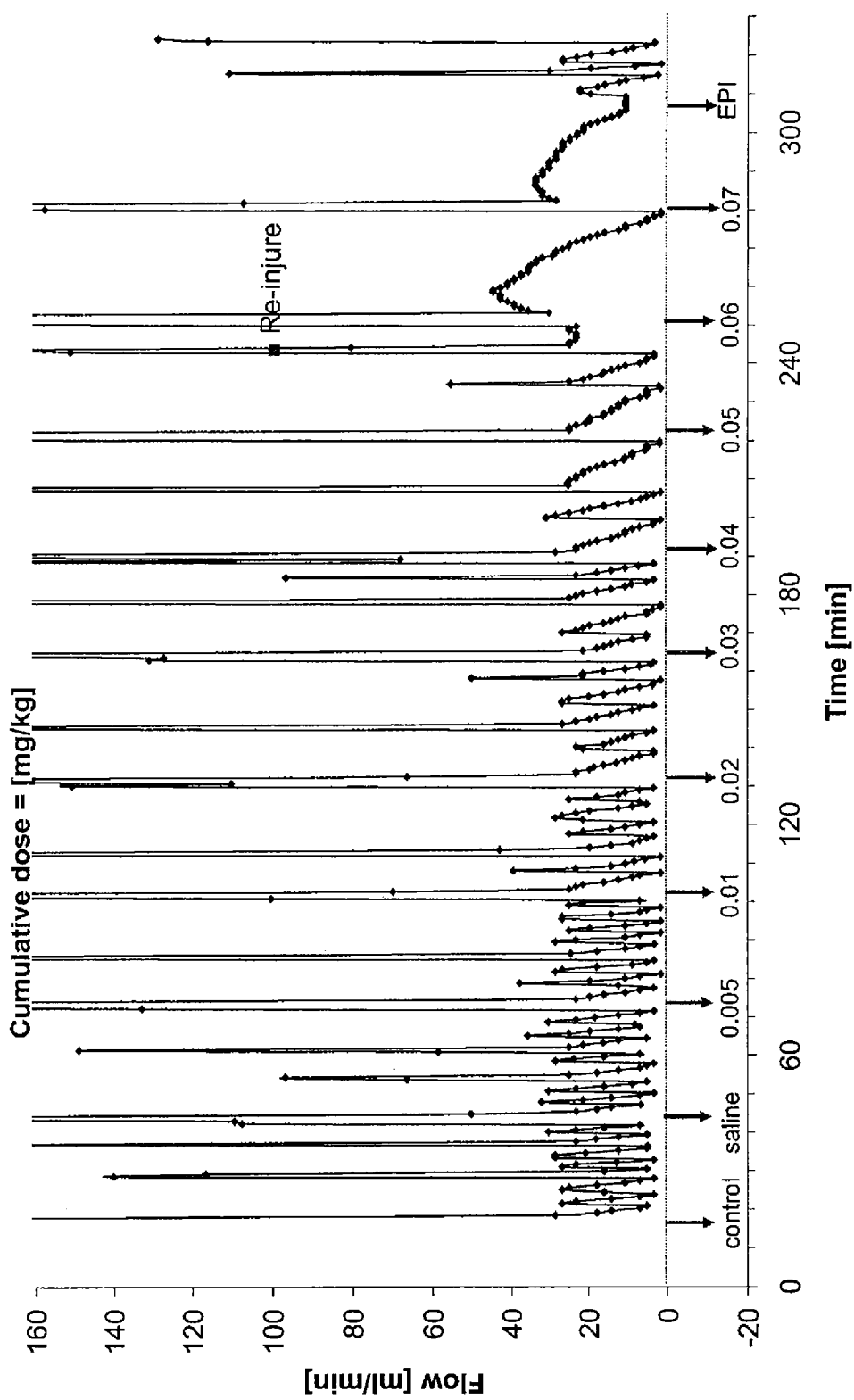
FIG. 7 shows the effect of cumulative doses (0.005-0.07 mg/kg) of GBR600 on CFRs in baboons.
Figure 8:
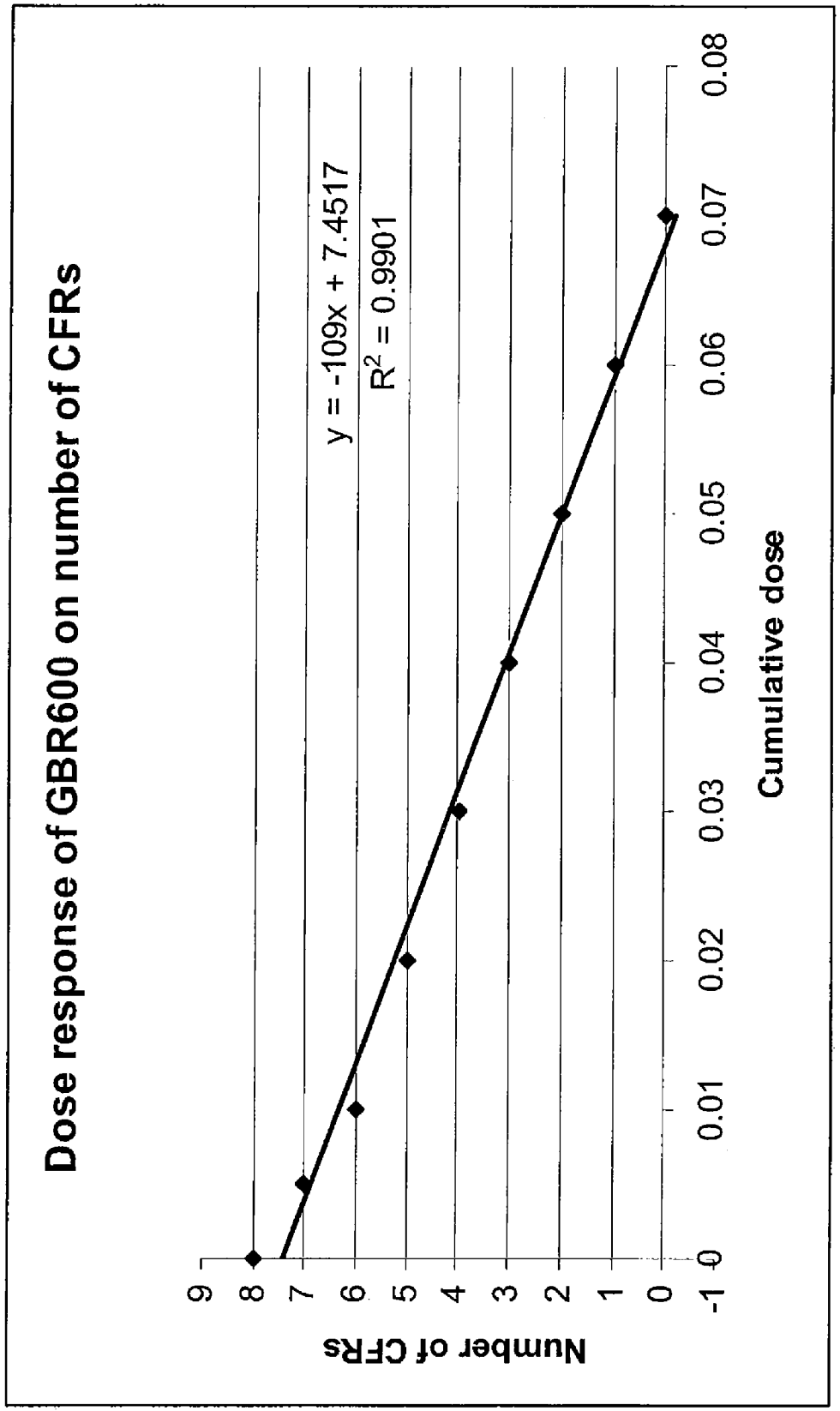
FIG. 8 shows dose response curve of cumulative doses of GBR600 on CFRs in baboons.

In Study 3 (see, e.g., FIG. 7), an effect on CFRs (reduction of 8 CFRs/30 min to 7 CFRs) by infusion of 0.005 mg/kg GBR 600 is observed. CFRs decreased in a linear fashion with increasing doses of GBR 600. The number of CFRs per dose period are shown in Table 23 and FIG. 8. FIG. 8 depicts the linear decrease in the number of CFRs associated with increasing doses of GBR 600. The relationship between number of CFRs and dose of GBR 600 is expressed by the following equation. The data fit this equation with $R2=0.9901$.

Number of CFRs/dose period=−109×dose GBR 600 (mg/kg)+7.4517.

In Study 3, the $ED_{100}$ is 0.07 mg/kg compared to complete inhibition in Study 2 caused by a cumulative dose of 0.04 mg/kg. The time between increasing doses is thirty minutes in Study 3. This discrepancy in observed $ED_{100}$s may be caused by a reduction of the GBR 600 concentration in blood as a result of initial clearance of the drug. Infusion of epinephrine reverses the inhibition of CFRs. This might be related to the shape of the CFR curve at the 0.07 mg/kg cumulative dose. The inhibition is slowly reversing at 0.07 mg/kg cumulative dose, which is indicative of a growing thrombus. Under these particular conditions, epinephrine seems to be able to reverse the CFR.

TABLE 23

Effect of cumulative doses of GBR 600 on CFRs (0.005-0.07 mg/kg)

| Dose (mg/kg) | Cumulative Dose (mg/kg) | Number of CFRs |
|---|---|---|
| Baseline | 0 | 8 |
| Saline | 0 | 8 |
| 0.005 | 0.005 | 7 |
| 0.005 | 0.01 | 6 |
| 0.01 | 0.02 | 5 |
| 0.01 | 0.03 | 4 |
| 0.01 | 0.04 | 3 |
| 0.01 | 0.05 | 2 |
| 0.01 | 0.06 | 1 |
| 0.01 | 0.07 | 0 |

Study 4: Study 4 is carried out in a manner similar to Study 1, with the exception that Clopidogrel is used as a positive control in three Baboons to compare efficacy and bleeding tendency of GBR 600 dosed at 1, 1.5, 2.5, 5 and 10 mg/kg against clopidogrel.

Figure 9:
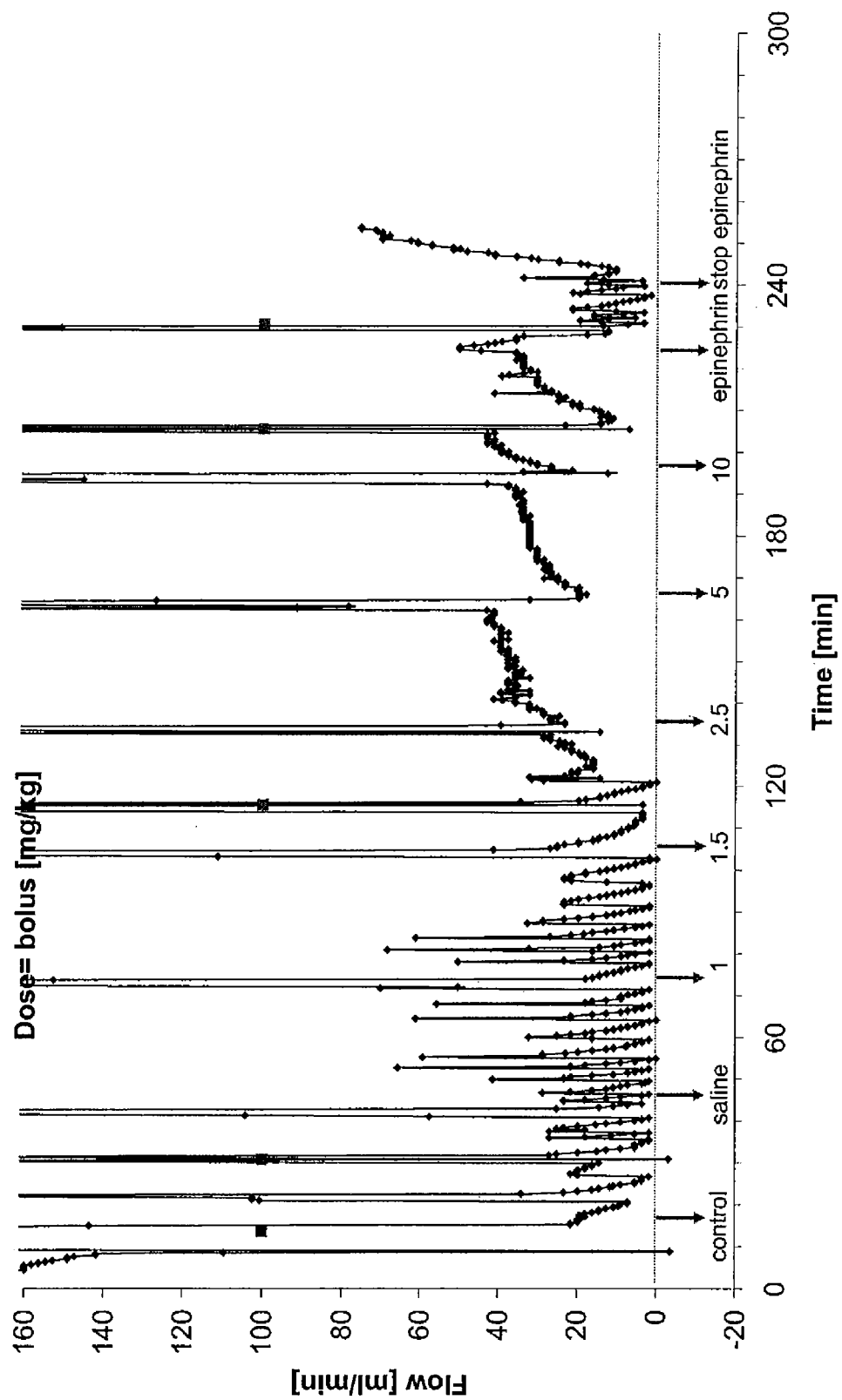
FIG. 9 shows the effect of increasing doses (1-10 mg/kg) of clopidogrel in baboons.

In Study 4, clopidogrel inhibited CFRs completely at a cumulative dose of 10 mg/kg in Baboon 1 and 5 mg/kg in Baboon 2&3 as shown in Table 24 and FIG. 9 which illustrates the results of Baboon 3 in Table 24. Infusion of epinephrine reversed the inhibition of CFRs.

TABLE 24

Effect of increasing doses (1-10 mg/kg) of clopidogrel in baboons.

| Dose (mg/kg) | Cumulative Dose (mg/kg) | Number of CFRs Baboon 1 | Number of CFRs Baboon 2 | Number of CFRs Baboon 3 |
|---|---|---|---|---|
| Baseline | 0 | 13 | 8 | 6 |
| Saline | 0 | 13 | 7 | 8 |
| 1 | 1 | 8 | 8 | 7 |
| 1.5 | 2.5 | 5 | 2 | 2 |
| 2.5 | 5 | 2 | 0 | 0 |
| 5 | 10 | 0 | 0 | 0 |
| 10 | 20 | 0 | 0 | 0 |

Template Bleeding Times: In Studies 1 and 2 the template bleeding times are longer than fifteen minutes at all doses higher than 0.04 mg/kg. In the positive control study with clopidogrel (Bristol-Myers Squibb/Sanofi Pharmaceuticals) the template bleeding times are prolonged to the same extent at cumulative doses greater than 2.5 mg/kg. In Study 3 the template bleeding times are never prolonged longer than fifteen minutes. Template bleeding times are not a very precise measure of bleeding tendency since they show a high baseline variability (see, e.g. the baseline values in clopidogrel Baboon 1, 2, 3). As such, template bleeding times are not considered very predictive for clinically relevant bleeding, such as in a preoperative setting (see, e.g., Lind et al. *Platelets*, second edition, p485-493, Michelson A D ed., Academic Press.). The incisional bleeding test shows less variation as it quantifies the actual amount of blood lost through the incision and has a higher dynamic range. Therefore, the incisional bleeding test is run in addition to the template bleeding test. These data are summarized in Table 25 and 26.

TABLE 25

GBR 600 Template Bleeding Time [minutes]

| Dose (mg/kg) | Cumulative Dose (mg/kg) | Study 1 | Study 2 | Study 3 |
|---|---|---|---|---|
| Baseline | 0 | 5.5 | 6.25 | 2 |
| Saline | 0 | 2.5 | 7 | 4.45 |
| 0.005 | 0.005 | n.a. | n.a. | 5.25 |
| 0.005 | 0.01 | n.a. | n.a. | 5.25 |
| 0.01 | 0.02 | n.a. | n.a. | 6 |
| 0.01 | 0.03 | n.a. | n.a. | 7.45 |
| 0.01 | 0.04 | n.a. | n.a. | 2.5 |
| 0.01 | 0.05 | n.a. | n.a. | 3.5 |
| 0.01 | 0.06 | n.a. | n.a. | 7.45 |
| 0.01 | 0.07 | n.a. | n.a. | 5.45 |
| 0.01 | 0.01 | n.a. | 2.45 | n.a. |
| 0.03 | 0.03/0.04 | 5.25 | >15 | n.a. |
| 0.1 | 0.13/0.14 | >15 | >15 | n.a. |
| 0.3 | 0.43/0.44 | >15 | >15 | n.a. |
| 1 | 0.143/1.44 | >15 | >15 | n.a. |
| 10 | 11.43/11.44 | >15 | >15 | n.a. |

TABLE 26

Clopidogrel Template Bleeding Time [minutes]

| Dose (mg/kg) | Cumulative Dose (mg/kg) | Baboon 1 | Baboon 2 | Baboon 3 |
|---|---|---|---|---|
| Baseline | 0 | >15 | 5.5 | 13 |
| Saline | 0 | n.d. | n.d. | n.d. |
| 1 | 1 | 3.5 | n.d. | 7 |

TABLE 26-continued

Clopidogrel Template Bleeding Time [minutes]

| Dose (mg/kg) | Cumulative Dose (mg/kg) | Baboon 1 | Baboon 2 | Baboon 3 |
|---|---|---|---|---|
| 1.5 | 2.5 | >15 | >15 | >15 |
| 2.5 | 5 | >15 | >15 | >15 |
| 5 | 10 | >15 | >15 | >15 |
| 10 | 20 | >15 | >15 | >15 |

Table 27 and 28 show results obtained with the incisional bleeding test for clopidogrel and GBR 600. The amount of blood absorbed by the gauze increased initially with dose and is self limiting at high doses. In all studies the highest bleeding observed is with the fourth dose after which blood volume absorbed by the gauze decreases and healing of the wound seems to take place. In Studies 1 and 2 the maximal bleeding is similar to that for clopidogrel, although clopidogrel is tested in an $ED_{100}$ multiple of 2-4 and GBR 600 in a multiple up to 250. In Study 3 negligible bleeding is seen with all doses injected.

TABLE 27

GBR 600 Incisional Bleeding Test [multiples of saline value]

| Dose (mg/kg) | Cumulative Dose (mg/kg) | Study 1 | Study 2 | Study 3 |
|---|---|---|---|---|
| Baseline | 0 | n.a. | n.a. | n.a. |
| Saline | 0 | 1 | 1 | 1 |
| 0.005 | 0.005 | n.a. | n.a. | 0.13 |
| 0.005 | 0.01 | n.a. | n.a. | 0.08 |
| 0.01 | 0.02 | n.a. | n.a. | 0.05 |
| 0.01 | 0.03 | n.a. | n.a. | 0.05 |
| 0.01 | 0.04 | n.a. | n.a. | 0.02 |
| 0.01 | 0.05 | n.a. | n.a. | 0.03 |
| 0.01 | 0.06 | n.a. | n.a. | n.d. |
| 0.01 | 0.07 | n.a. | n.a. | n.d. |
| 0.01 | 0.01 | n.a. | 2.5 | n.a. |
| 0.03 | 0.03/0.04 | 0.125 | 0.5 | n.a. |
| 0.1 | 0.13/0.14 | 0.625 | 4.75 | n.a. |
| 0.3 | 0.43/0.44 | 3.125 | 7.75 | n.a. |
| 1 | 0.143/1.44 | 7.625 | 5.75 | n.a. |
| 10 | 11.43/11.44 | 4 | 1.75 | n.a. |

TABLE 28

Clopidogrel Incisional Bleeding Test [multiples of saline value]

| Dose (mg/kg) | Cumulative Dose (mg/kg) | Baboon 1 | Baboon 2 | Baboon 3 |
|---|---|---|---|---|
| Baseline | 0 | n.a | n.a. | n.a |
| Saline | 0 | 1 | 1 | 1 |
| 1 | 1 | 1.59 | 1.21 | 1.28 |
| 1.5 | 2.5 | 1.06 | 1 | 1.1 |
| 2.5 | 5 | 1.41 | 6.64 | 3.32 |
| 5 | 10 | 5.82 | 13.64 | 0.95 |
| 10 | 20 | 9.12 | 2.64 | 0.92 |

Figure 10:
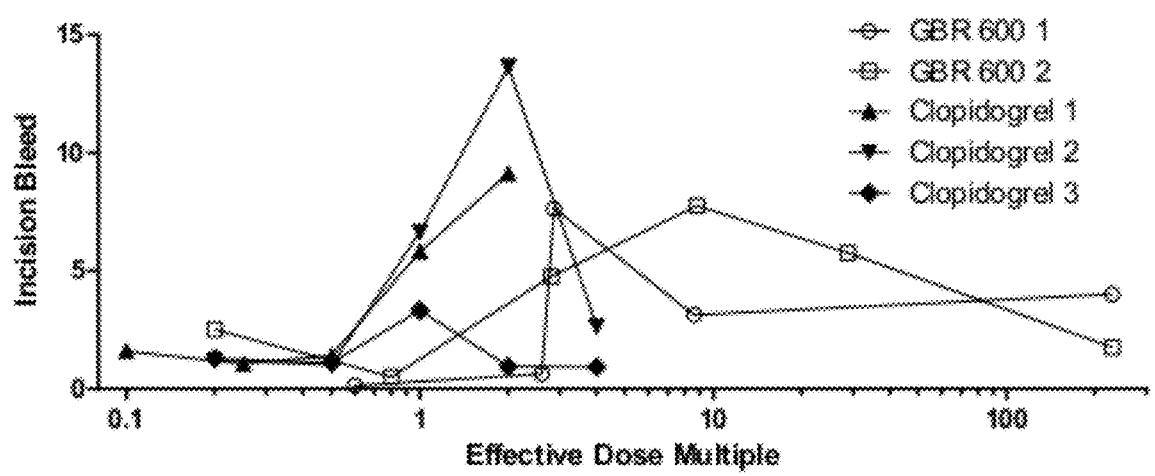
FIG. 10 shows a comparison of the effect of infusion of increasing doses of GBR600 and clopidogrel on the incisional bleeding test. Doses have been expressed as multiples of the effective dose (e.g., the cumulative dose, at which CFRs are reduced to zero).

Therapeutic Window and Bleedscore of GBR600: In FIG. 10, the results from the incision bleeding test of Study 1 and 2 and the three clopidogrel studies are plotted against the doses of GBR 600 and clopidogrel (Doses are expressed as multiples of their $ED_{100}$s and plotted on a logarithmic scale).

GBR 600, even at doses greater than 100-fold its $ED_{100}$, causes bleeding at a level seen in clopidogrel at only up to 4-fold its $ED_{100}$. Unexpectedly, GBR 600 has an unprecedented therapeutic window of safety in terms of bleeding risk.

The only clinically relevant increase in bleeding observed in this study is an increase in self-limiting bleeding from superficial cuts as determined by template bleeding and incisional bleeding methods. Animals are closely observed for a period of forty-eight hours after the surgical operation and no additional signs of superficial bleeding such as easy bruising, petechia or echymosis are detected. More important no signs of internal bleeding such as hematoma, epistaxis, blood loss from mouth, vagina, melena, eye bleed, hematuria, hematemesis. The operation wound did not bleed and healed normally.

Both clopidogrel and GBR 600 have a score of 1 in the BleedScore scoring scheme, as shown in Table 29. Apart from the increased bleeding in superficial wounds, no other symptoms are detected in the animals during the experiment or during a forty-eight hour observation period following the conclusion of the studies.

TABLE 29

BleedScore determination for clopidogrel and GBR 600
BleedScore Determination

| Bleed Severity | Symptoms | Score | Clopidogrel | GBR600 |
|---|---|---|---|---|
| Superficial Bleeding | Easy bruising | 1 | 0 | 0 |
| | Bleeding from small cuts | 1 | 1 | 1 |
| | Petechia | 1 | 0 | 0 |
| | Ecchymosis | 1 | 0 | 0 |
| Internal Bleeding | Hematoma | 3 | 0 | 0 |
| | Epistaxis | 3 | 0 | 0 |
| | Bood loss from mouth, vagina | 3 | 0 | |
| | Melena | 3 | 0 | 0 |
| | Eye bleed | 3 | 0 | 0 |
| | Hematuria | 3 | 0 | 0 |
| | Hematemesis | 3 | 0 | 0 |
| Alarming Bleeding | Transfusion needed | 6 | 0 | 0 |
| | Intracranial | 6 | 0 | 0 |
| | Life threatening | 6 | 0 | 0 |
| BleedScore | | | 1 | 1 |

Findings from Efficacy and Safety Studies: Tables 30-32 show the effect of GBR 600 on vWF levels, Factor VIII levels, White Cell count, Haemoglobin concentration (Hb), Platelet count (Plt) and Prothrombin time (PT) and activated Partial Thromboplastin Time (aPTT) in Studies 1 to 3.

With regard to the von Willebrand levels obtained in Studies 1 to 3 no pattern is observed in Study 1, but in Studies 2 and 3 a clear decrease in von Willebrand levels is observed. In Study 2, where much higher doses are used, the effect is more pronounced than in Study 3 where relatively low doses are used. In the study with a control humanized monoclonal IgG4 antibody which do not bind vWF no effect on von Willebrand levels is observed. This effect and the implications of it should be carefully monitored in future studies. GBR 600 did not have a marked effect on Factor VIII levels in all Studies.

Although an increase in WBC is observed, this is a known effect of the invasive procedure and correlates well with results observed for the control monoclonal IgG4 antibody which do not bind vWF and all other drugs tested in this model so far. No marked effect on Haemoglobin concentration caused by infusion of GBR 600 can be observed. As an effect of infusion of GBR 600 on platelet count, platelets are consumed during these procedures as platelet deposition is responsible for occlusion of the artery during CFRs. Effective inhibition of CFRs will therefore decrease the amount of platelet consumption. This explains the higher platelet consumption seen with the control humanized monoclonal IgG4 antibody which do not bind vWF, where no inhibition of CFRs is observed.

There seems to be no marked effect of GBR 600 on PT and aPTT, which are indicators of the integrity of the coagulation proteins. Similar results are observed for the control humanized monoclonal IgG4 antibody which do not bind vWF.

TABLE 30

Study 1

| | Baseline | Saline | 0.03 mg/kg | 0.1 mg/kg | 0.3 mg/kg | 1.0 mg/kg | 10 mg/kg |
|---|---|---|---|---|---|---|---|
| WBC × 109/l | 7.48 | 6.92 | 7.89 | 9.32 | 11.57 | 12.29 | 11.52 |
| RBC × 1012/l | 5.7 | 5.88 | 5.75 | 5.86 | 5.83 | 5.79 | 5.8 |
| haemoglobuin g/dl | 13.4 | 14.3 | 14.1 | 14.1 | 14.4 | 14 | 14 |
| haematocrit l/l | 40.5 | 43.5 | 42.5 | 43.5 | 43.4 | 0.4 | 41.4 |
| MCV fl | 71.1 | 74.0 | 73.9 | 74.2 | 74.4 | 74.6 | 71.4 |
| MCH pg | 23.5 | 24.3 | 24.5 | 24.1 | 24.7 | 24.2 | 24.1 |
| MCMC g/dl | 33.1 | 32.9 | 33.2 | 32.4 | 33.2 | 32.4 | 33.8 |
| plt × 109/l | 306 | 249 | 234 | 236 | 245 | 257 | 262 |
| neut × 109/l | 3.46 | 3.32 | 4.35 | 5.92 | 8.16 | 8.89 | 8.44 |
| lymph × 109/l | 3.62 | 3.21 | 3.04 | 2.80 | 2.75 | 2.88 | 2.32 |
| monocytes × 109/l | 0.36 | 0.36 | 0.46 | 0.58 | 0.61 | 0.50 | 0.73 |
| eosinophils × 109/l | 0.03 | 0.02 | 0.04 | 0.03 | 0.03 | 0.01 | 0.02 |
| basophils × 109/l | 0.01 | 0.01 | 0.01 | 0.00 | 0.01 | 0.01 | 0.01 |
| PT | 9 | 10 | 10 | 10.00 | 10 | 10 | 10 |
| aPTT | 42 | 42 | 44 | 43 | 42 | 42 | 45 |
| F VIII | 107 | 89 | 83 | 88 | 80 | 78 | 78 |
| vWF concentration | 25 | 46 | 39 | 15 | 26 | 48 | 17 |
| % aggregation | no | no | no | no | no | no | no |

TABLE 31

Study 2

| | Baseline | Saline | 0.01 mg/kg | 0.03 mg/kg | 0.1 mg/kg | 0.3 mg/kg | 1.0 mg/kg | 10 mg/kg |
|---|---|---|---|---|---|---|---|---|
| WBC × 109/l | 11.98 | 12.42 | 12.49 | 11.89 | 11.14 | 10.91 | 11.01 | 13.92 |
| RBC × 1012/l | 5.24 | 5.36 | 5.34 | 5.34 | 5.42 | 5.57 | 5.57 | 5.54 |
| haemoglobuin g/dl | 12.2 | 12.7 | 12.8 | 12.8 | 12.9 | 13.2 | 13.4 | 13.2 |
| haematocrit l/l | 34.1 | 34.9 | 34.8 | 34.7 | 35.1 | 36.1 | 36.1 | 36.1 |
| MCV fl | 65.1 | 65.1 | 65.2 | 65.0 | 64.8 | 64.8 | 64.8 | 65.2 |
| MCH pg | 23.3 | 23.7 | 24.0 | 24.0 | 23.8 | 23.7 | 24.1 | 23.8 |
| MCMC g/dl | 35.8 | 36.4 | 36.8 | 36.9 | 36.8 | 36.6 | 37.1 | 36.6 |
| plt × 109/l | 313 | 281 | 276 | 281 | 287 | 283 | 283 | 268 |
| neut × 109/l | 9.37 | 9.44 | 9.12 | 8.60 | 8.03 | 7.98 | 8.15 | 11.33 |
| lymph × 109/l | 2.20 | 2.55 | 2.84 | 2.82 | 2.68 | 2.51 | 2.46 | 2.10 |
| monocytes × 109/l | 0.38 | 0.40 | 0.47 | 0.42 | 0.37 | 0.36 | 0.32 | 0.38 |
| eosinophils × 109/l | 0.01 | 0.02 | 0.05 | 0.04 | 0.04 | 0.05 | 0.08 | 0.10 |
| basophils × 109/l | 0.01 | 0.01 | 0.01 | 0.02 | 0.01 | 0.01 | 0.01 | 0.01 |
| PT | 9 | 9 | 9 | 9 | 9 | 9 | 9 | 9 |
| aPTT | 55 | ?>120 | 53 | 60 | 61 | 55 | 55 | 58 |
| F VIII | 49 | 56 | 48 | 54 | 54 | 56 | 58 | 68 |
| vWF concentration | 34 | 31 | 28 | 21 | 16 | 14 | 14 | 10 |
| % aggregation | no | no | no | | no | no | no | no |

TABLE 32

Study 3

| | Baseline | Saline | 0.005 mg/kg | 0.01 mg/kg | 0.02 mg/kg | 0.03 mg/kg | 0.04 mg/kg | 0.05 mg/kg | 0.06 mg/kg | 0.07 mg/kg |
|---|---|---|---|---|---|---|---|---|---|---|
| WBC × 109/l | 4.97 | 5.63 | 5.10 | 6.36 | 7.22 | 8.8 | 11.56 | 13.5 | 14.06 | 14.38 |
| RBC × 1012/l | 6.13 | 6.25 | 6.2 | 6.1 | 6.22 | 6.19 | 6.27 | 6.17 | 6.16 | 5.65 |
| haemoglobuin g/dl | 14.0 | 14.6 | 14.8 | 14.7 | 14.5 | 14.4 | 14.7 | 14.7 | 14.8 | 13.5 |
| haematocrit l/l | 44.1 | 45.2 | 46.4 | 45.8 | 45.1 | 44.7 | 45.2 | 46.6 | 46.5 | 42.7 |
| MCV fl | 71.9 | 72.3 | 74.8 | 75.1 | 72.5 | 72.2 | 72.1 | 75.5 | 75.5 | 75.6 |
| MCH pg | 22.8 | 23.4 | 23.9 | 24.1 | 23.3 | 23.3 | 23.4 | 23.8 | 24.0 | 23.9 |
| MCMC g/dl | 31.7 | 32.3 | 31.9 | 32.1 | 32.2 | 32.2 | 32.5 | 31.5 | 31.8 | 31.6 |
| plt × 109/l | 373 | 331 | 327 | 342 | 342 | 334 | 360 | 321 | 318 | 286 |
| neut × 109/l | 3.21 | 3.83 | 3.11 | 4.13 | 5.26 | 6.85 | 9.73 | 11.80 | 12.36 | 12.80 |
| lymph × 109/l | 1.59 | 1.54 | 1.73 | 1.97 | 1.60 | 1.56 | 1.45 | 1.38 | 1.34 | 1.14 |
| monocytes × 109/l | 0.15 | 0.23 | 0.20 | 0.25 | 0.34 | 0.36 | 0.36 | 0.31 | 0.37 | 0.42 |
| eosinophils × 109/l | 0.01 | 0.01 | 0.05 | 0.00 | 0.01 | 0.02 | 0.01 | 0.01 | 0.00 | 0.01 |
| basophils × 109/l | 0.01 | 0.01 | 0.00 | 0.01 | 0.01 | 0.02 | 0.01 | 0.01 | 0.00 | 0.01 |
| PT | 9 | 9 | 8 | 8 | 9 | 9 | 9 | 9 | 9 | 10 |
| aPTT | 39 | 41 | 40 | 40 | 39 | 39 | 39 | 38 | 41 | 42 |

TABLE 32-continued

Study 3

|  | Baseline | Saline | 0.005 mg/kg | 0.01 mg/kg | 0.02 mg/kg | 0.03 mg/kg | 0.04 mg/kg | 0.05 mg/kg | 0.06 mg/kg | 0.07 mg/kg |
|---|---|---|---|---|---|---|---|---|---|---|
| F VIII | 84 | 79 | 80 | 88 | 80 | 85 | 82 | 80 | 85 | 81 |
| vWF concentration | 53 | 50 | 48 | 51 | 46 | 44 | 42 | 35 | 36 | 35 |
| % aggregation | no | no |  | no | no | no | no |  |  | no |

GBR 600 appears to be a potent inhibitor of platelet deposition during arterial thrombosis. Epinephrine did not reverse the inhibition, as it does with clopidogrel. No serious adverse bleeding is seen with GBR 600, even when the drug is infused at what currently looks like a dose of up to 250 times the effective dose. At these doses bleeding measured by the incisional bleeding model yielded similar results to clopidogrel infused at four to eight times the effective dose. GBR 600 had no effect on the coagulation proteins which is shown by the PT and aPTT results. However, there is a decrease in von Willebrand Factor levels. No clear-cut effect is seen on Factor VIII levels, however. This need not be a problem as warfarin inhibits the coagulation system by decreasing circulating levels of the functional vitamin K dependant coagulation proteins. No unexpected effects on Full Blood Count parameters (WBC, Hb and Plt) were observed in this study.

Example 11

Thermostability of Humanized NMC-4 Variants

The thermal stability of humanized NMC-4 variants, of the murine NMC-4 FAB fragment and of a chimeric NMC4-IgG1 was compared using calorimetric measurements. Monoclonal antibodies melting profiles are characteristic of their isotypes (Garber and Demarest (2007), BBRC 355:751-7); however the mid-point melting temperature of the FAB fragment can be easily identified even in context of a full-length IgG. Such mid-point melting of FAB portion was used to monitor monoclonal stability of humanized candidates.

Figure 11:
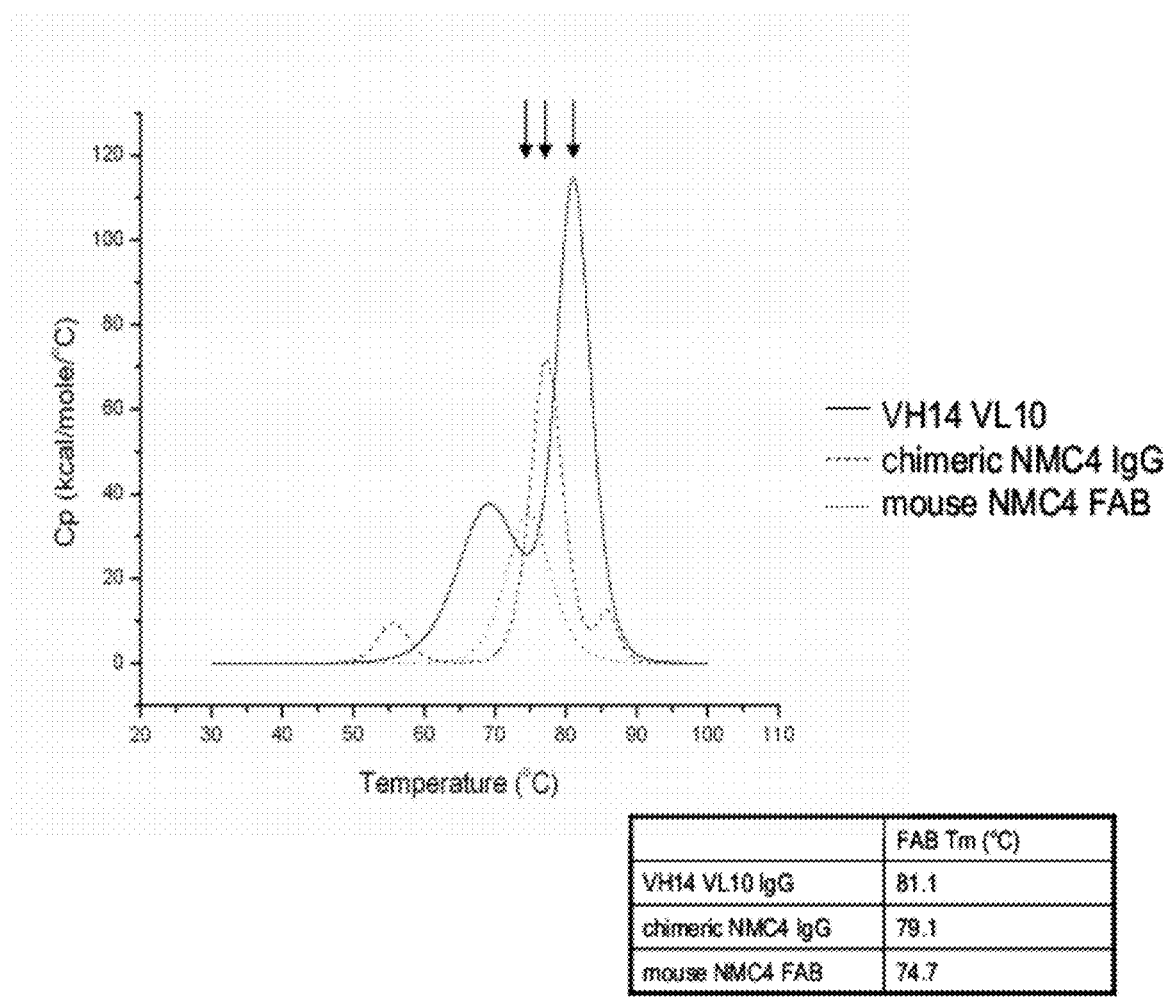
FIG. 11 shows thermostability of humanized NMC-4 variants by differential scanning calorimetry.

Calorimetric measurements were carried out on a VP-DSC differential scanning microcalorimeter (MicroCal, Northampton, UK). The cell volume was 0.128 ml; the heating rate was 1° C./min; and the excess pressure was kept at 64 p.s.i. All protein fragments were used at a concentration of 1-0.5 mg/mL (74 μM) in PBS (pH 7.4). The molar heat capacity of each protein was estimated by comparison with duplicate samples containing identical buffer from which the protein had been omitted. The partial molar heat capacities and melting curves were analyzed using standard procedures. Thermograms were baseline corrected and concentration normalized before being further analysed using a Non-Two State model in the software Origin v7.0. An example of the data obtained for H14L10-IgG4 as described in Example 3, is shown in FIG. 11. Murine NMC-4 FAB fragment display a single transition at 74.7° C., while H14L10-IgG4 FAB fragment transition appears at 81.1° C., which corresponds to a significant difference in stability (6.4° C.). To probe the influence of human FAB constant domains, a chimera consisting of murine NMC-4 variable domains grafted onto the human IgG1 (the most stable human isotype; Garber and Demarest (2007), BBRC 355:751-7) was prepared. The apparent FAB Tm values for H14L10-IgG4 and chimeric NMC4-IgG1 (79.1° C.) still show a significant increase in stability for H14-L10 FAB (delta Tm>1° C.).

Example 12

Cloning of the Genes Encoding for GBR600 Heavy (VH9) and Light Chain (VL9)

Materials and Methods used for cloning of the genes encoding for GBR600 were as follows:
PfuUltra (Stratagene, Cat.-No.: 600380)
SpeI (NEB, Cat.-No.: R0133)
HindIII (NEB, Cat.-No.: R0104)
CIP (NEB, Cat.-No.:M0290)
pCR-blunt (Invitrogen, Cat.-No.: 44-0302)
Primers: Operon, Cologne, Germany

```
GLNPR107:   TAACTAGTCGTGAGGCTCCGGTGCCCGTC

GLNPR108:   AAGCTTACGGCTAGCTCACGACACCTGAAATGGAAG

GLNPR139:   CCTCAGACAGTGGTTCAAAG

GLNPR176    GCTAGCGCCACCATGGAGACAGACACAC

GLNPR177    TAAGCTTCTATCATTTACCCAGAGACAGGG

GLNPR178    TAAGCTTCTATCAACACTCTCCCCTGTTG
```

BGHREV: provided by fasteris
TMC vectors pCI-NMC4-VL9 (p156) and pCI-NMC4-VH9 (p158) provided by Chromos.
Qiaquick Gel extraction kit (Qiagen, Cat.-No.: 28706)
1 kb+ladder (Fermentas, Cat.-No.:R0491)
pcDNA3.1 (−) (Invitrogen, Cat.-No.: V795-20)
pEF-Dest51-[CD19] (RZPD, Cat.-No.: RzPDo839G0167-pEF-DEST51)
Sequencing: Fasteris SA (Geneva, Switzerland)
Gigaprep kit (Macherey-Nagel, Cat.-No.: Nucleobond PC10000)

Cloning of the expression vector pEFcDNA3.1

The expression vector pEFcDNA was created by replacing the CMV promoter from pcDNA3.1(−) (Invitrogen) with the EF1-alpha promoter from pEF-DEST51. For this purpose, the EF1-alpha promoter was amplified using the primers GLNPR107 and 108 using PfuUltra (Stratagene, annealing temperature 55° C., 30 cycles). The primers amplify the complete EF1alpha promoter and attach an SpeI side on the 5' end and a HindIII side on the 3' end of the amplified fragment. The PCR amplicon was cloned into pCR-blunt (Invitrogen) and the clones were analyzed by a SpeI/HindIII digest. The SpeI/HindIII fragment from clone #4 was cut out and cloned into the pcDNA3.1(−) backbone that was digested using the same enzyme combination and CIPed. The clones were analyzed using SpeI and HindIII and clone #2 seemed to be positive. A second digest with the backbone and the insert further confirmed the correct size of the promoter fragment.

Cloning of GBR600 into pEFcDNA

GBR600 VH9 was amplified using PfuUltra (standard conditions, annealing temperature 55° C., 30 cycles) and primers GLNPR176 and 177. The template was the TMC vector p156.

GBR600 VL9 was amplified using the primers GLNPR176 and 178 as described for the heavy chain. The template used was the TMC vector p158. The primers add an NheI restriction site 5' and a HindIII restriction site 3' to the respective amplicon. The obtained PCR fragments were cloned into pCR-blunt and analyzed by restriction digest using NheI and HindIII. Clone #1 for the light chain and clone #3 for the heavy chain were cut out and cloned into pEFcDNA that was opened using the enzymes NheI and HindIII and CIPed. The restriction digest showed that clone #1 for the light chain and clone #6 for the light chain contained fragments of the correct size. These two clones were sent to Fasteris for sequencing control as samples GS256 and GS257. The sequencing files were aligned with reference sequences. Due to the bad quality of the miniprep DNA the heavy chain sequence GS257 could not be confirmed to 100%. The plasmids encoding GBR600 heavy chain VH9 (GS257) and GBR600 light chain VL9 (GS256) were used for the preparation of Gigapreps. The plasmid preps were sent again for sequence confirmation to fasteris. The sample names this time were GS265 for GBR600 heavy chain VH9 and GS264 for GBR600 light chain VL9. Due to the better DNA quality, the sequence identity to the reference sequence could be confirmed for heavy and light chain.

While the present disclosure has been described and illustrated herein by references to various specific materials, procedures and examples, it is understood that the disclosure is not restricted to the particular combinations of material and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A humanized antibody or an antigen binding fragment thereof specific for von Willebrand factor (vWF), the humanized antibody or antigen binding fragment thereof comprising: (a) the heavy chain variable region sequence as set forth in SEQ ID NO: 19; and (b) the light chain variable region sequence as set forth in SEQ ID NO: 28.

2. A humanized antibody or binding fragment thereof specific for vWF, the humanized antibody comprising: (a) a heavy chain sequence as set forth in SEQ ID NO: 237; and (b) a light chain sequence as set forth in SEQ ID NO: 238.

3. The humanized antibody or antigen binding fragment thereof of claim 1, wherein the humanized antibody or antigen binding fragment thereof binds to vWF with an affinity (Kd) of 10 nM or less.

4. The humanized antibody or antigen binding fragment thereof of claim 1, wherein the humanized antibody or antigen binding fragment thereof competes for binding to vWF with an affinity (Ki) of 100 nM or less.

5. The humanized antibody or antigen binding fragment thereof of claim 1, wherein the humanized antibody or antigen binding fragment thereof binds to the A1 domain of vWF with an affinity (Kd) of 10 nM or less.

6. The humanized antibody or antigen binding fragment thereof of claim 1, wherein the humanized antibody or antigen binding fragment thereof competes for binding to the A1 domain of vWF with an affinity (Ki) of 100 nM or less.

7. The humanized antibody or antigen binding fragment thereof of claim 1, wherein the humanized antibody or antigen binding fragment thereof has a FAB fragment thermostability temperature greater than 65° C.

8. The humanized antibody or antigen binding fragment thereof of claim 1, wherein the humanized antibody or antigen binding fragment thereof has a FAB fragment thermostability temperature greater than the parent non-humanized antibody.

9. The humanized antibody or antigen binding fragment thereof of claim 1, wherein the humanized antibody or antigen binding fragment thereof retains the same activity as the parent non-humanized antibody or as a chimeric antibody comprising variable regions from the parent non-humanized antibody and a human Fc region.

10. The humanized antibody or antigen binding fragment thereof of claim 9, wherein the activity is measured as ristocetin-induced platelet agglutination activity.

11. The humanized antibody or antigen binding fragment thereof of claim 1, wherein the humanized antibody or antigen binding fragment thereof comprises an Fc region derived from IgG4.

12. The humanized antibody or antigen binding fragment thereof of claim 1, wherein the humanized antibody or antigen binding fragment thereof is specific for the A1 domain of human vWF.

13. The humanized antibody of claim 1, wherein the humanized antibody is a full length antibody.

14. The binding fragment of claim 1, wherein the antigen binding fragment is an antibody fragment selected from the group consisting of Fab, Fab', Fab'-SH, Fv, scFv, F(ab')2, and a diabody.

15. An isolated nucleic acid encoding the antibody or binding fragment thereof of claim 1.

16. An isolated nucleic acid encoding a humanized antibody or binding fragment thereof specific for vWF that comprises a heavy chain variable region sequence as set forth in SEQ ID NO: 19 and a light chain variable region sequence as set forth in SEQ ID NO: 28.

17. An isolated nucleic acid encoding a humanized antibody or binding fragment thereof specific for vWF that comprises a heavy chain sequence as set forth in SEQ ID NO: 237 and a light chain sequence as set forth in SEQ ID NO: 238.

18. A vector comprising the isolated nucleic acid of claim 15.

19. A host cell comprising the isolated nucleic acid of claim 15 or the vector of claim 18.

20. A method of producing a humanized antibody or binding fragment thereof comprising culturing the host cell of claim 19 so that the nucleic acid is expressed and the antibody produced.

21. The method of claim 20 further comprising recovering the antibody from the host cell culture.

22. The method of claim 20, wherein the antibody is recovered from the host cell medium.

23. The method of claim 20, wherein before culturing, the host cell is co-transfected with a vector comprising nucleic acid encoding a heavy chain variable region and with a vector comprising nucleic acid encoding a light chain variable region.

24. A composition comprising the humanized antibody or antigen binding fragment thereof of claim 1 and a pharmaceutically acceptable carrier.

25. A composition comprising a first humanized antibody or antigen binding fragment thereof of claim 1 and a second antibody that binds to the A1 domain of vWF.

26. The composition of claim 25, wherein the second antibody is AJW-200.

27. A method for treating a vWF mediated disease or disorder in a subject, wherein the vWF mediated disorder is a thrombotic disease or disorder, the method comprising administering to the subject a therapeutically effective amount of the humanized antibody or antigen binding fragment thereof of claim 1.

28. The method of claim 27, wherein the subject is a human.

29. The method of claim 27, wherein the thrombotic disease or disorder is cardiovascular disease or cerebrovascular disease such as ischemic stroke.

30. The method of claim 29, wherein the cardiovascular disease is atherosclerosis, restenosis, angina, acute myocardial infarction, acute coronary syndrome or cardiovascular disorders associated with diabetes.

31. The method of claim 27, wherein the thrombotic disease or disorder is vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes.

32. The method of claim 29, wherein the cerebrovascular disease is vascular dementia, ischemic stroke, or prevention of recurrent strokes.

33. The method of claim 27, wherein the therapeutically effective amount is from about 0.001 to about 100 mg/kg.

34. The method of claim 27, wherein the therapeutically effective amount is from about 0.002 to about 20 mg/kg.

35. The method of claim 27, wherein the therapeutically effective amount is from about 0.002 to about 10 mg/kg.

36. The method of claim 27, wherein a single or multiple sub-doses of the therapeutically effective amount of the humanized antibody or binding fragment thereof are administered to the subject.

37. The method of claim 27, wherein the therapeutically effective amount is sufficient to inhibit platelet aggregation but insufficient to cause significant clinical signs of bleeding.

38. The method of claim 27, wherein the therapeutically effective amount is from about 1 to about 250 times an $ED_{100}$ without causing significant clinical signs of bleeding.

39. A pharmaceutical composition comprising a therapeutically effective amount of the humanized antibody or antigen binding fragment thereof of claim 1 and a pharmaceutically acceptable carrier or diluent.

40. A pharmaceutical composition for the treatment of a vWF mediated disease or disorder, wherein the vWF mediated disorder is a thrombotic disease or disorder, comprising a therapeutically effective amount of the humanized antibody or antigen binding fragment thereof of claim 1 and a pharmaceutically acceptable carrier or diluent.

41. The composition of claim 40, wherein the thrombotic disorder is cardiovascular disease or cerebrovascular disease such as ischemic stroke.

42. The composition of claim 41, wherein the cardiovascular disease is atherosclerosis, restenosis, angina, acute myocardial infarction, acute coronary syndrome or cardiovascular disorders associated with diabetes.

43. The composition of claim 40, wherein the thrombotic disease is vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes.

44. The composition of claim 41, wherein the cerebrovascular disease is vascular dementia, ischemic stroke, or prevention of recurrent strokes.

45. The composition of claim 39, wherein the therapeutically effective amount is from about 0.001 to about 100 mg/kg.

46. The composition of claim 39, wherein the therapeutically effective amount is from about 0.002 to about 20 mg/kg.

47. The composition of claim 39, wherein the therapeutically effective amount is from about 0.002 to about 10 mg/kg.

48. The composition of claim 39, wherein a single or multiple sub-doses of the therapeutically effective amount of the humanized antibody or binding fragment thereof are administered to the subject.

49. The composition of claim 39, wherein the therapeutically effective amount is sufficient to inhibit platelet aggregation but insufficient to cause significant clinical signs of bleeding.

50. The composition of claim 39, wherein the humanized antibody or antigen binding fragment thereof is administered in a therapeutically effective amount from about 1 to about 250 times an $ED_{100}$ without causing significant clinical signs of bleeding.

51. A method for administering the humanized antibody or binding fragment thereof of claim 1 to a subject in need thereof comprising administering a therapeutically effective amount of the humanized antibody or binding fragment thereof sufficient to inhibit platelet aggregation without significant clinical signs of bleeding.

52. The method of claim 51, wherein the humanized antibody or binding fragment thereof is administered subcutaneously.

53. The method of claim 51, wherein the humanized antibody or binding fragment thereof is administered intravenously.

54. The method of claim 51, wherein the humanized antibody or binding fragment thereof is administered intravenously in combination with radiological treatments.

55. The method of claim 51, wherein the therapeutically effective amount of the humanized antibody or binding fragment thereof is from about 1 to about 250 times the $ED_{100}$.

56. The composition of claim 39, wherein the humanized antibody or antigen binding fragment thereof is administered in an amount from about 1 to about 250 times the $ED_{100}$.

57. An article of manufacture comprising the humanized antibody or antigen binding fragment thereof of claim 1 for the treatment of a vWF mediated disease or disorder.

58. A kit comprising the humanized antibody or antigen binding fragment thereof of claim 1 for the treatment of a vWF mediated disease or disorder.

59. A kit comprising the humanized antibody or antigen binding fragment thereof of claim 1 for use in non-therapeutic applications.

60. The kit of claim 59, wherein the non-therapeutic application is a diagnostic assay.

61. A humanized antibody or an antigen binding fragment thereof specific for von Willebrand factor (vWF), the humanized antibody or antigen binding fragment thereof comprising a heavy chain variable region and a light chain variable region, wherein the heavy chain variable region comprises the sequence as set forth in SEQ ID NO: 19.

62. The humanized antibody or antigen binding fragment thereof of claim 61, wherein the humanized antibody or antigen binding fragment thereof binds to vWF with an affinity (Kd) of 10 nM or less.

63. The humanized antibody or antigen binding fragment thereof of claim 61, wherein the humanized antibody or antigen binding fragment thereof competes for binding to vWF with an affinity (Ki) of 100 nM or less.

64. The humanized antibody or antigen binding fragment thereof of claim 61, wherein the humanized antibody or antigen binding fragment thereof binds to the A1 domain of vWF with an affinity (Kd) of 10 nM or less.

65. The humanized antibody or antigen binding fragment thereof of claim 61, wherein the humanized antibody or antigen binding fragment thereof competes for binding to the A1 domain of vWF with an affinity (Ki) of 100 nM or less.

66. The humanized antibody or antigen binding fragment thereof of claim 61, wherein the humanized antibody or antigen binding fragment thereof has a FAB fragment thermostability temperature greater than 65° C.

67. The humanized antibody or antigen binding fragment thereof of claim 61, wherein the humanized antibody or antigen binding fragment thereof has a FAB fragment thermostability temperature greater than the parent non-humanized antibody.

68. The humanized antibody or antigen binding fragment thereof of claim 61, wherein the humanized antibody or antigen binding fragment thereof retains the same activity as the parent non-humanized antibody or as a chimeric antibody comprising variable regions from the parent non-humanized antibody and a human Fc region.

69. The humanized antibody or antigen binding fragment thereof of claim 68, wherein the activity is measured as ristocetin-induced platelet agglutination activity.

70. The humanized antibody or antigen binding fragment thereof of claim 61, wherein the humanized antibody or antigen binding fragment thereof comprises an Fc region derived from IgG4.

71. The humanized antibody or antigen binding fragment thereof of claim 61, wherein the humanized antibody or antigen binding fragment thereof is specific for the A1 domain of human vWF.

72. The humanized antibody of claim 61, wherein the humanized antibody is a full length antibody.

73. The binding fragment of claim 61, wherein the antigen binding fragment is an antibody fragment selected from the group consisting of Fab, Fab', Fab'-SH, Fv, scFv, F(ab')2, and a diabody.

74. A composition comprising the humanized antibody or antigen binding fragment thereof of claim 61 and a pharmaceutically acceptable carrier.

75. A composition comprising a first humanized antibody or antigen binding fragment thereof of claim 61 and a second antibody that binds to the A1 domain of vWF.

76. The composition of claim 75, wherein the second antibody is AJW-200.

77. A pharmaceutical composition comprising a therapeutically effective amount of the humanized antibody or antigen binding fragment thereof of claim 61 and a pharmaceutically acceptable carrier or diluent.

78. A pharmaceutical composition for the treatment of a vWF mediated disease or disorder, wherein the vWF mediated disorder is a thrombotic disease or disorder, comprising a therapeutically effective amount of the humanized antibody or antigen binding fragment thereof of claim 61 and a pharmaceutically acceptable carrier or diluent.

79. The composition of claim 78, wherein the thrombotic disorder is cardiovascular disease or cerebrovascular disease such as ischemic stroke.

80. The composition of claim 79, wherein the cardiovascular disease is atherosclerosis, restenosis, angina, acute myocardial infarction, acute coronary syndrome or cardiovascular disorders associated with diabetes.

81. The composition of claim 78, wherein the thrombotic disease is vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes.

82. The composition of claim 79, wherein the cerebrovascular disease is vascular dementia, ischemic stroke, or prevention of recurrent strokes.

83. The composition of claim 77, wherein the therapeutically effective amount is from about 0.001 to about 100 mg/kg.

84. The composition of claim 77, wherein the therapeutically effective amount is from about 0.002 to about 20 mg/kg.

85. The composition of claim 77, wherein the therapeutically effective amount is from about 0.002 to about 10 mg/kg.

86. The composition of claim 77, wherein a single or multiple sub-doses of the therapeutically effective amount of the humanized antibody or binding fragment thereof are administered to the subject.

87. The composition of claim 77, wherein the therapeutically effective amount is sufficient to inhibit platelet aggregation but insufficient to cause significant clinical signs of bleeding.

88. The composition of claim 77, wherein the humanized antibody or antigen binding fragment thereof is administered in a therapeutically effective amount from about 1 to about 250 times an $ED_{100}$ without causing significant clinical signs of bleeding.

89. The composition of claim 77, wherein the humanized antibody or antigen binding fragment thereof is administered in an amount from about 1 to about 250 times the $ED_{100}$.

90. An article of manufacture comprising the humanized antibody or antigen binding fragment thereof of claim 61 for the treatment of a vWF mediated disease or disorder.

91. A kit comprising the humanized antibody or antigen binding fragment thereof of claim 61 for the treatment of a vWF mediated disease or disorder.

92. A kit comprising the humanized antibody or antigen binding fragment thereof of claim 61 for use in non-therapeutic applications.

93. The kit of claim 92, wherein the non-therapeutic application is a diagnostic assay.

94. A humanized antibody or an antigen binding fragment thereof specific for von Willebrand factor (vWF), the humanized antibody or antigen binding fragment thereof comprising a heavy chain variable region and a light chain variable region, wherein the light chain variable region comprises the sequence as set forth in SEQ ID NO: 28.

95. The humanized antibody or antigen binding fragment thereof of claim 94, wherein the humanized antibody or antigen binding fragment thereof binds to vWF with an affinity (Kd) of 10 nM or less.

96. The humanized antibody or antigen binding fragment thereof of claim 94, wherein the humanized antibody or antigen binding fragment thereof competes for binding to vWF with an affinity (Ki) of 100 nM or less.

97. The humanized antibody or antigen binding fragment thereof of claim 94, wherein the humanized antibody or antigen binding fragment thereof binds to the A1 domain of vWF with an affinity (Kd) of 10 nM or less.

98. The humanized antibody or antigen binding fragment thereof of claim 94, wherein the humanized antibody or antigen binding fragment thereof competes for binding to the A1 domain of vWF with an affinity (Ki) of 100 nM or less.

99. The humanized antibody or antigen binding fragment thereof of claim 94, wherein the humanized antibody or antigen binding fragment thereof has a FAB fragment thermostability temperature greater than 65° C.

100. The humanized antibody or antigen binding fragment thereof of claim 94, wherein the humanized antibody or antigen binding fragment thereof has a FAB fragment thermostability temperature greater than the parent non-humanized antibody.

101. The humanized antibody or antigen binding fragment thereof of claim 94, wherein the humanized antibody or antigen binding fragment thereof retains the same activity as the parent non-humanized antibody or as a chimeric antibody comprising variable regions from the parent non-humanized antibody and a human Fc region.

102. The humanized antibody or antigen binding fragment thereof of claim 101, wherein the activity is measured as ristocetin-induced platelet agglutination activity.

103. The humanized antibody or antigen binding fragment thereof of claim 94, wherein the humanized antibody or antigen binding fragment thereof comprises an Fc region derived from IgG4.

104. The humanized antibody or antigen binding fragment thereof of claim 94, wherein the humanized antibody or antigen binding fragment thereof is specific for the A1 domain of human vWF.

105. The humanized antibody of claim 94, wherein the humanized antibody is a full length antibody.

106. The binding fragment of claim 94, wherein the antigen binding fragment is an antibody fragment selected from the group consisting of Fab, Fab', Fab'-SH, Fv, scFv, F(ab')2, and a diabody.

107. A composition comprising the humanized antibody or antigen binding fragment thereof of claim 94 and a pharmaceutically acceptable carrier.

108. A composition comprising a first humanized antibody or antigen binding fragment thereof of claim 94 and a second antibody that binds to the A1 domain of vWF.

109. The composition of claim 108, wherein the second antibody is AJW-200.

110. A pharmaceutical composition comprising a therapeutically effective amount of the humanized antibody or antigen binding fragment thereof of claim 94 and a pharmaceutically acceptable carrier or diluent.

111. A pharmaceutical composition for the treatment of a vWF mediated disease or disorder, wherein the vWF mediated disorder is a thrombotic disease or disorder, comprising a therapeutically effective amount of the humanized antibody or antigen binding fragment thereof of claim 94 and a pharmaceutically acceptable carrier or diluent.

112. The composition of claim 111, wherein the thrombotic disorder is cardiovascular disease or cerebrovascular disease such as ischemic stroke.

113. The composition of claim 112, wherein the cardiovascular disease is atherosclerosis, restenosis, angina, acute myocardial infarction, acute coronary syndrome or cardiovascular disorders associated with diabetes.

114. The composition of claim 111, wherein the thrombotic disease is vascular inflammation, venous thrombosis, sickle cell disease, xenograft rejection, peripheral vascular disease, thrombotic thrombocytopenic purpura, cystic fibrosis, vascular dementia, Raynaud's disease, rheumatoid arthritis or diabetes.

115. The composition of claim 112, wherein the cerebrovascular disease is vascular dementia, ischemic stroke, or prevention of recurrent strokes.

116. The composition of claim 110, wherein the therapeutically effective amount is from about 0.001 to about 100 mg/kg.

117. The composition of claim 110, wherein the therapeutically effective amount is from about 0.002 to about 20 mg/kg.

118. The composition of claim 110, wherein the therapeutically effective amount is from about 0.002 to about 10 mg/kg.

119. The composition of claim 110, wherein a single or multiple sub-doses of the therapeutically effective amount of the humanized antibody or binding fragment thereof are administered to the subject.

120. The composition of claim 110, wherein the therapeutically effective amount is sufficient to inhibit platelet aggregation but insufficient to cause significant clinical signs of bleeding.

121. The composition of claim 110, wherein the humanized antibody or antigen binding fragment thereof is administered in a therapeutically effective amount from about 1 to about 250 times an $ED_{100}$ without causing significant clinical signs of bleeding.

122. The composition of claim 110, wherein the humanized antibody or antigen binding fragment thereof is administered in an amount from about 1 to about 250 times the $ED_{100}$.

123. An article of manufacture comprising the humanized antibody or antigen binding fragment thereof of claim 94 for the treatment of a vWF mediated disease or disorder.

124. A kit comprising the humanized antibody or antigen binding fragment thereof of claim 94 for the treatment of a vWF mediated disease or disorder.

125. A kit comprising the humanized antibody or antigen binding fragment thereof of claim 94 for use in non-therapeutic applications.

126. The kit of claim 125, wherein the non-therapeutic application is a diagnostic assay.

* * * * *

SEQUENCE LISTING

```
<160> NUMBER OF SEQ ID NOS: 238

<210> SEQ ID NO 1
<211> LENGTH: 218
<212> TYPE: PRT
<213> ORGANISM: artificial
<220> FEATURE:
<223> OTHER INFORMATION: NMC-4 (heavy chain of the murine mAb)

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asp Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Arg Tyr Tyr Cys Val
                85                  90                  95

Arg Asp Pro Ala Asp Tyr Gly Asn Tyr Asp Tyr Ala Leu Asp Tyr Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys
    210                 215
```

<210> SEQ ID NO 2
<211> LENGTH: 208
<212> TYPE: PRT
<213> ORGANISM: artificial
<220> FEATURE:
<223> OTHER INFORMATION: NMC-4 (light chain of the murine mAb)

<400> SEQUENCE: 2

Asp Ile Gln Met Thr Gln Ser Pro Ser Leu Ser Ala Ser Leu Gly
1               5                   10                  15

Asp Arg Val Thr Ile Ser Cys Ser Ala Ser Gln Asp Ile Asn Lys Tyr
            20                  25                  30

Leu Asn Trp Tyr Gln Gln Lys Pro Asp Gly Ala Val Lys Leu Leu Ile
        35                  40                  45

Phe Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Lys Leu Pro Trp
                85                  90                  95

Thr Phe Gly Gly Gly Thr Lys Leu Glu Val Lys Arg Ala Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

<210> SEQ ID NO 3
<211> LENGTH: 65
<212> TYPE: PRT
<213> ORGANISM: artificial
<220> FEATURE:
<223> OTHER INFORMATION: Human germline VH, 4-59

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser
65

<210> SEQ ID NO 4
<211> LENGTH: 122
<212> TYPE: PRT
<213> ORGANISM: artificial
<220> FEATURE:
<223> OTHER INFORMATION: Human antibody AAC18165.1

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Arg Pro Gly Val Ala Ala His Ser Pro Phe Asp Tyr Trp
            100                 105                 110

Gly Gln Gly Thr Leu Val Thr Val Ser Ser
            115                 120

<210> SEQ ID NO 5
<211> LENGTH: 88
<212> TYPE: PRT
<213> ORGANISM: artificial
<220> FEATURE:
<223> OTHER INFORMATION: Human germline VL, O18

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys
                85

<210> SEQ ID NO 6
<211> LENGTH: 107
<212> TYPE: PRT
<213> ORGANISM: artificial
<220> FEATURE:
<223> OTHER INFORMATION: Human antibody AAK94808

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Tyr Asp Asn Leu Pro Leu
                85                  90                  95
Thr Phe Gly Gly Gly Thr Lys Val Glu Ile Lys
            100                 105

<210> SEQ ID NO 7
<211> LENGTH: 10
<212> TYPE: PRT
<213> ORGANISM: artificial
<220> FEATURE:
<223> OTHER INFORMATION: HDCDR1

<400> SEQUENCE: 7

Gly Phe Ser Leu Thr Asp Tyr Gly Val Asp
1               5                   10

<210> SEQ ID NO 8
<211> LENGTH: 16
<212> TYPE: PRT
<213> ORGANISM: artificial
<220> FEATURE:
<223> OTHER INFORMATION: HCDR2

<400> SEQUENCE: 8

Met Ile Trp Gly Asp Gly Ser Thr Asp Tyr Asn Ser Ala Leu Lys Ser
1               5                   10                  15

<210> SEQ ID NO 9
<211> LENGTH: 14
<212> TYPE: PRT
<213> ORGANISM: artificial
<220> FEATURE:
<223> OTHER INFORMATION: HCDR3

<400> SEQUENCE: 9

Asp Pro Ala Asp Tyr Gly Asn Tyr Asp Tyr Ala Leu Asp Tyr
1               5                   10

<210> SEQ ID NO 10
<211> LENGTH: 11
<212> TYPE: PRT
<213> ORGANISM: artificial
<220> FEATURE:
<223> OTHER INFORMATION: LCDR1

<400> SEQUENCE: 10

Ser Ala Ser Gln Asp Ile Asn Lys Tyr Leu Asn
1               5                   10

<210> SEQ ID NO 11
<211> LENGTH: 7
<212> TYPE: PRT
<213> ORGANISM: artificial
<220> FEATURE:
<223> OTHER INFORMATION: LCDR2

<400> SEQUENCE: 11

Tyr Thr Ser Ser Leu His Ser
1               5

<210> SEQ ID NO 12
<211> LENGTH: 9
<212> TYPE: PRT
<213> ORGANISM: artificial
<220> FEATURE:
<223> OTHER INFORMATION: LCDR3

<400> SEQUENCE: 12
```

```
Gln Gln Tyr Glu Lys Leu Pro Trp Thr
1               5
```

<210> SEQ ID NO 13
<211> LENGTH: 122
<212> TYPE: PRT
<213> ORGANISM: artificial
<220> FEATURE:
<223> OTHER INFORMATION: H2

<400> SEQUENCE: 13

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
                20                  25                  30

Gly Val Asp Trp Ile Arg Gln Pro Pro Gly Lys Gly Leu Glu Trp Ile
            35                  40                  45

Gly Met Ile Trp Gly Asp Gly Ser Thr Asp Tyr Asn Ser Ala Leu Lys
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Asp Pro Ala Asp Tyr Gly Asn Tyr Asp Tyr Ala Leu Asp Tyr Trp
            100                 105                 110

Gly Gln Gly Thr Ser Leu Thr Val Ser Ser
        115                 120
```

<210> SEQ ID NO 14
<211> LENGTH: 122
<212> TYPE: PRT
<213> ORGANISM: artificial
<220> FEATURE:
<223> OTHER INFORMATION: H4

<400> SEQUENCE: 14

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
                20                  25                  30

Gly Val Asp Trp Ile Arg Gln Pro Pro Gly Lys Gly Leu Glu Trp Ile
            35                  40                  45

Gly Met Ile Trp Gly Asp Gly Ser Thr Asp Tyr Asn Ser Ala Leu Lys
        50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Pro Ala Asp Tyr Gly Asn Tyr Asp Tyr Ala Leu Asp Tyr Trp
            100                 105                 110

Gly Gln Gly Thr Ser Leu Thr Val Ser Ser
        115                 120
```

<210> SEQ ID NO 15
<211> LENGTH: 122
<212> TYPE: PRT
<213> ORGANISM: artificial
<220> FEATURE:
<223> OTHER INFORMATION: H5

```
<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Asp Trp Ile Arg Gln Pro Pro Gly Lys Gly Leu Glu Trp Ile
        35                  40                  45

Gly Met Ile Trp Gly Asp Gly Ser Thr Asp Tyr Asn Ser Ala Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Asp Pro Ala Asp Tyr Gly Asn Tyr Asp Tyr Ala Leu Asp Tyr Trp
            100                 105                 110

Gly Gln Gly Thr Ser Leu Thr Val Ser Ser
        115                 120

<210> SEQ ID NO 16
<211> LENGTH: 122
<212> TYPE: PRT
<213> ORGANISM: artificial
<220> FEATURE:
<223> OTHER INFORMATION: H6

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Asp Trp Ile Arg Gln Pro Pro Gly Lys Gly Leu Glu Trp Ile
        35                  40                  45

Gly Met Ile Trp Gly Asp Gly Ser Thr Asp Tyr Asn Ser Ala Leu Lys
    50                  55                  60

Ser Arg Leu Thr Ile Ser Val Asp Asn Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Asp Pro Ala Asp Tyr Gly Asn Tyr Asp Tyr Ala Leu Asp Tyr Trp
            100                 105                 110

Gly Gln Gly Thr Ser Leu Thr Val Ser Ser
        115                 120

<210> SEQ ID NO 17
<211> LENGTH: 122
<212> TYPE: PRT
<213> ORGANISM: artificial
<220> FEATURE:
<223> OTHER INFORMATION: H7

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Asp Trp Ile Arg Gln Pro Pro Gly Lys Gly Leu Glu Trp Ile
        35                  40                  45

Gly Met Ile Trp Gly Asp Gly Ser Thr Asp Tyr Asn Ser Ala Leu Lys
```

```
                   50                  55                  60
Ser Arg Leu Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Val
                     85                  90                  95

Arg Asp Pro Ala Asp Tyr Gly Asn Tyr Asp Tyr Ala Leu Asp Tyr Trp
                    100                 105                 110

Gly Gln Gly Thr Ser Leu Thr Val Ser Ser
                115                 120

<210> SEQ ID NO 18
<211> LENGTH: 122
<212> TYPE: PRT
<213> ORGANISM: artificial
<220> FEATURE:
<223> OTHER INFORMATION: H8

<400> SEQUENCE: 18

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Leu Thr Asp Tyr
                20                  25                  30

Gly Val Asp Trp Ile Arg Gln Pro Pro Gly Lys Gly Leu Glu Trp Ile
             35                  40                  45

Gly Met Ile Trp Gly Asp Gly Ser Thr Asp Tyr Asn Ser Ala Leu Lys
 50                  55                  60

Ser Arg Leu Thr Ile Ser Lys Asp Asn Ser Lys Asn Gln Phe Ser Leu
 65                  70                  75                  80

Lys Leu Ser Ser Val Thr Ala Ala Asp Thr Ala Val Tyr Tyr Cys Val
                     85                  90                  95

Arg Asp Pro Ala Asp Tyr Gly Asn Tyr Asp Tyr Ala Leu Asp Tyr Trp
                    100                 105                 110

Gly Gln Gly Thr Ser Leu Thr Val Ser Ser
                115                 120

<210> SEQ ID NO 19
<211> LENGTH: 122
<212> TYPE: PRT
<213> ORGANISM: artificial
<220> FEATURE:
<223> OTHER INFORMATION: H9

<400> SEQUENCE: 19

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Leu Thr Asp Tyr
                20                  25                  30

Gly Val Asp Trp Ile Arg Gln Pro Pro Gly Lys Gly Leu Glu Trp Ile
             35                  40                  45

Gly Met Ile Trp Gly Asp Gly Ser Thr Asp Tyr Asn Ser Ala Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                     85                  90                  95

Arg Asp Pro Ala Asp Tyr Gly Asn Tyr Asp Tyr Ala Leu Asp Tyr Trp
                    100                 105                 110

Gly Gln Gly Thr Leu Val Thr Val Ser Ser
```

```
                    115                 120

<210> SEQ ID NO 20
<211> LENGTH: 122
<212> TYPE: PRT
<213> ORGANISM: artificial
<220> FEATURE:
<223> OTHER INFORMATION: H12

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Tyr
            20                  25                  30

Gly Val Asp Trp Ile Arg Gln Pro Pro Gly Lys Gly Leu Glu Trp Ile
        35                  40                  45

Gly Met Ile Trp Gly Asp Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Ala Asp Tyr Gly Asn Tyr Asp Tyr Ala Leu Asp Tyr Trp
            100                 105                 110

Gly Gln Gly Thr Leu Val Thr Val Ser Ser
        115                 120

<210> SEQ ID NO 21
<211> LENGTH: 122
<212> TYPE: PRT
<213> ORGANISM: artificial
<220> FEATURE:
<223> OTHER INFORMATION: H13

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asp Tyr
            20                  25                  30

Gly Trp Asp Trp Ile Arg Gln Pro Pro Gly Lys Gly Leu Glu Trp Ile
        35                  40                  45

Gly Met Ile Trp Gly Asp Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Ala Asp Tyr Gly Asn Tyr Asp Tyr Ala Leu Asp Tyr Trp
            100                 105                 110

Gly Gln Gly Thr Leu Val Thr Val Ser Ser
        115                 120

<210> SEQ ID NO 22
<211> LENGTH: 122
<212> TYPE: PRT
<213> ORGANISM: human
<220> FEATURE:
<221> NAME/KEY: H14
<222> LOCATION: (1)..(122)

<400> SEQUENCE: 22
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Asp Tyr
            20                  25                  30

Gly Trp Asp Trp Ile Arg Gln Pro Pro Gly Lys Gly Leu Glu Trp Ile
            35                  40                  45

Gly Met Ile Trp Gly Asp Gly Ser Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Ala Asp Tyr Gly Asn Tyr Asp Tyr Ala Leu Asp Tyr Trp
            100                 105                 110

Gly Gln Gly Thr Leu Val Thr Val Ser Ser
            115                 120
```

<210> SEQ ID NO 23
<211> LENGTH: 107
<212> TYPE: PRT
<213> ORGANISM: artificial
<220> FEATURE:
<223> OTHER INFORMATION: L5

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Asn Lys Tyr
            20                  25                  30

Leu Asn Trp Tyr Gln Gln Lys Pro Gly Lys Ala Val Lys Leu Leu Ile
            35                  40                  45

Phe Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105
```

<210> SEQ ID NO 24
<211> LENGTH: 107
<212> TYPE: PRT
<213> ORGANISM: artificial
<220> FEATURE:
<223> OTHER INFORMATION: L4

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Asn Lys Tyr
            20                  25                  30

Leu Asn Trp Tyr Gln Gln Lys Pro Gly Lys Ala Pro Lys Leu Leu Ile
            35                  40                  45

Phe Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Ile Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105

<210> SEQ ID NO 25
<211> LENGTH: 107
<212> TYPE: PRT
<213> ORGANISM: artificial
<220> FEATURE:
<223> OTHER INFORMATION: L6

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Asn Lys Tyr
            20                  25                  30

Leu Asn Trp Tyr Gln Gln Lys Pro Gly Lys Ala Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: artificial
<220> FEATURE:
<223> OTHER INFORMATION: L7

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Asn Lys Tyr
            20                  25                  30

Leu Asn Trp Tyr Gln Gln Lys Pro Gly Lys Ala Val Lys Leu Leu Ile
        35                  40                  45

Phe Tyr Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105

<210> SEQ ID NO 27
<211> LENGTH: 107
<212> TYPE: PRT
<213> ORGANISM: artificial
<220> FEATURE:
<223> OTHER INFORMATION: L8

<400> SEQUENCE: 27

Asp Ile Gln Met Thr Gln Ser Pro Ser Ser Leu Ser Ala Ser Val Gly
```

```
                1               5                  10                  15
Asp Arg Val Thr Ile Thr Cys Ser Ala Ser Gln Asp Ile Asn Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105

<210> SEQ ID NO 28
<211> LENGTH: 107
<212> TYPE: PRT
<213> ORGANISM: artificial
<220> FEATURE:
<223> OTHER INFORMATION: L9

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Asn Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105

<210> SEQ ID NO 29
<211> LENGTH: 107
<212> TYPE: PRT
<213> ORGANISM: artificial
<220> FEATURE:
<223> OTHER INFORMATION: L10

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Lys Leu Pro Trp
                85                  90                  95

Thr Phe Gly Gln Gly Thr Lys Val Glu Ile Lys
```

<210> SEQ ID NO 30
<211> LENGTH: 107
<212> TYPE: PRT
<213> ORGANISM: artificial
<220> FEATURE:
<223> OTHER INFORMATION: L11

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Phe Ser Ser Leu Gln Pro
65                  70                  75                  80

Glu Asp Phe Ala Thr Tyr Tyr Cys Gln Gln Tyr Glu Lys Leu Pro Trp
                85                  90                  95

Thr Phe Gly Gln Gly Thr Lys Val Glu Ile Lys
            100                 105

<210> SEQ ID NO 31
<211> LENGTH: 6
<212> TYPE: DNA
<213> ORGANISM: artificial
<220> FEATURE:
<223> OTHER INFORMATION: Transcriptional element
<220> FEATURE:
<221> NAME/KEY: misc_feature
<222> LOCATION: (2)..(2)
<223> OTHER INFORMATION: n is a, c, g, or t

<400> SEQUENCE: 31 cncaat                                                                      6

<210> SEQ ID NO 32
<211> LENGTH: 6
<212> TYPE: DNA
<213> ORGANISM: artificial
<220> FEATURE:
<223> OTHER INFORMATION: Transcriptional element 1

<400> SEQUENCE: 32 aataaa                                                                      6

<210> SEQ ID NO 33
<211> LENGTH: 1602
<212> TYPE: DNA
<213> ORGANISM: artificial
<220> FEATURE:
<223> OTHER INFORMATION: IMAGE clone #4764579

<400> SEQUENCE: 33
ggcaccgagg gtttctgtcc tccaccatca tggggtcaac cgccatcctc gccctcctcc      60
tggctgttct ccaaggagtc tgtgccgagg tgcgcctgga gcagtctggg acagaggtga     120
aaaagccggg ggagtctctg aaaatctcct gtcaggcttc tggattcacc tttaccgact     180
actggatcgg ctgggtgcgc cagctgcccg ggcaaggcct ggagtggatg ggcttcatcg     240
atcgtcttga ctctaaaata agatataacc cgtccttcca aggccaagtc accatgtcag     300

```
ccgacacgtc gataaccgcc gtctacctgc agtggagccg cctgaaggcc tcggacaccg    360
gcatctatta ttgtgcgacc tcggatacac ctctggactc ttactccttt gaattttggg    420
gccagggaag cctcgtcatc gtctcctcag cctccaccaa gggcccatcg gtcttccccc    480
tggcaccctc ctccaagagc acctctgggg gcacagcggc cctgggctgc ctggtcaagg    540
actacttccc cgaaccggtg acggtgtcat ggaactcagg cgccctgacc agcggcgtgc    600
acaccttccc ggctgtccta cagtcctcag gactctactc cctcagcagc gtggtgaccg    660
tgccctccag cagcttgggc acccagacct acatctgcaa cgtgaatcac aagcccagca    720
acaccaaggt ggacaagaaa gttgagccca aatcttgtga caaaactcac acatgcccac    780
cgtgcccagc acctgaactc ctggggggac cgtcagtctt cctcttcccc ccaaaaccca    840
aggacaccct catgatctcc cggacccctg aggtcacatg cgtggtggtg gacgtgagcc    900
acgaagaccc tgaggtcaag ttcaactggt acgtggacgg cgtggaggtg cataatgcca    960
agacaaagcc gcgggaggag cagtacaaca gcacgtaccg tgtggtcagc gtcctcaccg   1020
tcctgcacca ggactggctg aatggcaagg agtacaagtg caaggtctcc aacaaagccc   1080
tcccagcccc catcgagaaa accatctcca aagccaaagg gcagcccga gaaccacagg   1140
tgtacaccct gcccccatcc cgggatgagc tgaccaagaa ccaggtcagc ctgacctgcc   1200
tggtcaaagg cttctatccc agcgacatcg ccgtggagtg ggagagcaat gggcagccgg   1260
agaacaacta caagaccacg cctcccgtgc tggactccga cggctccttc ttcctctaca   1320
gcaagctcac cgtggacaag agcaggtggc agcaggggaa cgtcttctca tgctccgtga   1380
tgcatgaggc tctgcacaac cactacacgc agaagagcct ctccctgtct ccgggtaaat   1440
gagtgcgacg gccggcaagc ccccgctccc cgggctctcg cggtcgcacg aggatgcttg   1500
gcacgtaccc cctgtacata cttcccgggc gcccagcatg gaaataaagc acccagcgct   1560
gccctgggcc cctgcgaaaa aaaaaaaaa aaaaaaaaa aa                        1602
```

<210> SEQ ID NO 34
<211> LENGTH: 33
<212> TYPE: DNA
<213> ORGANISM: artificial
<220> FEATURE:
<223> OTHER INFORMATION: NMC-VH-coRI-F

<400> SEQUENCE: 34
gacgcgaatt cgcaggtgca gctgaaggag agc                                 33

<210> SEQ ID NO 35
<211> LENGTH: 43
<212> TYPE: DNA
<213> ORGANISM: artificial
<220> FEATURE:
<223> OTHER INFORMATION: NMC-VH-gG4lgG1-R

<400> SEQUENCE: 35
cggatgggcc cttggtggaa gcgctgctca cggtcacgct ggt                      43

<210> SEQ ID NO 36
<211> LENGTH: 22
<212> TYPE: DNA
<213> ORGANISM: artificial
<220> FEATURE:
<223> OTHER INFORMATION: hIgG-F

<400> SEQUENCE: 36
gcttccacca agggcccatc cg                                             22

<210> SEQ ID NO 37
<211> LENGTH: 24
<212> TYPE: DNA
<213> ORGANISM: artificial
<220> FEATURE:
<223> OTHER INFORMATION: hIgG-R

<400> SEQUENCE: 37
cagagacagg gagaggctct tctg                                          24

<210> SEQ ID NO 38
<211> LENGTH: 40
<212> TYPE: DNA
<213> ORGANISM: artificial
<220> FEATURE:
<223> OTHER INFORMATION: hIgG BamH1-R

<400> SEQUENCE: 38
attaggatcc ttatcattta cccagagaca gggagaggct                         40

<210> SEQ ID NO 39
<211> LENGTH: 29
<212> TYPE: DNA
<213> ORGANISM: artificial
<220> FEATURE:
<223> OTHER INFORMATION: hFc-L235E-F

<400> SEQUENCE: 39 ctcgagggg gaccgtcagt cttcctctt                                      29

<210> SEQ ID NO 40
<211> LENGTH: 29
<212> TYPE: DNA
<213> ORGANISM: artificial
<220> FEATURE:
<223> OTHER INFORMATION: IgG1-L235E-R

<400> SEQUENCE: 40
aagaggaaga ctgacggtcc cccctcgag                                     29

<210> SEQ ID NO 41
<211> LENGTH: 30
<212> TYPE: DNA
<213> ORGANISM: artificial
<220> FEATURE:
<223> OTHER INFORMATION: CH2-C1q(-)-F

<400> SEQUENCE: 41
ggcgtacgcg tgcgcggtct ccaacaaagc                                    30

<210> SEQ ID NO 42
<211> LENGTH: 31
<212> TYPE: DNA
<213> ORGANISM: artificial
<220> FEATURE:
<223> OTHER INFORMATION: CH2-C1q(-)-R

<400> SEQUENCE: 42
ccgcgcacgc gtacgccttg ccattcagcc a                                  31

<210> SEQ ID NO 43
<211> LENGTH: 96
<212> TYPE: DNA
<213> ORGANISM: artificial
<220> FEATURE:
<223> OTHER INFORMATION: 4-59 leader-Hindlll-NMC-4

<400> SEQUENCE: 43
attaagcttg ccgccaccat gaaacatctg tggttcttcc ttctcctggt ggcagctccc    60
aggtgggtcc tgtcccaggt gcagctgaag gagagc    96

<210> SEQ ID NO 44
<211> LENGTH: 36
<212> TYPE: DNA
<213> ORGANISM: artificial
<220> FEATURE:
<223> OTHER INFORMATION: lgG1-BamH1-R

<400> SEQUENCE: 44
taaggatcct tatcatttac ccggagacag ggagag    36

<210> SEQ ID NO 45
<211> LENGTH: 34
<212> TYPE: DNA
<213> ORGANISM: artificial
<220> FEATURE:
<223> OTHER INFORMATION: NMC-VL-EcoRl-F

<400> SEQUENCE: 45
gacgcgaatt cggacatcca gatgacccag agcc    34

<210> SEQ ID NO 46
<211> LENGTH: 48
<212> TYPE: DNA
<213> ORGANISM: artificial
<220> FEATURE:
<223> OTHER INFORMATION: NMC-VL-Kappa-R

<400> SEQUENCE: 46
gaagacagat ggtgcagcca cagttcgctt cacctccagc ttggtgcc    48

<210> SEQ ID NO 47
<211> LENGTH: 26
<212> TYPE: DNA
<213> ORGANISM: artificial
<220> FEATURE:
<223> OTHER INFORMATION: Kappa-F

<400> SEQUENCE: 47
cgaactgtgg ctgcaccatc tgtctt    26

<210> SEQ ID NO 48
<211> LENGTH: 41
<212> TYPE: DNA
<213> ORGANISM: artificial
<220> FEATURE:
<223> OTHER INFORMATION: Kappa-BamH1-R

<400> SEQUENCE: 48
aattcggatc cttactaaca ctctcccctg ttgaagctct t    41

<210> SEQ ID NO 49
<211> LENGTH: 48
<212> TYPE: DNA
<213> ORGANISM: artificial
<220> FEATURE:
<223> OTHER INFORMATION: Hind lll-Ko-AJW-F

<400> SEQUENCE: 49
gttaagcttg ccgccaccat ggattttggg ctgatttttt ttattgtt    48

```
<210> SEQ ID NO 50
<211> LENGTH: 43
<212> TYPE: DNA
<213> ORGANISM: artificial
<220> FEATURE:
<223> OTHER INFORMATION: HuFab-H-R

<400> SEQUENCE: 50
gaatgggccc ttggtggaag cggaggaaac ggtcacgagg gta            43

<210> SEQ ID NO 51
<211> LENGTH: 43
<212> TYPE: DNA
<213> ORGANISM: artificial
<220> FEATURE:
<223> OTHER INFORMATION: XhoI-Ko-AJW-F

<400> SEQUENCE: 51
aatctcgagg ccgccaccat gagtgtgccc actcaggtcc tgg            43

<210> SEQ ID NO 52
<211> LENGTH: 56
<212> TYPE: PRT
<213> ORGANISM: artificial
<220> FEATURE:
<223> OTHER INFORMATION: NMC-4 VL

<400> SEQUENCE: 52

Asp Ile Gln Met Thr Gln Ser Pro Ser Ser Leu Ser Ala Ser Leu Gly
1               5                   10                  15

Asp Arg Val Thr Ile Ser Cys Ser Ala Ser Gln Asp Ile Asn Lys Leu
            20                  25                  30

Tyr Asn Trp Tyr Gln Gln Lys Pro Asp Gly Ala Val Lys Leu Leu Ile
        35                  40                  45

Phe Tyr Thr Ser Ser Leu His Ser
    50                  55

<210> SEQ ID NO 53
<211> LENGTH: 65
<212> TYPE: PRT
<213> ORGANISM: artificial
<220> FEATURE:
<223> OTHER INFORMATION: NMC-4 VH

<400> SEQUENCE: 53

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asp Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser
65

<210> SEQ ID NO 54
<211> LENGTH: 98
<212> TYPE: DNA
<213> ORGANISM: artificial
<220> FEATURE:
<223> OTHER INFORMATION: 4-59 huNMC-F

<400> SEQUENCE: 54
```

```
gttaagcttg ccgccaccat gaaacatctg tggttcttcc ttctcctggt ggcagctccc    60
aggtgggtcc tgtcccaggt gcagctgcag gaatccgg                            98
```

<210> SEQ ID NO 55
<211> LENGTH: 43
<212> TYPE: DNA
<213> ORGANISM: artificial
<220> FEATURE:
<223> OTHER INFORMATION: Hu-VH-R

<400> SEQUENCE: 55

```
ggatgggccc ttggtggaag cggaggaaac ggtcacgagg gta                      43
```

<210> SEQ ID NO 56
<211> LENGTH: 26
<212> TYPE: DNA
<213> ORGANISM: artificial
<220> FEATURE:
<223> OTHER INFORMATION: pcDNA6-F

<400> SEQUENCE: 56

```
cactgcttac tggcttatcg aaatta                                         26
```

<210> SEQ ID NO 57
<211> LENGTH: 40
<212> TYPE: DNA
<213> ORGANISM: artificial
<220> FEATURE:
<223> OTHER INFORMATION: VH-93A-For

<400> SEQUENCE: 57

```
gacaccgctg tttactactg cgctcgtgac ccggctgact                          40
```

<210> SEQ ID NO 58
<211> LENGTH: 40
<212> TYPE: DNA
<213> ORGANISM: artificial
<220> FEATURE:
<223> OTHER INFORMATION: VH-V93A-Rev

<400> SEQUENCE: 58

```
agtcagccgg gtcacgaccg cagtagtaaa cagcggtgtc                          40
```

<210> SEQ ID NO 59
<211> LENGTH: 30
<212> TYPE: DNA
<213> ORGANISM: artificial
<220> FEATURE:
<223> OTHER INFORMATION: HC-L67V-F

<400> SEQUENCE: 59

```
ctgaaatccc gtgttaccat ctccaaagac                                     30
```

<210> SEQ ID NO 60
<211> LENGTH: 30
<212> TYPE: DNA
<213> ORGANISM: artificial
<220> FEATURE:
<223> OTHER INFORMATION: HC-L67V-R

<400> SEQUENCE: 60

```
gtctttggag atggtaacac gggatttcag                                     30
```

<210> SEQ ID NO 61
<211> LENGTH: 27
<212> TYPE: DNA

<210> SEQ ID NO 61
<211> LENGTH: 27
<212> TYPE: DNA
<213> ORGANISM: artificial
<220> FEATURE:
<223> OTHER INFORMATION: HC-N73T-F

<400> SEQUENCE: 61
accatctcca aagacacctc caaaaac                                          27

<210> SEQ ID NO 62
<211> LENGTH: 27
<212> TYPE: DNA
<213> ORGANISM: artificial
<220> FEATURE:
<223> OTHER INFORMATION: HC-N73T-R
<220> FEATURE:
<221> NAME/KEY: HC-N73T-R
<222> LOCATION: (1)..(27)

<400> SEQUENCE: 62
gtttttggag gtgtctttgg agatggt                                          27

<210> SEQ ID NO 63
<211> LENGTH: 28
<212> TYPE: DNA
<213> ORGANISM: artificial
<220> FEATURE:
<223> OTHER INFORMATION: HC-V78F-F

<400> SEQUENCE: 63
aactccaaaa accagttctc cctgaaac                                         28

<210> SEQ ID NO 64
<211> LENGTH: 28
<212> TYPE: DNA
<213> ORGANISM: artificial
<220> FEATURE:
<223> OTHER INFORMATION: HC-V78F-R

<400> SEQUENCE: 64
gtttcaggga gaactggttt ttggagtt                                         28

<210> SEQ ID NO 65
<211> LENGTH: 30
<212> TYPE: DNA
<213> ORGANISM: artificial
<220> FEATURE:
<223> OTHER INFORMATION: HC-K71V-F(H9)

<400> SEQUENCE: 65
cttaccatct ccgtagacaa ctccaaaaac                                       30

<210> SEQ ID NO 66
<211> LENGTH: 30
<212> TYPE: DNA
<213> ORGANISM: artificial
<220> FEATURE:
<223> OTHER INFORMATION: HC-K71V-R

<400> SEQUENCE: 66
gtttttggag ttgtctacgg agatggtaag                                       30

<210> SEQ ID NO 67
<211> LENGTH: 30
<212> TYPE: DNA
<213> ORGANISM: artificial
<220> FEATURE:
<223> OTHER INFORMATION: hu-VH-K71V-F(H9)

<400> SEQUENCE: 67
cgtgttacca tctccgtaga cacctccaaa                                           30

<210> SEQ ID NO 68
<211> LENGTH: 30
<212> TYPE: DNA
<213> ORGANISM: artificial
<220> FEATURE:
<223> OTHER INFORMATION: hu-VH-K71V-R(H9)

<400> SEQUENCE: 68
tttggaggtg tctacggaga tggtaacacg                                           30

<210> SEQ ID NO 69
<211> LENGTH: 30
<212> TYPE: DNA
<213> ORGANISM: artificial
<220> FEATURE:
<223> OTHER INFORMATION: Fab-L-For

<400> SEQUENCE: 69
atacatatgg acatccagat gacccagagc                                           30

<210> SEQ ID NO 70
<211> LENGTH: 36
<212> TYPE: DNA
<213> ORGANISM: artificial
<220> FEATURE:
<223> OTHER INFORMATION: Fab-L-Rev

<400> SEQUENCE: 70
agactcgagt tatcaacact ctcccctgtt gaagct                                    36

<210> SEQ ID NO 71
<211> LENGTH: 34
<212> TYPE: DNA
<213> ORGANISM: artificial
<220> FEATURE:
<223> OTHER INFORMATION: NMC4-VL-EcoRl-F

<400> SEQUENCE: 71
gacgcgaatt cggacatcca gatgacccag agcc                                      34

<210> SEQ ID NO 72
<211> LENGTH: 14
<212> TYPE: DNA
<213> ORGANISM: artificial
<220> FEATURE:
<223> OTHER INFORMATION: 5'-IRES

<400> SEQUENCE: 72
agctggttta gtga                                                            14

<210> SEQ ID NO 73
<211> LENGTH: 17
<212> TYPE: DNA
<213> ORGANISM: artificial
<220> FEATURE:
<223> OTHER INFORMATION: 3'-IRES

<400> SEQUENCE: 73
caagcggctt cggccag                                                         17

<210> SEQ ID NO 74
<211> LENGTH: 24
<212> TYPE: DNA
<213> ORGANISM: artificial

```
<220> FEATURE:
<223> OTHER INFORMATION: LC-Y49F-F

<400> SEQUENCE: 74
ccaagctgct gatcttctac acca                                          24

<210> SEQ ID NO 75
<211> LENGTH: 24
<212> TYPE: DNA
<213> ORGANISM: artificial
<220> FEATURE:
<223> OTHER INFORMATION: LC-Y49F-R

<400> SEQUENCE: 75
tggtgtagaa gatcagcagc ttgg                                          24

<210> SEQ ID NO 76
<211> LENGTH: 30
<212> TYPE: DNA
<213> ORGANISM: artificial
<220> FEATURE:
<223> OTHER INFORMATION: LC-F83I-F

<400> SEQUENCE: 76
cagcccgagg acatcgccac ctactactgc                                    30

<210> SEQ ID NO 77
<211> LENGTH: 30
<212> TYPE: DNA
<213> ORGANISM: artificial
<220> FEATURE:
<223> OTHER INFORMATION: LC-F83I-R

<400> SEQUENCE: 77
gcagtagtag gtggcgatgt cctcgggctg                                    30

<210> SEQ ID NO 78
<211> LENGTH: 30
<212> TYPE: DNA
<213> ORGANISM: artificial
<220> FEATURE:
<223> OTHER INFORMATION: LC-P44V-F

<400> SEQUENCE: 78
aagcccggca aggccgtcaa gctgctgatc                                    30

<210> SEQ ID NO 79
<211> LENGTH: 30
<212> TYPE: DNA
<213> ORGANISM: artificial
<220> FEATURE:
<223> OTHER INFORMATION: LC-P44V-R

<400> SEQUENCE: 79
gatcagcagc ttgacggcct tgccgggctt                                    30

<210> SEQ ID NO 80
<211> LENGTH: 29
<212> TYPE: DNA
<213> ORGANISM: artificial
<220> FEATURE:
<223> OTHER INFORMATION: LC-F49Y-F

<400> SEQUENCE: 80
gccgtcaagc tgctgatcta ctacaccag                                     29
```

<210> SEQ ID NO 81
<211> LENGTH: 29
<212> TYPE: DNA
<213> ORGANISM: artificial
<220> FEATURE:
<223> OTHER INFORMATION: LC-F49Y-R

<400> SEQUENCE: 81
ctggtgtagt agatcagcag cttgacggc                                    29

<210> SEQ ID NO 82
<211> LENGTH: 30
<212> TYPE: DNA
<213> ORGANISM: artificial
<220> FEATURE:
<223> OTHER INFORMATION: LC-Y71F-F

<400> SEQUENCE: 82
ggcagcggca ccgacttcac cctgaccatc                                   30

<210> SEQ ID NO 83
<211> LENGTH: 30
<212> TYPE: DNA
<213> ORGANISM: artificial
<220> FEATURE:
<223> OTHER INFORMATION: LC-Y71F-R

<400> SEQUENCE: 83
gatggtcagg gtgaagtcgg tgccgctgcc                                   30

<210> SEQ ID NO 84
<211> LENGTH: 35
<212> TYPE: DNA
<213> ORGANISM: artificial
<220> FEATURE:
<223> OTHER INFORMATION: HuLC-V44P, F49Y-F

<400> SEQUENCE: 84
ggcaaggccc ccaagctgct gatctactac accag                             35

<210> SEQ ID NO 85
<211> LENGTH: 35
<212> TYPE: DNA
<213> ORGANISM: artificial
<220> FEATURE:
<223> OTHER INFORMATION: HuLC-V44P, F49Y-R

<400> SEQUENCE: 85
ctggtgtagt agatcagcag cttgggggcc ttgcc                             35

<210> SEQ ID NO 86
<211> LENGTH: 48
<212> TYPE: DNA
<213> ORGANISM: artificial
<220> FEATURE:
<223> OTHER INFORMATION: huL10-F

<400> SEQUENCE: 86
accatcacct gccaagccag ccaggacatc agcaactacc tgaactgg               48

<210> SEQ ID NO 87
<211> LENGTH: 48
<212> TYPE: DNA
<213> ORGANISM: artificial
<220> FEATURE:
<223> OTHER INFORMATION: huL10-R

<400> SEQUENCE: 87

-continued ccagttcagg tagttgctga tgtcctggct ggcttggcag gtgatggt        48

<210> SEQ ID NO 88
<211> LENGTH: 48
<212> TYPE: DNA
<213> ORGANISM: artificial
<220> FEATURE:
<223> OTHER INFORMATION: huL11-F

<400> SEQUENCE: 88
cccaagctgc tgatctacga cgccagcaac ctggaaaccg gcgtgccc        48

<210> SEQ ID NO 89
<211> LENGTH: 48
<212> TYPE: DNA
<213> ORGANISM: artificial
<220> FEATURE:
<223> OTHER INFORMATION: huL11-R

<400> SEQUENCE: 89
gggcacgccg gtttccaggt tgctggcgtc gtagatcagc agcttggg        48

<210> SEQ ID NO 90
<211> LENGTH: 40
<212> TYPE: DNA
<213> ORGANISM: artificial
<220> FEATURE:
<223> OTHER INFORMATION: huH12-F

<400> SEQUENCE: 90
gtttccggtg gctccatctc cgactacggt gttgactgga        40

<210> SEQ ID NO 91
<211> LENGTH: 40
<212> TYPE: DNA
<213> ORGANISM: artificial
<220> FEATURE:
<223> OTHER INFORMATION: huH12-R

<400> SEQUENCE: 91
tccagtcaac accgtagtcg gagatggagc caccggaaac        40

<210> SEQ ID NO 92
<211> LENGTH: 47
<212> TYPE: DNA
<213> ORGANISM: artificial
<220> FEATURE:
<223> OTHER INFORMATION: huH13-F

<400> SEQUENCE: 92
gtttccggtg gctccatctc cgatacggtt gggactggat ccgtcag        47

<210> SEQ ID NO 93
<211> LENGTH: 48
<212> TYPE: DNA
<213> ORGANISM: artificial
<220> FEATURE:
<223> OTHER INFORMATION: huH13-R

<400> SEQUENCE: 93
ctgcaggatc cagtcccaac cgtagtcgga gatggagcca ccggaaac        48

<210> SEQ ID NO 94
<211> LENGTH: 35
<212> TYPE: DNA
<213> ORGANISM: artificial

```
<220> FEATURE:
<223> OTHER INFORMATION: huH14-F

<400> SEQUENCE: 94
gttccaccga ctacaacccc tctctgaaat cccgt                                35

<210> SEQ ID NO 95
<211> LENGTH: 35
<212> TYPE: DNA
<213> ORGANISM: artificial
<220> FEATURE:
<223> OTHER INFORMATION: huH14-R

<400> SEQUENCE: 95
acgggatttc agagaggggt tgtagtcggt ggaac                                35

<210> SEQ ID NO 96
<211> LENGTH: 48
<212> TYPE: DNA
<213> ORGANISM: artificial
<220> FEATURE:
<223> OTHER INFORMATION: huH15-F

<400> SEQUENCE: 96
gtttccggtg gctccatctc ctcctactat tggtcctgga tccgtcag                  48

<210> SEQ ID NO 97
<211> LENGTH: 48
<212> TYPE: DNA
<213> ORGANISM: artificial
<220> FEATURE:
<223> OTHER INFORMATION: huH15-R

<400> SEQUENCE: 97
ctgacggatc caggaccaat agtaggagga gatggagcca ccggaaac                  48

<210> SEQ ID NO 98
<211> LENGTH: 51
<212> TYPE: DNA
<213> ORGANISM: artificial
<220> FEATURE:
<223> OTHER INFORMATION: huH16-F

<400> SEQUENCE: 98
gaatggatcg gttatatcta ttattccggt tccaccaact acaaccctc t               51

<210> SEQ ID NO 99
<211> LENGTH: 51
<212> TYPE: DNA
<213> ORGANISM: artificial
<220> FEATURE:
<223> OTHER INFORMATION: huH16-R

<400> SEQUENCE: 99
agaggggttg tagttggtgg aaccggaata atagatataa ccgatccatt c              51

<210> SEQ ID NO 100
<211> LENGTH: 42
<212> TYPE: DNA
<213> ORGANISM: artificial
<220> FEATURE:
<223> OTHER INFORMATION: lgKLF

<400> SEQUENCE: 100
cctatctcga gaagcttcca ccatggagac agacacactc ct                        42
```

```
<210> SEQ ID NO 101
<211> LENGTH: 55
<212> TYPE: DNA
<213> ORGANISM: artificial
<220> FEATURE:
<223> OTHER INFORMATION: lgKHnmcR

<400> SEQUENCE: 101
acccggaccg gattcctgca gctgcacctg tccagtggaa cctggaaccc agagc    55

<210> SEQ ID NO 102
<211> LENGTH: 27
<212> TYPE: DNA
<213> ORGANISM: artificial
<220> FEATURE:
<223> OTHER INFORMATION: 14VHF

<400> SEQUENCE: 102
caggtgcagc tgcaggaatc cggtccg                                    27

<210> SEQ ID NO 103
<211> LENGTH: 42
<212> TYPE: DNA
<213> ORGANISM: artificial
<220> FEATURE:
<223> OTHER INFORMATION: 14VHR

<400> SEQUENCE: 103
cctatgcggc cgcgggccct tggtggaagc ggaggaaacg gt                   42

<210> SEQ ID NO 104
<211> LENGTH: 55
<212> TYPE: DNA
<213> ORGANISM: artificial
<220> FEATURE:
<223> OTHER INFORMATION: lgKLNMCR

<400> SEQUENCE: 104
gctgctgggg ctctgggtca tctggatgtc tccagtggaa cctggaaccc agagc    55

<210> SEQ ID NO 105
<211> LENGTH: 22
<212> TYPE: DNA
<213> ORGANISM: artificial
<220> FEATURE:
<223> OTHER INFORMATION: 10VLF

<400> SEQUENCE: 105
gacatccaga tgacccagag cc                                         22

<210> SEQ ID NO 106
<211> LENGTH: 47
<212> TYPE: DNA
<213> ORGANISM: artificial
<220> FEATURE:
<223> OTHER INFORMATION: hKcR

<400> SEQUENCE: 106
cctatgcggc cgcggatcct atcaacactc tcccctgttg aagctct             47

<210> SEQ ID NO 107
<211> LENGTH: 21
<212> TYPE: PRT
<213> ORGANISM: artificial
<220> FEATURE:
<223> OTHER INFORMATION: lg leader sequence

<400> SEQUENCE: 107
```

Met Glu Thr Asp Thr Leu Leu Leu Trp Val Leu Leu Leu Trp Val Pro
1               5                   10                  15

Gly Ser Thr Gly Asp
            20

<210> SEQ ID NO 108
<211> LENGTH: 973
<212> TYPE: DNA
<213> ORGANISM: artificial
<220> FEATURE:
<223> OTHER INFORMATION: I.M.A.G.E clone #4704496

<400> SEQUENCE: 108

```
gatcaggact cctcagttca ccttctcaca atgaggctcc ctgctcagct cctggggctg    60
ctaatgctct gggtcccagg atccagtggg gatgttgtga tgactcagtc tccactctcc   120
ctgcccgtca cccttggaca gccggcctcc atctcctgca ggtctactca aagcctcgta   180
tacagtgatg gaaacaccta cttgaattgg tttcagcaga ggccaggcca atctccaagg   240
cgcctaattt ataaggtttc taaccgggac tctggggtcc cagacagatt cagcggcagt   300
gggtcaggca ctgatttcac actgaaaatc accagggtgg aggctgagga tgttggggtt   360
tatttctgca tgcagggtac acactggccg tccacttttg gccaggggac caagctggag   420
atcaaacgaa ctgtggctgc accatctgtc ttcatcttcc cgccatctga tgagcagttg   480
aaatctggaa ctgcctctgt tgtgtgcctg ctgaataact tctatcccag agaggccaaa   540
gtacagtgga aggtggataa cgccctccaa tcgggtaact cccaggagag tgtcacagag   600
caggacagca aggacagcac ctacagcctc agcagcaccc tgacgctgag caaagcagac   660
tacgagaaac acaaagtcta cgcctgcgaa gtcacccatc agggcctgag ctcgcccgtc   720
acaaagagct tcaacagggg agagtgttag agggagaagt gcccccacct gctcctcagt   780
tccagcctga ccccctccca tcctttggcc tctgacccct tttccacagg gacctacccc   840
ctattgcggt cctccagctc atctttcacc tcacccccct cctcctcctt ggctttaatt   900
atgctaatgt tggaggagaa tgaataaata aagtgaatct ttcaaaaaaa aaaaaaaaa   960
aaaaaaaaaa aaa                                                     973
```

<210> SEQ ID NO 109
<211> LENGTH: 19
<212> TYPE: PRT
<213> ORGANISM: artificial
<220> FEATURE:
<223> OTHER INFORMATION: leader sequence from the human germline 4-59
      VH

<400> SEQUENCE: 109

Met Lys His Leu Trp Phe Phe Leu Leu Leu Val Ala Ala Pro Arg Trp
1               5                   10                  15

Val Leu Ser

<210> SEQ ID NO 110
<211> LENGTH: 10
<212> TYPE: PRT
<213> ORGANISM: artificial
<220> FEATURE:
<223> OTHER INFORMATION: H15 CDRH1

<400> SEQUENCE: 110

Gly Gly Ser Ile Ser Ser Tyr Tyr Trp Ser
1               5                   10

<210> SEQ ID NO 111
<211> LENGTH: 10
<212> TYPE: PRT
<213> ORGANISM: artificial
<220> FEATURE:
<223> OTHER INFORMATION: H14 CDRH1

<400> SEQUENCE: 111

Gly Gly Ser Ile Ser Asp Tyr Gly Trp Asp
1               5                   10

<210> SEQ ID NO 112
<211> LENGTH: 29
<212> TYPE: DNA
<213> ORGANISM: artificial
<220> FEATURE:
<223> OTHER INFORMATION: vWf-A1-For

<400> SEQUENCE: 112
cccaggaatt cctcggaacc gcgttgcac                                    29

<210> SEQ ID NO 113
<211> LENGTH: 31
<212> TYPE: DNA
<213> ORGANISM: artificial
<220> FEATURE:
<223> OTHER INFORMATION: vWF-A1-Rev

<400> SEQUENCE: 113
ccgatgcggc cgctcacctc ttgggcccca g                                 31

<210> SEQ ID NO 114
<211> LENGTH: 34
<212> TYPE: DNA
<213> ORGANISM: artificial
<220> FEATURE:
<223> OTHER INFORMATION: Rat-VWF-A1-F

<400> SEQUENCE: 114
agcgaattcc cccgaacccc ccctgcacaa cttc                              34

<210> SEQ ID NO 115
<211> LENGTH: 42
<212> TYPE: DNA
<213> ORGANISM: artificial
<220> FEATURE:
<223> OTHER INFORMATION: Rat-VWPVWF-A1-R

<400> SEQUENCE: 115
agtgcggccg cttatcacct tttgggtcct ggtgatgaaa cc                     42

<210> SEQ ID NO 116
<211> LENGTH: 426
<212> TYPE: DNA
<213> ORGANISM: artificial
<220> FEATURE:
<223> OTHER INFORMATION: Human antibody AAC18165.1 (mRNA accession
      number AF062129.1)

<400> SEQUENCE: 116
atgaaacatc tgtggttctt ccttctcctg gtggcagctc ccagatgggt cctgtcccag    60
gtgcagctgc aggagtcggg cccaggactg gtgaagcctt cggagaccct gtccctcacc   120
tgcactgtct ctggtggctc catcagtagt tactactgga gctggatccg gcagccccca   180
gggaagggac tggagtggat tgggtatatc tattacagtg ggagcaccaa ctacaacccc   240

```
tccctcaaga gtcgagtcac catatcagta gacacgtcca agaaccagtt ctccctgaag    300
ctgagctctg tgaccgctgc ggacacggcc gtgtattact gtgcgagagg ctacagaccg    360
ggggtagctg cccacagccc atttgactac tggggccagg gaaccctggt caccgtctcc    420
tcaggg                                                                426

<210> SEQ ID NO 117
<211> LENGTH: 322
<212> TYPE: DNA
<213> ORGANISM: artificial
<220> FEATURE:
<223> OTHER INFORMATION: Human antibody AAK94808 (mRNA)

<400> SEQUENCE: 117
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgataatc tccctctcac tttcggcgga    300
gggaccaagg tggagatcaa ac                                             322

<210> SEQ ID NO 118
<211> LENGTH: 7
<212> TYPE: PRT
<213> ORGANISM: artificial
<220> FEATURE:
<223> OTHER INFORMATION: human germline O18 CDR-L2

<400> SEQUENCE: 118

Asp Ala Ser Asn Leu Glu Thr
1               5

<210> SEQ ID NO 119
<211> LENGTH: 16
<212> TYPE: PRT
<213> ORGANISM: artificial
<220> FEATURE:
<223> OTHER INFORMATION: VH4-59 CDR H2

<400> SEQUENCE: 119

Tyr Ile Tyr Tyr Ser Gly Ser Thr Asn Tyr Asn Pro Ser Leu Lys Ser
1               5                   10                  15

<210> SEQ ID NO 120
<211> LENGTH: 321
<212> TYPE: DNA
<213> ORGANISM: artificial
<220> FEATURE:
<223> OTHER INFORMATION: L5 DNA

<400> SEQUENCE: 120
gacatccaga tgacccagag ccccagcagc ctgagcgcca gcgtgggcga ccgcgtgacc     60
atcacctgca gcgccagcca ggacatcaac aagtacctga actggtacca gcagaagccc    120
ggcaaggccg tcaagctgct gatcttctac accagcagcc tgcacagcgg cgtgcccagc    180
cgcttcagcg gcagcggcag cggcaccgac tacaccctga ccatcagcag cctgcagccc    240
gaggacatcg ccacctacta ctgccagcag tacgagaagc tgccctggac cttcggccag    300
ggcaccaagg tggagatcaa g                                              321

<210> SEQ ID NO 121
```

```
<211> LENGTH: 321
<212> TYPE: DNA
<213> ORGANISM: artificial
<220> FEATURE:
<223> OTHER INFORMATION: L4 (DNA)

<400> SEQUENCE: 121
gacatccaga tgacccagag ccccagcagc ctgagcgcca gcgtgggcga ccgcgtgacc      60
atcacctgca gcgccagcca ggacatcaac aagtacctga actggtacca gcagaagccc     120
ggcaaggccc ccaagctgct gatcttctac accagcagcc tgcacagcgg cgtgcccagc     180
cgcttcagcg gcagcggcag cggcaccgac tacaccctga ccatcagcag cctgcagccc     240
gaggacatcg ccacctacta ctgccagcag tacgagaagc tgccctggac cttcggccag     300
ggcaccaagg tggagatcaa g                                               321

<210> SEQ ID NO 122
<211> LENGTH: 321
<212> TYPE: DNA
<213> ORGANISM: artificial
<220> FEATURE:
<223> OTHER INFORMATION: L6 (DNA)

<400> SEQUENCE: 122
gacatccaga tgacccagag ccccagcagc ctgagcgcca gcgtgggcga ccgcgtgacc      60
atcacctgca gcgccagcca ggacatcaac aagtacctga actggtacca gcagaagccc     120
ggcaaggccg tcaagctgct gatctactac accagcagcc tgcacagcgg cgtgcccagc     180
cgcttcagcg gcagcggcag cggcaccgac tacaccctga ccatcagcag cctgcagccc     240
gaggacatcg ccacctacta ctgccagcag tacgagaagc tgccctggac cttcggccag     300
ggcaccaagg tggagatcaa g                                               321

<210> SEQ ID NO 123
<211> LENGTH: 321
<212> TYPE: DNA
<213> ORGANISM: artificial
<220> FEATURE:
<223> OTHER INFORMATION: L7 (DNA)

<400> SEQUENCE: 123
gacatccaga tgacccagag ccccagcagc ctgagcgcca gcgtgggcga ccgcgtgacc      60
atcacctgca gcgccagcca ggacatcaac aagtacctga actggtacca gcagaagccc     120
ggcaaggccg tcaagctgct gatcttctac accagcagcc tgcacagcgg cgtgcccagc     180
cgcttcagcg gcagcggcag cggcaccgac ttcaccctga ccatcagcag cctgcagccc     240
gaggacatcg ccacctacta ctgccagcag tacgagaagc tgccctggac cttcggccag     300
ggcaccaagg tggagatcaa g                                               321

<210> SEQ ID NO 124
<211> LENGTH: 321
<212> TYPE: DNA
<213> ORGANISM: artificial
<220> FEATURE:
<223> OTHER INFORMATION: L8 (DNA)

<400> SEQUENCE: 124
gacatccaga tgacccagag ccccagcagc ctgagcgcca gcgtgggcga ccgcgtgacc      60
atcacctgca gcgccagcca ggacatcaac aagtacctga actggtacca gcagaagccc     120
ggcaaggccc ccaagctgct gatctactac accagcagcc tgcacagcgg cgtgcccagc     180
```

```
cgcttcagcg gcagcggcag cggcaccgac ttcaccctga ccatcagcag cctgcagccc      240
gaggacatcg ccacctacta ctgccagcag tacgagaagc tgccctggac cttcggccag      300
ggcaccaagg tggagatcaa g                                                321
```

<210> SEQ ID NO 125
<211> LENGTH: 321
<212> TYPE: DNA
<213> ORGANISM: artificial
<220> FEATURE:
<223> OTHER INFORMATION: L9 (DNA)

<400> SEQUENCE: 125

```
gacatccaga tgacccagag ccccagcagc ctgagcgcca gcgtgggcga ccgcgtgacc      60
atcacctgca gcgccagcca ggacatcaac aagtacctga actggtacca gcagaagccc      120
ggcaaggccc ccaagctgct gatctactac accagcagcc tgcacagcgg cgtgcccagc      180
cgcttcagcg gcagcggcag cggcaccgac ttcaccctga ccatcagcag cctgcagccc      240
gaggacttcg ccacctacta ctgccagcag tacgagaagc tgccctggac cttcggccag      300
ggcaccaagg tggagatcaa g                                                321
```

<210> SEQ ID NO 126
<211> LENGTH: 321
<212> TYPE: DNA
<213> ORGANISM: artificial
<220> FEATURE:
<223> OTHER INFORMATION: L10 (DNA)

<400> SEQUENCE: 126

```
gacatccaga tgacccagag ccccagcagc ctgagcgcca gcgtgggcga ccgcgtgacc      60
atcacctgcc aagccagcca ggacatcagc aactacctga actggtacca gcagaagccc      120
ggcaaggccc ccaagctgct gatctactac accagcagcc tgcacagcgg cgtgcccagc      180
cgcttcagcg gcagcggcag cggcaccgac ttcaccctga ccatcagcag cctgcagccc      240
gaggacttcg ccacctacta ctgccagcag tacgagaagc tgccctggac cttcggccag      300
ggcaccaagg tggagatcaa g                                                321
```

<210> SEQ ID NO 127
<211> LENGTH: 321
<212> TYPE: DNA
<213> ORGANISM: artificial
<220> FEATURE:
<223> OTHER INFORMATION: L11 (DNA)

<400> SEQUENCE: 127

```
gacatccaga tgacccagag ccccagcagc ctgagcgcca gcgtgggcga ccgcgtgacc      60
atcacctgcc aagccagcca ggacatcagc aactacctga actggtacca gcagaagccc      120
ggcaaggccc ccaagctgct gatctacgac gccagcaacc tggaaaccgg cgtgcccagc      180
cgcttcagcg gcagcggcag cggcaccgac ttcaccctga ccatcagcag cctgcagccc      240
gaggacttcg ccacctacta ctgccagcag tacgagaagc tgccctggac cttcggccag      300
ggcaccaagg tggagatcaa g                                                321
```

<210> SEQ ID NO 128
<211> LENGTH: 369
<212> TYPE: DNA
<213> ORGANISM: artificial
<220> FEATURE:
<223> OTHER INFORMATION: H2 (DNA)

<400> SEQUENCE: 128

```
caggtgcagc tgcaggaatc cggtccgggt ctggttaaac cgtccgaaac cctgtccctg    60
acctgcaccg tttccggttt ctccctgacc gactacggtg ttgactggat ccgtcagccg   120
ccgggtaaag gtctggaatg gatcggtatg atctggggtg acggttccac cgactacaac   180
tccgctctga atcccgtct taccatctcc aaagacaact ccaaaaacca ggtctccctg   240
aaactgtcct ccgttaccgc tgctgacacc gctgtttact actgcgttcg tgacccggct   300
gactacggta actacgacta cgctctggac tactggggtc agggtaccctc cctgaccgtt   360
tcctccgct                                                            369
```

<210> SEQ ID NO 129
<211> LENGTH: 369
<212> TYPE: DNA
<213> ORGANISM: artificial
<220> FEATURE:
<223> OTHER INFORMATION: H4 (DNA)

<400> SEQUENCE: 129

```
caggtgcagc tgcaggaatc cggtccgggt ctggttaaac cgtccgaaac cctgtccctg    60
acctgcaccg tttccggttt ctccctgacc gactacggtg ttgactggat ccgtcagccg   120
ccgggtaaag gtctggaatg gatcggtatg atctggggtg acggttccac cgactacaac   180
tccgctctga atcccgtct taccatctcc aaagacaact ccaaaaacca ggtctccctg   240
aaactgtcct ccgttaccgc tgctgacacc gctgtttact actgcgctcg tgacccggct   300
gactacggta actacgacta cgctctggac tactggggtc agggtaccctc cctgaccgtt   360
tcctccgct                                                            369
```

<210> SEQ ID NO 130
<211> LENGTH: 369
<212> TYPE: DNA
<213> ORGANISM: artificial
<220> FEATURE:
<223> OTHER INFORMATION: H5 (DNA)

<400> SEQUENCE: 130

```
caggtgcagc tgcaggaatc cggtccgggt ctggttaaac cgtccgaaac cctgtccctg    60
acctgcaccg tttccggttt ctccctgacc gactacggtg ttgactggat ccgtcagccg   120
ccgggtaaag gtctggaatg gatcggtatg atctggggtg acggttccac cgactacaac   180
tccgctctga atcccgtgt taccatctcc aaagacaact ccaaaaacca ggtctccctg   240
aaactgtcct ccgttaccgc tgctgacacc gctgtttact actgcgttcg tgacccggct   300
gactacggta actacgacta cgctctggac tactggggtc agggtaccctc cctgaccgtt   360
tcctccgct                                                            369
```

<210> SEQ ID NO 131
<211> LENGTH: 369
<212> TYPE: DNA
<213> ORGANISM: artificial
<220> FEATURE:
<223> OTHER INFORMATION: H6 (DNA)

<400> SEQUENCE: 131

```
caggtgcagc tgcaggaatc cggtccgggt ctggttaaac cgtccgaaac cctgtccctg    60
acctgcaccg tttccggttt ctccctgacc gactacggtg ttgactggat ccgtcagccg   120
ccgggtaaag gtctggaatg gatcggtatg atctggggtg acggttccac cgactacaac   180
```

```
tccgctctga aatcccgtct taccatctcc gtagacaact ccaaaaacca ggtctccctg      240
aaactgtcct ccgttaccgc tgctgacacc gctgtttact actgcgttcg tgacccggct      300
gactacggta actacgacta cgctctggac tactggggtc agggtaccctc cctgaccgtt     360 tcctccgct                                                              369

<210> SEQ ID NO 132
<211> LENGTH: 369
<212> TYPE: DNA
<213> ORGANISM: artificial
<220> FEATURE:
<223> OTHER INFORMATION: H7 (DNA)

<400> SEQUENCE: 132
caggtgcagc tgcaggaatc cggtccgggt ctggttaaac cgtccgaaac cctgtccctg       60
acctgcaccg tttccggttt ctccctgacc gactacggtg ttgactggat ccgtcagccg      120
ccgggtaaag gtctggaatg gatcggtatg atctggggtg acggttccac cgactacaac      180
tccgctctga atcccgtct taccatctcc aaagacacct ccaaaaacca ggtctccctg       240
aaactgtcct ccgttaccgc tgctgacacc gctgtttact actgcgttcg tgacccggct      300
gactacggta actacgacta cgctctggac tactggggtc agggtaccctc cctgaccgtt     360 tcctccgct                                                              369

<210> SEQ ID NO 133
<211> LENGTH: 369
<212> TYPE: DNA
<213> ORGANISM: artificial
<220> FEATURE:
<223> OTHER INFORMATION: H8 (DNA)

<400> SEQUENCE: 133
caggtgcagc tgcaggaatc cggtccgggt ctggttaaac cgtccgaaac cctgtccctg       60
acctgcaccg tttccggttt ctccctgacc gactacggtg ttgactggat ccgtcagccg      120
ccgggtaaag gtctggaatg gatcggtatg atcggggtg acggttccac cgactacaac       180
tccgctctga atcccgtct taccatctcc aaagacaact ccaaaaacca gttctccctg       240
aaactgtcct ccgttaccgc tgctgacacc gctgtttact actgcgttcg tgacccggct      300
gactacggta actacgacta cgctctggac tactggggtc agggtaccctc cctgaccgtt     360 tcctccgct                                                              369

<210> SEQ ID NO 134
<211> LENGTH: 369
<212> TYPE: DNA
<213> ORGANISM: artificial
<220> FEATURE:
<223> OTHER INFORMATION: H9 (DNA)

<400> SEQUENCE: 134
caggtgcagc tgcaggaatc cggtccgggt ctggttaaac cgtccgaaac cctgtccctg       60
acctgcaccg tttccggttt ctccctgacc gactacggtg ttgactggat ccgtcagccg      120
ccgggtaaag gtctggaatg gatcggtatg atctggggtg acggttccac cgactacaac      180
tccgctctga atcccgtgt taccatctcc gtagacacct ccaaaaacca gttctccctg       240
aaactgtcct ccgttaccgc tgctgacacc gctgtttact actgcgctcg tgacccggct      300
gactacggta actacgacta cgctctggac tactggggtc agggtaccct cgtgaccgtt      360
tcctccgct                                                              369
```

<210> SEQ ID NO 135
<211> LENGTH: 369
<212> TYPE: DNA
<213> ORGANISM: artificial
<220> FEATURE:
<223> OTHER INFORMATION: H12 (DNA)

<400> SEQUENCE: 135

| | | | | | |
|---|---|---|---|---|---|
| caggtgcagc | tgcaggaatc | cggtccgggt | ctggttaaac | cgtccgaaac | cctgtccctg | 60 |
| acctgcaccg | tttccggtgg | ctccatctcc | gactacggtg | ttgactggat | ccgtcagccg | 120 |
| ccgggtaaag | gtctggaatg | gatcggtatg | atctggggtg | acggttccac | cgactacaac | 180 |
| tccgctctga | atcccgtgt | taccatctcc | gtagacacct | ccaaaaacca | gttctccctg | 240 |
| aaactgtcct | ccgttaccgc | tgctgacacc | gctgtttact | actgcgctcg | tgacccggct | 300 |
| gactacggta | actacgacta | cgctctggac | tactggggtc | agggtaccct | cgtgaccgtt | 360 |
| tcctccgct | | | | | | 369 |

<210> SEQ ID NO 136
<211> LENGTH: 369
<212> TYPE: DNA
<213> ORGANISM: artificial
<220> FEATURE:
<223> OTHER INFORMATION: H13 (DNA)

<400> SEQUENCE: 136

| | | | | | |
|---|---|---|---|---|---|
| caggtgcagc | tgcaggaatc | cggtccgggt | ctggttaaac | cgtccgaaac | cctgtccctg | 60 |
| acctgcaccg | tttccggtgg | ctccatctcc | gactacggtt | gggactggat | ccgtcagccg | 120 |
| ccgggtaaag | gtctggaatg | gatcggtatg | atctggggtg | acggttccac | cgactacaac | 180 |
| tccgctctga | atcccgtgt | taccatctcc | gtagacacct | ccaaaaacca | gttctccctg | 240 |
| aaactgtcct | ccgttaccgc | tgctgacacc | gctgtttact | actgcgctcg | tgacccggct | 300 |
| gactacggta | actacgacta | cgctctggac | tactggggtc | agggtaccct | cgtgaccgtt | 360 |
| tcctccgct | | | | | | 369 |

<210> SEQ ID NO 137
<211> LENGTH: 369
<212> TYPE: DNA
<213> ORGANISM: artificial
<220> FEATURE:
<223> OTHER INFORMATION: H14 (DNA)

<400> SEQUENCE: 137

| | | | | | |
|---|---|---|---|---|---|
| caggtgcagc | tgcaggaatc | cggtccgggt | ctggttaaac | cgtccgaaac | cctgtccctg | 60 |
| acctgcaccg | tttccggtgg | ctccatctcc | gactacggtt | gggactggat | ccgtcagccg | 120 |
| ccgggtaaag | gtctggaatg | gatcggtatg | atctggggtg | acggttccac | cgactacaac | 180 |
| ccctctctga | atcccgtgt | taccatctcc | gtagacacct | ccaaaaacca | gttctccctg | 240 |
| aaactgtcct | ccgttaccgc | tgctgacacc | gctgtttact | actgcgctcg | tgacccggct | 300 |
| gactacggta | actacgacta | cgctctggac | tactggggtc | agggtaccct | cgtgaccgtt | 360 |
| tcctccgct | | | | | | 369 |

<210> SEQ ID NO 138
<211> LENGTH: 369
<212> TYPE: DNA
<213> ORGANISM: artificial
<220> FEATURE:
<223> OTHER INFORMATION: H15 (DNA)

```
<400> SEQUENCE: 138
caggtgcagc tgcaggaatc cggtccgggt ctggttaaac cgtccgaaac cctgtccctg    60
acctgcaccg tttccggtgg ctccatctcc tcctactatt ggtcctggat ccgtcagccg   120
ccgggtaaag gtctggaatg gatcggtatg atctggggtg acggttccac cgactacaac   180
ccctctctga atcccgtgt taccatctcc gtagacacct ccaaaaacca gttctccctg    240
aaactgtcct ccgttaccgc tgctgacacc gctgtttact actgcgctcg tgacccggct   300
gactacggta actacgacta cgctctggac tactggggtc agggtaccct cgtgaccgtt   360
tcctccgct                                                           369

<210> SEQ ID NO 139
<211> LENGTH: 369
<212> TYPE: DNA
<213> ORGANISM: artificial
<220> FEATURE:
<223> OTHER INFORMATION: H16 (DNA)

<400> SEQUENCE: 139
caggtgcagc tgcaggaatc cggtccgggt ctggttaaac cgtccgaaac cctgtccctg    60
acctgcaccg tttccggtgg ctccatctcc tcctactatt ggtcctggat ccgtcagccg   120
ccgggtaaag gtctggaatg gatcggttat atctattatt ccggttccac caactacaac   180
ccctctctga atcccgtgt taccatctcc gtagacacct ccaaaaacca gttctccctg    240
aaactgtcct ccgttaccgc tgctgacacc gctgtttact actgcgctcg tgacccggct   300
gactacggta actacgacta cgctctggac tactggggtc agggtaccct cgtgaccgtt   360
tcctccgct                                                           369

<210> SEQ ID NO 140
<211> LENGTH: 60
<212> TYPE: DNA
<213> ORGANISM: artificial
<220> FEATURE:
<223> OTHER INFORMATION: VL-leader (DNA)

<400> SEQUENCE: 140
atggagacag acacactcct gctatgggta ctgctgctct gggttccagg ttccactgga    60

<210> SEQ ID NO 141
<211> LENGTH: 321
<212> TYPE: DNA
<213> ORGANISM: artificial
<220> FEATURE:
<223> OTHER INFORMATION: Kappa constant region (DNA)

<400> SEQUENCE: 141
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                              321

<210> SEQ ID NO 142
<211> LENGTH: 78
<212> TYPE: DNA
<213> ORGANISM: artificial
<220> FEATURE:
```

```
<223> OTHER INFORMATION: VH-leader (DNA)

<400> SEQUENCE: 142
atgaaacatc tgtggttctt ccttctcctg gtggcagcta tgaaacatct gtggttcttc      60
cttctcctgg tggcagct                                                   78

<210> SEQ ID NO 143
<211> LENGTH: 993
<212> TYPE: DNA
<213> ORGANISM: artificial
<220> FEATURE:
<223> OTHER INFORMATION: lgG1-constant region (DNA)

<400> SEQUENCE: 143
tccaccaagg gcccatccgt cttccccctg gcaccctcct ccaagagcac ctctgggggc      60
acagcggccc tgggctgcct ggtcaaggac tacttccccg aaccggtgac ggtgtcatgg     120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tgagcccaaa    300
tcttgtgaca aaactcacac atgcccaccg tgcccagcac ctgaactcga gggggggaccg   360 tcagtcttcc tcttccccc aaaacccaag gacaccctca tgatctcccg acccctgag      420 gtcacatgcg tggtggtgga cgtgagccac gaagaccctg aggtcaagtt caactggtac    480
gtggacggcg tggaggtgca taatgccaag acaaagccgc gggaggagca gtacaacagc    540
acgtaccgtg tggtcagcgt cctcaccgtc ctgcaccagg actggctgaa tggcaaggcg    600
tacgcgtgcg cggtctccaa caaagccctc ccagccccca tcgagaaaac catctccaaa    660
gccaaagggc agccccgaga accacaggtg tacaccctgc cccatcccg ggatgagctg     720 accaagaacc aggtcagcct gacctgcctg gtcaaaggct tctatcccag cgacatcgcc    780
gtggagtggg agagcaatgg gcagccggag aacaactaca agaccacgcc tcccgtgctg    840
gactccgacg gctccttctt cctctacagc aagctcaccg tggacaagag caggtggcag    900
caggggaacg tcttctcatg ctccgtgatg catgaggctc tgcacaacca ctacacgcag    960
aagagcctct ccctgtctct gggtaaatga taa                                 993

<210> SEQ ID NO 144
<211> LENGTH: 997
<212> TYPE: DNA
<213> ORGANISM: artificial
<220> FEATURE:
<223> OTHER INFORMATION: lgG4-constant region (DNA)
<220> FEATURE:
<221> NAME/KEY: IgG4-constant region (DNA)
<222> LOCATION: (1)..(997)

<400> SEQUENCE: 144
tccaccaagg gcccatccgt cttccccctg gcgccctgct ccaggagcac ctccgagagc      60
acagccgccc tgggctgcct ggtcaaggac tacttccccg aaccggtgac ggtgtcgtgg     120
aactcaggcg ccctgaccag cggcgtgcac accttcccgg ctgtcctaca gtcctcagga    180
ctctactccc tcagcagcgt ggtgaccgtg ccctccagca gcttgggcac gaagacctac    240
acctgcaacg tagatcacaa gcccagcaac accaaggtgg acaagagagt tgagtccaaa    300
tatggtcccc catgcccatc atgcccagca cctgagttcc tggggggacc atcagtcttc    360
ctgttccccc caaaacccaa ggacactctc atgatctccc ggacccctga ggtcacgtgc    420
gtggtggtgg acgtgagcca ggaagacccc gaggtccagt tcaactggta cgtggatggc    480
```

```
gtggaggtgc ataatgccaa gacaaagccg cgggaggagc agttcaacag cacgtaccgt    540
gtggtcagcg tcctcaccgt cctgcaccag gactggctga acggcaagga gtacaagtgc    600
aaggtctcca acaaaggcct cccgtcctcc atcgagaaaa ccatctccaa agccaaaggg    660
cagccccgag agccacaggt gtacaccctg cccccatccc aggaggagat gaccaagaac    720
caggtcagcc tgacctgcct ggtcaaaggc ttctacccca gcgacatcgc cgtggagtgg    780
gagagcaatg ggcagccgga gaacaactac aagaccacgc tcccgtgctg ggactccgac    840
ggctccttct cctctacag caggctaacc gtggacaaga gcaggtggca gaggggaat     900 gtcttctcat gctccgtgat gcatgaggct ctgcacaacc actacacaca gaagagcctc    960
tccctgtctc tgggtaaatg ataggatccg cggccgc                            997
```

```
<210> SEQ ID NO 145
<211> LENGTH: 122
<212> TYPE: PRT
<213> ORGANISM: artificial
<220> FEATURE:
<223> OTHER INFORMATION: H15

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Met Ile Trp Gly Asp Gly Ser Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Ala Asp Tyr Gly Asn Tyr Asp Tyr Ala Leu Asp Tyr Trp
            100                 105                 110

Gly Gln Gly Thr Leu Val Thr Val Ser Ser
        115                 120

<210> SEQ ID NO 146
<211> LENGTH: 122
<212> TYPE: PRT
<213> ORGANISM: artificial
<220> FEATURE:
<223> OTHER INFORMATION: H16

<400> SEQUENCE: 146

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Asp Pro Ala Asp Tyr Gly Asn Tyr Asp Tyr Ala Leu Asp Tyr Trp
            100                 105                 110

Gly Gln Gly Thr Leu Val Thr Val Ser Ser
        115                 120

<210> SEQ ID NO 147
<211> LENGTH: 25
<212> TYPE: PRT
<213> ORGANISM: artificial
<220> FEATURE:
<223> OTHER INFORMATION: VH4 (4-04, framework region 1)

<400> SEQUENCE: 147

Gln Val Gln Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 148
<211> LENGTH: 14
<212> TYPE: PRT
<213> ORGANISM: artificial
<220> FEATURE:
<223> OTHER INFORMATION: VH4 (4-04, framework region 2

<400> SEQUENCE: 148

Trp Val Arg Gln Pro Pro Gly Lys Gly Leu Glu Trp Ile Gly
1               5                   10

<210> SEQ ID NO 149
<211> LENGTH: 32
<212> TYPE: PRT
<213> ORGANISM: artificial
<220> FEATURE:
<223> OTHER INFORMATION: VH4 (4-04, framework region 3)

<400> SEQUENCE: 149

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 150
<211> LENGTH: 25
<212> TYPE: PRT
<213> ORGANISM: artificial
<220> FEATURE:
<223> OTHER INFORMATION: VH4 (4-28, framework region 1)

<400> SEQUENCE: 150

Gln Val Gln Leu Gln Glu Ser Gly Pro Gly Leu Val Lys Pro Ser Asp
1               5                   10                  15

Thr Leu Ser Leu Thr Cys Ala Val Ser
            20                  25

<210> SEQ ID NO 151
<211> LENGTH: 14
<212> TYPE: PRT
<213> ORGANISM: artificial
<220> FEATURE:
<223> OTHER INFORMATION: VH4 (4-28, framework region 2)

<400> SEQUENCE: 151

Trp Ile Arg Gln Pro Pro Gly Lys Gly Leu Glu Trp Ile Gly
1               5                   10
```

<210> SEQ ID NO 152
<211> LENGTH: 32
<212> TYPE: PRT
<213> ORGANISM: artificial
<220> FEATURE:
<223> OTHER INFORMATION: VH4 (4-28, framework region 3)

<400> SEQUENCE: 152

Arg Val Thr Met Ser Val Asp Thr Ser Lys Asn Gln Phe Ser Leu Lys
1               5                   10                  15

Leu Ser Ser Val Thr Ala Val Asp Thr Ala Val Tyr Tyr Cys Ala Arg
            20                  25                  30

<210> SEQ ID NO 153
<211> LENGTH: 25
<212> TYPE: PRT
<213> ORGANISM: artificial
<220> FEATURE:
<223> OTHER INFORMATION: VH4 (4-30.1, framework region 1)

<400> SEQUENCE: 153

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 154
<211> LENGTH: 14
<212> TYPE: PRT
<213> ORGANISM: artificial
<220> FEATURE:
<223> OTHER INFORMATION: VH4 (4-30.1, framework region 2)

<400> SEQUENCE: 154

Trp Ile Arg Gln His Pro Gly Lys Gly Leu Glu Trp Ile Gly
1               5                   10

<210> SEQ ID NO 155
<211> LENGTH: 32
<212> TYPE: PRT
<213> ORGANISM: artificial
<220> FEATURE:
<223> OTHER INFORMATION: VH4 (4-30.1, framework region 3)

<400> SEQUENCE: 155

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 156
<211> LENGTH: 25
<212> TYPE: PRT
<213> ORGANISM: artificial
<220> FEATURE:
<223> OTHER INFORMATION: VH4 (4-30.2, framework region 1)

<400> SEQUENCE: 156

Gln Leu Gln Leu Gln Glu Ser Gly Ser Gly Leu Val Lys Pro Ser Gln
1               5                   10                  15

Thr Leu Ser Leu Thr Cys Ala Val Ser
            20                  25

<210> SEQ ID NO 157

```
<211> LENGTH: 14
<212> TYPE: PRT
<213> ORGANISM: artificial
<220> FEATURE:
<223> OTHER INFORMATION: VH4 (4-30.2, framework region 2)

<400> SEQUENCE: 157

Trp Ile Arg Gln Pro Pro Gly Lys Gly Leu Glu Trp Ile Gly
1               5                   10

<210> SEQ ID NO 158
<211> LENGTH: 32
<212> TYPE: PRT
<213> ORGANISM: artificial
<220> FEATURE:
<223> OTHER INFORMATION: VH4 (4-30.2, framework region 3)

<400> SEQUENCE: 158

Arg Val Thr Ile Ser Val Asp Arg Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 159
<211> LENGTH: 25
<212> TYPE: PRT
<213> ORGANISM: artificial
<220> FEATURE:
<223> OTHER INFORMATION: VH4 (4-30.4, framework region 1)

<400> SEQUENCE: 159

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 160
<211> LENGTH: 14
<212> TYPE: PRT
<213> ORGANISM: artificial
<220> FEATURE:
<223> OTHER INFORMATION: VH4 (4-30.4, framework region 2)

<400> SEQUENCE: 160

Trp Ile Arg Gln Pro Pro Gly Lys Gly Leu Glu Trp Ile Gly
1               5                   10

<210> SEQ ID NO 161
<211> LENGTH: 32
<212> TYPE: PRT
<213> ORGANISM: artificial
<220> FEATURE:
<223> OTHER INFORMATION: VH4 (4-30.4, framework region 3)

<400> SEQUENCE: 161

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 162
<211> LENGTH: 25
<212> TYPE: PRT
<213> ORGANISM: artificial
<220> FEATURE:
<223> OTHER INFORMATION: VH4 (4-31, framework region 1)
```

<400> SEQUENCE: 162

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 163
<211> LENGTH: 14
<212> TYPE: PRT
<213> ORGANISM: artificial
<220> FEATURE:
<223> OTHER INFORMATION: VH4 (4-31, framework region 2)

<400> SEQUENCE: 163

Trp Ile Arg Gln His Pro Gly Lys Gly Leu Glu Trp Ile Gly
1               5                   10

<210> SEQ ID NO 164
<211> LENGTH: 32
<212> TYPE: PRT
<213> ORGANISM: artificial
<220> FEATURE:
<223> OTHER INFORMATION: VH4 (4-31, framework region 3)

<400> SEQUENCE: 164

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 165
<211> LENGTH: 25
<212> TYPE: PRT
<213> ORGANISM: artificial
<220> FEATURE:
<223> OTHER INFORMATION: VH4 (4-34, framework region 1)

<400> SEQUENCE: 165

Gln Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 166
<211> LENGTH: 14
<212> TYPE: PRT
<213> ORGANISM: artificial
<220> FEATURE:
<223> OTHER INFORMATION: VH4 (4-34, framework region 2)

<400> SEQUENCE: 166

Trp Ile Arg Gln Pro Pro Gly Lys Gly Leu Glu Trp Ile Gly
1               5                   10

<210> SEQ ID NO 167
<211> LENGTH: 32
<212> TYPE: PRT
<213> ORGANISM: artificial
<220> FEATURE:
<223> OTHER INFORMATION: VH4 (4-34, framework region 3)

<400> SEQUENCE: 167

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg 20                  25                  30

<210> SEQ ID NO 168
<211> LENGTH: 25
<212> TYPE: PRT
<213> ORGANISM: artificial
<220> FEATURE:
<223> OTHER INFORMATION: VH4 (4-39, framework region 1)

<400> SEQUENCE: 168

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 169
<211> LENGTH: 14
<212> TYPE: PRT
<213> ORGANISM: artificial
<220> FEATURE:
<223> OTHER INFORMATION: VH4 (4-39, framework region 2)

<400> SEQUENCE: 169

Trp Ile Arg Gln Pro Pro Gly Lys Gly Leu Glu Trp Ile Gly
1               5                   10

<210> SEQ ID NO 170
<211> LENGTH: 32
<212> TYPE: PRT
<213> ORGANISM: artificial
<220> FEATURE:
<223> OTHER INFORMATION: VH4 (4-39, framework region 3)

<400> SEQUENCE: 170

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 171
<211> LENGTH: 25
<212> TYPE: PRT
<213> ORGANISM: artificial
<220> FEATURE:
<223> OTHER INFORMATION: VH4 (4-59, framework region 1)

<400> SEQUENCE: 171

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 172
<211> LENGTH: 14
<212> TYPE: PRT
<213> ORGANISM: artificial
<220> FEATURE:
<223> OTHER INFORMATION: VH4 (4-59, framework region 2)

<400> SEQUENCE: 172

Trp Ile Arg Gln Pro Pro Gly Lys Gly Leu Glu Trp Ile Gly
1               5                   10

<210> SEQ ID NO 173
<211> LENGTH: 32
<212> TYPE: PRT

```
<213> ORGANISM: artificial
<220> FEATURE:
<223> OTHER INFORMATION: VH4 (4-59, framework region 3)

<400> SEQUENCE: 173

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 174
<211> LENGTH: 25
<212> TYPE: PRT
<213> ORGANISM: artificial
<220> FEATURE:
<223> OTHER INFORMATION: VH4 (4-61, framework region 1)

<400> SEQUENCE: 174

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 175
<211> LENGTH: 14
<212> TYPE: PRT
<213> ORGANISM: artificial
<220> FEATURE:
<223> OTHER INFORMATION: VH4 (4-61, framework region 2)

<400> SEQUENCE: 175

Trp Ile Arg Gln Pro Pro Gly Lys Gly Leu Glu Trp Ile Gly
1               5                   10

<210> SEQ ID NO 176
<211> LENGTH: 32
<212> TYPE: PRT
<213> ORGANISM: artificial
<220> FEATURE:
<223> OTHER INFORMATION: VH4 (4-61, framework region 3)

<400> SEQUENCE: 176

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 177
<211> LENGTH: 25
<212> TYPE: PRT
<213> ORGANISM: artificial
<220> FEATURE:
<223> OTHER INFORMATION: VH4 (4-b, framework region 1)

<400> SEQUENCE: 177

Gln Val Gln Leu Gln Glu Ser Gly Pro Gly Leu Val Lys Pro Ser Glu
1               5                   10                  15

Thr Leu Ser Leu Thr Cys Ala Val Ser
            20                  25

<210> SEQ ID NO 178
<211> LENGTH: 14
<212> TYPE: PRT
<213> ORGANISM: artificial
<220> FEATURE:
<223> OTHER INFORMATION: VH4 (4-b, framework region 2)
```

```
<400> SEQUENCE: 178

Trp Ile Arg Gln Pro Pro Gly Lys Gly Leu Glu Trp Ile Gly
1               5                   10

<210> SEQ ID NO 179
<211> LENGTH: 32
<212> TYPE: PRT
<213> ORGANISM: artificial
<220> FEATURE:
<223> OTHER INFORMATION: VH4 (4-b, framework region 3)

<400> SEQUENCE: 179

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 180
<211> LENGTH: 23
<212> TYPE: PRT
<213> ORGANISM: artificial
<220> FEATURE:
<223> OTHER INFORMATION: VK1 (O12, framework region 1)

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 181
<211> LENGTH: 15
<212> TYPE: PRT
<213> ORGANISM: artificial
<220> FEATURE:
<223> OTHER INFORMATION: VK1 (O12 ,framework region 2)

<400> SEQUENCE: 181

Trp Tyr Gln Gln Lys Pro Gly Lys Ala Pro Lys Leu Leu Ile Tyr
1               5                   10                  15

<210> SEQ ID NO 182
<211> LENGTH: 32
<212> TYPE: PRT
<213> ORGANISM: artificial
<220> FEATURE:
<223> OTHER INFORMATION: VK1 (O12 , framework region 3)

<400> SEQUENCE: 182

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 183
<211> LENGTH: 23
<212> TYPE: PRT
<213> ORGANISM: artificial
<220> FEATURE:
<223> OTHER INFORMATION: VK1 (O2, framework region 1)

<400> SEQUENCE: 183

Asp Ile Gln Met Thr Gln Ser Pro Ser Ser Leu Ser Ala Ser Val Gly
1               5                   10                  15
```

```
Asp Arg Val Thr Ile Thr Cys
            20

<210> SEQ ID NO 184
<211> LENGTH: 15
<212> TYPE: PRT
<213> ORGANISM: artificial
<220> FEATURE:
<223> OTHER INFORMATION: VK1 (O2 ,framework region 2)

<400> SEQUENCE: 184

Trp Tyr Gln Gln Lys Pro Gly Lys Ala Pro Lys Leu Leu Ile Tyr
1               5                   10                  15

<210> SEQ ID NO 185
<211> LENGTH: 32
<212> TYPE: PRT
<213> ORGANISM: artificial
<220> FEATURE:
<223> OTHER INFORMATION: VK1 (O2 , framework region 3)

<400> SEQUENCE: 185

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 186
<211> LENGTH: 23
<212> TYPE: PRT
<213> ORGANISM: artificial
<220> FEATURE:
<223> OTHER INFORMATION: VK1 (O18 derived antibody AAK94808, framework
      region 1)

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 187
<211> LENGTH: 15
<212> TYPE: PRT
<213> ORGANISM: artificial
<220> FEATURE:
<223> OTHER INFORMATION: VK1 (O18 derived antibody AAK94808,framework
      region 2)

<400> SEQUENCE: 187

Trp Tyr Gln Gln Lys Pro Gly Lys Ala Pro Lys Leu Leu Ile Tyr
1               5                   10                  15

<210> SEQ ID NO 188
<211> LENGTH: 32
<212> TYPE: PRT
<213> ORGANISM: artificial
<220> FEATURE:
<223> OTHER INFORMATION: VK1 (O18 derived antibody AAK94808, framework
      region 3)

<400> SEQUENCE: 188

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30
```

<210> SEQ ID NO 189
<211> LENGTH: 23
<212> TYPE: PRT
<213> ORGANISM: artificial
<220> FEATURE:
<223> OTHER INFORMATION: VK1 (08, framework region 1)

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 190
<211> LENGTH: 15
<212> TYPE: PRT
<213> ORGANISM: artificial
<220> FEATURE:
<223> OTHER INFORMATION: VK1 (08 ,framework region 2)

<400> SEQUENCE: 190

Trp Tyr Gln Gln Lys Pro Gly Lys Ala Pro Lys Leu Leu Ile Tyr
1               5                   10                  15

<210> SEQ ID NO 191
<211> LENGTH: 32
<212> TYPE: PRT
<213> ORGANISM: artificial
<220> FEATURE:
<223> OTHER INFORMATION: VK1 (08 , framework region 3)

<400> SEQUENCE: 191

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 192
<211> LENGTH: 23
<212> TYPE: PRT
<213> ORGANISM: artificial
<220> FEATURE:
<223> OTHER INFORMATION: VK1 (A20, framework region 1)

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 193
<211> LENGTH: 15
<212> TYPE: PRT
<213> ORGANISM: artificial
<220> FEATURE:
<223> OTHER INFORMATION: VK1 (A20 ,framework region 2)

<400> SEQUENCE: 193

Trp Tyr Gln Gln Lys Pro Gly Lys Val Pro Lys Leu Leu Ile Tyr
1               5                   10                  15

<210> SEQ ID NO 194
<211> LENGTH: 32
<212> TYPE: PRT
<213> ORGANISM: artificial
<220> FEATURE:

<223> OTHER INFORMATION: VK1 (A20 , framework region 3)

<400> SEQUENCE: 194

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 195
<211> LENGTH: 23
<212> TYPE: PRT
<213> ORGANISM: artificial
<220> FEATURE:
<223> OTHER INFORMATION: VK1 (A30, framework region 1)

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 196
<211> LENGTH: 15
<212> TYPE: PRT
<213> ORGANISM: artificial
<220> FEATURE:
<223> OTHER INFORMATION: VK1 (A30 ,framework region 2)

<400> SEQUENCE: 196

Trp Tyr Gln Gln Lys Pro Gly Lys Ala Pro Lys Arg Leu Ile Tyr
1               5                   10                  15

<210> SEQ ID NO 197
<211> LENGTH: 32
<212> TYPE: PRT
<213> ORGANISM: artificial
<220> FEATURE:
<223> OTHER INFORMATION: VK1 (A30 , framework region 3)

<400> SEQUENCE: 197

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 198
<211> LENGTH: 23
<212> TYPE: PRT
<213> ORGANISM: artificial
<220> FEATURE:
<223> OTHER INFORMATION: VK1 (L14, framework region 1)

<400> SEQUENCE: 198

Asn Ile Gln Met Thr Gln Ser Pro Ser Ala Met Ser Ala Ser Val Gly
1               5                   10                  15

Asp Arg Val Thr Ile Thr Cys
            20

<210> SEQ ID NO 199
<211> LENGTH: 15
<212> TYPE: PRT
<213> ORGANISM: artificial
<220> FEATURE:
<223> OTHER INFORMATION: VK1 (L14 ,framework region 2)

<400> SEQUENCE: 199

```
<210> SEQ ID NO 200
<211> LENGTH: 32
<212> TYPE: PRT
<213> ORGANISM: artificial
<220> FEATURE:
<223> OTHER INFORMATION: VK1 (L14 , framework region 3)

<400> SEQUENCE: 200
```

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

```
<210> SEQ ID NO 201
<211> LENGTH: 23
<212> TYPE: PRT
<213> ORGANISM: artificial
<220> FEATURE:
<223> OTHER INFORMATION: VK1 (L1, framework region 1)

<400> SEQUENCE: 201
```

Asp Ile Gln Met Thr Gln Ser Pro Ser Ser Leu Ser Ala Ser Val Gly
1               5                   10                  15

Asp Arg Val Thr Ile Thr Cys
            20

```
<210> SEQ ID NO 202
<211> LENGTH: 15
<212> TYPE: PRT
<213> ORGANISM: artificial
<220> FEATURE:
<223> OTHER INFORMATION: VK1 (L1 ,framework region 2)

<400> SEQUENCE: 202
```

Trp Phe Gln Gln Lys Pro Gly Lys Ala Pro Lys Ser Leu Ile Tyr
1               5                   10                  15

```
<210> SEQ ID NO 203
<211> LENGTH: 32
<212> TYPE: PRT
<213> ORGANISM: artificial
<220> FEATURE:
<223> OTHER INFORMATION: VK1 (L1 , framework region 3)

<400> SEQUENCE: 203
```

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

```
<210> SEQ ID NO 204
<211> LENGTH: 23
<212> TYPE: PRT
<213> ORGANISM: artificial
<220> FEATURE:
<223> OTHER INFORMATION: VK1 (L15, framework region 1)

<400> SEQUENCE: 204
```

Asp Ile Gln Met Thr Gln Ser Pro Ser Ser Leu Ser Ala Ser Val Gly
1               5                   10                  15

Asp Arg Val Thr Ile Thr Cys
            20

```
<210> SEQ ID NO 205
<211> LENGTH: 15
<212> TYPE: PRT
<213> ORGANISM: artificial
<220> FEATURE:
<223> OTHER INFORMATION: VK1 (L15,framework region 2)

<400> SEQUENCE: 205

Trp Tyr Gln Gln Lys Pro Glu Lys Ala Pro Lys Ser Leu Ile Tyr
1               5                   10                  15

<210> SEQ ID NO 206
<211> LENGTH: 32
<212> TYPE: PRT
<213> ORGANISM: artificial
<220> FEATURE:
<223> OTHER INFORMATION: VK1 (L15, framework region 3)

<400> SEQUENCE: 206

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 207
<211> LENGTH: 23
<212> TYPE: PRT
<213> ORGANISM: artificial
<220> FEATURE:
<223> OTHER INFORMATION: VK1 (L4, framework region 1)

<400> SEQUENCE: 207

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 208
<211> LENGTH: 15
<212> TYPE: PRT
<213> ORGANISM: artificial
<220> FEATURE:
<223> OTHER INFORMATION: VK1 (L4 ,framework region 2)

<400> SEQUENCE: 208

Trp Tyr Gln Gln Lys Pro Gly Lys Ala Pro Lys Leu Leu Ile Tyr
1               5                   10                  15

<210> SEQ ID NO 209
<211> LENGTH: 32
<212> TYPE: PRT
<213> ORGANISM: artificial
<220> FEATURE:
<223> OTHER INFORMATION: VK1 (L4 , framework region 3)

<400> SEQUENCE: 209

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 210
<211> LENGTH: 23
<212> TYPE: PRT
<213> ORGANISM: artificial
```

```
<220> FEATURE:
<223> OTHER INFORMATION: VK1 (L18, framework region 1)

<400> SEQUENCE: 210

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 211
<211> LENGTH: 15
<212> TYPE: PRT
<213> ORGANISM: artificial
<220> FEATURE:
<223> OTHER INFORMATION: VK1 (L18 ,framework region 2)

<400> SEQUENCE: 211

Trp Tyr Gln Gln Lys Pro Gly Lys Ala Pro Lys Leu Leu Ile Tyr
1               5                   10                  15

<210> SEQ ID NO 212
<211> LENGTH: 32
<212> TYPE: PRT
<213> ORGANISM: artificial
<220> FEATURE:
<223> OTHER INFORMATION: VK1 (L18 , framework region 3)

<400> SEQUENCE: 212

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 213
<211> LENGTH: 23
<212> TYPE: PRT
<213> ORGANISM: artificial
<220> FEATURE:
<223> OTHER INFORMATION: VK1 (L5, framework region 1)

<400> SEQUENCE: 213

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 214
<211> LENGTH: 15
<212> TYPE: PRT
<213> ORGANISM: artificial
<220> FEATURE:
<223> OTHER INFORMATION: VK1 (L5 ,framework region 2)

<400> SEQUENCE: 214

Trp Tyr Gln Gln Lys Pro Gly Lys Ala Pro Lys Leu Leu Ile Tyr
1               5                   10                  15

<210> SEQ ID NO 215
<211> LENGTH: 32
<212> TYPE: PRT
<213> ORGANISM: artificial
<220> FEATURE:
<223> OTHER INFORMATION: VK1 (L5 , framework region 3)

<400> SEQUENCE: 215

Gly Val Pro Ser Arg Phe Ser Gly Ser Gly Ser Gly Thr Asp Phe Thr
```

```
                1               5                  10                 15
Leu Thr Ile Ser Ser Leu Gln Pro Glu Asp Phe Ala Thr Tyr Tyr Cys
                20                  25                 30
```

<210> SEQ ID NO 216
<211> LENGTH: 23
<212> TYPE: PRT
<213> ORGANISM: artificial
<220> FEATURE:
<223> OTHER INFORMATION: VK1 (L19, framework region 1)

<400> SEQUENCE: 216

```
Asp Ile Gln Met Thr Gln Ser Pro Ser Ser Val Ser Ala Ser Val Gly
1               5                   10                  15
Asp Arg Val Thr Ile Thr Cys
                20
```

<210> SEQ ID NO 217
<211> LENGTH: 15
<212> TYPE: PRT
<213> ORGANISM: artificial
<220> FEATURE:
<223> OTHER INFORMATION: VK1 (L19 ,framework region 2)

<400> SEQUENCE: 217

```
Trp Tyr Gln Gln Lys Pro Gly Lys Ala Pro Lys Leu Leu Ile Tyr
1               5                   10                  15
```

<210> SEQ ID NO 218
<211> LENGTH: 32
<212> TYPE: PRT
<213> ORGANISM: artificial
<220> FEATURE:
<223> OTHER INFORMATION: VK1 (L19 , framework region 3)

<400> SEQUENCE: 218

```
Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
                20                  25                 30
```

<210> SEQ ID NO 219
<211> LENGTH: 23
<212> TYPE: PRT
<213> ORGANISM: artificial
<220> FEATURE:
<223> OTHER INFORMATION: VK1 (L8, framework region 1)

<400> SEQUENCE: 219

```
Asp Ile Gln Leu Thr Gln Ser Pro Ser Phe Leu Ser Ala Ser Val Gly
1               5                   10                  15
Asp Arg Val Thr Ile Thr Cys
                20
```

<210> SEQ ID NO 220
<211> LENGTH: 15
<212> TYPE: PRT
<213> ORGANISM: artificial
<220> FEATURE:
<223> OTHER INFORMATION: VK1 (L8 ,framework region 2)

<400> SEQUENCE: 220

```
Trp Tyr Gln Gln Lys Pro Gly Lys Ala Pro Lys Leu Leu Ile Tyr
1               5                   10                  15
```

```
<210> SEQ ID NO 221
<211> LENGTH: 32
<212> TYPE: PRT
<213> ORGANISM: artificial
<220> FEATURE:
<223> OTHER INFORMATION: VK1 (L8 , framework region 3)

<400> SEQUENCE: 221

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 222
<211> LENGTH: 23
<212> TYPE: PRT
<213> ORGANISM: artificial
<220> FEATURE:
<223> OTHER INFORMATION: VK1 (L23, framework region 1)

<400> SEQUENCE: 222

Ala Ile Arg Met Thr Gln Ser Pro Phe Ser Leu Ser Ala Ser Val Gly
1               5                   10                  15

Asp Arg Val Thr Ile Thr Cys
            20

<210> SEQ ID NO 223
<211> LENGTH: 15
<212> TYPE: PRT
<213> ORGANISM: artificial
<220> FEATURE:
<223> OTHER INFORMATION: VK1 (L12 ,framework region 2)

<400> SEQUENCE: 223

Trp Tyr Gln Gln Lys Pro Ala Lys Ala Pro Lys Leu Phe Ile Tyr
1               5                   10                  15

<210> SEQ ID NO 224
<211> LENGTH: 32
<212> TYPE: PRT
<213> ORGANISM: artificial
<220> FEATURE:
<223> OTHER INFORMATION: VK1 (L23 , framework region 3)

<400> SEQUENCE: 224

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 225
<211> LENGTH: 23
<212> TYPE: PRT
<213> ORGANISM: artificial
<220> FEATURE:
<223> OTHER INFORMATION: VK1 (L9, framework region 1)

<400> SEQUENCE: 225

Ala Ile Arg Met Thr Gln Ser Pro Ser Ser Phe Ser Ala Ser Thr Gly
1               5                   10                  15

Asp Arg Val Thr Ile Thr Cys
            20

<210> SEQ ID NO 226
<211> LENGTH: 15
<212> TYPE: PRT
```

```
<213> ORGANISM: artificial
<220> FEATURE:
<223> OTHER INFORMATION: VK1 (L9 ,framework region 2)

<400> SEQUENCE: 226

Trp Tyr Gln Gln Lys Pro Gly Lys Ala Pro Lys Leu Leu Ile Tyr
1               5                   10                  15

<210> SEQ ID NO 227
<211> LENGTH: 32
<212> TYPE: PRT
<213> ORGANISM: artificial
<220> FEATURE:
<223> OTHER INFORMATION: VK1 (L9, framework region 3)

<400> SEQUENCE: 227

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 228
<211> LENGTH: 23
<212> TYPE: PRT
<213> ORGANISM: artificial
<220> FEATURE:
<223> OTHER INFORMATION: VK1 (L24, framework region 1)

<400> SEQUENCE: 228

Val Ile Trp Met Thr Gln Ser Pro Ser Leu Leu Ser Ala Ser Thr Gly
1               5                   10                  15

Asp Arg Val Thr Ile Ser Cys
            20

<210> SEQ ID NO 229
<211> LENGTH: 15
<212> TYPE: PRT
<213> ORGANISM: artificial
<220> FEATURE:
<223> OTHER INFORMATION: VK1 (L24 ,framework region 2)

<400> SEQUENCE: 229

Trp Tyr Gln Gln Lys Pro Gly Lys Ala Pro Glu Leu Leu Ile Tyr
1               5                   10                  15

<210> SEQ ID NO 230
<211> LENGTH: 32
<212> TYPE: PRT
<213> ORGANISM: artificial
<220> FEATURE:
<223> OTHER INFORMATION: VK1 (L24 , framework region 3)

<400> SEQUENCE: 230

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 231
<211> LENGTH: 23
<212> TYPE: PRT
<213> ORGANISM: artificial
<220> FEATURE:
<223> OTHER INFORMATION: VK1 (L11, framework region 1)

<400> SEQUENCE: 231
```

```
Ala Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 232
<211> LENGTH: 15
<212> TYPE: PRT
<213> ORGANISM: artificial
<220> FEATURE:
<223> OTHER INFORMATION: VK1 (L11 ,framework region 2)

<400> SEQUENCE: 232

```
Trp Tyr Gln Gln Lys Pro Gly Lys Ala Pro Lys Leu Leu Ile Tyr
1               5                   10                  15
```

<210> SEQ ID NO 233
<211> LENGTH: 32
<212> TYPE: PRT
<213> ORGANISM: artificial
<220> FEATURE:
<223> OTHER INFORMATION: VK1 (L11 , framework region 3)

<400> SEQUENCE: 233

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 234
<211> LENGTH: 23
<212> TYPE: PRT
<213> ORGANISM: artificial
<220> FEATURE:
<223> OTHER INFORMATION: VK1 (L12, framework region 1)

<400> SEQUENCE: 234

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 235
<211> LENGTH: 15
<212> TYPE: PRT
<213> ORGANISM: artificial
<220> FEATURE:
<223> OTHER INFORMATION: VK1 (L12 ,framework region n2)

<400> SEQUENCE: 235

```
Trp Tyr Gln Gln Lys Pro Gly Lys Ala Pro Lys Leu Leu Ile Tyr
1               5                   10                  15
```

<210> SEQ ID NO 236
<211> LENGTH: 32
<212> TYPE: PRT
<213> ORGANISM: artificial
<220> FEATURE:
<223> OTHER INFORMATION: VK1 (L12 , framework region 3)

<400> SEQUENCE: 236

```
Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30
```

-continued

<210> SEQ ID NO 237
<211> LENGTH: 449
<212> TYPE: PRT
<213> ORGANISM: artificial
<220> FEATURE:
<223> OTHER INFORMATION: H9IgG4 (heavy chain)

<400> SEQUENCE: 237

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Asp Trp Ile Arg Gln Pro Pro Gly Lys Gly Leu Glu Trp Ile
        35                  40                  45

Gly Met Ile Trp Gly Asp Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Ala Asp Tyr Gly Asn Tyr Asp Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
                    370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 238
<211> LENGTH: 214
<212> TYPE: PRT
<213> ORGANISM: artificial
<220> FEATURE:
<223> OTHER INFORMATION: L9IgG4 (light chain)

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Asn Lys Tyr
            20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Lys Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210
```